US010801078B2

(12) United States Patent
Chen et al.

(10) Patent No.: US 10,801,078 B2
(45) Date of Patent: Oct. 13, 2020

(54) METHODS AND COMPOSITIONS FOR DETECTING BK VIRUS

(71) Applicant: Quest Diagnostics Infectious Disease, Inc., San Juan Capistrano, CA (US)

(72) Inventors: Fan Chen, Fullerton, CA (US); Lilly I. Kong, Covina, CA (US); Jules Chen, Walnut, CA (US); Mehrdad Jannatipour, Oceanside, CA (US)

(73) Assignee: Quest Diagnostics Infectious Disease, Inc., San Juan Capistrano, CA (US)

( * ) Notice: Subject to any disclaimer, the term of this patent is extended or adjusted under 35 U.S.C. 154(b) by 0 days.

(21) Appl. No.: 15/683,036

(22) Filed: Aug. 22, 2017

(65) Prior Publication Data
US 2018/0044742 A1    Feb. 15, 2018

Related U.S. Application Data

(63) Continuation of application No. 14/264,462, filed on Apr. 29, 2014, now Pat. No. 9,745,638, which is a continuation of application No. 13/005,490, filed on Jan. 12, 2011, now Pat. No. 8,748,092, which is a continuation of application No. 11/246,904, filed on Oct. 6, 2005, now Pat. No. 7,892,795.

(60) Provisional application No. 60/705,217, filed on Aug. 2, 2005.

(51) Int. Cl.
*C07H 21/04* (2006.01)
*C12Q 1/70* (2006.01)

(52) U.S. Cl.
CPC .... *C12Q 1/701* (2013.01); *C12N 2710/22011* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,213,796 A | 5/1993 | Garcea et al. | |
| 5,541,308 A | 7/1996 | Hogan et al. | |
| 6,605,602 B1 | 8/2003 | Vats | |
| 7,691,824 B2 | 4/2010 | Tan | |
| 7,892,795 B2 | 2/2011 | Chen et al. | |
| 2002/0146690 A1* | 10/2002 | Meyer, Jr. ............ | C12Q 1/6818 435/6.11 |

FOREIGN PATENT DOCUMENTS

| | | |
|---|---|---|
| WO | WO-92/19774 | 11/1992 |
| WO | WO-01/66148 | 9/2001 |
| WO | WO-2007/130519 | 11/2007 |

OTHER PUBLICATIONS

Bergallo, et al, Detection and typing of BKV, JCV, and SV40 by multiplex nested polymerase chain reaction, Molecular Biotech, (2007), 35:243-252.
Communication pursuant to Article 94(3) EPC dated Dec. 1, 2010 in EP application 06788689.
Degener et al, Identification of a New Control Region in the Genome of the DDP Stain ofBK Virus Isolated from PBMC, J Medical Virology 58:413 (1999).
Del Valle et al, Primary Central Nervous System Lymphoma Expressing the Human Neurotropic Polyomavirus, JC Virus, Genome, Journal of Virology, 78:3462-3469, 2004.
GenBank Accession No. AY628224 (NCBI Jun. 22, 2004).
International Search Report dated Apr. 1, 2008 in application PCT/US06/29243.
MacKenzie et al, Screening for herpesvirus genomes in common acute lymphoblasitc leukemia, Leukemia, 15:415-421, 2001.
McNees, et al, Specific and quantitative detection of human polyomaviruses BKV, JCV, and SV40 by real time PCR, J Clin Virol, (2005), 34:52-62.
Schatzl et al, Detection by PCR of human polyomaviruses BK and JC in immunocompromised individuals and partial sequencing of control regions, J. of Medical Virology, 42(2):138-145, 1994.
Search Report dated Nov. 10, 2009 for EP Application No. 06788689. 5.
Stoner et al., BK Virus Regulatory Region Rearrangements in Brain and Cerebrospinal Fluid from a Leukemia Patient with Tubulointerstitial Nephritis and Meningoencephalitis, American J of Kidney Diseases. 39:1102-1112(2002).
U.S. Notice of Allowance dated Oct. 12, 2010 in U.S. Appl. No. 11/246,904.
U.S. Office Action dated Apr. 30, 2008 in U.S. Appl. No. 11/246,904.
U.S. Office Action dated Apr. 17, 2009 in U.S. Appl. No. 11/246,904.
Vanchiere et al, Detection of BK virus and simian virus 40 in the urine of healthy children, J. of Medical Virology, 74(3):447-454, 2005.
Watzinger et al, Real-Time Quantitative PCR Assays for Detection and Monitoring of Pathogenic Human Viruses in Immunosuppressed Pediatric Patients, Journal of Clinical Microbiology, 42(11):5189-5198 (2004).
Whiley et al, Detection and Differentiation of Human Polyomaviruses JC and BK by LightCycler PCR, Journal of Clincal Microbiolgoy, 39:4357-4361, 2001.
Yang et al, BK Virus DNA Complete Nucleotide Sequence of a Human Tumor Virus, Science, 206:456-462, 1979.
Diffenbach, "General concepts for PCR primer design," PCR Methods and Applications, vol. 3, pp. 30-37, 1993.
Roux, "Optimization and troubleshooting in PCR," PCR Methods and Applications, vol. 4, pp. 185-194, 1995.
Examination Report dated Jun. 21, 2011 for AU Application No. 2006275803.

(Continued)

*Primary Examiner* — Katherine D Salmon

(57) ABSTRACT

The invention provides methods and compositions for rapid, sensitive, and highly specific nucleic acid-based (e.g., DNA based) detection of a BK virus in a sample. In general, the methods involve detecting a target nucleic acid having a target sequence of a conserved region of BK viral genomes. The invention also features compositions, including primers, probes, and kits, for use in the methods of the invention.

12 Claims, 54 Drawing Sheets

Specification includes a Sequence Listing.

(56) References Cited

OTHER PUBLICATIONS

Office Action issued in U.S. Appl. No. 13/005,490 dated Feb. 26, 2013.
Office Action issued in U.S. Appl. No. 13/005,490 dated Aug. 1, 2013.
Notice of Allowance issued in U.S. Appl. No. 13/005,490 dated Jan. 27, 2014.
NCBI GenBank Accession NC_001699 Apr. 5, 2012.
Office Action issued in U.S. Appl. No. 14/264,426 dated Aug. 10, 2015.
Final Office Action issued in U.S. Appl. No. 14/264,426 dated May 31, 2016.
Notice of Allowance issued in U.S. Appl. No. 14/264,426 dated May 5, 2017.

* cited by examiner

```
Consensus #1  CCTTCA.GCAGGGTC.CA.AAAGT.CATGA..ATGGTGGAGG.AAAACCT.T.C.AGGCAG.AATTT.CACTT.TTTGCTGT.GGTGG..GA.CCCTTGGAA
Majority      CCTTCATGCAGGGTCACAAAAAGTCACATGAGCATGGTGGAGGCATGGTGGAGGTAAACCTATTCAAGGCAGTAATTTCCACTTCTTTGCTGTTGGTGGAGACCCTTGGAA
ay628224      CCTTCACGCAGGGTCACAAAAAGTCACATGAGCATGGTGGAGGCATGGTGGAGGTAAACCTATTCAAGGCAGTAATTTCCACTTCTTTGCTGTTGGTGGAGACCCTTGGAA 2034
ay628225      CCTTCATGCAGGGTCACAAAAAGTCACATGAGCATGGTGGAGGCATGGTGGAGGTAAACCTATTCGAGGCAGTAATTTCCACTTCTTTGCTGTTGGTGGAGACCCTTGGAA 2034
ay628226      CCTTCATGCAGGGTCACAAAAAGTCACATGAGCATGGTGGAGGCATGGTGGAGGTAAACCTATTCAAGGCAGTAATTTCCACTTCTTTGCTGTTGGTGGAGACCCTTGGAA 2034
ay628227      CCTTCATGCAGGGTCACAAAAAGTCACATGAGCATGGTGGAGGCATGGTGGAGGTAAACCTATTCAAGGCAGTAATTTCCACTTCTTTGCTGTTGGTGGAGACCCTTGGAA 2034
ay628228      CCTTCATGCAGGGTCACAAAAAGTCACATGAGCATGGTGGAGGCATGGTGGAGGTAAACCTATTCAAGGCAGTAATTTCCACTTCTTTGCTGTTGGTGGAGACCCTTGGAA 2034
ay628229      CCTTCATGCAGGGTCACAAAAAGTCACATGAGCATGGTGGAGGCATGGTGGAGGTAAACCTATTCAAGGCAGTAATTTCCACTTCTTTGCTGTTGGTGGAGACCCTTGGAA 2034
ay628230      CCTTCATGCAGGGTCACAAAAAGTCACATGAGCATGGTGGAGGCATGGTGGAGGTAAACCTATTCAAGGCAGTAATTTCCACTTCTTTGCTGTTGGTGGAGACCCTTGGAA 2034
ay628231      CCTTCATGCAGGGTCACAAAAAGTCACATGAGCATGGTGGAGGCATGGTGGAGGTAAACCTATTCAAGGCAGTAATTTCCACTTCTTTGCTGTTGGTGGAGACCCTTGGAA 2034
ay628232      CCTTCATGCAGGGTCACAAAAAGTCACATGAGCATGGTGGAGGCATGGTGGAGGTAAACCTATTCAAGGCAGTAATTTCCACTTCTTTGCTGTTGGTGGAGACCCTTGGAA 2034
ay628233      CCTTCATGCAGGGTCACAAAAAGTCACATGAGCATGGTGGAGGCATGGTGGAGGTAAACCTATTCAAGGCAGTAATTTCCACTTCTTTGCTGTTGGTGGAGACCCTTGGAA 2034
ay628234      CCTTCATGCAGGGTCACAAAAAGTCACATGAGCATGGTGGAGGCATGGTGGAGGTAAACCTATTCAAGGCAGTAATTTCCACTTTTTTGCTGTTGGTGGAGACCCTTGGAA 1985
ay628235      CCTTCATGCAGGGTCACAAAAAGTCACATGAGCATGGTGGAGGCATGGTGGAGGTAAACCTATTCAAGGCAGTAATTTCCACTTTTTTGCTGTTGGTGGAGACCCTTGGAA 2034
ay628236      CCTTCATGCAGGGTCACAAAAAGTCACATGAGCATGGTGGAGGCATGGTGGAGGTAAACCTATTCAAGGCAGTAATTTCCACTTTTTTGCTGTTGGTGGAGACCCTTGGAA 2034
ay628237      CCTTCATGCAGGGTCACAAAAAGTCACATGAGCATGGTGGAGGCATGGTGGAGGTAAACCTATTCAAGGCAGTAATTTCCACTTCTTTGCTGTTGGTGGAGATCCTTGGAA 2022
ay628238      CCTTCATGCAGGGTCACAAAAAGTCACATGAGCATGGTGGAGGCATGGTGGAGGTAAACCTATTCGTCAAGGCAGTAATTTCCACTTTTTTGCTGTTGGTGGGGTAGACCCTTGGAA 2025
m23122        CCTTCATGCAGGGTCCCAAAAAGTCACATGAGAATGGTGGAGGCATGGTGGAGGTAAACCTATTCAAGGCAGTAATTTCCACTTCTTTGCTGTTAGTGGAGAACCCTTGGAA 2001
nc_001538     CCTTCATGCAGGGTCACAAAAAGTCACATGAGCATGGTGGAGGCATGGTGGAGGTAAACCTATTCAAGGCAGTAATTTCCACTTCTTTGCTGTTGGTGGAGAACCCTTGGAA 2046
v01108        CCTTCATGCAGGGTCACAAAAAGTCACATGAGCATGGTGGAGGCATGGTGGAGGTAAACCTATTCAAGGCAGTAATTTCCACTTCTTTGCTGTTGGTGGAGAACCCTTGGAA 2046
v01109        CCTTCATGCAGGGTCACAAAAAGTCACATGAGCATGGTGGAGGCATGGTGGAGGTAAACCTATTCAAGGCAGTAATTTCCACTTCTTTGCTGTTGGTGGAGACCCTTGGAA 1838
Focus2        CCTTCATGCAGGGTCACAAAAAGTCACATGAGCATGGTGGAGGCATGGTGGAGGAAAAACCTATTCAAGGCAGTAATTTCCACTTCTTTTTTGCTGTTGGTGGAGACCCTTGGAA 2040
Focus4        CCTTCATGCAGGGTCACAAAAAGTCACATGAGCATGGTGGAGGCATGGTGGAGGAAAAACCTATTCAAGGCAGTAATTTCCACTTTTTTTGCTGTTGGTGGAGACCCTTGGAA 2040
Focus9        CCTTCATGCAGGGTCACAGAAAGTCACATGAGCATGGTGGAGGCATGGTGGAGGAAAAACCTATTCAAGGCAGTAATTTCCACTTTTTTTGCTGTTGGTGGAGACCCTTGGAA 2089
Focus11       CCTTCATGCAGGGTCACAGAAAGTCACATGAGTACATGGTGGAGGCATGGTGGAGGAAATGGCAAACCTATTCGAGAAATGGAGGCAGTAATTTCCAATTTCACTTTTTTGCTGTTGGTGGGGGAGACCCTTGGAA 2042
Focus13       CCTTCATGCAGGGTCACAAAAAGTCACATGAGCATGGTGGAGGCATGGTGGAGGAAATGGAGGCAGTAATTTCCACTTTTTTGCTGTTGGTGGAGACCCTTGGAA 2042
Focus14       CCTTCATGCAGGGTCACAAAAAGTCACATGAGCATGGTGGAGGCATGGTGGAGGAAATGGAGGCAGTAATTTCCACTTTTTTGCTGTTGGTGGGGTAGACCCTTGGAA 2039
Focus18       CCTTCATGCAGGGTCACAGAAAGTCACATGAGTACATGGTGGAGGCATGGTGGAGGAAATGAAAATGGAGGCAGCAATTTCCACTTTTTCACTTCTTTGCTGTTGGTGGGGGAGACCCTTGGAA 2042
Focus19       CCTTCATGCAGGGTCACAAAAAGTCACATGAGCATGGTGGAGGCATGGTGGAGGAAAAACCTATTCAAGGCAGTAATTTCCACTTCTTTGCTGTTGGTGGAGACCCTTGGAA 2040
Focus23       CCTTCATGCAGGGTCACAAAAAGTCACATGAGCATGGTGGAGGCATGGTGGAGGAAAAACCTATTCAAGGAAATGGAGGCAGTAATTTCCACTTTTTTGCTGTTGGTGGAGACCCTTGGAA 2040
Focus29       CCTTCATGCAGGGTCACAAAAAGTCACATGAGCATGGTGGAGGCATGGTGGAGGAAAAACCTATTCAAGGAAATGGAGGCAGTAATTTCCACTTTTTTGCTGTTGGTGGAGACCCTTGGAA 2041
Focus30       CCTTCATGCAGGGTCACAAAAAGTCACATGAGCATGGTGGAGGCATGGTGGAGGAAAAACCTATTCAAGGCAGTAATTTCCACTTTTTTGCTGTTGGTGGAGACCCTTGGAA 2040
Focus31       CCTTCATGCAGGGTCACAAAAAGTCACATGAGCATGGTGGAGGCATGGTGGAGGAAAAACCTATTCAAGGCAGTAATTTCCACTTTTTTGCTGTTGGTGGAGACCCTTGGAA 2041
Focus32       CCTTCATGCAGGGTCACAAAAAGTCACATGAGCATGGTGGAGGAAGGCATGGTGGAGGAGAAAATGGAGGCAGTAATTTCCACTTCTTTGCTGTTGGTGGAGACCCTTGGAA 2004
```

```
Consensus    #1  G.GAATCTGCTGTTGC.TC.TCATCACTGGCAAACATATC.TCATGGCA..AATAA.TCTTCATCCCATTTTTCATTAAAGGA..CTCCACCA.GACTCCCA
Majority         GAGAATCTGCTGTTGCTTGCTTCTTCATCACTGGCAAACATATCTTCATGGCAAAATAAATCTTCATCCCATTTTTCATTAAAGGAGCTCCACCAGACTCCCA
ay628224         GAGAATCTGCTGTTGCTTGCTTCTTCATCACTGGCAAACATATCTTCATGGCAAAATAAATCTTCATCCCATTTTTCATTAAAGGAGCTCCACCAGACTCCCA  4530
ay628225         GAGAATCTGCTGTTGCTTGCTTCTTCATCACTGGCAAACATATCTTCATGGCAAAATAAATCTTCATCCCATTTTTCATTAAAGGAGCTCCACCAGACTCCCA  4530
ay628226         GAGAATCTGCTGTTGCTTGCTTCTTCATCACTGGCAAACATATCTTCATGGCAAAATAAATCTTCATCCCATTTTTCATTAAAGGAGCTCCACCAGACTCCCA  4530
ay628227         GAGAATCTGCTGTTGCTTGCTTCTTCATCACTGGCAAACATATCTTCATGGCAAAATAAATCTTCATCCCATTTTTCATTAAAGGAGCTCCACCAGACTCCCA  4530
ay628228         GAGAATCTGCTGTTGCTTGCTTCTTCATCACTGGCAAACATATCTTCATGGCAAAATAAATCTTCATCCCATTTTTCATTAAAGGAGCTCCACCAGACTCCCA  4530
ay628229         GAGAATCTGCTGTTGCTTGCTTCTTCATCACTGGCAAACATATCTTCATGGCAAAATAAATCTTCATCCCATTTTTCATTAAAGGAGCTCCACCAGACTCCCA  4530
ay628230         GAGAATCTGCTGTTGCTTGCTTCTTCATCACTGGCAAACATATCTTCATGGCAAAATAAATCTTCATCCCATTTTTCATTAAAGGAGCTCCACCAGACTCCCA  4530
ay628231         GAGAATCTGCTGTTGCTTGCTTCTTCATCACTGGCAAACATATCTTCATGGCAAAATAAATCTTCATCCCATTTTTCATTAAAGGAGCTCCACCAGACTCCCA  4530
ay628232         GAGAATCTGCTGTTGCTTGCTTCTTCATCACTGGCAAACATATCTTCATGGCAAAATAAATCTTCATCCCATTTTTCATTAAAGGAGCTCCACCAGACTCCCA  4530
ay628233         GAGAATCTGCTGTTGCTTGCTTCTTCATCACTGGCAAACATATCTTCATGGCAAAATAAATCTTCATCCCATTTTTCATTAAAGGAGCTCCACCAGACTCCCA  4530
ay628234         GAGAATCTGCTGTTGCTTGCTTCTTCATCACTGGCAAACATATCTTCATGGCAAAATAAATCTTCATCCCATTTTTCATTAAAGGAGCTCCACCAGACTCCCA  4481
ay628235         GAGAATCTGCTGTTGCTTGCTTCTTCATCACTGGCAAACATATCTTCATGGCAAAATAAATCTTCATCCCATTTTTCATTAAAGGAGCTCCACCAGACTCCCA  4530
ay628236         GAGAATCTGCTGTTGCTTGCTTCTTCATCACTGGCAAACATATCTTCATGGCAAAATAAATCTTCATCCCATTTTTCATTAAAGGAGCTCCACCAGACTCCCA  4530
ay628237         GAGAATCTGCTGTTGCTTGCTTCTTCATCACTGGCAAACATATCTTCATGGCAAAATAAATCTTCATCCCATTTTTCATTAAAGGAGCTCCACCAGACTCCCA  4518
ay628238         GAGAATCTGCTGTTGCTTGCTTCTTCATCACTGGCAAACATATCCTCATGGCAGAAATAAATCTTCATCCCATTTTTCATTAAAGGAGCTCCACCAGACTCCCA  4521
m23122           GGGAATCTGCTGTTGCTTGCTTCTTCATCACTGGCAAACATATCTTCATGGCAAAATAAATCTTCATCCCATTTTTCATTAAAGGAGCTCCACCAGACTCCCA  4485
nc_001538        GAGAATCTGCTGTTGCTTGCTTCTTCATCACTGGCAAACATATCTTCATGGCAAAATAAATCTTCATCCCATTTTTCATTAAAGGAACTCCACCAGACTCCCA  4542
v01108           GAGAATCTGCTGTTGCTTGCTTCTTCATCACTGGCAAACATATCTTCATGGCAAAATAAATCTTCATCCCATTTTTCATTAAAGGAACTCCACCAGACTCCCA  4542
v01109           GAGAATCTGCTGTTGCTTGCCTCTTCTTCATCACTGGCAAACATATCTTCATGGCAAAATAAATCTTCATCCCATTTTTCATTAAAGGAACTCCACCAGACTCCCA  4334
Focus2           GAGAATCTGCTGTTGCTTGCTTCCTCCTTCATCACTGGCAAACATATCTTCATGGCAAAATAAATCTTCATCCCATTTTTCATTAAAGGAACTCCACCAGACTCCCA  4536
Focus4           GAGAATCTGCTGTTGCTTGCTTCTTCTTCATCACTGGCAAACATATCTTCATGGCAAAATAAATCTTCATCCCATTTTTCATTAAAGGAACTCCACCAAGACTCCCA  4536
Focus9           GGGAATCTGCTGTTGCTTGCTTCTTCCCTCATCACTGGCAAACATATCTTCATGGCAAAATAAGTAAATAAATCTTCATCCCATTTTTCATTAAAGGAACTCCACCAGACTCCCA  4585
Focus11          GAGAATCTGCTGTTGCTTGCTTCTTCTTCATCACTGGCAAACATATCTTCATGGCAGAAATAAATCTTCATCCCATTTTTCATTAAAGGAACTCCACCAGACTCCCA  4541
Focus13          GAGAATCTGCTGTTGCTTGCTTCTTCTTCATCACTGGCAAACATATCTTCATGGCAGAAATAAATCTTCATCCCATTTTTCATTAAAGGACCTCCACCAAGACTCCCA  4538
Focus14          GAGAATCTGCTGTTGCTTGCTTCTTCTTCATCACTGGCAAACATATCTTCATGGCAAAATAAATCTTCATCCCATTTTTCATTAAAGGAACTCCACAAGACTCCCA  4535
Focus18          GGGAATCTGCTGTTGCTTGCCTCTTCTTCATCACTGGCAAACATATCTTCATGGCAAAATAAATCTTCATCCCATTTTTCATTAAAGGAACTCCACCAGACTCCCA  4542
Focus19          GAGAATCTGCTGTTGCTTGCTTCTTCTTCATCACTGGCAAACATATCTTCATGGCAAAATAAATCTTCATCCCATTTTTCATTAAAGGAGCTCCACCAGACTCCCA  4536
Focus23          GAGAATCTGCTGTTGCTTGCTTCTTCTTCATCACTGGCAAACATATCTTCATGGCAAAATAAGTAAATCTTCATCCCATTTTTCATTAAAGGAACTCCACCAGACTCCCA  4536
Focus29          GAGAATCTGCTGTTGCTTGCTTCTTCTTCATCACTGGCAAACATATCTTCATGGCAAAATAAATCTTCATCCCATTTTTCATTAAAGGAACTCCACCAGACTCCCA  4537
Focus30          GAGAATCTGCTGTTGCTTGCTTCTTCTTCATCACTGGCAAACATATCTTCATGGCAAAATAAATCTTCATCCCATTTTTCATTAAAGGAACTCCACCAGACTCCCA  4536
Focus31          GAGAATCTGCTGTTGCTTGCTTCTTCTTCATCACTGGCAAACATATCTTCATGGCAAAATAAATCTTCATCCCATTTTTCATTAAAGGAACTCCACCAGACTCCCA  4537
Focus32          GAGAATCTGCTGTTGCTTGCTTCTTCTTCATCACTGGCAAACATATCTTCATGGCAAAATAAGTCTTCATCCCATTTTTCATTAAAGGAACTCCACCAGACTCCCA  4500
```

| | | | |
|---|---|---|---|
| Consensus #1 | | | |
| Majority | ...AA.AG....A......CC.T..A.TC...C.T....A...A.T..A.CCA. | | |
| ay628224 | -CTAAAAGGTCCATGAGCTCCATGGATTCTTCCCTGTTAA-GCACTTTATCCAT | (SEQ ID NO.:22) | 5141 |
| ay628225 | -CTAAAAGGTCCATGAGCTCCATGGATTCTTCCCTGTTAA-GCACTTTATCCAT | (SEQ ID NO.:23) | 5141 |
| ay628226 | -CTAAAAGGTCCATGAGCTCCATGGATTCTTCCCTGTTAA-GCACTTTATCCAT | (SEQ ID NO.:24) | 5141 |
| ay628227 | -CTAAAAGGTCCATGAGCTCCATGGATTCTTCCCTGTTAA-GCACTTTATCCAT | (SEQ ID NO.:25) | 5141 |
| ay628228 | -CTAAAAGGTCCATGAGCTCCATGGATTCTTCCCTGTTAA-GCACTTTATCCAT | (SEQ ID NO.:26) | 5141 |
| ay628229 | -CTAAAAGGTCCATGAGCTCCATGGATTCTTCCCTGTTAA-GCACTTTATCCAT | (SEQ ID NO.:27) | 5141 |
| ay628230 | -CTAAAAGGTCCATGAGCTCCATGGATTCTTCCCTGTTAA-GCACTTTATCCAT | (SEQ ID NO.:28) | 5141 |
| ay628231 | -CTAAAAGGTCCATGAGCTCCATGGATTCTTCCCTGTTAA-GCACTTTATCCAT | (SEQ ID NO.:29) | 5141 |
| ay628232 | -CTAAAAGGTCCATGAGCTCCATGGATTCTTCCCTGTTAA-GCACTTTATCCAT | (SEQ ID NO.:30) | 5141 |
| ay628233 | -CTAAAAGGTCCATGAGCTCCATGGATTCTTCCCTGTTAA-GCACTTTATCCAT | (SEQ ID NO.:31) | 5141 |
| ay628234 | -CCAAAAGGTCCATGAGCTCCATGGATTCTTCCCTGTTAA-GCACTTTATCCAT | (SEQ ID NO.:32) | 5141 |
| ay628235 | -CCAAAAGGTCCATGAGCTCCATGGATTCTTCCCTGTTAA-GCACTTTATCCAT | (SEQ ID NO.:33) | 5092 |
| ay628236 | -CCAAAAGGTCCATGAGCTCCATGGATTCTTCCCTGTTAA-GCACTTTATCCAT | (SEQ ID NO.:34) | 5141 |
| ay628237 | -CCAAAAGGTCCATGAGCTCCATGGATTCTTCCCTGTTAA-GCACTTTATCCAT | (SEQ ID NO.:35) | 5141 |
| ay628238 | -CTAAAAGGTCCATGAGCTCCATGGATTCTTCCCTGTTAA-GCACTTTATCCAT | (SEQ ID NO.:36) | 5129 |
| m23122 | -CTAAAAGGTCCATGAGCTCCATGGATTCTTCCCTGTTTA-AGACTTTATCCAT | (SEQ ID NO.:37) | 5132 |
| nc_001538 | -CTAAAAGGTCCATGAGCTCCATGGATTCTTCCCTGTTAA-GAACTTTATCCAT | (SEQ ID NO.:38) | 5098 |
| v01108 | -CTAAAAGGTCCATGAGCTCCATGGATTCTTCCCTGTTAA-GAACTTTATCCAT | (SEQ ID NO.:39) | 5153 |
| v01109 | GTTAATAGTGAAACCCGCCCCCTAAAATCTCTTCCCTGTTAA-CCACCATGGAATGCAGCAA | (SEQ ID NO.:40) | 5153 |
| Focus2 | -CTAAAAGGTCCATGAGCTCCATGGATTCTTCCCTGTTAA-GCACTTTATCCAT | (SEQ ID NO.:41) | 4963 |
| Focus4 | -CCAAAAGGTCCATGAGCTCCATGGATTCTTCCCTGTTAA-GCACTTTATCCAT | (SEQ ID NO.:42) | 5147 |
| Focus9 | -CCAAAAGGTCCATGAGCTCCATGGATTCTTCCCTGTTAA-GCACTTTATCCAT | (SEQ ID NO.:43) | 5147 |
| Focus11 | -CTAAAAGGTCCATGAGCTCCATGGATTCCTCCCTGTTTA-GAACTTTATCCAT | (SEQ ID NO.:44) | 5196 |
| Focus13 | -CCAAAAGGTCCATGAGCTCCATGGATTCTTCCCTGTTAA-GCACTTTATCCAT | (SEQ ID NO.:45) | 5154 |
| Focus14 | -CCAAAAGGTCCATGAGCTCCATGGATTCTTCCCTGTTAA-GCACTTTATCCAT | (SEQ ID NO.:46) | 5149 |
| Focus18 | -CCAAAAGGTCCATGAGCTCCATGGATTCCTCCCTGTTTA-GCACTTTATCCAT | (SEQ ID NO.:47) | 5146 |
| Focus19 | -CTAAAAGGTCCATGAGCTCCATGGATTCTTCCCTGTTTA-GCACTTTATCCAT | (SEQ ID NO.:48) | 5153 |
| Focus23 | -CTAAAAGGTCCATGAGCTCCATGGATTCTTCCCTGTTAA-GCACTTTATCCAT | (SEQ ID NO.:49) | 5147 |
| Focus29 | -CTAAAAGGTCCATGAGCTCCATGGATTCTTCCCTGTTAA-GCACTTTATCCAT | (SEQ ID NO.:50) | 5147 |
| Focus30 | -CCAAAAGGTCCATGAGCTCCATGGATTCTTCCCTGTTAA-GCACTTTATCCAT | (SEQ ID NO.:51) | 5196 |
| Focus31 | -CTAAAAGGTCCATGAGCTCCATGGATTCTTCCCTGTTAA-GCACTTTATCCAT | (SEQ ID NO.:52) | 5147 |
| Focus32 | -CTAAAAGGTCCATGAGCTCCATGGATTCTTCCCTGTTAA-GCACTTTATCCAT | (SEQ ID NO.:53) | 5148 |
| | -CTAAAAGGTCCATGAGCTCCATGGATTCTTCCCTGTTAA-GCACTTTATCCAT | (SEQ ID NO.:54) | 5111 |

FIG. 1AAA

METHODS AND COMPOSITIONS FOR DETECTING BK VIRUS

CROSS-REFERENCE

This application is a Continuation of U.S. Application. No. 14/264,462, filed Apr. 29, 2014, which issued as U.S. Pat. No. 9,745,638 on Aug. 29, 2017, which is a Continuation of U.S. application Ser. No. 13/005,490, filed Jan. 12, 2011, which issued as U.S. Pat. No. 8,748,092 on Jun. 10, 2014, which is a Continuation of U.S. application Ser. No. 11/246,904, filed Oct. 6, 2005, which issued as U.S. Pat. No. 7,892,795 on Feb. 22, 2011, which claims the benefit of U.S. Provisional application Ser. No. 60/705,217, filed Aug. 2, 2005, which application is incorporated herein by reference in its entirety.

FIELD OF THE INVENTION

The invention relates to detection of BK viruses.

BACKGROUND OF THE INVENTION

Human polyomavirus type BK (BK virus) is a non-enveloped virus with a circular, double-stranded-DNA genome of about 5,300 bp. BK virus was first recognized as a member of the polyomavirus family in 1971, after isolation from the urine of a renal-transplant recipient. Subsequent studies documented a worldwide rate of seroprevalence in adults of more than 80 percent. Typically, primary infection with the BK virus occurs during childhood by the respiratory route, followed by latency of the virus in the urogenital tract. Asymptomatic reactivation and intermittent shedding of virus in the urine occur spontaneously in immunocompetent persons but are more frequent among those with altered cellular immunity, such as pregnant women, patients with cancer who are receiving chemotherapy, HIV-1 infected individuals and recipients of renal or other allografts. Overt clinical disease from BK virus infection is rare and is clearly linked to the degree of immunosuppression.

BK-virus associated nephropathy has become an increasingly recognized cause of renal dysfunction in renal transplant patients. According to retrospective studies, BK virus nephropathy develops in 1 to 5 percent of renal-transplant recipients, with loss of allograft function occurring in as many as 45 percent of the affected patients. Although BK virus-specific antiviral therapy is not available, in some cases, BK virus replication may be controlled by reducing the level of maintenance immunosuppression. Recent evidence suggests that detection of BK virus DNA closely follows the course of BK virus nephropathy and may serve as a noninvasive tool for diagnosis and monitoring. Therefore, quantification of BK virus load in renal transplant patients would be useful both for diagnosing BK virus nephropathy and for monitoring the response to therapy, i.e., reduction in immunosuppression. In addition, BK virus has been implicated in other diseases, such as prostate cancer.

Accordingly, there remains a need for the development of reliable diagnostic tests to detect BK virus with a sensitivity that allows detection of low titers of virus, as well as for detection of different BK virus genotypes. In addition, there remains a need for a reliable diagnostic test to distinguish between BK virus and other polyoma viruses, such as JC virus. Such assays are critical to prevent transmission of the virus through blood and plasma derivatives or by close personal contact. The present invention addresses these needs.

Literature

Literature of interest includes:
U.S. Pat. No. 5,213,796; U.S. Pat. No. 6,605,602; WO 92/19774; Watzinger et al., Journal of Clinical Microbiology, 42(11):5189-5198 (2004); Anna Marta Degener, et al., J Medical Virology 58:413 (1999); and Stoner et al., American J of Kidney Diseases. 33:1102 (2002).

SUMMARY OF THE INVENTION

The invention provides methods and compositions for rapid, sensitive, and highly specific nucleic acid-based (e.g., DNA based) detection of a BK virus in a sample. In general, the methods involve detecting a target nucleic acid having a target sequence of conserved regions of BK viral genome. The invention also features compositions, including primers, probes, and kits, for use in the methods of the invention.

An advantage of the invention is that it provides for detection of BK virus while avoiding detection of viruses that are closely related genetically. Thus, the invention decreases the incidence of false positives.

Another advantage of the invention is that it decreases the incidence of false negative results that can result from failure to detect genetic variants of the BK virus (e.g., BK viruses of different genotype or strain).

Still another advantage is that the invention encompasses embodiments that require detection of only a relatively short target sequence. This can be particularly advantageous where the assay uses amplification-based technology, such as real-time PCR.

The present invention can be developed into assays or manufactured into kits to be use in reference laboratories or hospitals for the diagnostics of BK virus. The assay can also be utilized in the development and clinical trials of therapeutic drugs for treating diseases caused by BKV infection.

These and other advantages will be readily apparent to the ordinarily skilled artisan upon reading the present specification.

BRIEF DESCRIPTION OF THE DRAWINGS

Figure 1A:
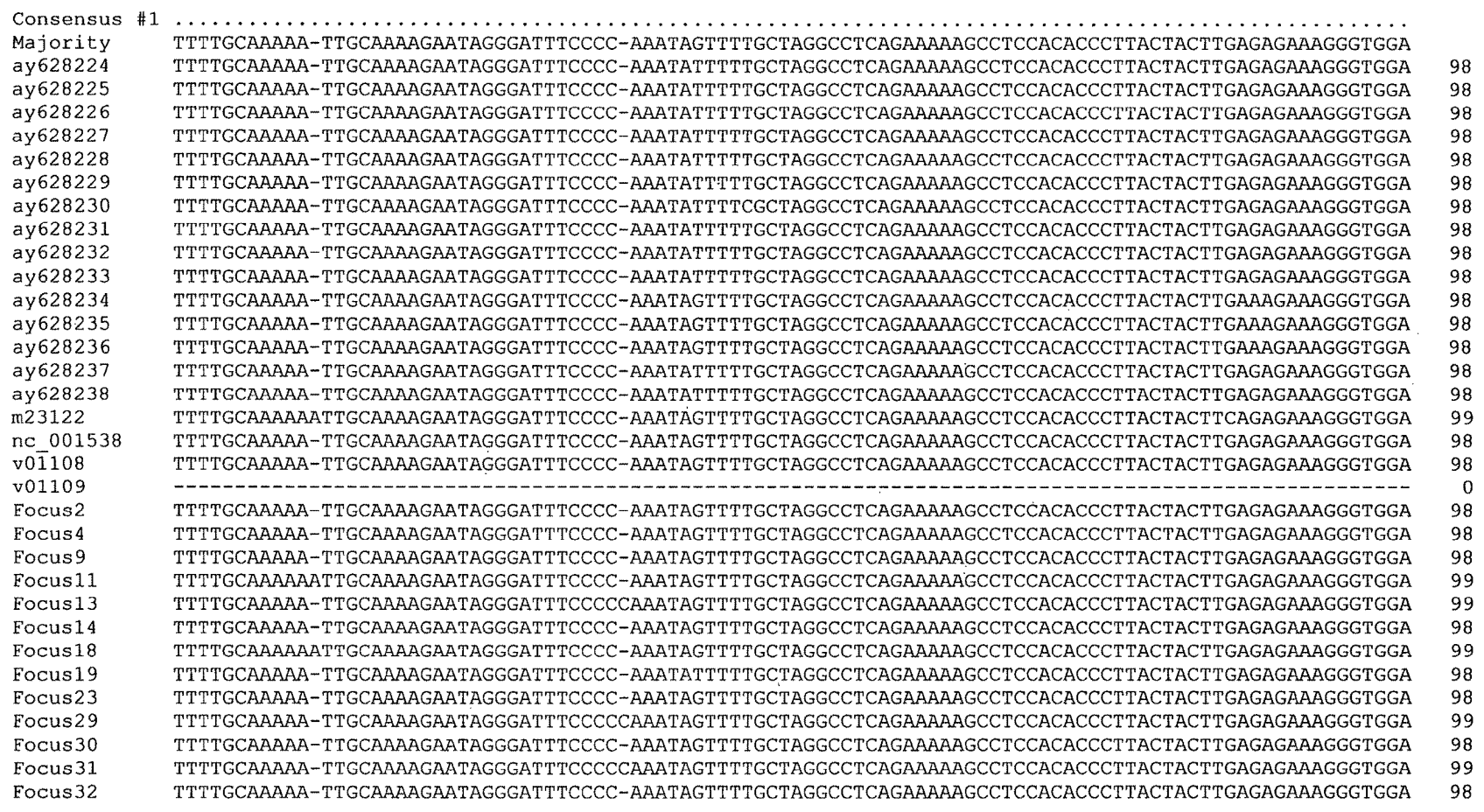
Figure 1B:
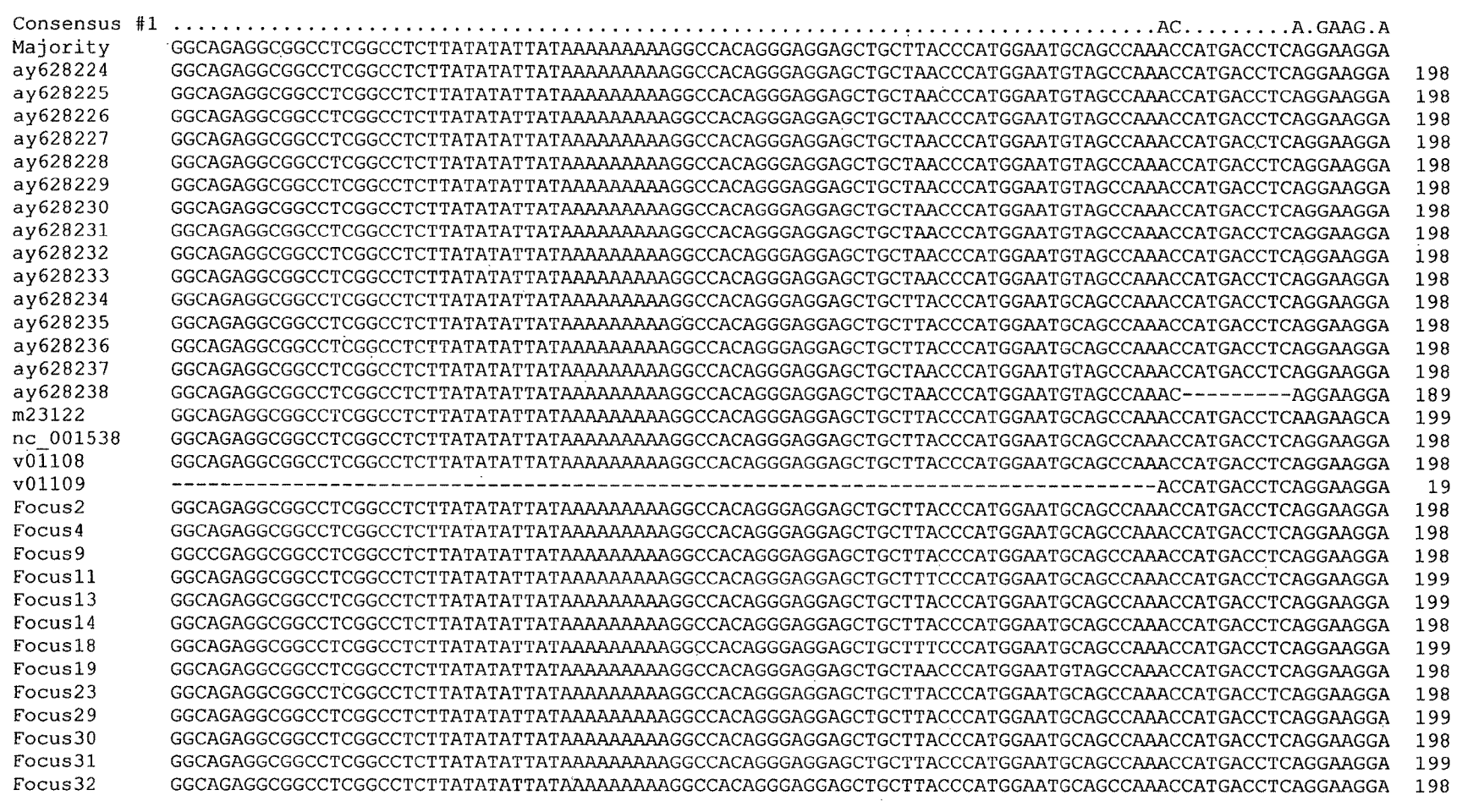
Figure 1C:
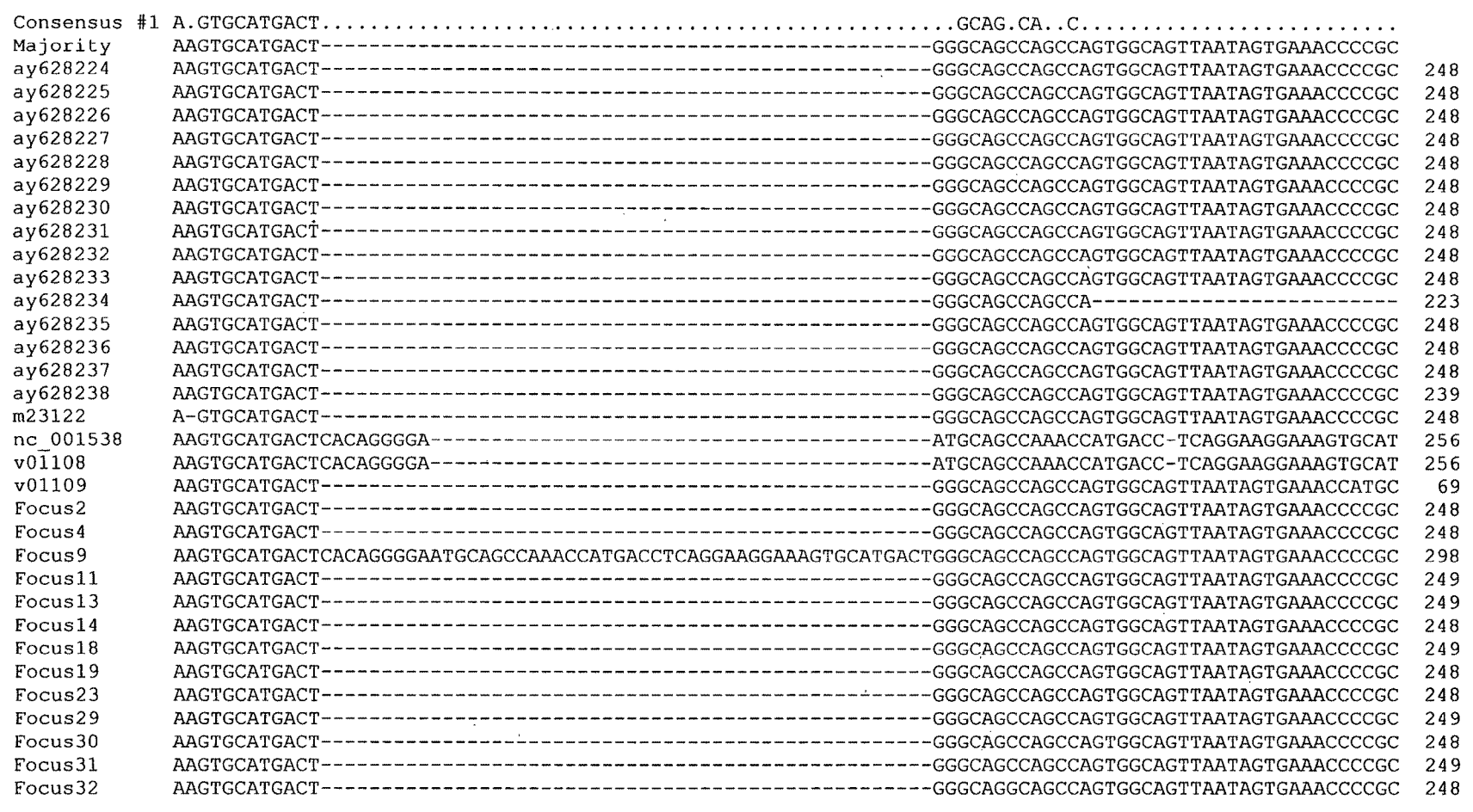
Figure 1D:
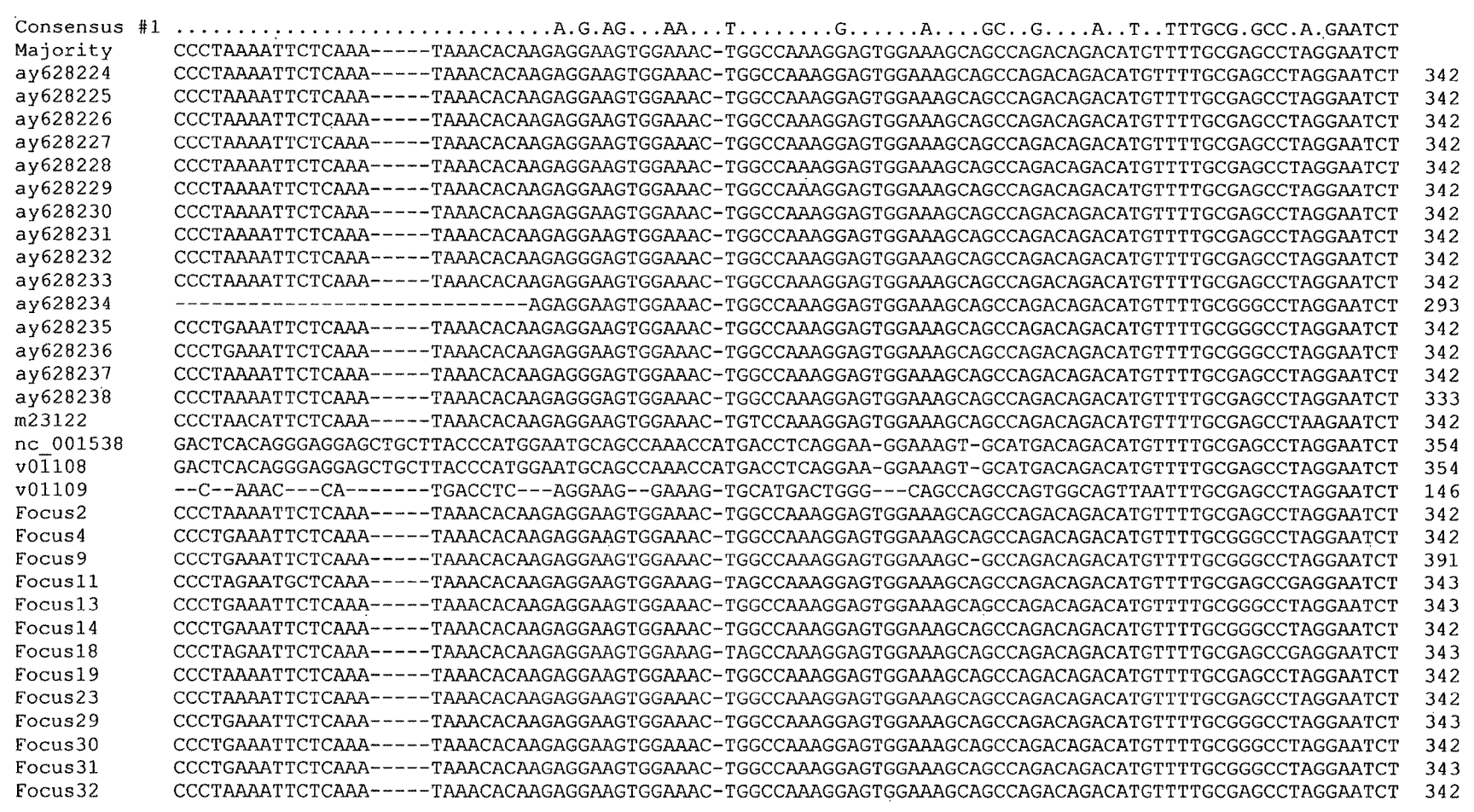
Figure 1E:
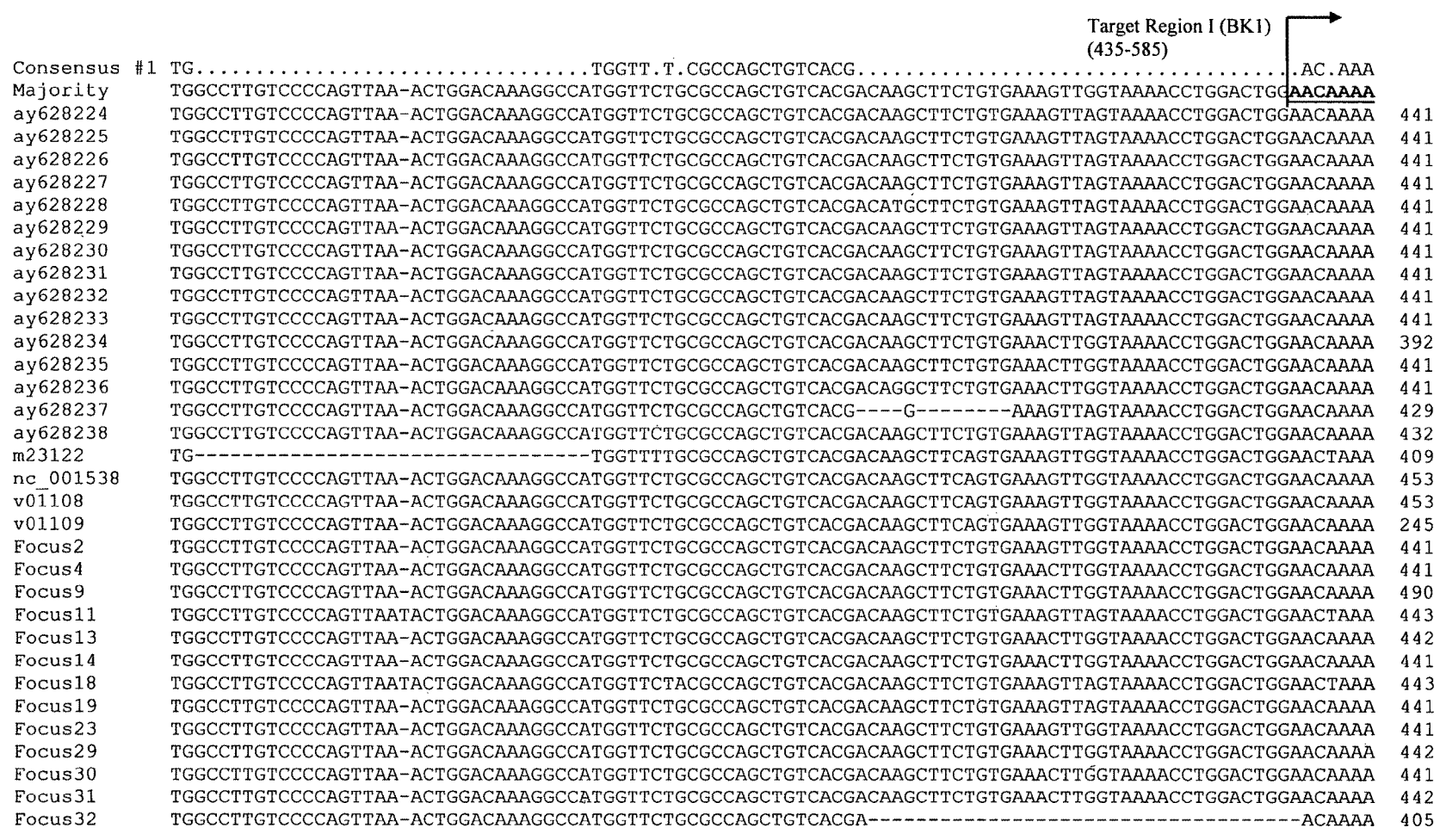
Figure 1F:
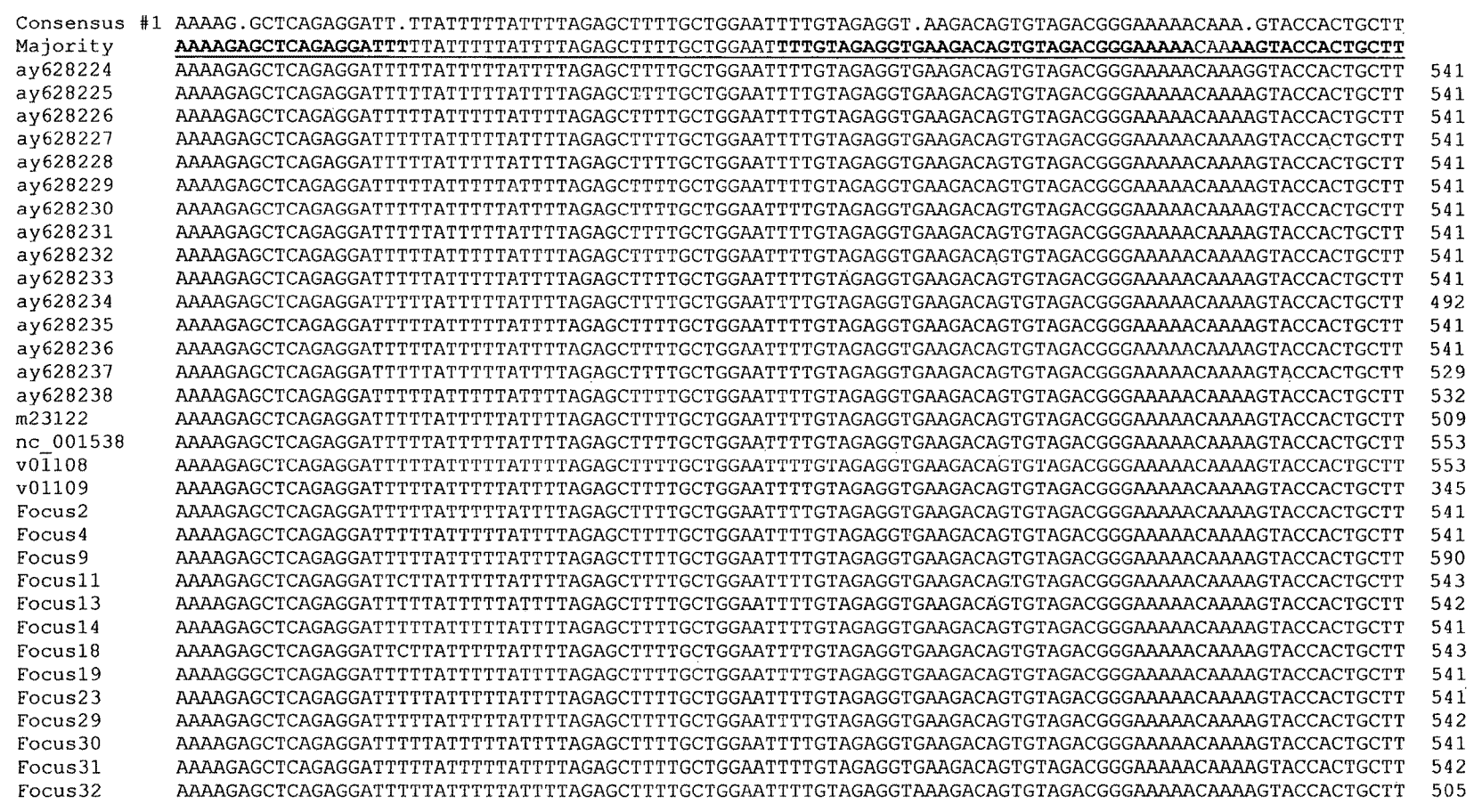
Figure 1G:
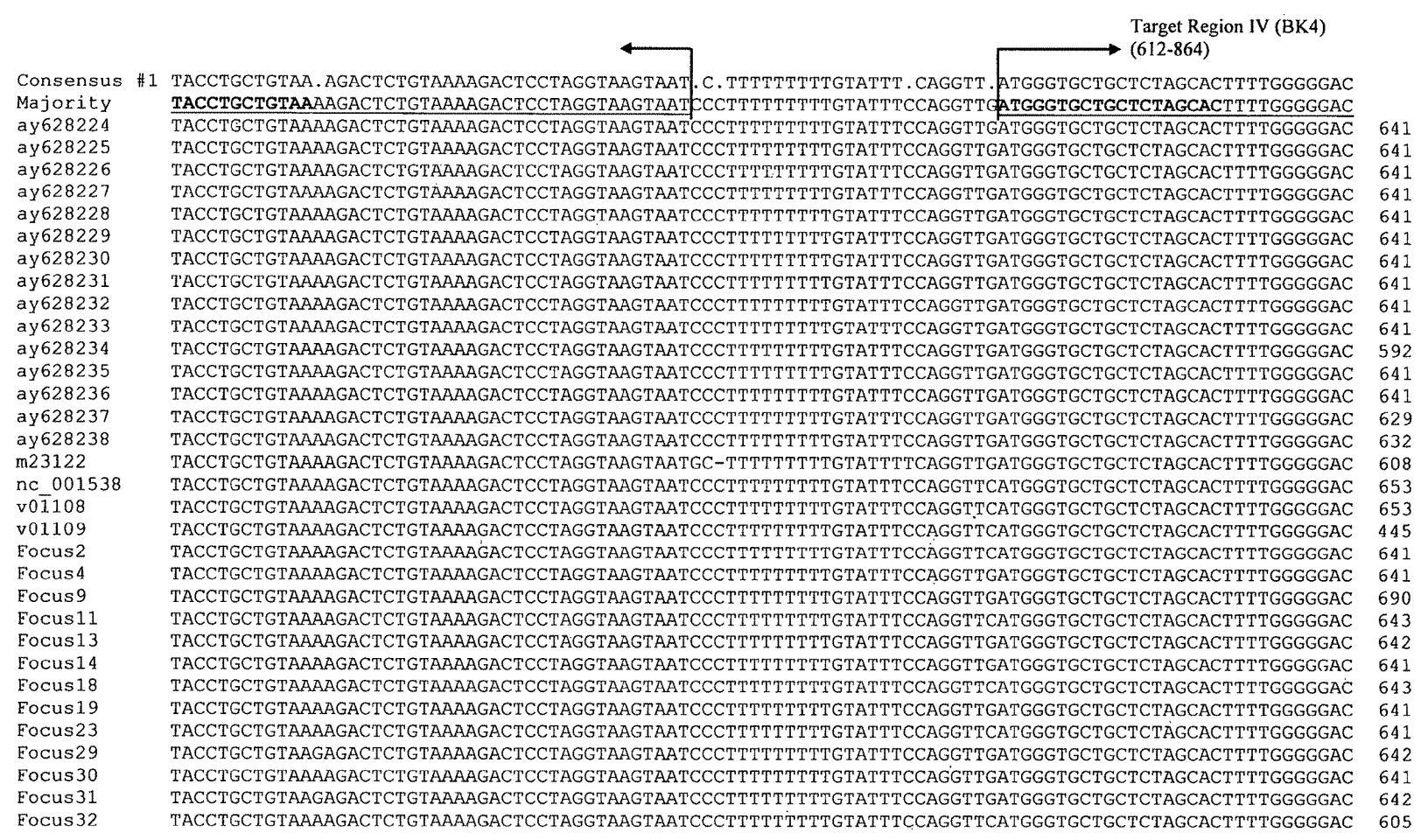
Figure 1H:
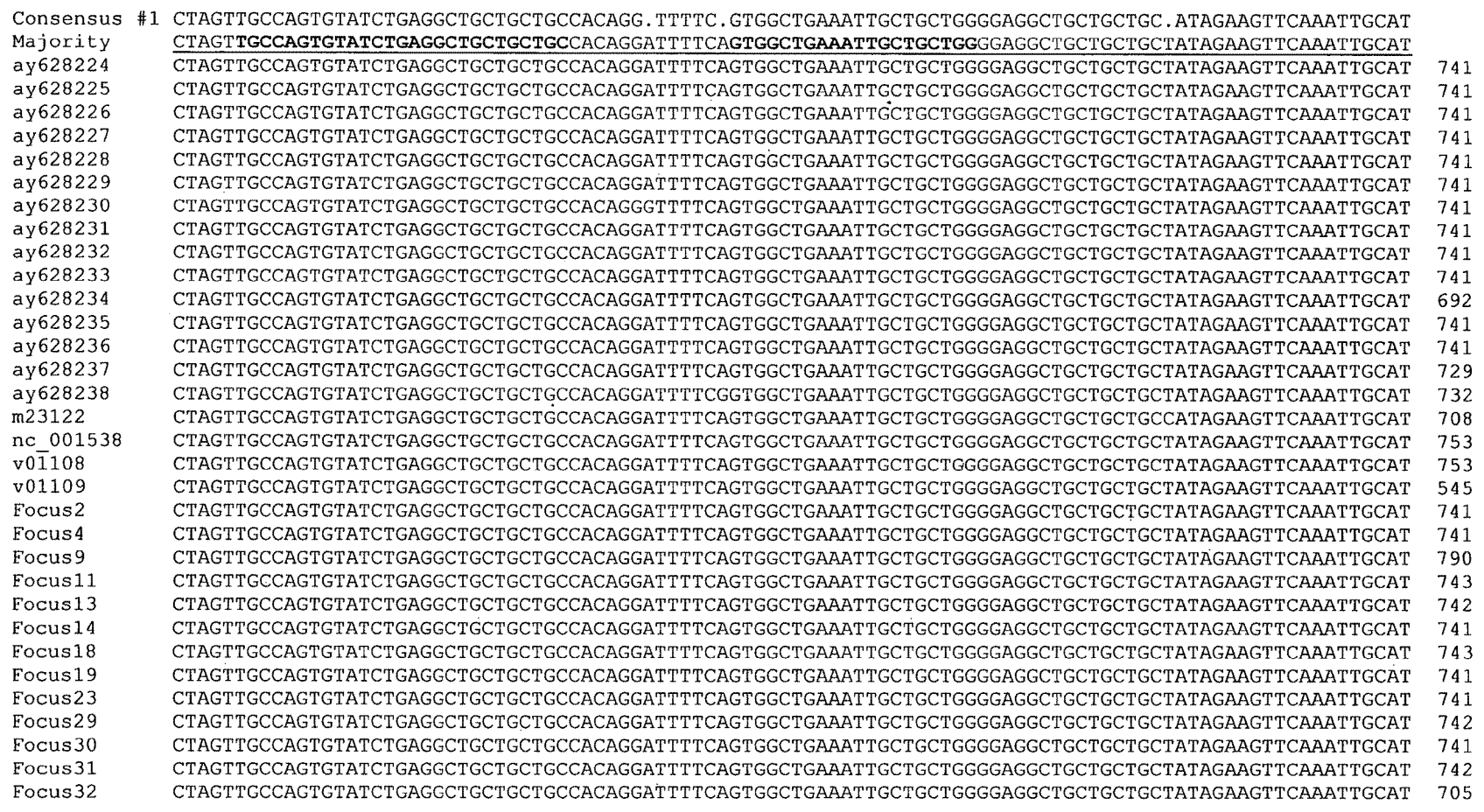
Figure 1I:
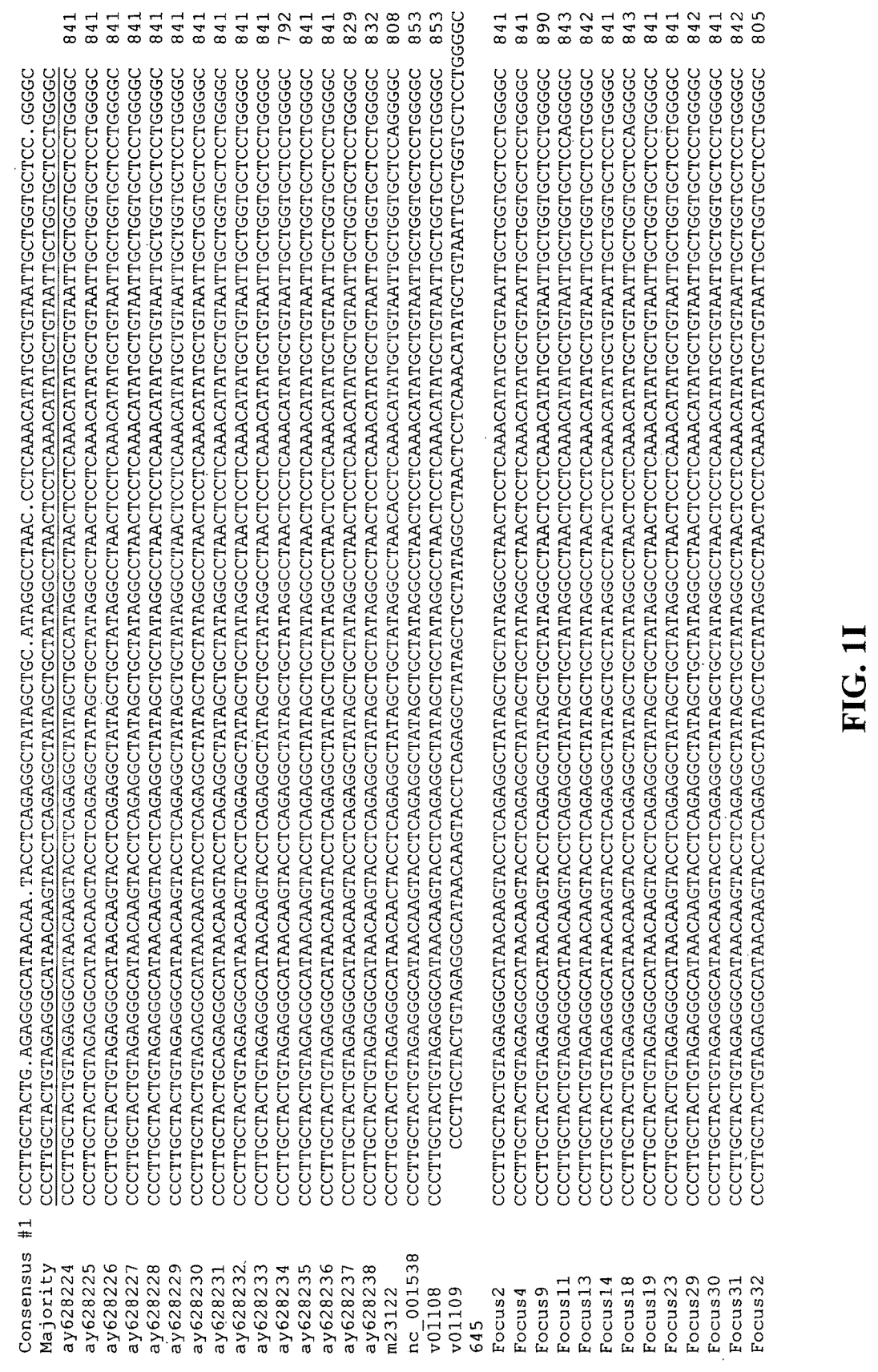
Figure 1J:
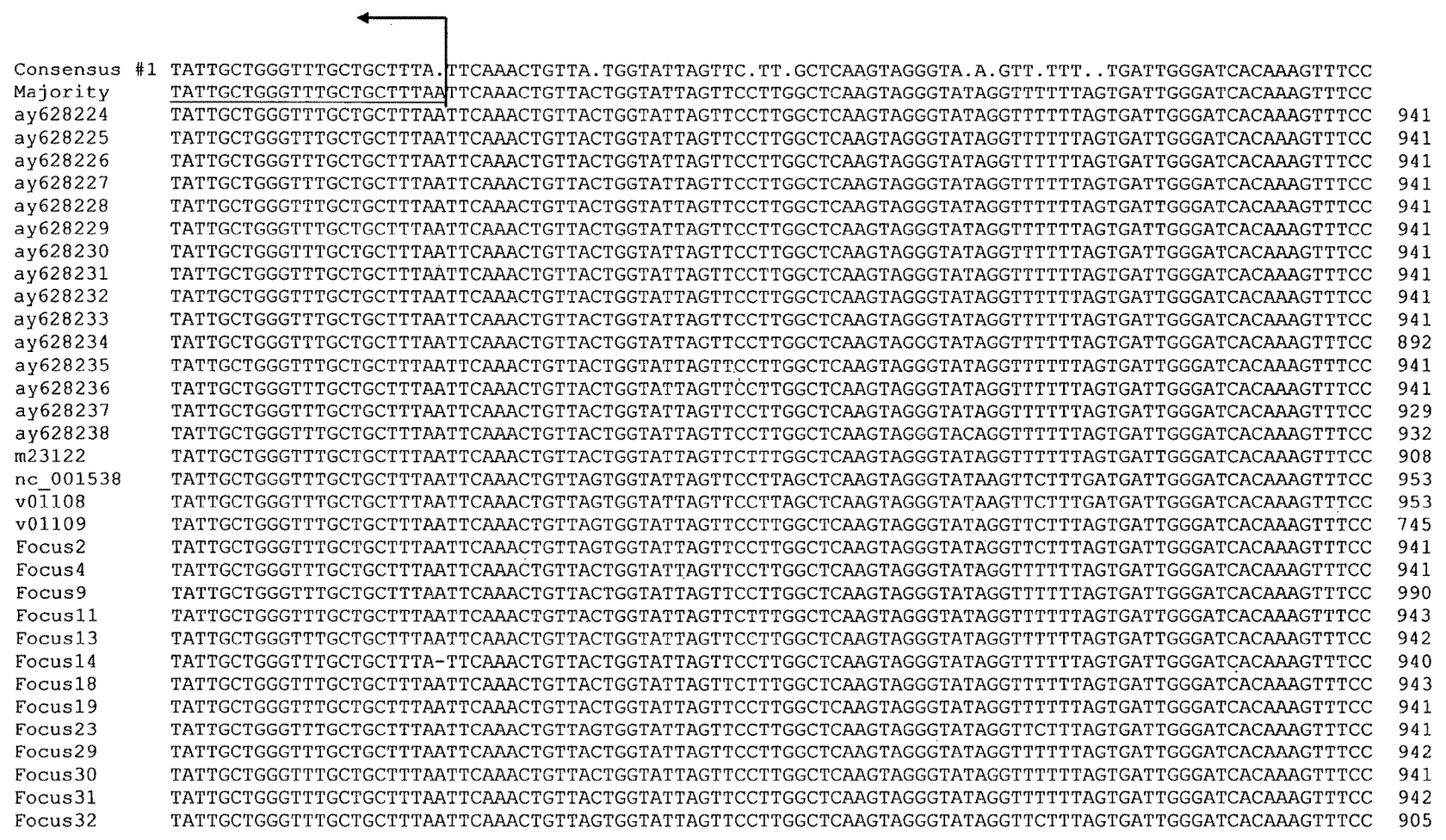
Figure 1K:
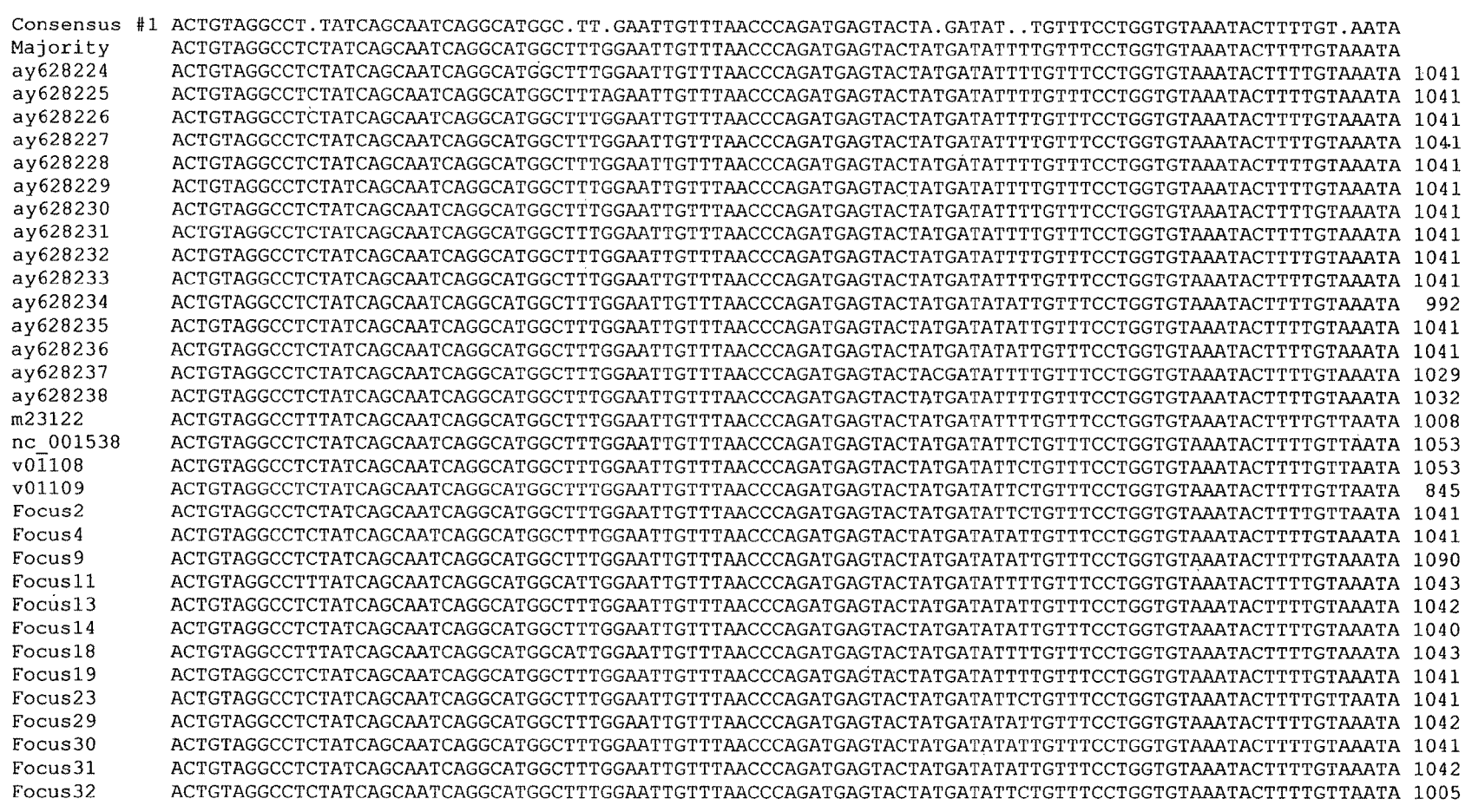
Figure 1L:
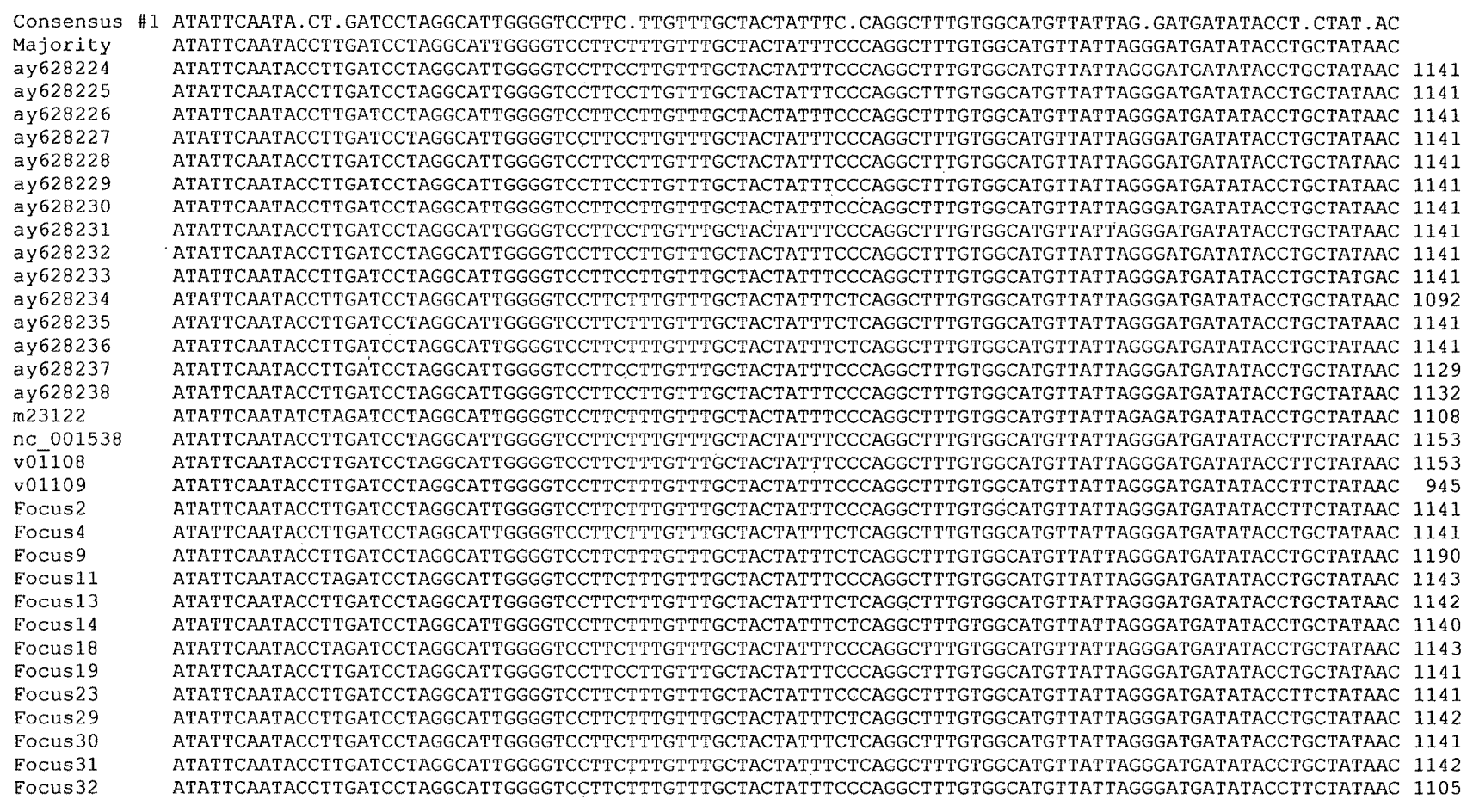
Figure 1M:
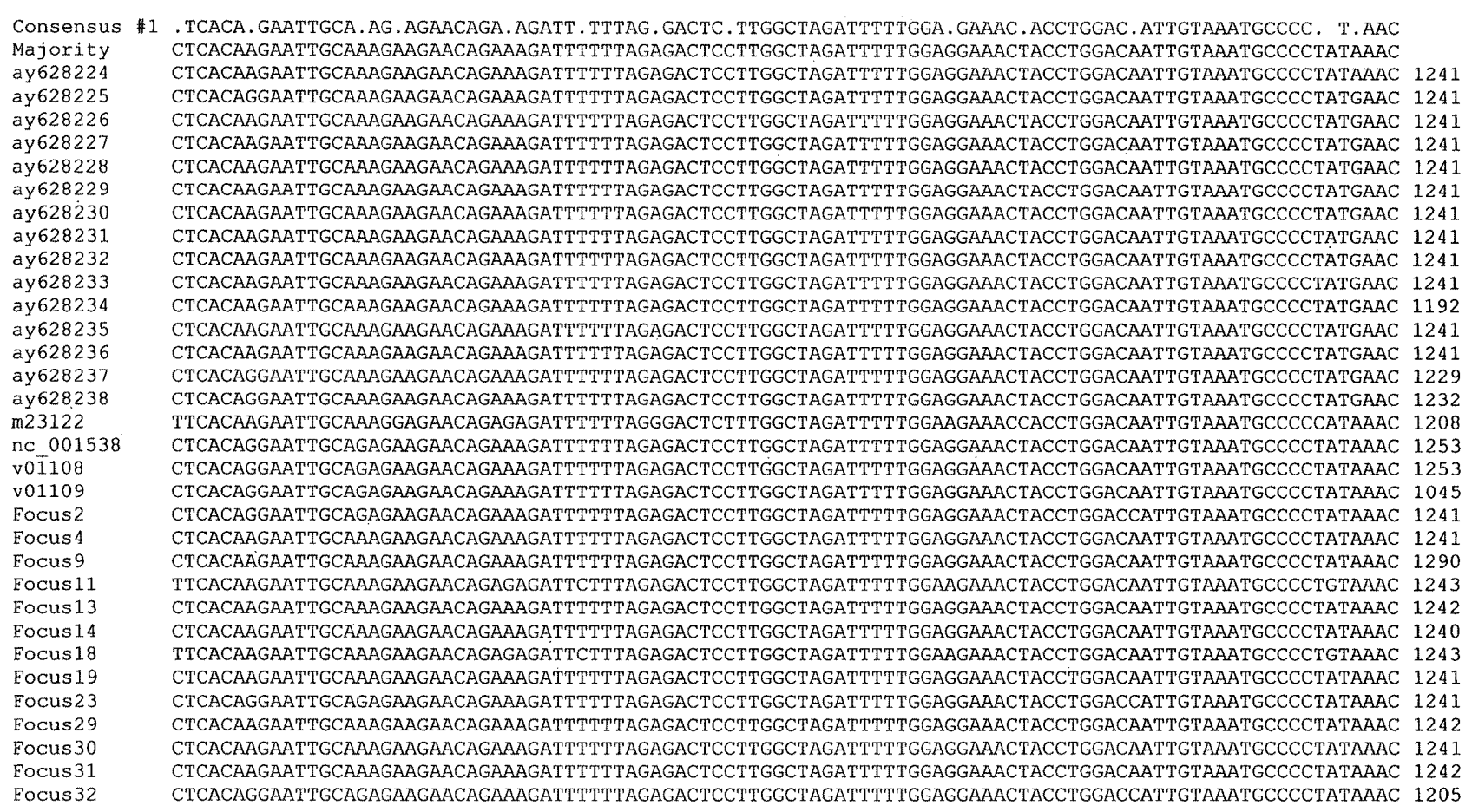
Figure 1N:
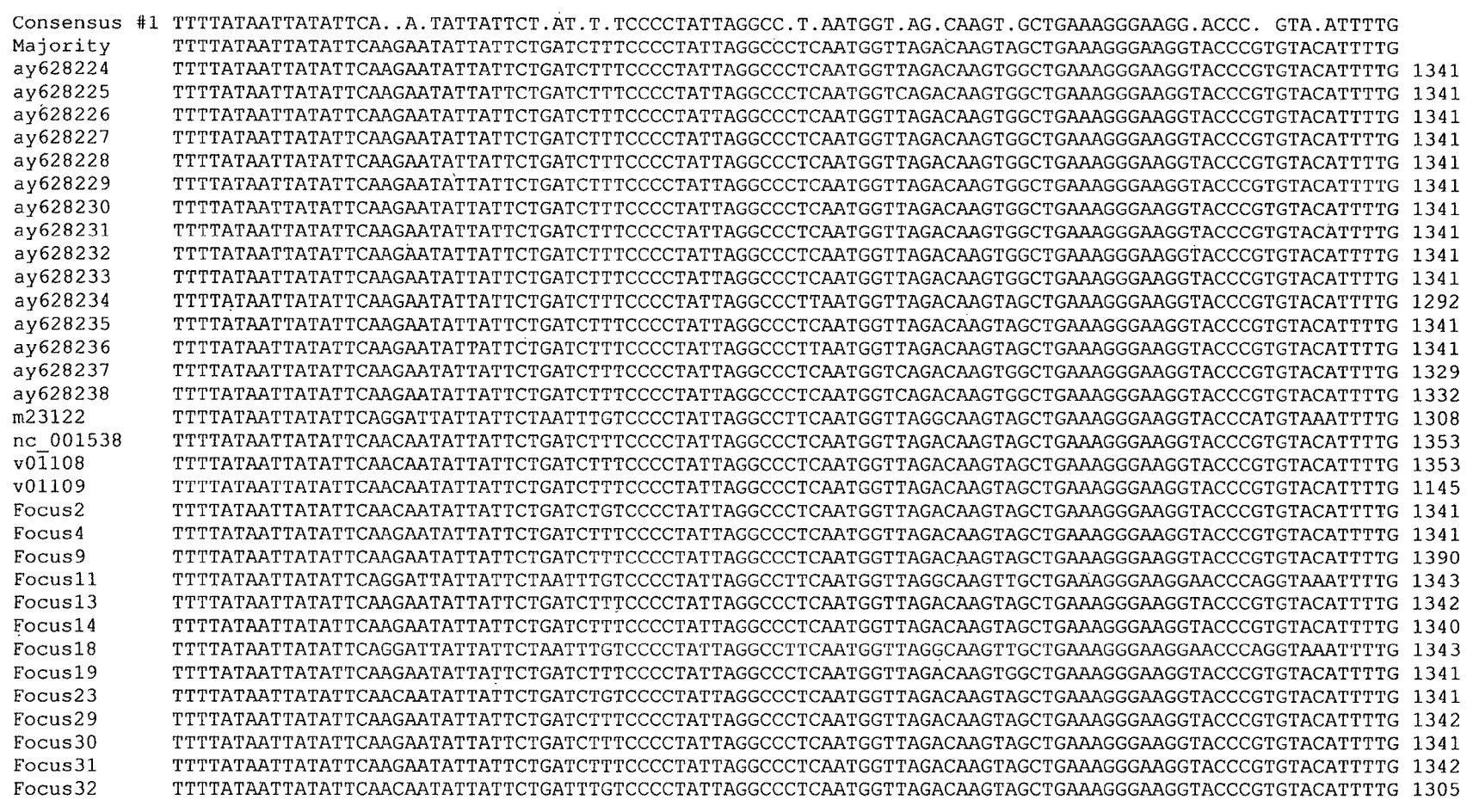
Figure 1P:
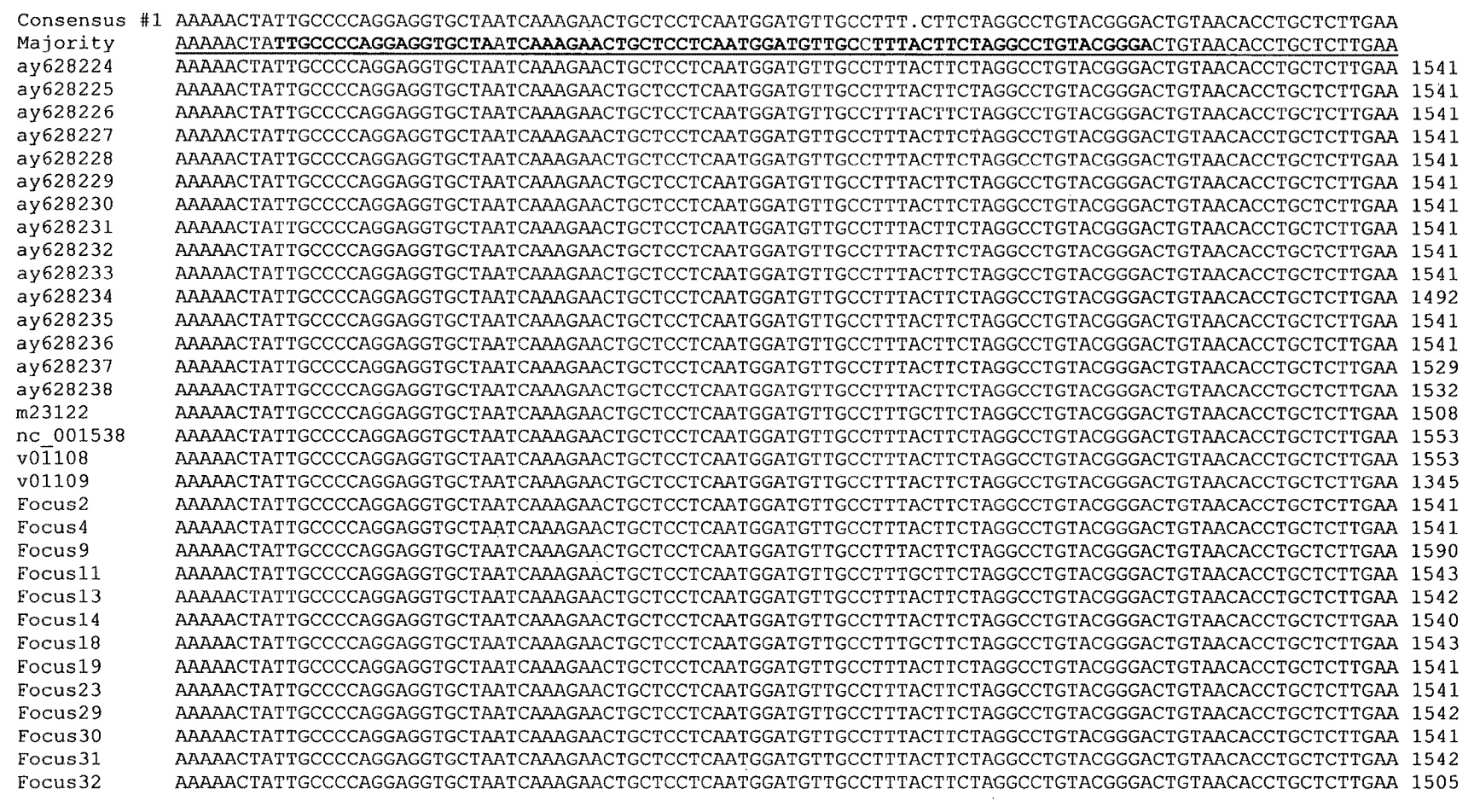
Figure 1Q:
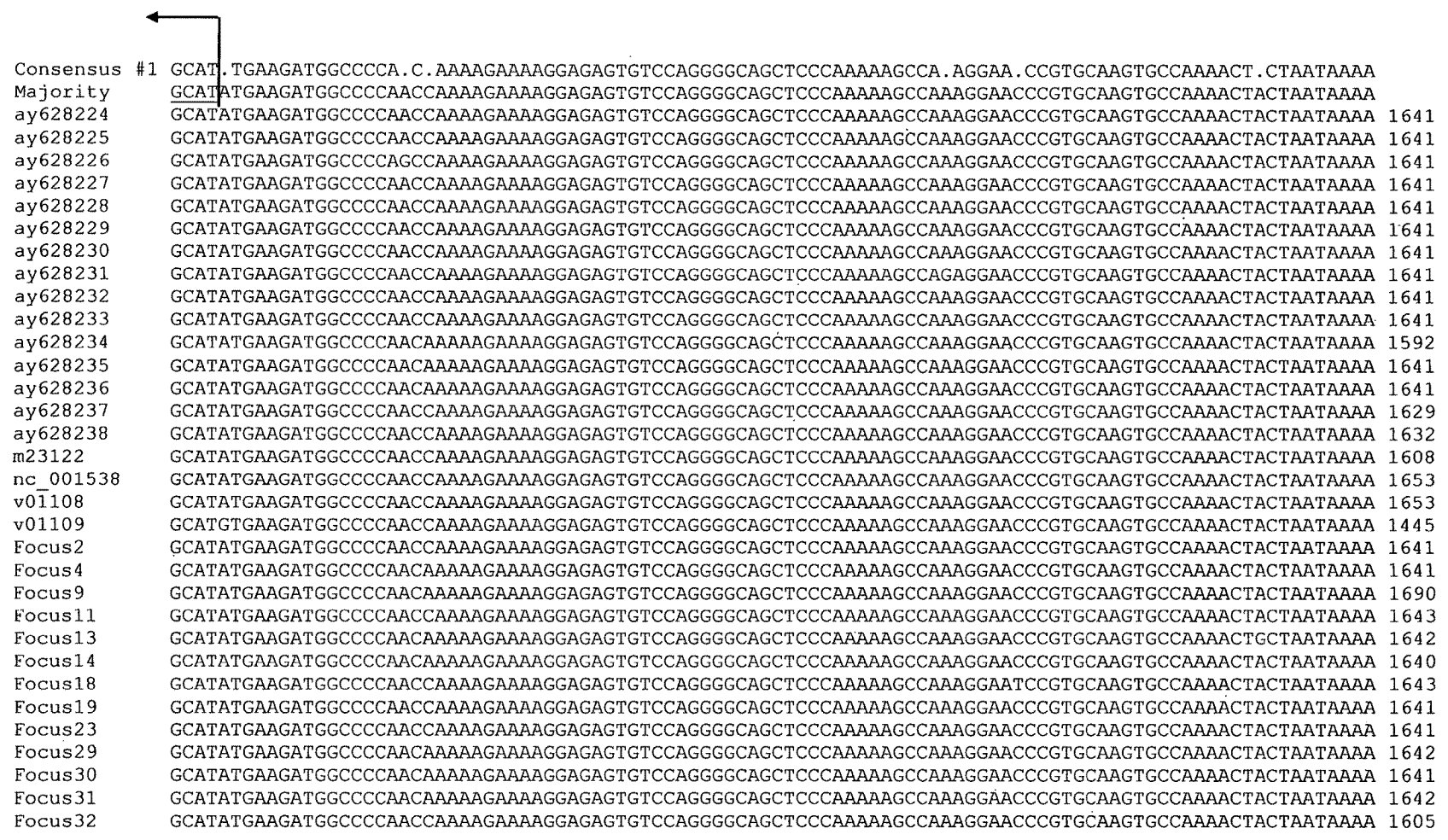
Figure 1R:
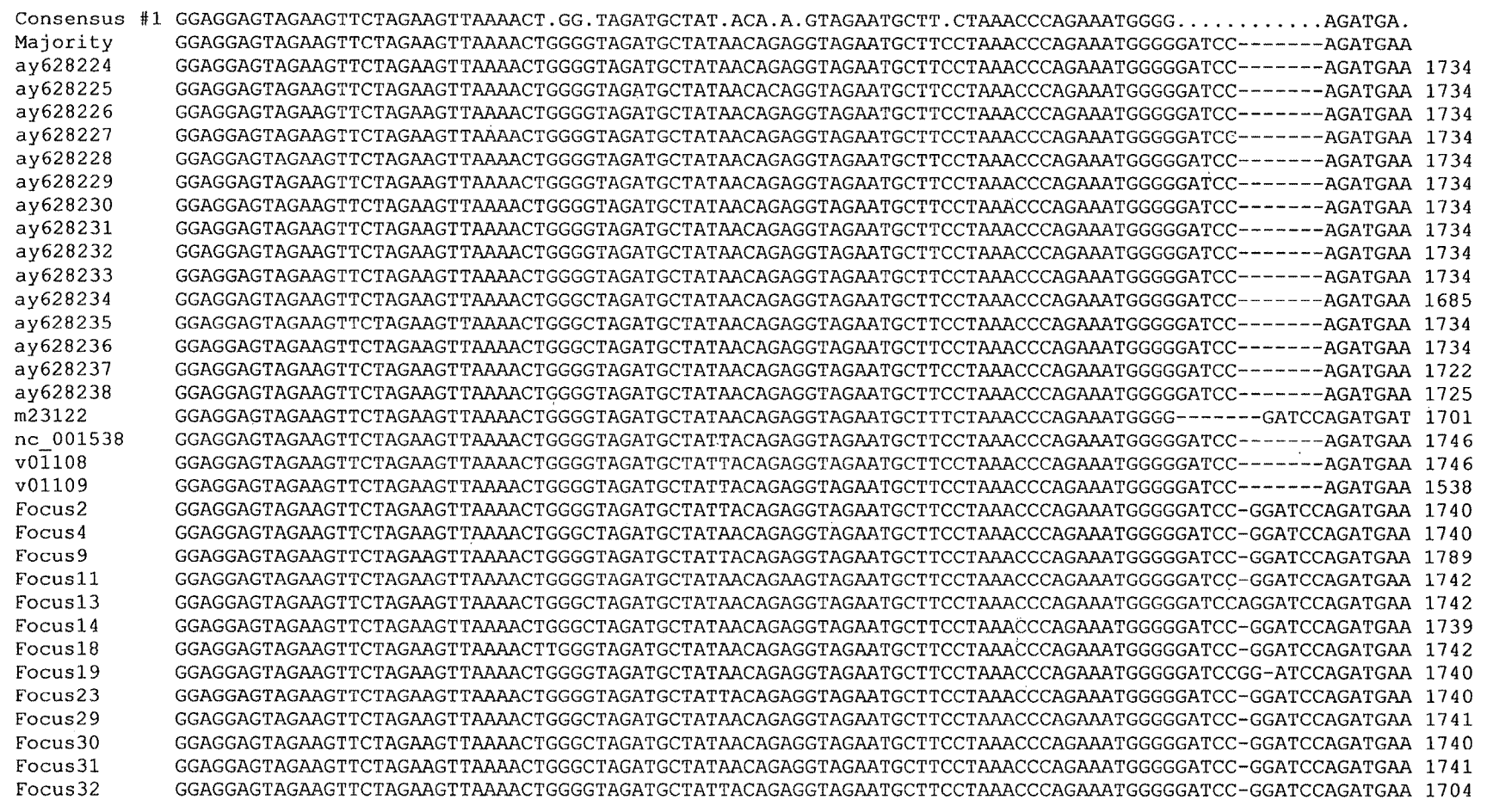
Figure 1S:
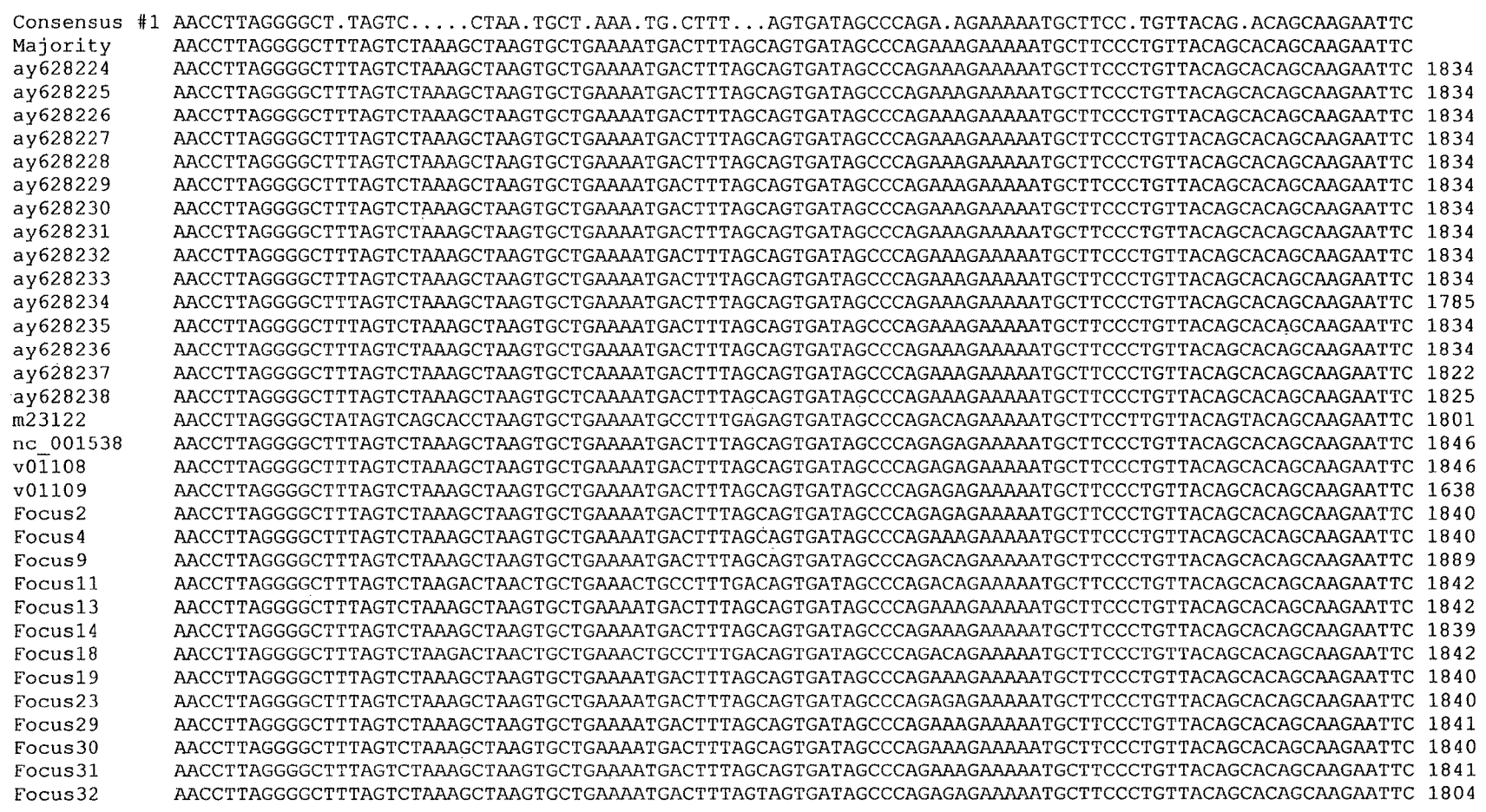
Figure 1T:
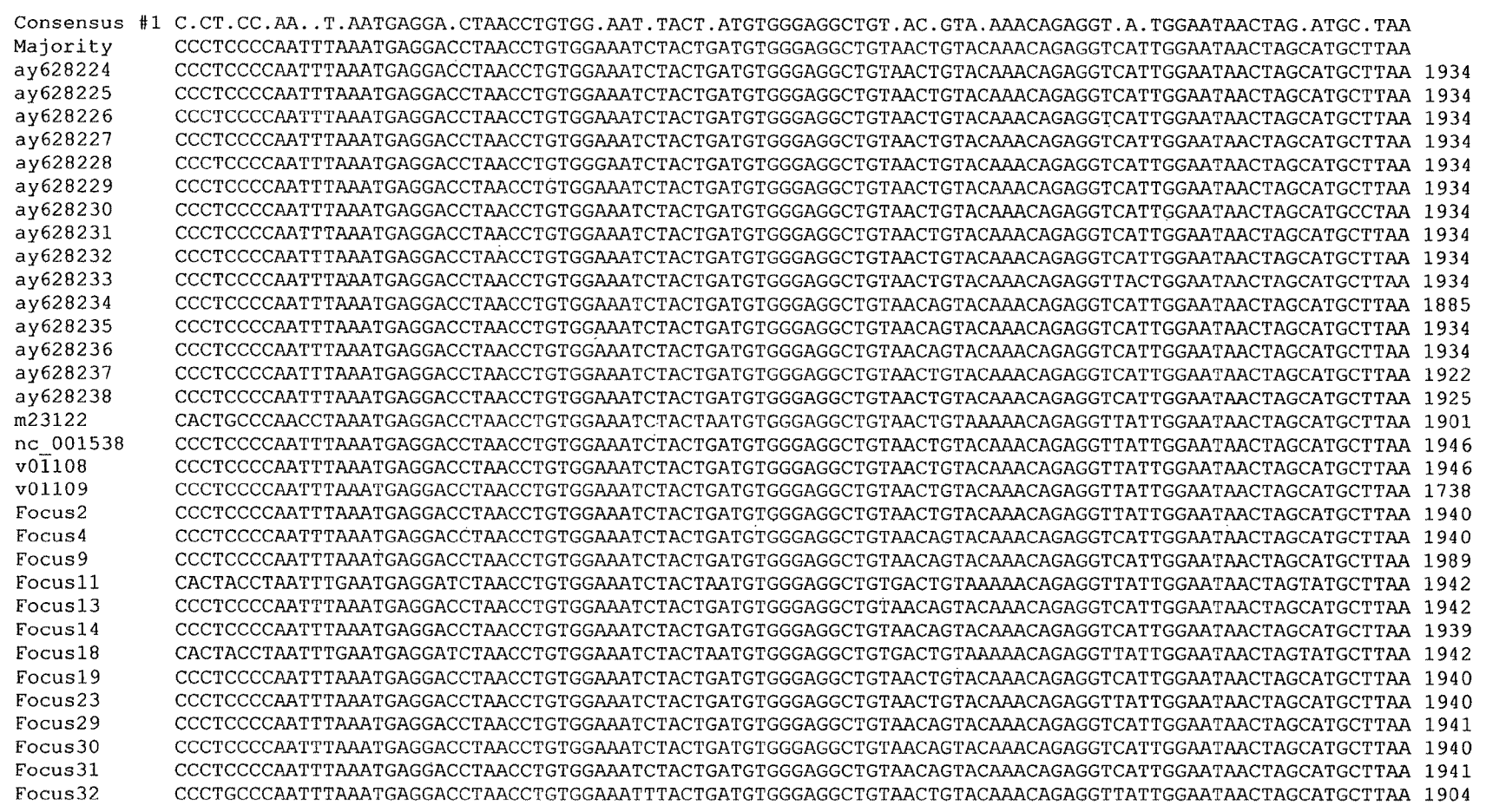
Figure 1V:
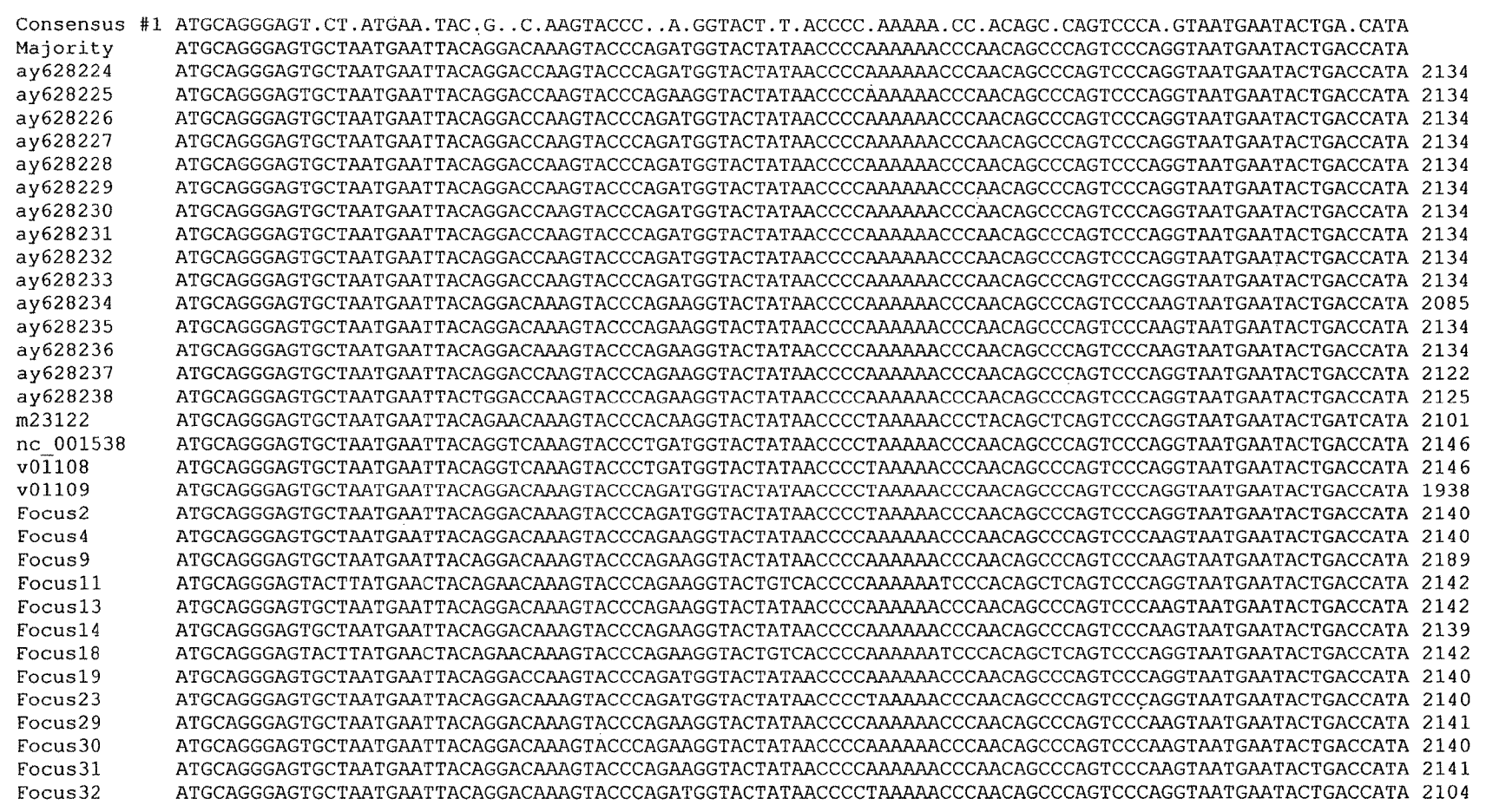
Figure 1W:
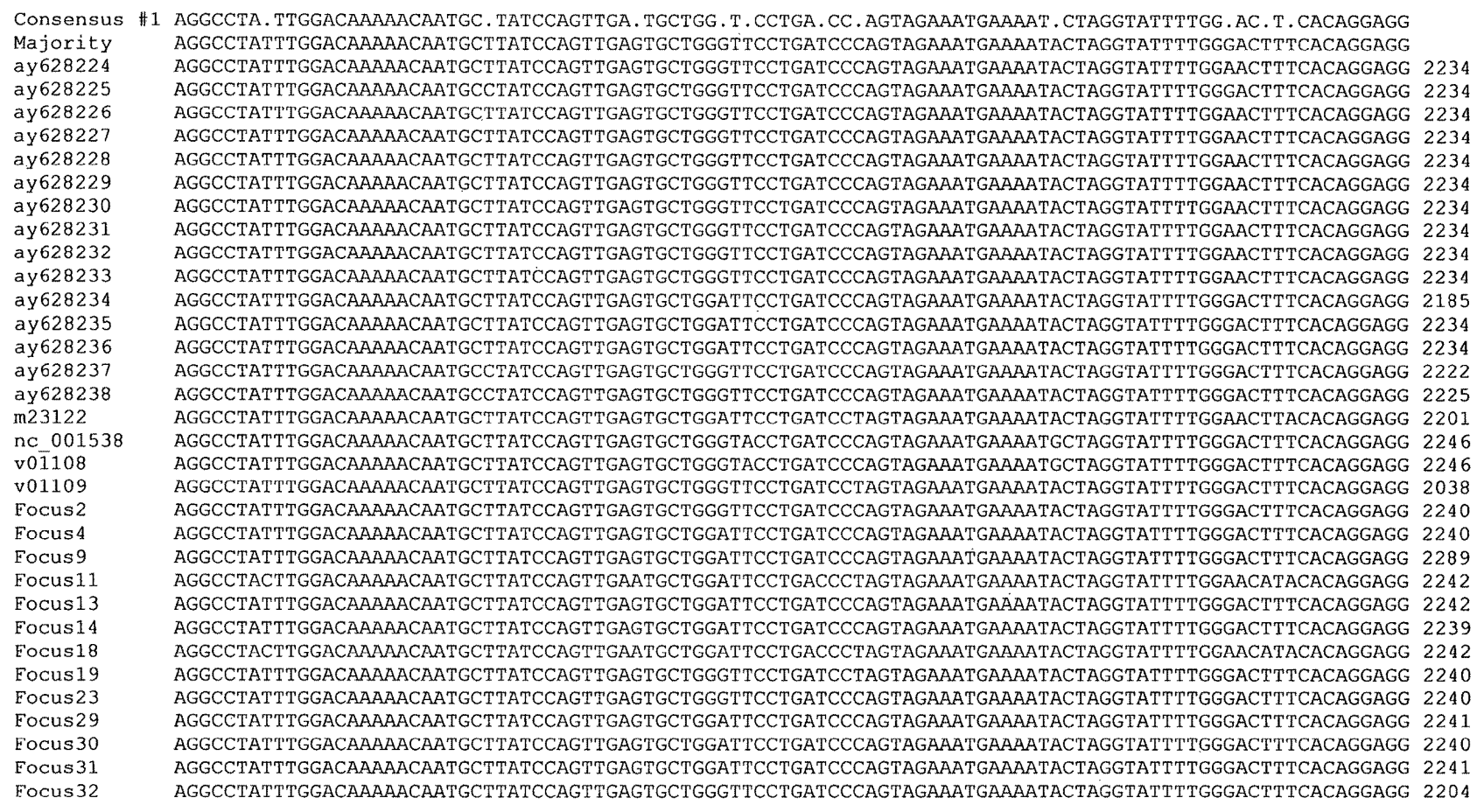
Figure 1X:
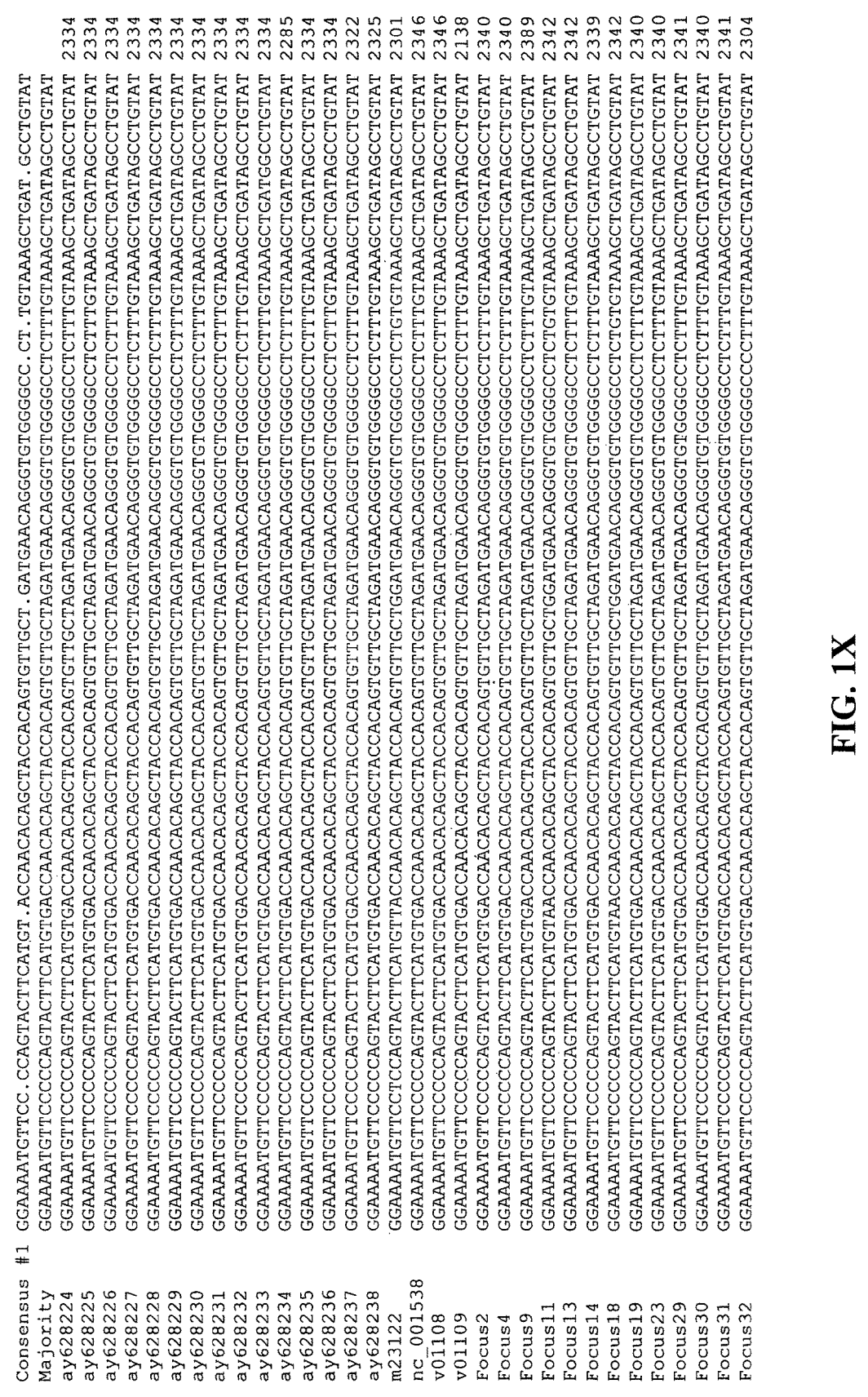
Figure 1Y:
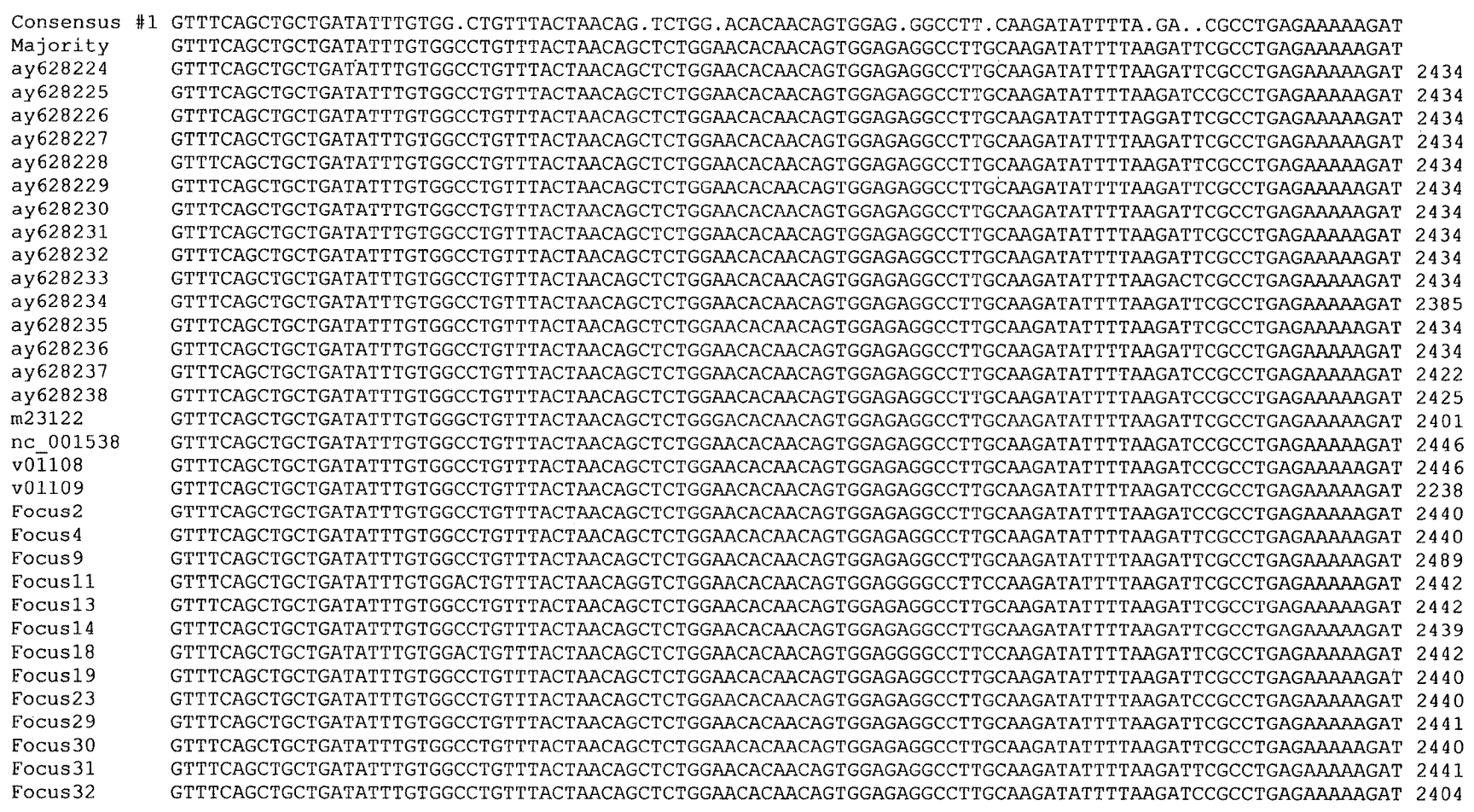
Figure 1Z:
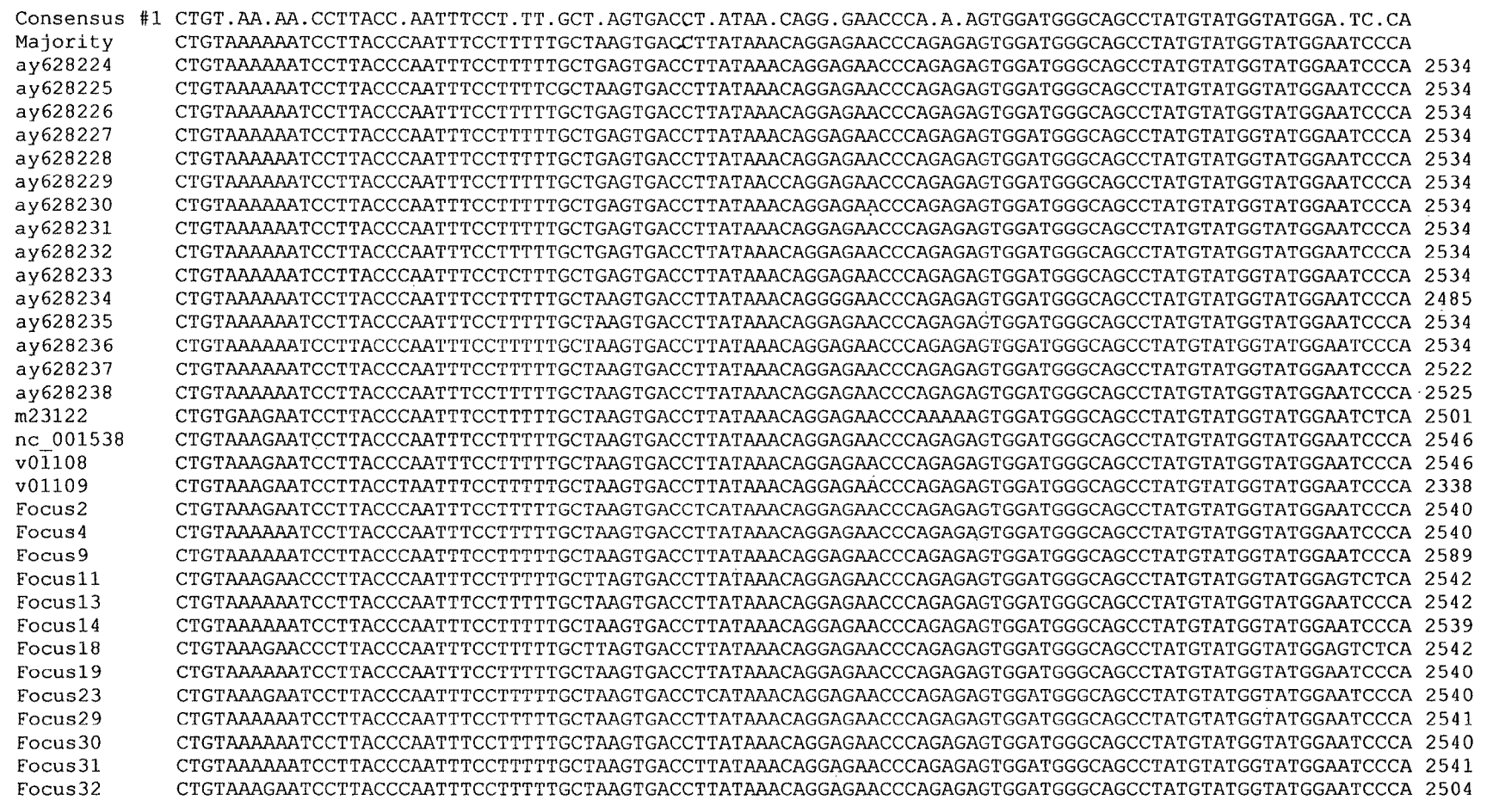

FIG. 1A-FIG. 1AAA shows the alignment of the nucleic acid sequences of the 32 BK virus genotypes. The target nucleic acid regions for detection of BK virus (BKV) according to the invention, which regions are designated as BK1, BK2, BK3, BK4, and BK5 (also referred to herein as Target Regions I, II, III, IV and V, respectively) as denoted in underline typeface and start and end arrows.

Figure 2:
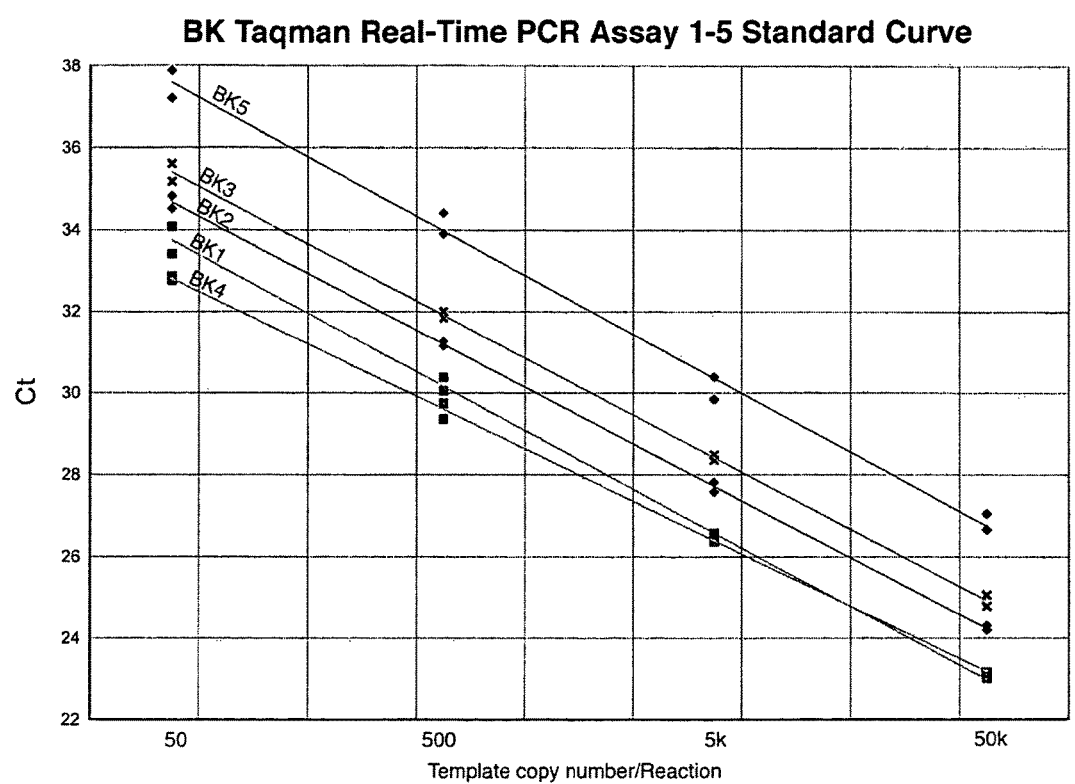

The numbering system on the right side of the figure represents the sequence numbering for each of the genotypes according to the respective GenBank Accession Numbers for each genotype or the numbering for a sequenced genome. All references to sequences numbering herein are based on the sequence numbering for GenBank Accession No. AY628224, unless stated otherwise. Exemplary primers and probes within the Target Regions I-V suitable for use in the methods of the invention are indicated by bold typeface. Probes suitable for use in the invention include any sequence positioned within the sequence of an amplification product that would be produced using two selected primers.

FIG. 2 is a graph showing the standard curves for the Taqman real-time assay for each of BK1, BK2, BK3, BK4, and BK5. Template concentrations ranged from 50 copies per reaction to 50.000 per reaction. All assays were performed in duplicate. For the BK1 assay: slope=−3.58, intercept=43.428, and $R^2$=0.997. For the BK2 assay: slope=−

3.48, intercept=44.053, R²=0.999. For the BK3 assay: slope=−3.49, intercept=44.819, R²=0.999. For the BK4 assay: slope=−3.21, intercept=41.466, R²=0.999. For the BK5 assay: slope=−3.61, intercept=47.324, R²=0.994.

DEFINITIONS

The terms "BK virus" or "BKV" as used herein refer to a virus from the polyomavirus family that has been associated with nephropathy and renal dysfunction. BK virus is a small non-enveloped virus whose genome includes a circular, double-stranded-DNA molecule around 5,300 bp.

The terms "polynucleotide," "oligonucleotide," "nucleic acid" and "nucleic acid molecule" are used interchangeably herein to include a polymeric form of nucleotides, either ribonucleotides or deoxyribonucleotides. This term refers only to the primary structure of the molecule. Thus, the terms include triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA.

Unless specifically indicated otherwise, there is no intended distinction in length between the terms "polynucleotide," "oligonucleotide," "nucleic acid" and "nucleic acid molecule" and these terms will be used interchangeably. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA. DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

Throughout the specification, abbreviations are used to refer to nucleotides (also referred to as bases), including abbreviations that refer to multiple nucleotides. As used herein, G=guanine, A=adenine, T=thymine, C=cytosine, and U=uracil. In addition, R=a purine nucleotide (A or G); Y=a pyrimidine nucleotide (A or T (U)); S=C or G; W=A or T (U); M=A or C; K=G or T (U); V=A, C or G; and N=any nucleotide (A, T (U), C, or G). Nucleotides can be referred to throughout using lower or upper case letters. It is also understood that nucleotides sequences provided for DNA in the specification also represent nucleotide sequences for RNA, where T is substituted by U.

The terms "deoxyribonucleic acid" and "DNA" as used herein mean a polymer composed of deoxyribonucleotides.

The terms "ribonucleic acid" and "RNA" as used herein refer to a polymer composed of ribonucleotides. Where sequences of a nucleic acid are provided using nucleotides of a DNA sequence, it is understood that such sequences encompass complementary DNA sequences and further also encompass RNA sequences based on the given DNA sequence or its complement, where uracil (U) replaces thymine (T) in the DNA sequence or its complement.

Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified. The term "isolated" encompasses instances in which the recited material is unaccompanied by at least some of the material with which it is normally associated in its natural state, preferably constituting at least about 0.5%, more preferably at least about 5% by weight of the total protein in a given sample. For example, the term "isolated" with respect to a polynucleotide generally refers to a nucleic acid molecule devoid, in whole or part, of sequences normally associated with it in nature; or a sequence, as it exists in nature, but having heterologous sequences in association therewith; or a molecule disassociated from the chromosome.

"Purified" as used herein means that the recited material comprises at least about 75% by weight of the total material, with at least about 80% being preferred, and at least about 90% being particularly preferred. As used herein, the term "substantially pure" refers to a compound that is removed from its natural environment and is at least 60% free, preferably 75% free, and most preferably 90% free from other components with which it is naturally associated.

A polynucleotide "derived from" or "specific for" a designated sequence, such as a target sequence of a target nucleic acid, refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding to, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived or specific for. Polynucleotides that are derived from or "specific for" a designated sequence include polynucleotides that are in a sense or an antisense orientations relative to the original polynucleotide.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%, at least about 85%, preferably at least about 90%, and most preferably at least about 95% or at least about 98% sequence similarity over a defined length of the molecules. As used herein, substantially homologous also refers to sequences showing complete Identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis of homology and identity, such as Lasergene from DNASTAR, Inc., and ALIGN, Dayhoff, M. O. in Atlas of Protein Sequence and Structure M. O. Dayhoff ed., 5 Suppl. 3:353-358, National biomedical Research Foundation, Washington, D.C., which adapts the local homology algorithm of Smith and Waterman Advances in Appl. Math. 2:482-489, 1981 for peptide analysis. Programs for determining nucleotide sequence homology are available in the Wisconsin Sequence Analysis Package, Version 8 (available from Genetics Computer Group, Madison, Wis.) for example, the BESTFIT, PASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet on a website sponsored by the National Center for Biotechnology Information (NCBI) and the National Library of Medicine (see the world wide website at ncbi.nlm.gov/cgi-bin/BLAST).

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule refers to a polynucleotide of genomic, cDNA, mammalian, bacterial, viral, semisynthetic, synthetic or other origin which, by virtue of its origin, manipulation, or both is not associated with all or a portion of the polynucleotide with which it is associated in nature. The term "recombinant" as used with respect to a protein or polypeptide means a polypeptide produced by expression of a recombinant polynucleotide.

A "control element" refers to a polynucleotide sequence which aids in the transcription and/or translation of a nucleotide sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for or facilitate the transcription and translation of a coding sequence in a host cell.

A "DNA-dependent DNA polymerase" is an enzyme that synthesizes a complementary DNA copy from a DNA template. Examples include DNA polymerase I from *E. coli* and bacteriophage T7 DNA polymerase. All known DNA-dependent DNA polymerases require a complementary primer to initiate synthesis. Under suitable conditions, a DNA-dependent DNA polymerase may synthesize a complementary DNA copy from an RNA template.

As used herein, the term "target nucleic acid region" or "target nucleic acid" or "target molecules" refers to a nucleic acid molecule with a "target sequence" to be detected (e.g., by amplification). The target nucleic acid may be either single-stranded or double-stranded and may or may not include other sequences besides the target sequence (e.g., the target nucleic acid may or may not include nucleic acid sequences upstream or 5' flanking sequence, may or may not include downstream or 3' flanking sequence, and in some embodiments may not include either upstream (5') or downstream (3') nucleic acid sequence relative to the target sequence. Where detection is by amplification, these other sequences in addition to the target sequence may or may not be amplified with the target sequence.

The term "target sequence" or "target nucleic acid sequence" refers to the particular nucleotide sequence of the target nucleic acid to be detected (e.g., through amplification). The target sequence may include a probe-hybridizing region contained within the target molecule with which a probe will form a stable hybrid under desired conditions. The "target sequence" may also include the complexing sequences to which the oligonucleotide primers complex and be extended using the target sequence as a template. Where the target nucleic acid is single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands. The invention also contemplates target regions having the full-length of the sequences provided herein, as well as fragments or subsequences of such target regions, and complementary sequences thereof. The terms "fragment" and "subsequence" are used interchangeably in this context. Moreover, where sequences of a "target sequence" are provided herein, it is understood that the sequence may be either DNA or RNA. Thus where a DNA sequence is provided, the RNA sequence is also contemplated and is readily provided by substituting "T" of the DNA sequence with "U" to provide the RNA sequence.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal concentration, and salt concentration. Primers are generally of a length compatible with its use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein, the term "probe" or "oligonucleotide probe", used interchangeable herein, refers to a structure comprised of a polynucleotide, as defined above, that contains a nucleic acid sequence complementary to a nucleic acid sequence present in the target nucleic acid analyte (e.g., a nucleic acid amplification product). The polynucleotide regions of probes may be composed of DNA, and/or RNA, and/or synthetic nucleotide analogs. Probes are generally of a length compatible with its use in specific detection of all or a portion of a target sequence of a target nucleic acid, and are usually are in the range of between 8 to 100 nucleotides in length, such as 8 to 75, 10 to 74, 12 to 72, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. The typical probe is in the range of between 10-50 nucleotides long, such as 15-45, 18-40, 20-30, 21-28, 22-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Probes contemplated herein include probes that include a detectable label. For example, when an "oligonucleotide probe" is to be used in a 5' nuclease assay, such as the TaqMan™ assay, the probe includes at least one fluorescer and at least one quencher which is digested by the 5' endonuclease activity of a polymerase used in the reaction in order to detect any amplified target oligonucleotide sequences. In this context, the oligonucleotide probe will have a sufficient number of phosphodiester linkages adjacent to its 5' end so that the 5' to 3' nuclease activity employed can efficiently degrade the bound probe to separate the fluorescers and quenchers. When an oligonucleotide probe is used in the TMA technique, it will be suitably labeled, as described below.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in the detectable range.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

The term "stringent conditions" refers to conditions under which a primer will hybridize preferentially to, or specifically bind to, its complementary binding partner, and to a lesser extent to, or not at all to, other sequences. Put another way, the term "stringent hybridization conditions" as used herein refers to conditions that are compatible to produce duplexes on an array surface between complementary binding members, e.g., between probes and complementary targets in a sample, e.g., duplexes of nucleic acid probes, such as DNA probes, and their corresponding nucleic acid targets that are present in the sample, e.g., their corresponding mRNA analytes present in the sample.

As used herein, the term "binding pair" refers to first and second molecules that specifically bind to each other, such as complementary polynucleotide pairs capable of forming nucleic acid duplexes. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent.

By "selectively bind" is meant that the molecule binds preferentially to the target of interest or binds with greater affinity to the target than to other molecules. For example, a DNA molecule will bind to a substantially complementary sequence and not to unrelated sequences.

A "stringent hybridization" and "stringent hybridization wash conditions" in the context of nucleic acid hybridization (e.g., as in array, Southern or Northern hybridizations) are sequence dependent, and are different under different environmental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mnM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a probe. Wash conditions used to identify nucleic acids may include, e.g.: a salt concentration of about 0.02 molar at pH 7 and a temperature of at least about 50. ° C. or about 55° C. to about 60° C.; or, a salt concentration of about 0.15 M NaCl at 72° C. for about 15 minutes; or, a salt concentration of about 0.2×SSC at a temperature of at least about 50° C. or about 55. ° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37. ° C. (for 14-base oligos), 48. ° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

The "melting temperature" or "Tm" of double-stranded DNA is defined as the temperature at which half of the helical structure of DNA is lost due to heating or other dissociation of the hydrogen bonding between base pairs, for example, by acid or alkali treatment, or the like. The $T_m$ of a DNA molecule depends on its length and on its base composition. DNA molecules rich in GC base pairs have a higher $T_m$ than those having an abundance of AT base pairs. Separated complementary strands of DNA spontaneously reassociate or anneal to form duplex DNA when the temperature is lowered below the $T_m$. The highest rate of nucleic acid hybridization occurs approximately 25.degree. C. below the $T_m$. The $T_m$ may be estimated using the following relationship: $T_m$=69.3+0.41(GC) % (Marmur et al. (1962) J. Mol. Biol. 5:109-118).

As used herein, a "biological sample" refers to a sample of tissue or fluid isolated from a subject, which in the context of the invention generally refers to samples suspected of containing nucleic acid and/or viral particles of BK virus, which samples, after optional processing, can be analyzed in an in vitro assay. Typical samples of interest include, but are not necessarily limited to, respiratory secretions (e.g., samples obtained from fluids or tissue of nasal passages, lung, and the like), blood, plasma, serum, blood cells, cerebrospinal fluid, fecal matter, urine, tears, saliva, milk, organs, biopsies, and secretions of the intestinal and respiratory tracts. Samples also include samples of in vitro cell culture constituents including but not limited to conditioned media resulting from the growth of cells and tissues in culture medium, e.g., recombinant cells, and cell components.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

In the context of the methods involving nucleic acid-based amplification of a target sequence, the term "reference range" refers to a range of $C_T$ (threshold cycle) values from BK virus-negative specimens representative of results that are deemed to indicate that the sample (e.g., a patient specimen) is BK virus-negative.

In the context of the methods involving nucleic acid-based amplification of a target sequence, the term "reportable range" refers to a range of $C_T$ values generated by BK virus positive specimens that are representative of results to be reported as BK virus-positive patient specimens.

"Analytical specificity" as used herein refers to the ability of a detection system to specifically detect the target virus and not detect other related viruses, or pathogenic or commensal flora found in the specimen types being validated. For example, "analytical specificity" in reference to assays using BK virus primers and a probe refers to the ability of this detection system to specifically amplify and detect the target virus and not detect other related viruses, or pathogenic or commensal flora found in the specimen types being validated.

"Analytical sensitivity" in the context of the methods involving nucleic acid-based amplification of a target sequence refers to the lowest measurable amount of BK virus target DNA that can be detected for each specimen type validated.

"Precision" refers to the ability of an assay to reproducibly generate the same or comparable result for a given sample.

"Accuracy" refers to the ability of an assay to correctly detect a target molecule in a blinded panel containing both positive and negative specimens.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to a "oligonucleotide primer" includes a plurality of such primers and reference to "primer" includes reference to one or more the primers and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The practice of the present invention will employ, unless otherwise indicated, conventional methods of chemistry, biochemistry, recombinant DNA techniques and virology, within the skill of the art. Such techniques are explained fully in the literature. See, e.g., Fundamental Virology, 2nd Edition, vol. I & II (B. N. Fields and D. M. Knipe, eds.); A. L. Lehnineer, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Oligonucleotide Synthesis (N. Gait, ed., 1984); A Practical Guide to Molecular Cloning (1984).

The invention will now be described in more detail.

DETAILED DESCRIPTION OF THE INVENTION

The invention is based on the discovery of consensus target nucleic acid regions within the BK virus (BKV) genome that include target nucleic acid sequences (also referred to herein as target sequences) for detection of BKV in a sample, particularly a biological sample, with specificity and sensitivity. In particular the detection of one or more target nucleic acid sequence regions allows for detection of BKV in a sample, in general, while also being able to discriminate between, for example, BKV and JC virus (JCV) and/or BKV and SV40. The specificity and simplicity of these assays facilitate rapid, reliable and inexpensive assays for detection of BKV in general. The subject invention finds use in a variety of different applications, including research, medical, drug development and diagnostic applications.

In general, the subject methods provide for detection of BKV in a sample, such as a biological sample, by detection of a target nucleic acid region of the BKV genome. Five such target nucleic acid regions are described herein, termed as Target Regions I-V as designated in FIG. 1.

In some embodiments, the subject methods provide for detection of any BKV isolates, in a sample, such a biological sample. In such embodiments, the subject methods detect a target nucleic acid region, or fragment thereof, by using primers and probe that correspond to sequences within the target region. Exemplary primers within the Target Regions I-V suitable for use in the methods of the invention are provided in Table 1. Probes suitable for use in the invention include any sequence positioned within the sequence of an amplification product that would be produced using selected primers. A probe suitable for use with such an embodiment is selected such that it corresponds to a region that shares a nucleotide sequence between the different BKV isolates to be detected.

We note that the sequences provided herein, and particularly the consensus sequences are provided as DNA sequences. It is understood that the DNA sequences provided may be single stranded or double stranded, and as such the description of the DNA sequences below is intended to also provide the complementary sequence as well.

The compositions and methods of the invention will now be described in more detail.

Target Nucleic Acid Regions

Target nucleic acid sequence regions were identified by alignment of various BKV isolate genomes. The present invention provides for identification of BKV in a sample, such as a biological sample, by detecting one or more target nucleic acid region or a portion thereof. In general, detection is by nucleic acid amplification, which in some embodiments is followed by detection of the amplification product using a hybridization probe. The target nucleic acid regions are described in further detail below.

It will be appreciated that since BKV contains a double-stranded DNA genome from which RNA is generated during viral replication, the primers and probes described herein encompass those having the nucleic acid sequence described-herein, as well as primers and probes having the complement of such nucleic acid sequences.

Furthermore, it will be understood that primer pairs useful in the invention include a first primer having a sequence that is the same or similar to that of the BKV sequence provided herein, and a second primer having a sequence that is complementary to the BKV sequence provided herein to provide for amplification of a BKV target nucleic acid region described herein or a fragment thereof (e.g., the first primer is a "forward" primer and the second primer is a "reverse" primer). It will be further understood that primer pairs useful in the invention also include a first primer having a sequence that is complementary to that of the BKV sequence provided herein, and a second primer having a sequence that is the same or similar to the BKV sequence provided herein to provide for amplification of an BKV target nucleic acid region described herein or a fragment thereof (e.g., the first primer is a "reverse" primer and the second primer is a "forward" primer).

It also will be understood that the nucleic acid sequence of probes described herein can be the same or similar to that of the BKV sequence provided or a complement thereof. In addition, primers described herein can also be used as probes, e.g., to detect an amplification product.

Target Region I (BK1)

In one embodiment, the invention provides for detection of BKV in a sample, such as a biological sample, by detection of target nucleic acid sequence region I (FIG. 1, Target Region I (also referred to as BK1), alignment position 435-585 based on numbering of GenBank Accession No. AY628224) as follows:

(SEQ ID NO: 01)
AACAAAAAAAAGAGCTCAGAGGATTTTTATTTTTATTTTAGAGCTTTTGC

TGGAATTTTGTAGAGGTGAAGACAGTGTAGACGGGAAAAACAAAGGTACC

ACTGCTTTACCTGCTGTAAAAGACTCTGTAAAAGACTCCTAGGTAAGTAA

T or a complement thereof, or a fragment thereof, wherein the 5' and 3' end of the nucleic acid is contained within SEQ ID NO:01. This conserved sequence in BKV genome is shown in the alignment of in FIG. 1. In one embodiment of particular interest, the target region is a subsequence of Target Region I, such as (SEQ ID NO: 55)
AACAAAAAAAAGAGCTCAGAGGATTTTTATTTTTATTTTAGAGCTTTTGC

TGGAATTTTGTAGAGGTGAAGACAGTGTAGACGGGAAAAACAAAGTACC

ACTGCTTTACCTGCTGTAA or a complement thereof, or a fragment thereof.

Exemplary nucleic acid sequences suitable for design of primers for amplification of a Target Region I nucleic acid, and suitable for use in the methods of the invention, are indicated by underlined typeface in FIG. 1. Suitable sequences for primers for amplification of Target Region I nucleic acid correspond to nucleotides 1-26 and 94-119 of the nucleotide sequence of SEQ ID NO:01, or a complement thereof.

Probes suitable for use in the invention can be designed from any sequence positioned within the sequence of an amplification product that would be produced using two selected primers. Suitable sequences for use as a probe for detection of Target Region I nucleic acid correspond to nucleotides 57-90 of the nucleotide sequence of SEQ ID NO:01, or a complement thereof.

In one embodiment, detection of target region I nucleic acid involves production of an amplification product of at least 151, at least 145, at least 140, at least 135, at least 130, at least 125 at least 120, at least 115, at least 110, at least 105, at least 100, at least 95, at least 90, at least 85, at least 80, at least 75, at least 70, at least 65, at least 60, at least 55, at least 50, at least 45, at least 40, at least 35, at least 30, at least 28, at least 26, at least 24, at least 22, at least 20 consecutive nucleotides of SEQ ID NO:01.

The methods of the invention can involve detection of target region I nucleic acid either alone or in combination with detection of one or more of target regions II-V as described herein. For example, the methods of the invention can involve detection of target region I (BK1) and target region II (BK2); target region I (BK1) and target region III (BK3); target region I (BK1) and target region IV (BK4); target region I (BK1) and target region V (BK5); target region I (BK1), target region II (BK2), and target region III (BK3); target region I (BK1), target region IV (BK4), and target region V (BK5); target region I (BK1), target region III (BK3), and target region V (BK5) and the like. It will be understood that detection of all combination of target regions I-V are contemplates by the present methods.

Exemplary primers and probes are discussed in greater detail below.

Target Region II (BK2)

In one embodiment, the invention provides for detection of BKV in a sample, such as a biological sample, by detection of target nucleic acid sequence region I (FIG. 1, Target Region II (also referred to as BK2), alignment position 1418-1545 based on numbering of GenBank Accession No. AY628224) as follows:

(SEQ ID NO: 02)
TGTACATTCAGGAGAGTTTATAGAAAAAACTATTGCCCCAGGAGGTGCTA

ATCAAAGAACTGCTCCTCAATGGATGTTGCCTTTACTTCTAGGCCTGTAC

GGGACTGTAACACCTGCTCTTGAAGCAT or a complement thereof, or a fragment thereof, wherein the 5' and 3' end of the nucleic acid is contained within SEQ ID NO:02. This conserved sequence as found in the BKV genome is illustrated in the alignment of FIG. 1. In one embodiment of particular interest, the target region is a subsequence of Target Region II, such as:

(SEQ ID NO: 56)
TTGCCCCAGGAGGTGCTAATCAAAGAACTGCTCCTCAATGGATGTTGCCT

TTACTTCTAGGCCTGTACGGGA or a complement thereof, or a fragment thereof.

Exemplary nucleic acid sequences suitable for design of primers for amplification of a Target Region II nucleic acid, and suitable for use in the methods of the invention, are indicated by underlined typeface in FIG. 1. Suitable sequences for primers for amplification of Target Region II nucleic acid correspond to nucleotides 33-50 and 82-104 of the nucleotide sequence of SEQ ID NO:02, or a complement thereof.

Probes suitable for use in the invention can be designed from any sequence positioned within the sequence of an amplification product that would be produced using two selected primers. Suitable sequences for use as a probe for detection of Target Region II nucleic acid correspond to nucleotides 52-80 of the nucleotide sequence of SEQ ID NO:02, or a complement thereof.

In one embodiment, detection of target region II nucleic acid involves production of an amplification product of at least 128, at least 120, at least 110, at least 100, at least 90, at least 80, at least 75, at least 70, at least 65, at least 60, at least 55, at least 50, at least at least 45, 40, at least 35, at least 30, at least 28, at least 26, at least 24, at least 22, at least 20 consecutive nucleotides of SEQ ID NO:02.

The methods of the invention can involve detection of target region II nucleic acid either alone or in combination with detection of one or more of target regions I and III-V as described herein. For example, the methods of the invention can involve detection of target region II (BK2) and target region I (BK1); target region II (BK2) and target region III (BK3); target region II (BK2) and target region IV (BK4); target region II (BK2) and target region V (BK5); target region I (BK1), target region II (BK2), and target region III (BK3); target region II (BK2), target region IV (BK4), and target region V (BK5); or target region II (BK2), target region III (BK3), and target region V (BK5) and the like. It will be understood that detection of all combination of target regions I-V are contemplates by the present methods.

Exemplary primers and probes are discussed in greater detail below.

Target Region III (BK3)

In another embodiment, the invention provides for detection of BJKV in a sample, such as a biological sample, by detection of target nucleic acid sequence region III (FIG. 1, Target Region III (also referred to as BK3), alignment position 4097-4560 based on numbering of GenBank Accession No. AY628224) as follows:

```
                                                    (SEQ ID NO: 03)
AGTAAGTATTCCTTATTAACACCCTTACAAATTAAAAAACTAAAGGTACA

CAGCTTTTGACAGAAATTATTAATTGCAGAAACTCTATGTCTATGTGGAG

TTAAAAAGAATATAATATTATGCCCAGCACACATGTGTCTACTAATGAAA

GTTACAGAATATTTTTCCATAAGTTTTTTATACAGAATTTGAGCTTTTTC

TTTAGTAGTATACACAGCAAAGCAGGCAAGGGTTCTATTACTAAATACAG

CTTGACTAAGAAACTGGTGTAGATCAGAGGGAAAGTCTTTAGGGTCTTCT

ACCTTTCTCTTTTCTTGGGTGGTGTGGAGTGTTGAGAATCTGCTGTTGC

TTCTTCATCACTGGCAAACATATCTTCATGGCAAAATAAATCTTCATCCC

ATTTTTCATTAAAGGAGCTCCACCAGGACTCCCACTCTTCTGTTCCATAG

GTTGGCACCTATAA
``` or a complement thereof, or a fragment thereof, wherein the 5' and 3' end of the nucleic acid is contained within SEQ ID NO:03. This conserved sequence in the BKV genome is shown in the alignment of the three genomes in FIG. 1. In one embodiment of particular interest, the target region is a subsequence of Target Region III, such as:

```
                                                    (SEQ ID NO: 57)
GGAAAGTCTTTAGGGTCTTCTACCTTTCTCTTTTTCTTGGGTGGTGTGGA

GTGTTGAGAATCTGCTGTTGCTTCTTCATCACTGGCAAACATATCTTCAT

G
``` or a complement thereof, or a fragment thereof.

Exemplary nucleic acid sequences suitable for design of primers for amplification of a Target Region III nucleic acid, and suitable for use in the methods of the invention, are indicated by underlined typeface in FIG. 1. Suitable sequences for primers for amplification of Target Region III nucleic acid correspond to nucleotides 280-306 and 355-380 of the nucleotide sequence of SEQ ID NO:03, or a complement thereof.

Probes suitable for use in the invention can be designed from any sequence positioned within the sequence of an amplification product that would be produced using two selected primers. Suitable sequences for use as a probe for detection of Target Region III nucleic acid correspond to nucleotides 330-354 of the nucleotide sequence of SEQ ID NO:03, or a complement thereof.

In one embodiment, detection of target region III nucleic acid involves production of an amplification product of at least 464, at least 425, at least 400, at least 375, at least 350, at least 325, at least 300, at least 275, at least 250, at least 225, at least 200, at least 175, at least 150, at least 125, at least 120, at least 115, at least 110, at least 100, at least 95, at least 90, at least 85, at least 80, at least 75, at least 70, at least 65, at least 60, at least 55, at least 50, at least 45, at least 40, at least 35, at least 30, at least 28, at least 26, at least 24, at least 22, at least 20 consecutive nucleotides of SEQ ID NO:03.

The methods of the invention can involve detection of target region III nucleic acid either alone or in combination with detection of one or more of target regions I-II and IV-V as described herein. For example, the methods of the invention can involve detection of tweet region III (BK3) and target region IV (BK4); target region III (BK3) and target region V (BK5); target region III (BK3) and target region I (BK1); target region III (BK3) and target region II (BK); target region I (BK1), target region II (BK2), and target region III (BK3); target region III (BK3), target region IV (BK4), and target region V (BK5); or target region III (BK3), target region I (BK1), and target region V (BK5) and the like. It will be understood that detection of all combination of target regions I-V are contemplates by the present methods.

Exemplary primers and probes are discussed in greater detail below.

Target Region IV (BK4)

In another embodiment, the invention provides for detection of BKV in a sample, such as a biological sample, by detection of target nucleic acid sequence region IV (FIG. 1, Target Region IV (also referred to as BK4), alignment position 612-864 based on numbering of GenBank Accession No. AY628224) as follows:

```
                                                    (SEQ ID NO: 04)
ATGGGTGCTGCTCTAGCACTTTTGGGGGACCTAGTTGCCAGTGTATCTGA

GGCTGCTGCTGCCACAGGATTTTCAGTGGCTGAAATTGCTGCTGGGGAGG

CTGCTGCTGCTATAGAAGTTCAAATTGCATCCCTTGCTACTGTAGAGGGC

ATAACAAGTACCTCAGAGGCTATAGCTGCCATAGGCCTAACTCCTCAAAC
```

ATATGCTGTAATTGCTGGTGCTCCTGGGGCTATTGCTGGGTTTGCTGCTT

TAA or a complement thereof, or a fragment thereof, wherein the 5' and 3' end of the nucleic acid is contained within SEQ ID NO:04. This conserved sequence in the BKV genome is shown in the alignment of the three genomes in FIG. 1. In one embodiment of particular interest, the target region is a subsequence of Target Region IV, such as:

(SEQ ID NO: 58)
ATGGGTGCTGCTCTAGCACTTTTGGGGGACCTAGTTGCCAGTGTATCTGA

GGCTGCTGCTGCCACAGGATTTTCAGTGGCTGAAATTGCTGCTGG or a complement thereof, or a fragment thereof.

Exemplary nucleic acid sequences suitable for design of primers for amplification of a Target Region IV nucleic acid, and suitable for use in the methods of the invention, are indicated by underlined typeface in FIG. 1. Suitable sequences for primers for amplification of Target Region IV nucleic acid correspond to nucleotides 1-19 and 76-95 of the nucleotide sequence of SEQ ID NO:04, or a complement thereof.

Probes suitable for use in the invention can be designed from any sequence positioned within the sequence of an amplification product that would be produced using two selected primers. Suitable sequences for use as a probe for detection of Target Region IV nucleic acid correspond to nucleotides 36-62 of the nucleotide sequence of SEQ ID NO:04, or a complement thereof.

In one embodiment, detection of target region IV nucleic acid involves production of an amplification product of at least 253, at least 250, at least 225, at least 200, at least 175, at least 150, at least 125, at least 120, at least 115, at least 100, at least 95, at least 90, at least 85, at least 80, at least 75, at least 70, at least 65, at least 60, at least 55, at least 50, at least 45, at least 40, at least 35, at least 30, at least 28, at least 26, at least 24, at least 22, at least 20 consecutive nucleotides of SEQ ID NO:04.

The methods of the invention can involve detection of target region IV nucleic acid either alone or in combination with detection of one or more of target regions I-III and V as described herein. For example, the methods of the invention can involve detection of target region IV (BK4) and target region I (BK1); target region IV (BK4) and target region II (BK2); target region IV (BK4) and target region III (BK3); target region IV (BK4) and target region IV (BK5); target region I (BK1), target region II (BK2), and target region IV (BK4); target region III (BK3), target region IV (BK4) and target region V (BK5); or target region I (BK1), target region TV (BK4) and target region V (BK5) and the like. It will be understood that detection of all combination of target regions I-V are contemplates by the present methods.

Exemplary primers and probes are discussed in greater detail below.

Target Region V

In another embodiment, the invention provides for detection of BKV in a sample, such as a biological sample, by detection of target nucleic acid sequence region V (FIG. 1. Target Region V (also refereed to as BK5), alignment position 2810-2895 based on numbering of GenBank Accession No. AY628224) as follows:

(SEQ ID NO: 05)
GGGGCTGAAGTATCTGAGACTTGGGAAGAGCATTGTGATTGGGATTCAGT

GCTTGATCCATGTCCAGAGTCTTCAGTTTCTGAATC or complement thereof, or a fragment thereof, wherein the 5' and 3' end of the nucleic acid is contained within SEQ ID NO:05. This conserved sequence in the BKV genome is shown in the alignment of the three genomes in FIG. 1. In one embodiment of particular interest, the target region is a subsequence of Target Region V, such as:

(SEQ ID NO: 59)
GGGCTGAAGTATCTGAGACTTGGGAAGAGCATTGTGATTGGGATTCAGTG

CTTGATCCATGTC or complement thereof, or a fragment thereof.

Exemplary nucleic acid sequences suitable for design of primers for amplification of a Target Region V nucleic acid, and suitable for use in the methods of the invention, are indicated by underlined typeface in FIG. 1. Suitable sequences for primers for amplification of Target Region V nucleic acid correspond to nucleotides 2-18 and 47-64 of the nucleotide sequence of SEQ ID NO:05, or a complement thereof.

Probes suitable for use in the invention can be designed from any sequence positioned within the sequence of an amplification product that would be produced using two selected primers. Suitable sequences for use as a probe for detection of Target Region V nucleic acid correspond to nucleotides 19-41 of the nucleotide sequence of SEQ ID NO:05, or a complement thereof.

In one embodiment, detection of target region V nucleic acid involves production of an amplification product of at least 86, at least 80, at least 75, at least 70, at least 65, at least 60, at least 55, at least 50, at least 45, at least 40, at least 35, at least 30, at least 28, at least 26, at least 24, at least 22, at least 20 consecutive nucleotides of SEQ ID NO:05.

The methods of the invention can involve detection of target region V nucleic acid either alone or in combination with detection of one or more of target regions I-IV as described herein. For example, the methods of the invention can involve detection of target region V (BK5) and target region I (BK1); target region V (BK5) and target region II (BK2); target region V (BK5) and target region III (BK3); target region IV (BK4) and target region V (BKV); target region V (BK5), target region II (BK2), and target region III (BK3); target region III (BK3), target region IV (BK4), and target region V (BK5); or target region I (BK1), target region III (BK3), and target region V (BK5) and the like. It will be understood that detection of all combination of target regions I-V are contemplates by the present methods.

Exemplary primers and probes are discussed in greater detail below.

Primers and Probes

As described above, the target nucleic acid sequence regions I-V are conserved nucleic acid regions in different BKV genotypes. Primers and probes for use in these assays are preferably derived from the target nucleic acid sequence regions I-V as described above. In one embodiment of particular interest, primers and probes for use with the present assays are designed from the highly conserved nucleotide sequences of the target nucleic acid sequence regions I-V.

In general, the primers provide for amplification of target nucleic acid to produce as target nucleic acid amplification product (also referred to as an "amplicon"). Primers may be, and preferably are, used in connection with a probe, 5' primers generally bind to a region to provide for amplification of the target nucleic, and preferably bind to a 5' portion of the target sequence, as exemplified in FIG. 1. 3' primers generally bind to a sequence that is complementary to a 3' portion of the nucleic acid generated by extension from the 5' primer, as exemplified in FIG. 1. The 5' and 3' primers may be separated by about 10, 20, 30, or 40 contiguous nucleotides, usually about 30 contiguous nucleotides. In certain embodiments, primers are designed so as to have a sequence complementary to one or more variant nucleotides within a target region sequence and/or to have a 3' end adjacent a variant nucleotide of a sequence of a target region. Probes are generally designed so as to have a sequence complementary to one or more variant nucleotides within a target region sequence. In some embodiments involving amplification-based detection, probes are designed so as to have a sequence complementary to a sequence flanked by the sequence(s) complementary to one or more primers used for amplification.

Primers and probes for use in the assays herein are designed based on the sequence disclosed herein and are readily synthesized by standard techniques, e.g., solid phase synthesis via phosphoramidite chemistry, as disclosed in U.S. Pat. Nos. 4,458,066 and 4,415,732, incorporated herein by reference; Beaucage et at (1992) Tetrahedron 48:2223-2311; and Applied Biosystems User Bulletin No. 13 (1 Apr. 1987). Other chemical synthesis methods include, for example, the phosphotriester method described by Narang et al., Meth. Enzymol. (1979) 68:90 and the phosphodiester method disclosed by Brown et al., Meth. Enzymol. (1979) 68:109. Poly(A) or poly(C), or other non-complementary nucleotide extensions may be incorporated into probes using these same methods. Hexaethylene oxide extensions may be coupled to probes by methods known in the art. Cload et al. (1991) J. Am. Chem. Soc. 113:6324-6326; U.S. Pat. No. 4,914,210 to Levenson et al.; Durand et al. (1990) Nucleic Acids Res. 18:6353-6359; and Horn et al. (1986) Tet. Lett. 27:4705-4708.

Typically, the primer sequences are in the range of between 10-75 nucleotides in length, such as 10 to 70, 12 to 65, 15 to 60, 20 to 55, 25 to 50, 30 to 45, and the like. More typically, primers are in the range of between 18 to 40, 19 to 35, 20 to 30, 21 to 29, 22 to 28, 23 to 27, 24-25 nucleotides long, and any length between the stated ranges. Primers of about 20 to 22 nucleotides in length are of particular interest.

The typical probe is in the range of between 10-50 nucleotides long, such as such as 10 to 50, 12 to 45, 15 to 40, 20 to 35, 25 to 30 and the like. More typically, probes are in the range of between 18 to 40, 19 to 35, 20 to 30, 21 to 29, 22 to 28, 23 to 27, 24-25 nucleotides long, and any length between the stated ranges. Probes of about 20 to 22 nucleotides in length are of particular interest.

In some embodiments, the subject methods provide for detection of any BKV genotype in a sample, such a biological sample. In such embodiments, the subject methods detect a target nucleic acid region, or fragment thereof, by using primers and probe that correspond to sequences within the target region. Exemplary primers within the Target Regions I-V suitable for use in the methods of the invention are indicated by bold typeface in FIG. 1. Probes suitable for use in the invention can be designed from any sequence positioned within the sequence of an amplification product that would be produced using two selected primers. A probe suitable for use with such an embodiment is selected such that it corresponds to a region that shares a nucleotide sequence between the different BKV genotypes to be detected.

In other embodiments, the subject methods provide for detection and discrimination between different genotypes in a sample, such a biological sample. In such embodiments, the subject methods detect a target nucleic acid region, or fragment thereof, by using primers and probe that correspond to sequences within the target region. Exemplary primers within the Target Regions I-V suitable for use in the methods of the invention are indicated by bold typeface in FIG. 1. Probes suitable for use in the invention can be designed from any sequence positioned within the sequence of an amplification product that would be produced using two selected primers. In such embodiments the sequence of the probe is selected such that it corresponds to a region that differs in sequence by one or more nucleotides between the different BKV genotypes to be detected.

Exemplary nucleic acid sequences of the BKV genotypes that are suitable for use are primers and probes in the assays of the present invention are described in Table 1. The sequence numbering presented in Table 1 is the numbering of GenBank Accession No. AY628224 in FIG. 1.

TABLE 1

Exemplary Primer and Probe Sequences for Detection of Target Regions I-V of BKV Nucleic Acid (Sequence Provided Based on BKV Genome Sequence; Sequence Numbering Based on Numbering of GenBank Accession No. AY628224 of FIG. 1)

| SEQ ID NO.: | | Start | End | Length | Sequence 5' to 3' |
|---|---|---|---|---|---|
| Target Region I (BK1) (corresponding to nucleotides 435-585 of AY628224) | | | | | |
| SEQ ID NO: 06 | F | 435 | 460 | 26 | AACAAAAAAAAGAGCTCAGAGGATTT |
| SEQ ID NO: 07 | R | 527 | 552 | 26 | AAGTACCACTGCTTTACCTGCTGTAA |
| SEQ ID NO: 08 | P | 490 | 524 | 34 | TTTGTAGAGGTGAAGACAGTGTAGACGGGAAAAA |
| Target Region II (BK2) (corresponding to nucleotides 1418-1545 of AY628224) | | | | | |
| SEQ ID NO: 09 | F | 1450 | 1467 | 18 | TTGCCCCAGGAGGTGCTA |
| SEQ ID NO: 10 | R | 1498 | 1520 | 23 | TTTACTTCTAGGCCTGTACGGGA |
| SEQ ID NO: 11 | P | 1469 | 1497 | 29 | TCAAAGAACTGCTCCTCAATGGATGTTGC |
| Target Region III (BK3) (corresponding to nucleotides 4097-4560 of AY628224) | | | | | |
| SEQ ID NO: 12 | F | 4375 | 4404 | 27 | GGAAAGTCTTTAGGGTCTTCTACCTTT |
| SEQ ID NO: 13 | R | 4452 | 4478 | 26 | TCATCACTGGCAAACATATCTTCATG |
| SEQ ID NO: 14 | P | 4426 | 4450 | 25 | GTGTTGAGAATCTGCTGTTGCTTCT |

TABLE 1-continued

Exemplary Primer and Probe Sequences for Detection of Target Regions I-V
of BKV Nucleic Acid (Sequence Provided Based on BKV Genome Sequence; Sequence
Numbering Based on Numbering of GenBank Accession No. AY628224 of FIG. 1)

| SEQ ID NO.: | | Start | End | Length | Sequence 5' to 3' |
|---|---|---|---|---|---|
| Target Region IV (BK4) (corresponding to nucleotides 612-864 of AY628224) | | | | | |
| SEQ ID NO: 15 | F | 612 | 620 | 19 | ATGGGTGCTGCTCTAGCAC |
| SEQ ID NO: 16 | R | 677 | 696 | 20 | GTGGCTGAAATTGCTGCTGG |
| SEQ ID NO: 17 | P | 646 | 663 | 27 | TGCCAGTGTATCTGAGGCTGCTGCTGC |
| Target Region V (BK5) (corresponding to nucleotides 2810-2895 of AY628224) | | | | | |
| SEQ ID NO: 18 | F | 2811 | 2827 | 17 | GGGCTGAAGTATCTGAG |
| SEQ ID NO: 19 | R | 2856 | 2873 | 18 | CAGTGCTTGATCCATGTC |
| SEQ ID NO: 20 | P | 2828 | 2950 | 23 | CTTGGGAAGAGCATTGTGATTGG |

"F" refers to forward primer, "R" refers to reverse primer, and "P" refers to probe.

The probes may be coupled to labels for detection. There are several methods and compositions known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, Broken et al., Nucl. Acids Res. (1978) 5:363-384 which discloses the use of ferritin-avidin-biotin labels; and Chollet et al. Nucl. Acids Res. (1985) 13:1529-1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly (1987) Nucl. Acids Res. 15:3131-3139, Gibson et al. (1987) Nucl. Acids Res. 15:6455-6467 and U.S. Pat. No. 4,605,735 to Miyoshi et al. Methods are also available for synthesizing sulfhydryl-derivatized oligonucleotides which can be reacted with thiol-specific labels, see, e.g., U.S. Pat. No. 4,757,141 to Fung et al., Connolly et al. (1985) Nuc. Acids Res. 13:4485-4502 and Spoat et al. (1987) Nucl. Acids Res. 15:4837-4848. A comprehensive review of methodologies for labeling DNA fragments is provided in Matthews et al., Anal. Biochem. (1988) 169:1-25.

For example, probes may be fluorescently labeled by linking a fluorescent molecule to the non-ligating terminus of the probe. Guidance for selecting appropriate fluorescent labels can be found in Smith et al., Meth. Enzymol. (1987) 155:260-301; Karger et al., Nucl. Acids Res. (1991) 19:4955-4962; Haugland (1989) Handbook of Fluorescent Probes and Research Chemicals (Molecular Probes, Inc., Eugene, Oreg.). Preferred fluorescent labels include fluorescein and derivatives thereof, such as disclosed in U.S. Pat. No. 4,318,846 and Lee et al., Cytometry (1989) 10:151-164, and 6-FAM, JOE, TAMRA, ROX, HEX-1, HEX-2, ZOE, TET-1 or NAN-2, and the like.

Additionally, probes can be labeled with an acridinium ester (AE). Current technologies allow the AE label to be placed at any location within the probe. See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090. An AE molecule can be directly attached to the probe using non-nucleotide-based linker arm chemistry that allows placement of the label at any location within the probe. See, e.g., U.S. Pat. Nos. 5,585,481 and 5,185,439.

If a solid support is used in the assay (e.g., to capture amplicons of target nucleic acid using a probe), the oligonucleotide probe may be attached to the solid support in a variety of manners. For example, the probe may be attached to the solid support by attachment of the 3' or 5' terminal nucleotide of the probe to the solid support. More preferably, the probe is attached to the solid support by a linker which serves to distance the probe from the solid support. The linker is usually at least 15-30 atoms in length, more preferably at least 15-50 atoms in length. The required length of the linker will depend on the particular solid support used. For example, a six atom linker is generally sufficient when high cross-linked polystyrene is used as the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as functionalized polyethylene glycol can be used as the linker. Such polymers are preferred over homopolymeric oligonucleotides because they do not significantly interfere with the hybridization of probe to the target oligonucleotide. Polyethylene glycol is particularly preferred.

The linkages between the solid support, the linker and the probe are normally not cleaved during removal of base protecting groups under basic conditions at high temperature. Examples of preferred linkages include carbamate and amide linkages.

Examples of preferred types of solid supports for immobilization of the oligonucleotide probe include controlled pore glass, glass plates, polystyrene, avidin-coated polystyrene beads, cellulose, nylon, acrylamide gel and activated dextran.

In certain embodiments, an internal control (IC) or an internal standard is added to serve as a control to show that any negative result is not due to failure of the assay. The use of the IC permits the control of the separation process, the amplification process, and the detection system, and permits the monitoring of assay performance and quantification for the sample(s). The IC can be included at any suitable point, for example, in the lysis buffer. In one embodiment, the IC comprises phage nucleic acid. Where a solid support is used in the assay, the solid support may additionally include probes specific to the internal standard (IC probe), thereby facilitating capture when using the IC probe. The IC probe can optionally be coupled with a detectable label that is different from the detectable label for the target sequence. In embodiments where the detectable label is a fluorophore, the IC can be quantified spectrophotometrically and by limit of detection studies.

Detection of BKV in a Sample

In one aspect, the assay detects the presence of BKV in a sample. In such an aspect, the assay is an amplification-based assay using degenerate primers and probes, where the primers and probes are designed to provide for amplification of a target nucleic acid sequence region of the BKV genome.

As discussed above, the assay detects the presence of one or more target nucleic acid regions (e.g., Target Regions I-V), or a portion thereof. The target nucleic acid sequence regions I-V are conserved nucleic acid regions in different BKV genotypes. Primers and probes for use in these assays are preferably derived from the target nucleic acid sequence regions I-V as described above. Particularly preferred primers and probes for use with the present assays are designed from the highly conserved nucleotide sequences of the target nucleic acid sequence regions I-V.

As discussed above, in one embodiment, the primers and/or probes are designed for nucleic acid-based detection, particularly an amplification method, of a target nucleic acid having a target nucleic acid sequence described above, e.g., target nucleic acid sequence region I-V. That is, in such an embodiment, the primers are designed to amplify a target sequence having the nucleic acid sequence of a nucleic acid sequence described above, e.g., target nucleic acid sequence region I-V.

In another embodiment, the primers and/or probes are designed for nucleic acid-based detection, particularly an amplification method, of a target nucleic acid having a nucleic acid sequence that is a fragment of a target nucleic acid sequence described above, e.g., target nucleic acid sequence region I-V. That is, in such an embodiment, the primers are designed to amplify a target sequence having the nucleic acid sequence of a portion smaller than the entire nucleic acid sequence described above, e.g., target nucleic acid sequence region I-V.

Specific detection of BKV nucleic acid in a sample is generally accomplished by detection of one or more of the target sequence regions I-V, or a fragment thereof. In one embodiment. BKV target nucleic acid is detected by use of primers and probes designed upon the sequences of target sequence region V.

In an embodiment of particular interest, the target sequence is detected using primers having the sequence ATGGGTGCTGCTCTAGCAC (5' primer) (SEQ ID NO:15), GTGGCTGAAATTGCTGCTGG (3' primer) (SEQ ID NO:16), and a probe having the sequence TGCCAGTGTATCTGAGGCTGCTGCTGC (SEQ ID NO:17) is of particular interest.

In another embodiment of particular interest, the target sequence is detected using primers having the sequence GGGCTGAAGTATCTGAG (5' primer) (SEQ ID NO:18), CAGTGCTTGATCCATGTC (3' primer) (SEQ ID NO:19), and a probe having the sequence CTTGGGAAGAGCATTGTGATTGG (SEQ ID NO:20) is of particular interest.

Of particular interest is the use of these primers and probes in a real-time RT PCR method for detection of BKV in a sample, with use of a dual-labeled TaqMan Probe.

Methods of Detection

The invention provides DNA-based assay for detecting BKV in a sample. Detection may be done using a wide variety of methods, including direct sequencing, hybridization with sequence-specific oligomers, gel electrophoresis and mass spectrometry. These methods can use heterogeneous or homogeneous formats, isotopic or nonisotopic labels, as well as no labels at all.

Preferably, the methods involve amplifying nucleic acids from a sample. If a diagnostic nucleic acid is obtained, the presence of BKV in a sample is indicated. In general, the methods involve amplifying a nucleic acid from a sample using a detection primer and at least one other primer, as described above, and assessing the amplified nucleic acids. The methods are highly sensitive, and may detect as few as 5 copies of BKV per reaction, which is equivalent to 200 copies of DNA per mL of specimen, although detection may be limited by the limit of linear range detection. Thus, the invention generally provides for detection of BKV in a sample, where the BKV is present in at least 200 copies of DNA per mL of specimen.

As is known in the art, an amplified nucleic acid may be assessed by a number of methods, including, for example, determining the presence or absence of the nucleic acid, determining the size of the nucleic acid or determining the abundance of a nucleic acid in relation to another amplified nucleic acid. In most embodiments, an amplified nucleic acid is assessed using gel electrophoresis, nucleic acid hybridization, sequencing, and/or detection of a signal from a label bound to the amplified nucleic acid. Methods of amplifying (e.g., by polymerase chain reaction) nucleic acid, methods of performing primers extension, and methods of assessing nucleic acids are generally well known in the art (e.g., see Ausubel, et al, Short Protocols in Molecular Biology, 3rd ed., Wiley & Sons, 1995 and Sambrook, et al, Molecular Cloning: A Laboratory Manual, Third Edition, (2001) Cold Spring Harbor, N.Y.) and need not be described in any great detail.

For example, primers and probes described above may be used in polymerase chain reaction (PCR)-based techniques to detect BKV in biological samples. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) PCR Protocols (Academic Press, NY 1990); Taylor (1991) Polymerase chain reaction: basic principles and automation, in PCR: A Practical Approach, McPherson et al. (eds.) IRL Press, Oxford; Saiki et al. (1986) Nature 324:163; as well as in U.S. Pat. Nos. 4,683,195, 4,683,202 and 4,889,818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, preferably by heat, and hybridized with first and second primers which are present in molar excess. Polymerization is catalyzed in the presence of the four deoxyribonucleotide triphosphates (dNTPs— dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer). *Thermus thermophilus* (United States Biochemicals), *Bacillus stereothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands.

The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grow exponentially with each cycle. Preferably, PCR is carried out with a commercially available thermal cycler, e.g., Perkin Elmer.

The fluorogenic 5' nuclease assay, known as the TAQMAN™ assay (Perkin-Elmer), is a powerful and versatile PCR-based detection system for nucleic acid targets. For a detailed description of the TAQMAN™ assay, reagents and conditions for use therein, see, e.g., Holland et al., Proc. Natl. Acad. Sci, U.S.A. (1991) 88:7276-7280; U.S. Pat. Nos. 5,538,848, 5,723,591, and 5,876,930, all incorporated herein by reference in their entireties. Hence, primers and probes derived from regions of the BKV genome described herein can be used in TAQMAN™ analyses to detect the presence of infection in a biological sample. Analysis is performed in conjunction with thermal cycling by monitoring the generation of fluorescence signals. The assay system dispenses with the need for gel electrophoretic analysis, and has the capability to generate quantitative data allowing the determination of target copy numbers.

The fluorogenic 5' nuclease assay is conveniently performed using, for example, AMPLITAQ GOLD™ DNA polymerase, which has endogenous 5' nuclease activity, to digest an internal oligonucleotide probe labeled with both a fluorescent reporter dye and a quencher (see, Holland et al., Proc. Natl. Acad. Sci. USA (1991) 88:7276-7280; and Lee et al., Nucl. Acids Res. (1993) 21:3761-3766). Assay results are detected by measuring changes in fluorescence that occur during the amplification cycle as the fluorescent probe is digested, uncoupling the dye and quencher labels and causing an increase in the fluorescent signal that is proportional to the amplification of target nucleic acid.

The amplification products can be detected in solution or using solid supports. In this method, the TAQMAN™ probe is designed to hybridize to a target sequence within the desired PCR product. The 5' end of the TAQMAN™ probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence which can be detected.

In particular, the oligonucleotide probe is constructed such that the probe exists in at least one single-stranded conformation when unhybridized where the quencher molecule is near enough to the reporter molecule to quench the fluorescence of the reporter molecule. The oligonucleotide probe also exists in at least one conformation when hybridized to a target polynucleotide such that the quencher molecule is not positioned close enough to the reporter molecule to quench the fluorescence of the reporter molecule. By adopting these hybridized and unhybridized conformations, the reporter molecule and quencher molecule on the probe exhibit different fluorescence signal intensities when the probe is hybridized and unhybridized. As a result, it is possible to determine whether the probe is hybridized or unhybridized based on a change in the fluorescence intensity of the reporter molecule, the quencher molecule, or a combination thereof. In addition, because the probe can be designed such that the quencher molecule quenches the reporter molecule when the probe is not hybridized, the probe can be designed such that the reporter molecule exhibits limited fluorescence unless the probe is either hybridized or digested.

Accordingly, the present invention relates to methods for amplifying a target BKV nucleotide sequence using a nucleic acid polymerase having 5' to 3' nuclease activity, one or more primers capable of hybridizing to the target BKV sequence or its extension product, and an oligonucleotide probe capable of hybridizing to the target BKV sequence 3' relative to the primer. During amplification, the polymerase digests the oligonucleotide probe when it is hybridized to the target sequence, thereby separating the reporter molecule from the quencher molecule. As the amplification is conducted, the fluorescence of the reporter molecule is monitored, with fluorescence corresponding to the occurrence of nucleic acid amplification. The reporter molecule is preferably a fluorescein dye and the quencher molecule is preferably a rhodamine dye.

Another method of detection involves use of target sequence-specific oligonucleotide probes, which contain a region of complementarity to the target sequence described above. The probes may be used in hybridization protection assays (HPA). In this embodiment, the probes are conveniently labeled with acridinium ester (AE), a highly chemiluminescent molecule. See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090. One AE molecule is directly attached to the probe using a non-nucleotide-based linker arm chemistry that allows placement of the label at any location within the probe. See, e.g., U.S. Pat. Nos. 5,585,481 and 5,185,439. Chemiluminescence is triggered by reaction with alkaline hydrogen peroxide which yields an excited N-methyl acridone that subsequently collapses to ground state with the emission of a photon. Additionally, AE causes ester hydrolysis which yields the nonchemiluminescent-methyl acridinium carboxylic acid.

When the AE molecule is covalently attached to a nucleic acid probe, hydrolysis is rapid under mildly alkaline conditions. When the AE-labeled probe is exactly complementary to the target nucleic acid, the rate of AE hydrolysis is greatly reduced. Thus, hybridized and unhybridized AE-labeled probe can be detected directly in solution, without the need for physical separation.

HPA generally consists of the following steps: (a) the AE-labeled probe is hybridized with the target nucleic acid in solution for about 15 to about 30 minutes. A mild alkaline solution is then added and AE coupled to the unhybridized probe is hydrolyzed. This reaction takes approximately 5 to 10 minutes. The remaining hybrid-associated AE is detected as a measure of the amount of target present. This step takes approximately 2 to 5 seconds. Preferably, the differential hydrolysis step is conducted at the same temperature as the hybridization step, typically at 50 to 70 degrees celsius. Alternatively, a second differential hydrolysis step may be conducted at room temperature. This allows elevated pHs to be used, for example in the range of 10-11, which yields larger differences in the rate of hydrolysis between hybridized and unhybridized AE-labeled probe. HPA is described in detail in, e.g., U.S. Pat. Nos. 6,004,745; 5,948,899; and 5,283,174, the disclosures of which are incorporated by reference herein in their entireties.

The oligonucleotide molecules of the present invention may also be used in nucleic acid sequence-based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5' tail comprising a promoter, a second DNA primer, reverse transcriptase, RNAse-H, T7 RNA polymerase, MTP's and dNTP's. Using NASBA, large amounts of single-stranded RNA are generated from either single-stranded RNA or DNA, or double-stranded DNA. When RNA is to be amplified, the ssRNA serves as a template for the synthesis of a first DNA strand by elongation of a first primer containing an RNA polymerase recognition site. This DNA strand in turn serves as the template for the synthesis of a second, complementary, DNA strand by elongation of a second primer, resulting in a double-stranded active RNA-polymerase promoter site, and the second DNA strand serves as a template for the synthesis of large amounts of the first template, the ssRNA, with the aid of a RNA polymerase. The NASBA technique is known in the art and described in, e.g., European Patent 329,822, International Patent Application No. WO 91/02814, and U.S. Pat. Nos. 6,063,603, 5,554,517 and 5,409,818, all of which are incorporated herein in their entireties.

The BKV sequences described herein are also useful in nucleic acid hybridization and amplification techniques that utilize branched DNA molecules. In a basic nucleic acid hybridization assay, single-stranded analyte nucleic acid is hybridized to a labeled single-stranded nucleic acid probe and resulting labeled duplexes are detected. Variations of this basic scheme have been developed to facilitate separation of the duplexes to be detected from extraneous materials and/or to amplify the signal that is detected. One method for amplifying the signal uses amplification multimers that are polynucleotides with a first segment that hybridizes specifically to the analyte nucleic acid or a strand of nucleic acid bound to the analyte and iterations of a second segment that hybridizes specifically to a labeled probe. The amplification is theoretically proportional to the number of iterations of the second segment. The multimers may be either linear or branched. Two general types of branched multimers are useful in these techniques: forked and combed. Methods for making and using branched nucleic acid molecules are known in the art and described in, e.g., U.S. Pat. No. 5,849,481, incorporated herein by reference in its entirety.

As is readily apparent; design of the assays described herein are subject to a great deal of variation, and many formats are known in the art. The above descriptions are merely provided as guidance and one of skill in the art can readily modify the described protocols, using techniques well known in the art.

Kits

Kits for use in connection with the subject invention are also provided. The above-described assay reagents, including the primers, probes, solid support with bound probes, as well as other detection reagents, can be provided in kits, with suitable instructions and other necessary reagents, in order to conduct the assays as described above. The kit will normally contain in separate containers the combination of primers and probes (either already bound to a solid matrix or separate with reagents for binding them to the matrix), control formulations (positive and/or negative), labeled reagents when the assay format requires same and signal generating reagents (e.g., enzyme substrate) if the label does not generate a signal directly. Instructions (e.g., written, tape, VCR, CD-ROM, etc.) for carrying out the assay usually will be included in the kit. The kit can also contain, depending on the particular assay used, other packaged reagents and materials (i.e. wash buffers and the like). Standard assays, such as those described above, can be conducted using these kits.

The instructions are generally recorded on a suitable recording medium. For example, the instructions may be printed on a substrate, such as paper or plastic, etc. As such, the instructions may be present in the kits as a package insert, in the labeling of the container of the kit or components thereof (e.g., associated with the packaging or sub-packaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed from or from where the instructions can be downloaded.

Still further, the kit may be one in which the instructions are obtained are downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

In general, kits of the invention include at least one primer, usually at least two primers (a 5' and a 3' primer), usually at least two primers and a probe, as described above. Kits may also contain instructions for using the kit to detect BKV in a sample using the methods described above, including the above discussed PCR methods. Also included in the subject kits may be buffers, dNTPs, and controls, (e.g., positive and negative control nucleic acids) for performing the subject methods. Primers in the subject kits may be detectably labeled or unlabeled).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods

The following method and material were used in the Example(s) below.

Specimen Types and Handing.

Samples for use in detection of BKV according to the invention can be any suitable biological sample, such as serum, plasma, amniotic fluid, and tissue specimen. Tissue specimens should be stored frozen at −20±10° C. in saline or phosphate buffered saline (PBS). Serum, plasma, and amniotic fluid should be stored frozen at −20±10° C. All of the above specimen types, as needed, can be shipped on dry ice via overnight express, Primers and Probes.

Oligonucleotide primers and probes were designed and analyzed for their suitability for PCR and hybridization by computer analysis using standard program (Primer Express, Applied Biosystems). Oligonucleotide primers and fluorogenic probes were synthesized by qualified vendors. Oligonucleotide primers were desalted and lyophilized. Oligonucleotide primer pair sets for detection of BKV were as follows:

| SEQ ID NO.: | | Sequence 5' to 3' |
|---|---|---|
| Target Region I (BK1) | | |
| SEQ ID NO: 06 | F | AACAAAAAAAAGAGCTCAGAGGATTT |
| SEQ ID NO: 7 | R | AAGTACCACTGCTTTACCTGCTGTAA |
| SEQ ID NO: 8 | P | TTTGTAGAGGTGAAGACAGTGTAGACGGGAAAAA |
| Target Region II (BK2) | | |
| SEQ ID NO: 9 | F | TTGCCCCAGGAGGTGCTA |
| SEQ ID NO: 10 | R | TTTACTTCTAGGCCTGTACGGGA |
| SEQ ID NO: 11 | P | TCAAAGAACTGCTCCTCAATGGATGTTGC |
| Target Region III (BK3) | | |
| SEQ ID NO: 12 | F | GGAAAGTCTTTAGGGTCTTCTACCTTT |
| SEQ ID NO: 13 | R | TCATCACTGGCAAACATATCTTCATG |
| SEQ ID NO: 14 | P | GTGTTGAGAATCTGCTGTTGCTTCT |
| Target Region IV (BK4) | | |
| SEQ ID NO: 15 | F | ATGGGTGCTGCTCTAGCAC |
| SEQ ID NO: 16 | R | GTGGCTGAAATTGCTGCTGG |
| SEQ ID NO: 17 | P | TGCCAGTGTATCTGAGGCTGCTGCTGC |
| Target Region V (BK5) | | |
| SEQ ID NO: 18 | F | GGGCTGAAGTATCTGAG |
| SEQ ID NO: 19 | R | CAGTGCTTGATCCATGTC |
| SEQ ID NO: 20 | P | CTTGGGAAGAGCATTGTGATTGG |

"F" refers to the forward primer "R" to the reverse primer, and "P" refers to probe. Probes are frozen at a 100 μM concentration. The working concentration of the probes is 5 μM and are diluted 1:10 with 10 mM Tris-HCl, pH 8.0, and distributed into 100 μL aliquots. Probes can be stored at −20° C. or lower and protected from light.

Enzymes.

The following enzymes are used: 2×TaqMan® Universal PCR Master Mix Applied Biosystems Cat. #4304437 or 4318157, which includes the AmpliTaq Gold DNA Polymerase of Applied Biosystems Reagents and Buffers.

The following were used in the assays: QIAamp DNA Blood Mini Kit (QIAGEN Cat. No. 51106);

Equipment.

Equipment used included the ABI PRISM® Sequence Detection System 7500

Amplification.

DNA amplification was achieved by widely used PCR method described above (see, for example, Persing et al, 1993, Diagnostic Molecular Microbiology: Principles and Amplifications, American Society for Microbiology, Washing D.C.). Amplified DNA sequence was detected by hybridization and cleavage of dual labeled oligonucleotide probe by the Taqman method. Briefly, the amplification and detection protocols were as follows: extracted DNA from clinical specimens were amplified in 25 μl PCR reaction mixture (PCR Master Mix, Applied Biosystems) containing 500 nM of each primers, 100 nM of dual labeled probed (Taqman probe), 200 uM of each of the four dNTPs. The AmpliTaq Gold polymerase was used in the mix, which is a heat activation (hot start) enzyme to enhance the specificity and sensitivity of the amplification. The PCR reaction was subjected to thermal cycling (10 min at 95 C, followed by 40 cycles of 30 second at 95 C, 30 second at 60 C) by using ABI7500 Real Time PCR System. The amplification and detection was monitored at real time, and was analyzed after completion of PCR cycling by using ABI's Sequence Detection Software (v1.2.2).

Specificity.

The specificity of oligonucleotide primers and probes, derived from the sequenced DNA and the sequences available in GenBank, were tested on a panel of clinical BKV positive and negative samples. The primers and probes were also tested on JCV positive and negative samples, as well as a number of controls. The results were compared with the result by PCR assay currently used in clinical laboratories. Some of the amplified nucleic acids were sequenced in order to validate the specificity of the assay. The sequencing of the amplified nucleic acids confirmed that all PCR fragments were indeed BKV sequences. None of these sequences fragments correlated to JCV sequences or sequences from any other species.

Sensitivity.

The sensitivity of the assays was analyzed by titration of known concentration series of BKV DNA and converting the concentrations into standard curves. Since there are several primer/probe sets targeting different regions, the sensitivity varied slightly. Overall, the analytical sensitivity reached 5 copy or lower per reaction tube. Based on the sample preparation procedure and volume adjustment protocol, this analytical sensitivity was equivalent to about 200 copies per ml for clinical specimen (e.g., serum, urine, or other form of liquid specimen).

Example 1

Complete Sequencing of BKV Whole Genome

In order to understand the genomic diversity of BKV and to identify candidate sequences for its diagnostic applications, whole viral genome sequencing was performed. Urine samples were collected from 13 BKV positive patients. To avoid close clinical relationship, these patients were chosen from geographically diversified resources and were otherwise randomly selected. Samples were extracted for viral DNA by regular method. The extracted DNA was then amplified for its whole 5.1 kb genome by long PCR protocol (Stratagene). The amplified viral DNA was sequenced by four-color, dideoxy termination method with a set of pre-designed sequencing primers, and separated on AB1377 sequencer system. The sequence pieces were assembled into complete 5.1-5.2 kb contigs by Lasergene 6 software for each BKV genome for analysis.

Thirteen assembled BKV contigs were aligned against each other and also aligned against all published BKV sequences. Published sequence information was acquired from public databases (GenBank, EMBL and Swiss-Port). 32 complete BKV genome sequences were compared, including the 13 newly sequenced BKV sequences and the 19 published BKV sequences (GenBank Accession Nos.: AY628224, AY628225, AY628226, AY628227, AY628228, AY628229, AY628230, AY628231, AY628232, AY628233, AY628234, AY628235, AY628236, AY628237, AY628238, M23122, NC001538, V01108, and V0109).

First, all the sequences from the BKV strains were compared to one another. Then, the BKV sequences were then compared to genomes of other closely related species. Of all the species that were screened, of particular interest were the human polyomavirus JC viruses (JCV), another member in the polyomavirus family.

Complete sequence alignment within BKV genome allowed for the selection of several candidate sequence regions for diagnostic detection. These regions share consensus across all 32 BKV genomes, and have minimal variations in their sequences. Sequences outside these regions are either not consensus or are highly polymorphic, which make them very difficult to be used for ubiquity detection in diagnostic applications. A comparative analysis was further performed against sequences from all other species in public databases. Notably, JCV shares a high homology with BKV. Despite the homology, comparison of selected regions of BKV with JCV showed some sequence differences. These sequence differences, though limited, are critical for differential detection of BKV from JCV.

Of the 5100+ base pairs from the complete whole genome, there are a total of 142 previously unpublished nucleotide variations that were identified. Of these nucleotide variations, 105 were nucleotide substitutions (single or multiple base pairs) and 37 were deletions or insertions (multiple base pairs). The newly identified variations distributed throughout the entire BKV genome. A fine map of genetic diversity of BKV was created by combining the newly identified sequence variations with variations from public databases. As shown in FIG. 1, this map illustrates regions which are highly polymorphic and regions which are relatively conservative. Analysis of this fine map allows for selection of candidate sequence regions for diagnostic applications.

Example 2

Identification of Target Region I ("BK1")

As shown in FIG. 1, the comparison of sequences across all newly completed nucleic acid sequences and published nucleic acid sequences allowed the selection of more than one sequence regions that are conserved and will provide for specific and sensitive nucleic acid based detection of the presence or absence of BKV in a biological sample. The BK1 region comprising of nucleotides 435 to 585 of Gen-Bank Accession No. AY628224 was selected for PCR primer design. The nucleic acid sequence of the BK1 target sequence is:

(SEQ ID NO: 01)
AACAAAAAAAAGAGCTCAGAGGATTTTTATTTTTATTTTAGAGCTTTTG

CTGGAATTTTGTAGAGGTGAAGACAGTGTAGACGGGAAAAACAAAGGTA

CCACTGCTTTACCTGCTGTAAAAGACTCTGTAAAAGACTCCTAGGTAAG

TAAT

The strategy used to design the nucleic acid based amplification primers was based on the analysis of multiple sequences alignment of all BKV genomic sequences and sequences of closely related viruses. This analysis was designed to include all variants of BKV. This analysis was also designed to exclude any closely related, but non BKV sequences, such as sequence of JCV. A careful analysis of these alignments allowed the selection of oligonucleotide sequences which cover sequences of all BKV variants but discriminate sequences from any other closely related genera, thereby permitting the genus-specific amplification and ubiquitous detection and identification of BKV. The sequences of the primers and probe for the BK1 target region are as follows:

| SEQ ID NO.: | | Sequence 5' to 3' |
|---|---|---|
| Target Region I (BK1) | | |
| SEQ ID NO: 06 | F | AACAAAAAAAAGAGCTCAGAGGATTT |
| SEQ ID NO: 07 | R | AAGTACCACTGCTTTACCTGCTGTAA |
| SEQ ID NO: 08 | P | TTTGTAGAGGTGAAGACAGTGTAGAC GGGAAAAA |

For confirmation of specific detection of BKV, PCR amplification products from BKV specimens were sequenced and analyzed. The amplification product sequences were aligned well with the sequence of BKV, and none of the amplification product sequences were identified as sequence of JCV or of any other genera. The results of the assay are shown in FIG. 2. Template concentrations ranged from 50 copies per reaction to 50,000 per reaction, and the assay were performed in duplicate. BK1 assay: slope=−3.58, intercept=43.428, and $R^2$=0.997.

Example 3

Identification of Target Region II ("BK2")

The comparison of nucleic acid sequences across all newly completed BKV nucleic acid sequences and published BKV nucleic acid sequences allowed the selection of the BK2 target region. The BK2 target region comprises nucleotides 1418 to 1545 of GenBank Accession No. AY628224. The nucleic acid sequence of the BK2 target sequence is:

(SEQ ID NO: 02)
TGTACATTCAGGAGAGTTTATAGAAAAAACTATTGCCCAGGAGGTGCTAA

TCAAAGAACTGCTCCTCAATGGATGTTGCCTTTACTTCTAGGCCTGTACG

GGACTGTAACACCTGCTCTTGAAGCAT

The strategy used to design the nucleic acid based amplification primers and probes was based on the analysis of multiple sequences alignment of all BKV sequences and sequences of closely related viruses. This analysis was designed to include all variants of BKV. This analysis was also designed to exclude any closely related, but non BK sequences, such as sequence of JCV. A careful analysis of these alignments allowed the selection of oligonucleotide sequences which cover sequences of all BKV variants but discriminate sequences from any other closely related genera, thereby permitting the genus-specific amplification and ubiquitous detection and identification of BKV. The sequences of the primers and probe for the BK2 target region are as follows:

| SEQ ID NO.: | | Sequence 5' to 3' |
|---|---|---|
| Target Region II (BK2) | | |
| SEQ ID NO: 9 | F | TTGCCCCAGGAGGTGCTA |
| SEQ ID NO: 10 | R | TTTACTTCTAGGCCTGTACGGGA |
| SEQ ID NO: 11 | P | TCAAAGAACTGCTCCTCAATGGATGTTGC |

For confirmation of specific detection of BKV, PCR amplification products from BKV specimens were sequenced and analyzed. The amplification product sequences were aligned well with the sequence of BKV, and none of the amplification product sequences were identified as sequence of JCV or of any other genera. The results of the assay are shown in FIG. 2. Template concentrations ranged from 50 copies per reaction to 50,000 per reaction, and the assay were performed in duplicate. For the For the BK2 assay: slope=−3.48, intercept=44.053, $R^2$=0.0.999.

Example 4

Identification of Target Region III ("BK3")

The comparison of nucleic acid sequences across all newly completed BKV nucleic acid sequences and published BKV nucleic acid sequences allowed the selection of the BK2 target region. The BK3 target region comprises nucleotides 4097 to 4560 of GenBank Accession No. AY628224. The nucleic acid sequence of the BK3 target sequence is:

(SEQ ID NO: 03)
AGTAAGTATTCCTTATTAACACCCTTACAAATTAAAAAACTAAAGGTACA

CAGCTTTTGACAGAAATTATTAATTGCAGAAACTCTATGTCTATGTGGAG

TTAAAAAGAATATAATATTATGCCCAGCACACATGTGTCTACTAATGAAA

GTTACAGAATATTTTTCCATAAGTTTTTTATACAGAATTTGAGCTTTTTC

TTTAGTAGTATACACAGCAAAGCAGGCAAGGGTTCTATTACTAAATACAG

CTTGACTAAGAAACTGGTGTAGATCAGAGGGAAAGTCTTTAGGGTCTTCT

ACCTTTCTCTTTTTCTTGGGTGGTGTGGAGTGTTGAGAATCTGCTGTTGC

TTCTTCATCACTGGCAAACATATCTTCATGGCAAAATAAATCTTCATCCC

ATTTTTCATTAAAGGAGCTCCACCAGGACTCCCACTCTTCTGTTCCATAG

GTTGGCACCTATAA

The strategy used to design the nucleic acid based amplification primers and probes was based on the analysis of multiple sequences alignment of all BKV sequences and sequences of closely related viruses. This analysis was designed to include all variants of BKV. This analysis was also designed to exclude any closely related, but non BK sequences, such as sequence of JCV. A careful analysis of these alignments allowed the selection of oligonucleotide sequences which cover sequences of all BKV variants but discriminate sequences from any other closely related genera, thereby permitting the genus-specific amplification and ubiquitous detection and identification of BKV. The sequences of the primers and probe for the BK3 target region are as follows:

| SEQ ID NO.: | | Sequence 5' to 3' |
|---|---|---|
| Target Region III (BK3) | | |
| SEQ ID NO: 12 | F | GGAAAGTCTTTAGGGTCTTCTACCTTT |
| SEQ ID NO: 13 | R | TCATCACTGGCAAACATATCTTCATG |
| SEQ ID NO: 14 | P | GTGTTGAGAATCTGCTGTTGCTTCT |

For confirmation of specific detection of BKV, PCR amplification products from BKV specimens were sequenced and analyzed. The amplification product sequences were aligned well with the sequence of BKV, and none of amplification product sequences were identified as sequence of JCV or of any other genera. The results of the assay are shown in FIG. 2. Template concentrations ranged from 50 copies per reaction to 50,000 per reaction, and the assay were performed in duplicate. For the BK3 assay: slope=−3.49, intercept=44.819. $R^2$=0.999.

Example 5

Identification of Target Region IV ("BK4")

The comparison of nucleic acid sequences across all newly completed BKV nucleic acid sequences and published BKV nucleic acid sequences allowed the selection of the BK4 target region. The BK4 target region comprises nucleotides 612 to 864 of GenBank Accession No. AY628224. The nucleic acid sequence of the BK4 target sequence is:

(SEQ ID NO: 04)
ATGGGTGCTGCTCTAGCACTTTTGGGGGACCTAGTTGCCAGTGTATCTGA

GGCTGCTGCTGCCACAGGATTTTCAGTGGCTGAAATTGCTGCTGGGGAGG

CTGCTGCTGCTATAGAAGTTCAAATTGCATCCCTTGCTACTGTAGAGGGC

ATAACAAGTACCTCAGAGGCTATAGCTGCCATAGGCCTAACTCCTCAAAC

ATATGCTGTAATTGCTGGTGCTCCTGGGGCTATTGCTGGGTTTGCTGCTT

TAA

The strategy used to design the nucleic acid based amplification primers and probes was based on the analysis of multiple sequences alignment of all BKV sequences and sequences of closely related viruses. This analysis was designed to include all variants of BKV. This analysis was also designed to exclude any closely related, but non BK sequences, such as sequence of JCV. A careful analysis of these alignments allowed the selection of oligonucleotide sequences which cover sequences of all BKV variants but discriminate sequences from any other closely related genera, thereby permitting the genus-specific amplification and ubiquitous detection and identification of BKV. The sequences of the primers and probe for the BK4 target region are as follows:

| SEQ ID NO.: | | Sequence 5' to 3' |
|---|---|---|
| Target Region IV (BK4) | | |
| SEQ ID NO: 15 | F | ATGGGTGCTGCTCTAGCAC |
| SEQ ID NO: 16 | R | GTGGCTGAAATTGCTGCTGG |
| SEQ ID NO: 17 | P | TGCCAGTGTATCTGAGGCTGCTGCTGC |

For confirmation of specific detection of BKV, PCR amplification products from BKV specimens were sequenced and analyzed. The amplification product sequences were aligned well with the sequence of BKV, and none of amplification product sequences were identified as sequence of JCV or of any other genera. The results of the assay are shown in FIG. 2. Template concentrations ranged from 50 copies per reaction to 50,000 per reaction, and the assay were performed in duplicate. For the BK4 assay: slope=−3.21, intercept=41.466, $R^2$=0.999.

The analytical sensitivity of the oligonucleotide primer and probe was tested by titration of known concentration series of DNA and calculated by using standard curve analysis. It was demonstrated that the analytical sensitivity of the assay reached 5 copy or lower per reaction tube. Adjusted from the sample preparation procedure and volume adjustment protocol, this analytical sensitivity is equivalent to about 200 copies per ml of liquid clinical specimens.

The primer/probe set was tested on a panel of total 333 previously tested clinical samples. The panel included 47 of known BKV positive (detected), and 286 of known BKV negative (non detected) samples. The oligonucleotide primer/probe set detected all 47 positive samples. Furthermore, out of the 284 negative samples, it detected 34 as BKV positive. To validate those "missed" positive result, 28 were sequenced. All of the 28 sequenced amplification products were identified as BKV. The remaining 6 samples could not be sequenced due to insufficient sample volume. Overall, al least 10% of clinically negative samples was detected as BKV positive by the new primer/probe strategy and were validated by sequencing as true positive. The failure of detecting such percentage of true positive could be caused by primer/probe mismatch on variation sites or poor PCR efficiency or both.

Example 6

Identification of Target Region V ("BK5")

The comparison of nucleic acid sequences across all newly completed BKV nucleic acid sequences and published BKV nucleic acid sequences allowed the selection of the BK4 target region. The BK4 target region comprises nucleotides 2810 to 2895 of GenBank Accession No. AY628224. The nucleic acid sequence of the BK5 target sequence is:

(SEQ ID NO: 05)
GGGGCTGAAGTATCTGAGACTTGGGAAGAGCATTGTGATTGGGATTCAGT

GCTTGATCCATGTCCAGAGTCTTCAGTTTCTGAATC

The strategy used to design the nucleic acid based amplification primers and probes was based on the analysis of multiple sequences alignment of all BKV sequences and sequences of closely related viruses. This analysis was designed to include all variants of BKV. This analysis was also designed to exclude any closely related, but non BK sequences, such as sequence of JCV. A careful analysis of these alignments allowed the selection of oligonucleotide sequences which cover sequences of all BKV variants but discriminate sequences from any other closely related genera, thereby permitting the genus-specific amplification and ubiquitous detection and identification of BKV. The sequences of the primers and probe for the BK5 target region are as follows:

| SEQ ID NO.: | | Sequence 5' to 3' |
|---|---|---|
| Target Region V (BK5) | | |
| SEQ ID NO: 18 | F | GGGCTGAAGTATCTGAG |
| SEQ ID NO: 19 | R | CAGTGCTTGATCCATGTC |
| SEQ ID NO: 20 | P | CTTGGGAAGAGCATTGTGATTGG |

For confirmation of specific detection of BKV, PCR amplification products from BKV specimens were sequenced and analyzed. The amplification product sequences were aligned well with the sequence of BKV, and none of amplification product sequences were identified as sequence of JCV or of any other genera. The results of the assay are shown in FIG. 2. Template concentrations ranged from 50 copies per reaction to 50,000 per reaction, and the assay were performed in duplicate. For the BK5 assay: slope=−3.61, intercept=47.324, $R^2$=0.994.

It is evident from the above results and discussion that the subject invention provides an important new means for the detection of BK virus as well as differentiating between different BK virus genotypes or strains. As such, the subject methods and systems find use in a variety of different applications, including research, medical, therapeutic, diagnostic, military and other applications. Accordingly, the present invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A kit for detecting the presence of BK virus (BKV) nucleic acid in a sample comprising at least two oligonucleotide primers designed to hybridize to SEQ ID NO: 1 or a complement thereof but not to JC virus nucleic acid under conditions which discriminate between BKV and JCV nucleic acid, and at least one probe; wherein the at least two oligonucleotide primers comprise a first primer comprising SEQ ID NO: 6 and a second primer comprising SEQ ID NO: 7, and wherein the at least one probe comprises 8-44 nucleotides and hybridizes to nucleotides 57-90 of SEQ ID NO: 1 or a full complement thereof and comprises a detectable label selected from among a radioactive isotope, a fluorophore, a chemiluminescent molecule, a chromophore, an electron dense label, an enzyme, an enzyme substrate, an enzyme cofactor, an enzyme inhibitor, a dye, a metal ion, a metal sol, biotin, avidin, strepavidin or a hapten.

2. The kit of claim 1, further comprising a second primer pair selected from the group consisting of
   (a) a first primer comprising SEQ ID NO: 9 and a second primer comprising SEQ ID NO: 10;
   (b) a first primer comprising SEQ ID NO: 12 and a second primer comprising SEQ ID NO: 13;
   (c) a first primer comprising SEQ ID NO: 15 and a second primer comprising SEQ ID NO: 16; and
   (d) a first primer comprising SEQ ID NO: 18 and a second primer comprising SEQ ID NO: 19.

3. The kit of claim 1, wherein the detectable label is a fluorophore.

4. The kit of claim 3, wherein the at least one probe further comprises a quencher molecule.

5. The kit of claim 4, wherein the fluorophore and quencher molecule are attached to same probe.

6. The kit of claim 1, wherein the one or more oligonucleotide primers comprise a degenerate oligonucleotide.

7. The kit of claim 2, further comprising one or more additional probes selected from:
   (a) a probe comprising nucleotides 52-80 of SEQ ID NO: 2 or a complement thereof;
   (b) a probe comprising nucleotides 51-75 of SEQ ID NO: 57 or a complement thereof;
   (c) a probe comprising nucleotides 32-62 of SEQ ID NO: 4 or a complement thereof;
   (c) a probe comprising nucleotides 19-41 of SEQ ID NO: 5 or a complement thereof.

8. The kit of claim 7, wherein the one or more additional probes comprises a detectable label selected from among a radioactive isotope, a fluorophore, a chemiluminescent molecule, a chromophore, an electron dense label, an enzyme, an enzyme substrate, an enzyme cofactor, an enzyme inhibitor, a dye, a metal ion, a metal sol, biotin, avidin, strepavidin or a hapten.

9. The kit of claim 8, wherein the detectable label is a fluorophore.

10. The kit of claim 8, wherein the one or more additional probes further comprises a quencher molecule.

11. The kit of claim 9, wherein the fluorophore and quencher molecule are attached to same probe.

12. The kit of claim 1, wherein the at least one probe comprises nucleotides 57-90 of SEQ ID NO: 1 or a complement thereof.

* * * * *

SEQUENCE LISTING

<160> NUMBER OF SEQ ID NOS: 59

<210> SEQ ID NO 1
<211> LENGTH: 151
<212> TYPE: DNA
<213> ORGANISM: Human polyomavirus 1
<220> FEATURE:
<223> OTHER INFORMATION: Type BK virus

<400> SEQUENCE: 1
aacaaaaaaa agagctcaga ggatttttat ttttatttta gagcttttgc tggaattttg    60
tagaggtgaa gacagtgtag acgggaaaaa caaaggtacc actgctttac ctgctgtaaa   120
agactctgta aaagactcct aggtaagtaa t                                  151

<210> SEQ ID NO 2
<211> LENGTH: 128
<212> TYPE: DNA
<213> ORGANISM: Human polyomavirus 1
<220> FEATURE:
<223> OTHER INFORMATION: Type BK virus

<400> SEQUENCE: 2
tgtacattca ggagagttta tagaaaaaac tattgcccca ggaggtgcta atcaaagaac    60
tgctcctcaa tggatgttgc ctttacttct aggcctgtac gggactgtaa cacctgctct   120
tgaagcat                                                            128

<210> SEQ ID NO 3
<211> LENGTH: 464
<212> TYPE: DNA
<213> ORGANISM: Human polyomavirus 1
<220> FEATURE:
<223> OTHER INFORMATION: Type BK virus

<400> SEQUENCE: 3
agtaagtatt ccttattaac acccttacaa attaaaaaac taaaggtaca cagcttttga    60
cagaaattat taattgcaga aactctatgt ctatgtggag ttaaaaagaa tataatatta   120
tgcccagcac acatgtgtct actaatgaaa gttacagaat attttttccat aagttttta   180 tacagaattt gagcttttttc tttagtagta tacacagcaa agcaggcaag ggttctatta   240
ctaaatacag cttgactaag aaactggtgt agatcagagg gaaagtcttt agggtcttct   300
acctttctct ttttcttggg tggtgtggag tgttgagaat ctgctgttgc ttcttcatca   360
ctggcaaaca tatcttcatg gcaaaataaa tcttcatccc attttttcatt aaaggagctc   420 caccaggact cccactcttc tgttccatag gttggcacct ataa                    464

<210> SEQ ID NO 4
<211> LENGTH: 253
<212> TYPE: DNA
<213> ORGANISM: Human polyomavirus 1
<220> FEATURE:
<223> OTHER INFORMATION: Type BK virus

<400> SEQUENCE: 4
atgggtgctg ctctagcact tttgggggac ctagttgcca gtgtatctga ggctgctgct    60
gccacaggat tttcagtggc tgaaattgct gctgggagg ctgctgctgc tatagaagtt   120
caaattgcat cccttgctac tgtagagggc ataacaagta cctcagaggc tatagctgcc   180
ataggcctaa ctcctcaaac atatgctgta attgctggtg ctcctggggc tattgctggg   240
tttgctgctt taa                                                      253

<210> SEQ ID NO 5
<211> LENGTH: 86
<212> TYPE: DNA
<213> ORGANISM: Human polyomavirus 1
<220> FEATURE:
<223> OTHER INFORMATION: Type BK virus

<400> SEQUENCE: 5
ggggctgaag tatctgagac ttgggaagag cattgtgatt gggattcagt gcttgatcca    60
tgtccagagt cttcagtttc tgaatc                                        86

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aacaaaaaaa agagctcaga ggattt                                        26

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aagtaccact gctttacctg ctgtaa                                        26

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
tttgtagagg tgaagacagt gtagacggga aaaa                               34

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttgccccagg aggtgcta                                                 18

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tttacttcta ggcctgtacg gga                                           23

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
tcaaagaact gctcctcaat ggatgttgc                                       29

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggaaagtctt tagggtcttc taccttt                                         27

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tcatcactgg caaacatatc ttcatg                                          26

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
gtgttgagaa tctgctgttg cttct                                           25

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atgggtgctg ctctagcac                                                  19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtggctgaaa ttgctgctgg                                                 20

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
tgccagtgta tctgaggctg ctgctgc                                         27

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gggctgaagt atctgag                                                   17

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cagtgcttga tccatgtc                                                  18

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
cttgggaaga gcattgtgat tgg                                            23

<210> SEQ ID NO 21
<211> LENGTH: 4012
<212> TYPE: DNA
<213> ORGANISM: Human polyomavirus 1
<220> FEATURE:
<223> OTHER INFORMATION: Type BK virus consensus sequence

<400> SEQUENCE: 21
acagaagaag tgcatgactg cagcacagag aatgagcgat tttgcggcca gaatcttgtg     60
gtttcgccag ctgtcacgac aaaaaaaggc tcagaggatt ttatttttat tttagagctt    120
ttgctggaat tttgtagagg taagacagtg tagacgggaa aaacaaagta ccactgcttt    180
acctgctgta aagactctgt aaaagactcc taggtaagta atcttttttt ttgtatttca    240
ggttatgggt gctgctctag cacttttggg ggacctagtt gccagtgtat ctgaggctgc    300
tgctgccaca ggttttcgtg gctgaaattg ctgctgggga ggctgctgct gcatagaagt    360
tcaaattgca tcccttgcta ctgagagggc ataacaatac ctcagaggct atagctgcat    420
aggcctaacc ctcaaacata tgctgtaatt gctggtgctc cggggctatt gctgggtttg    480
ctgctttatt caaactgtta tggtattagt tcttgctcaa gtagggtaag tttttttgatt   540

```
gggatcacaa agtttccact gtaggcctta tcagcaatca ggcatggctt gaattgttta      600
acccagatga gtactagata ttgtttcctg gtgtaaatac ttttgtaata atattcaata      660
ctgatcctag gcattggggt ccttcttgtt tgctactatt tccaggcttt gtggcatgtt      720
attaggatga tatacctcta tactcacaga attgcaagag aacagaagat ttttaggact      780
cttggctaga ttttggaga aacacctgga cattgtaaat gccctaact tttataatta       840 tattcaatat tattctattt ccctattag gcctaatggt agcaagtgct gaaagggaag      900
gacccgtaat tttggccatc taagatagat atgctgacag tataaagaag ttaccaaaga    960
atggattaag aaataaatgt acattcagga gagtttatag aaaaaactat tgccccagga   1020
ggtgctaatc aaagaactgc tcctcaatgg atgttgcctt tcttctaggc ctgtacggga   1080
ctgtaacacc tgctcttgaa gcattgaaga tggccccaca aaagaaaagg agagtgtcca   1140
ggggcagctc ccaaaaagcc aaggaaccgt gcaagtgcca aaactctaat aaaaggagga   1200
gtagaagttc tagaagttaa aactggtaga tgctatacaa gtagaatgct tctaaaccca   1260
gaaatgggga gatgaaacct taggggctta gtcctaatgc taaatgcttt agtgatagcc   1320
cagaagaaaa atgcttcctg ttacagacag caagaattcc ctccaataat gaggactaac   1380
ctgtggaatt actatgtggg aggctgtacg taaaacagag gtatggaata actagatgct   1440
aaccttcagc agggtccaaa agtcatgaat ggtggaggaa accttcaggc agaatttcac   1500
tttttgctgt ggtgggaccc ttggaaatgc agggagtcta tgaatacgca agtacccagg   1560
tacttacccc aaaaaccaca gccagtccca gtaatgaata ctgacataag gcctattgga   1620
caaaaacaat gctatccagt tgatgctggt cctgaccagt agaaatgaaa atctaggtat   1680
tttggactca caggagggga aaatgttccc cagtacttca tgtaccaaca cagctaccac   1740
agtgttgctg atgaacaggg tgtggggccc ttgtaaagct gatgcctgta tgtttcagct   1800
gctgatattt gtggctgttt actaacagtc tggacacaac agtggagggc cttcaagata   1860
ttttagacgc ctgagaaaaa gatctgtaaa accttaccaa tttccttttgc tagtgaccta   1920 taacagggaa cccaaagtgg atgggcagcc tatgtatggt atggatccag tggaggtagg   1980
gtgtttgatg gcacagaact tccaggggac ccagatatga taagatatat tgaacaggac   2040
aattgcaaac aaaatgttta aacaggtgct ttattgtata tatttaataa atgctgcttt   2100
ttatacatta actttgttat tttggggggtg gtgttttagg cttttaaaac atgaaagcct   2160
ttacacaaat gactcttctt ggggttttct acggggctga agtatctgag acttgggaag   2220
agcattgtga ttgggattca gtgcttgatc catgtccaga gtcttcagtt tctgaatctc   2280
ttctcttgta tacaagaata catttcccat gcatatatta tatttcatcc ttgaaaaagt   2340
atacatactt atctcagaat ccagcctttc ttccattcaa caattctaga gtatatctg    2400 aaaatcagct acaggcctac caaattagag tagcaaaggt cattccactt tgtaattctt   2460
ttttcaagta aaatcgagtt tgaggatttc ttaaataatt ttggctaaaa tctattgtct   2520
tacaaatcta gctgagtttt ggacaggata ctcattcatt gtaacacctg gtggaaatat   2580
ttggtctttt gtttaatgtt tttttctaaa ttacttacac ttccactaat aatcctaaac   2640
tgtctaaatt gtttattcca tgtcctgaag gcaaatcctt tgattcagcc cgtccttaca   2700
tctcaaaaac aaccatactg atcatagcac accagtcaaa gtagccttcc atgggtatta   2760
catttaagct ttcccacaaa tctaaaccct gcagctagtt gttttccact atcatggacc   2820
tttaataacc agtatcttct tttaggtaca ttaaaacaaa cagtgaaaat caaaatacag   2880
```

```
aatccatttt aggtacaaac atgagccagc aaccctgcca tatattgttc atacgcattt    2940
ccatgagccc aaatataaat ccatttatct aatatatgat taatcttctg ttagcatttc    3000
ttcctgtcat atgaggtatc taccttttt agctaaactg tatcactgct tgctgacaaa     3060
tttttttttt actttctgca aaattagcat ttgcaatgct tttcatgata ttaaagtgta    3120
ggtgtctttt ttgacacttt ttcactctct acattgtatg aaattctaaa tacataccaa    3180
tataaacaca tctcacactt tgttctactg catatcagta ttaattccag aacctgcttt    3240
gttcttcagg tctctgggta aatcatgctc ctttagcccc cttgaatctt tctctattat    3300
tatggtccta gttaaggcac ttaagtaagt attccttatt aacacccta caaattaaaa     3360 aactaaagta cacagctttt gacagaatta ttaattgcag aaactctatg tctatgtgga    3420
gttaaaaaga atataatatt atgccagcaa catgtgtcta ctataaagtt acagatattt    3480
ttccataagt tttttataca gattagcttt ttctttagtg tatacacagc aaacaggcag    3540
gttctattac taaaacagct tgactaagaa actggtgtag atcaaggaaa gtctttaggg    3600
tcttctacct tcttttttt gggtggtgtg agtgttggaa tctgctgttg ctctcatcac     3660
tggcaaacat atctcatggc aaataatctt catcccattt ttcattaaag gactccacca    3720
gactcccact cttctgttcc ataggttggc acctataaaa aaaaattact tagggtttt      3780 ttaaaataca aacttctagg tcaatagaca ccttcatctc attacaatca tatcgtgcct    3840
tcaactttct taaattttct ttaagattcg cactcaaggc aagttgatgt cctgtatcga    3900
aagcaaatgt ccataggcta cctacactat ttaaaagtc ctcctttatt tgcaggggat     3960
cttacctaac tctcaaggaa gtcggcagcg gcaaagacct atcctaatac ca            4012
```

<210> SEQ ID NO 22
<211> LENGTH: 5141
<212> TYPE: DNA
<213> ORGANISM: Human polyomavirus 1
<220> FEATURE:
<223> OTHER INFORMATION: Type BK virus majority sequence

<400> SEQUENCE: 22

```
ttttgcaaaa attgcaaaag aatagggatt tccccaaata gttttgctag gcctcagaaa      60
aagcctccac acccttacta cttgagagaa agggtggagg cagaggcggc ctcggcctct     120
tatatattat aaaaaaaaag gccacaggga ggagctgctt acccatggaa tgcagccaaa     180
ccatgacctc aggaaggaaa gtgcatgact gggcagccag ccagtggcag ttaatagtga     240
aaccccgccc ctaaaattct caaataaaca caagaggaag tggaaactgg ccaaaggagt     300
ggaaagcagc cagacagaca tgttttgcga gcctaggaat cttggccttg tccccagtta     360
aactggacaa aggccatggt tctgcgccag ctgtcacgac aagcttctgt gaaagttggt     420
aaaacctgga ctggaacaaa aaaagagct cagaggattt ttatttttat tttagagctt      480
ttgctggaat tttgtagagg tgaagacagt gtagacggga aaacaaaag taccactgct      540 ttacctgctg taaaagactc tgtaaaagac tcctaggtaa gtaatccctt ttttttgta      600 tttccaggtt gatgggtgct gctctagcac ttttggggga cctagttgcc agtgtatctg     660
aggctgctgc tgccacagga ttttcagtgg ctgaaattgc tgctggggag ctgctgctg      720 ctatagaagt tcaaattgca tcccttgcta ctgtagaggg cataacaagt acctcagagg     780
ctatagctgc tataggccta actcctcaaa catatgctgt aattgctggt gctcctgggg     840
ctattgctgg gtttgctgct ttaattcaaa ctgttactgg tattagttcc ttggctcaag     900
tagggtatag gttttttagt gattgggatc acaaagtttc cactgtaggc ctctatcagc     960
```

```
aatcaggcat ggctttggaa ttgtttaacc cagatgagta ctatgatatt ttgtttcctg    1020
gtgtaaatac ttttgtaaat aatattcaat accttgatcc taggcattgg ggtccttctt    1080
tgtttgctac tatttcccag gctttgtggc atgttattag ggatgatata cctgctataa    1140
cctcacaaga attgcaaaga agaacagaaa gattttttag agactccttg gctagatttt    1200
tggaggaaac tacctggaca attgtaaatg cccctataaa cttttataat tatattcaag    1260
aatattattc tgatctttcc cctattaggc cctcaatggt tagacaagta gctgaaaggg    1320
aaggtacccg tgtacatttt ggccatactt atagtataga tgatgctgac agtatagaag    1380
aagttacaca aagaatggac ttaagaaatc aacaaactgt acattcagga gagtttatag    1440
aaaaaactat tgccccagga ggtgctaatc aaagaactgc tcctcaatgg atgttgcctt    1500
tacttctagg cctgtacggg actgtaacac ctgctcttga agcatatgaa gatggcccca    1560
accaaaagaa aaggagagtg tccaggggca gctcccaaaa agccaaagga acccgtgcaa    1620
gtgccaaaac tactaataaa aggaggagta gaagttctag aagttaaaac tggggtagat    1680
gctataacag aggtagaatg cttcctaaac ccagaaatgg gggatccaga tgaaaacctt    1740
aggggcttta gtctaaagct aagtgctgaa aatgacttta gcagtgatag cccagaaaga    1800
aaaatgcttc cctgttacag cacagcaaga attcccctcc ccaatttaaa tgaggaccta    1860
acctgtggaa atctactgat gtgggaggct gtaactgtac aaacagaggt cattggaata    1920
actagcatgc ttaaccttca tgcagggtca caaaaagtgc atgagcatgg tggaggtaaa    1980
cctattcaag gcagtaattt ccacttcttt gctgttggtg gagaccccctt ggaaatgcag    2040 ggagtgctaa tgaattacag gacaaagtac ccagatggta ctataacccc aaaaaacccca    2100 acagcccagt cccaggtaat gaatactgac cataaggcct atttggacaa aaacaatgct    2160
tatccagttg agtgctgggt tcctgatccc agtagaaatg aaaatactag gtattttggg    2220
actttcacag gaggggaaaa tgttccccca gtacttcatg tgaccaacac agctaccaca    2280
gtgttgctag atgaacaggg tgtggggcct cttttgtaaag ctgatagcct gtatgtttca    2340
gctgctgata tttgtggcct gtttactaac agctctggaa cacaacagtg gagaggcctt    2400
gcaagatatt ttaagattcg cctgagaaaa agatctgtaa aaaatcctta cccaatttcc    2460
tttttgctaa gtgaccttat aaacaggaga acccagagag tggatgggca gcctatgtat    2520
ggtatggaat cccaggtaga agaggtcagg gtgtttgatg gcacagaaag acttccaggg    2580
gacccagata tgataagata tattgacaaa caaggacaat tgcaaaccaa aatgctttaa    2640
acaggtgctt ttattgtaca tatacatttta ataaatgctg cttttgtata agccacttt    2700 aagcttgtgt tattttgggg gtggtgtttt aggccttta aaacactgaa agcctttaca    2760
caaatgcaac tcttgactat ggggctctga cctttgggaa tcttcagcag gggctgaagt    2820
atctgagact tgggaagagc attgtgattg ggattcagtg cttgatccat gtccagagtc    2880 ttcagttttct gaatcttctt ctcttgtgat atcaagaata catttcccca tgcatatatt    2940
atatttcatc cttgaaaaag tatacatact tatctcagaa tccagccttt ccttccattc    3000
aacaattcta gattgtatat ctgttgcaaa atcagctaca ggcctaaacc aaattagcag    3060
tagcaacaag gtcattccac tttgtaaaat tcttttttca gtaagaaact ctgagttttg    3120
taaggatttt cttaaatata ttttgggcct aaaatctatc tgtcttacaa atctagcctg    3180
cagggtttta gggacaggat actcattcat tgtaaccagg cctggtggaa atatttgggt    3240
tcttttgttt aaatgtttct tttctaaatt aaccttaaca cttccatcta aataatctct    3300
```

```
caaactgtct aaattgttta ttccatgtcc tgaaggcaaa tcctttgatt cagctcctgt    3360
tccttttaca tcttcaaaaa caaccatgta ctgatctata gctacaccta gttcaaaggt    3420
tagcctttcc atgggtaggt ttacatttaa ggctttacct ccacacaaat ctaataaccc    3480
tgcagctagt gttgttttc cactatcaat gggacctta aataaccagt atcttctttt     3540
aggtacatta aaacaatac agtgcaaaaa atcaaatata acagaatcca ttttaggtag    3600
caaacagtgc agccaagcaa cacctgccat atattgttct agtacagcat ttccatgagc    3660
tccaaatatt aaatccattt tatctaatat atgattaaat ctttctgtta gcatttcttc    3720
tctggtcata tgaagggtat ctactctttt tttagctaaa actgtatcta ctgcttgctg    3780
acaaatactt ttttgatttt tactttctgc aaaaatagta gcatttgcaa aatgcttttc    3840
atgatactta aagtgataag gttggtcttt tttctgacac tttttacact cctctacatt    3900
gtattgaaat tctaaataca tacctaataa taaaaacaca tcctcacact ttgtctctac    3960
tgcatactca gtaattaatt tccaagacac ctgctttgtt tcttcaggct cttctgggtt    4020
aaaatcatgc tcctttaagc ccccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc agcacacat gtgtctacta ataaaagtta cagaatattt     4260
ttccataagt tttttataca gaatttgagc ttttctctta gtagtataca cagcaaagca    4320
ggcaagggtt ctattactaa atacagcttg actaagaaac tggtgtagat cagaaggaaa    4380
gtctttaggg tcttctacct ttcttttttt cttgggtggt gttgagtgtt gagaatctgc    4440
tgttgcttct tcatcactgg caaacatatc ttcatggcaa aataaatctt catcccattt    4500
ttcattaaag gagctccacc aggactccca ctcttctgtt ccataggttg gcacctataa    4560
aaaaaataat tacttagggc ctttaaatat tttattattt atctaaatat aagttagtta    4620
ccttaaagct ttagatctct gaagggagtt tctccaatta tttggaccca ccattgcaga    4680
gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg cacagaaggc ttttggaac aaataggcca ttccttgcag     4860
tacagggtat ctgggcaaag aggaaaatca gcacaaacct ctgagctact ccaggttcca    4920
aaatcaggct gatgagctac ctttacatcc tgctccattt ttttatataa agtattcatt    4980
ctcttcattt tatcctcgtc gccccctttg tcagggtgaa attccttaca cttccttaaa    5040
taggcttttc tcattaaggg aaggtttccc caggcagctc tttcaaggcc taaaaggtcc    5100
atgagctcca tggattcttc cctgttaagc actttatcca t                        5141
```

<210> SEQ ID NO 23
<211> LENGTH: 5141
<212> TYPE: DNA
<213> ORGANISM: Human polyomavirus 1
<220> FEATURE:
<223> OTHER INFORMATION: Type BK virus

<400> SEQUENCE: 23

```
ttttgcaaaa attgcaaaag aatagggatt tccccaaata ttttttgctag gcctcagaaa    60
aagcctccac acccttacta cttgagagaa agggtggagg cagaggcggc ctcggcctct   120
tatatattat aaaaaaaag gccacaggga ggagctgcta acccatggaa tgtagccaaa    180
ccatgacctc aggaaggaaa gtgcatgact gggcagccag ccagtggcag ttaatagtga   240
```

-continued

```
aaccccgccc ctaaaattct caaataaaca caagaggaag tggaaactgg ccaaaggagt    300
ggaaagcagc cagacagaca tgttttgcga gcctaggaat cttggccttg tccccagtta    360
aactggacaa aggccatggt tctgcgccag ctgtcacgac aagcttctgt gaaagttagt    420
aaaacctgga ctggaacaaa aaaaagagct cagaggattt ttatttttat tttagagctt    480
ttgctggaat tttgtagagg tgaagacagt gtagacggga aaaacaaagg taccactgct    540
ttacctgctg taaaagactc tgtaaaagac tcctaggtaa gtaatccctt tttttttgta    600
tttccaggtt gatgggtgct gctctagcac ttttggggga cctagttgcc agtgtatctg    660
aggctgctgc tgccacagga ttttcagtgg ctgaaattgc tgctggggag gctgctgctg    720
ctatagaagt tcaaattgca tcccttgcta ctgtagaggg cataacaagt acctcagagg    780
ctatagctgc cataggccta actcctcaaa catatgctgt aattgctggt gctcctgggg    840
ctattgctgg gtttgctgct ttaattcaaa ctgttactgg tattagttcc ttggctcaag    900
tagggtatag gtttttttagt gattgggatc acaaagtttc cactgtaggc ctctatcagc    960
aatcaggcat ggctttggaa ttgtttaacc cagatgagta ctatgatatt ttgtttcctg   1020
gtgtaaatac ttttgtaaat aatattcaat accttgatcc taggcattgg ggtccttcct   1080
tgtttgctac tatttcccag gctttgtggc atgttattag ggatgatata cctgctataa   1140
cctcacaaga attgcaaaga agaacagaaa gatttttttag agactccttg gctagatttt   1200
tggaggaaac tacctggaca attgtaaatg cccctataaa cttttataat tatattcaag   1260
aatattattc tgatctttcc cctattaggc cctcaatggt tagacaagtg gctgaaaggg   1320
aaggtacccg tgtacatttt ggccatactt atagtataga tgatgctgac agtatagaag   1380
aagttacaca aagaatggac ttaagaaatc agcaaactgt acattcagga gagtttatag   1440
aaaaaactat tgccccagga ggtgctaatc aaagaactgc tcctcaatgg atgttgcctt   1500
tacttctagg cctgtacggg actgtaacac ctgctcttga agcatatgaa gatggcccca   1560
accaaaagaa aaggagagtg tccaggggca gctcccaaaa agccaaagga acccgtgcaa   1620
gtgccaaaac tactaataaa aggaggagta gaagttctag aagttaaaac tggggtagat   1680
gctataacag aggtagaatg cttcctaaac ccagaaatgg gggatccaga tgaaaacctt   1740
aggggcttta gtctaaagct aagtgctgaa aatgacttta gcagtgatag cccagaaaga   1800
aaaatgcttc cctgttacag cacagcaaga attcccctcc ccaatttaaa tgaggaccta   1860
acctgtggaa atctactgat gtgggaggct gtaactgtac aaacagaggt cattggaata   1920
actagcatgc ttaaccttca cgcagggtca caaaaaagtgc atgagcatgg tggaggtaaa   1980
cctattcaag gcagtaattt ccacttcttt gctgttggtg gagacccctt ggaaatgcag   2040
ggagtgctaa tgaattacag gaccaagtac ccagatggta ctataacccc aaaaaaccca   2100
acagcccagt cccaggtaat gaatactgac cataaggcct atttggacaa aaacaatgct   2160
tatccagttg agtgctgggt tcctgatccc agtagaaatg aaaatactag gtattttgga   2220
actttcacag gaggggaaaa tgttcccccca gtacttcatg tgaccaacac agctaccaca   2280
gtgttgctag atgaacaggg tgtggggcct ctttgtaaag ctgatagcct gtatgtttca   2340
gctgctgata tttgtggcct gtttactaac agctctggaa cacaacagtg gagaggcctt   2400
gcaagatatt ttaagattcg cctgagaaaa agatctgtaa aaaatcctta cccaatttcc   2460
tttttgctga gtgaccttat aaacaggaga acccagagag tggatgggca gcctatgtat   2520
ggtatggaat cccaggtaga agaggtcagg gtgtttgatg gcacagaaag acttccaggg   2580
```

```
gacccagata tgataagata tattgataga caaggacaat tgcaaaccaa aatgctttaa   2640
acaggtgctt ttattgtaca tatacattta ataaatgctg cttttgtata agccacttt    2700 aagcttgtgt tattttgggg gtggtgtttt aggcctttta aaacattgaa agcctttaca   2760
caaatgcaac tcttgactat ggggggtctga cctttgggaa tcttcagccg ggctgaagt   2820 atctgagact tgggaagagc attgtgattg ggattcagtg cttgatccat gtccagagtc   2880
ttcagtttct gaatcttctt ctcttgtgat atcaagaata catttcccca tgcatatatt   2940
atatttcatc cttgaaaaag tatacatact tatctcagaa tccagccttt ccttccattc   3000
aacaattcta gattgtatat ctgttgcaaa atcagctaca ggcctaaacc aaattagcag   3060
tagcaacaag gtcattccac tttgtaaaat tcttttttca agtaagaact ctgagttttg   3120
taaggatttt cttaaatata ttttgggtct aaaatctatc tgtcttacaa atctagcctg   3180
cagggtttta ggaacaggat actcattcat tgtaaccagg cctggtggaa atatttgggt   3240
tcttttgttt aaatgtttct tttctaaatt aaccttaaca cttccatcta ataatctct    3300 caaactgtct aaattgttta ttccatgtcc tgaaggcaaa tcctttgatt cagccccgt    3360 tccttttaca tcttcaaaaa caaccatgta ctgatctata gctacaccta gttcaaaggt   3420
tagcctttcc atgggtaggt ttacatttaa ggctttacct ccacacaaat ctaataaccc   3480
tgcagctagt gttgttttc cactatcaat gggacctta aataaccagt atcttctttt     3540
aggtacatta aaaacaatac agtgcaaaaa atcaaatata acagaatcca ttttaggtag   3600
caaacagtgc agccaagcaa cacctgccat atattgttcc agtacagcat tccatgagc    3660 tccaaatatt aaatccattt tatctaatat atgattaaat ctttctgtta gcatttcttc   3720
tctggtcata tgaagggtat ctactctttt tttagctaaa actgtatcta ctgcttgctg   3780
acaaatactt ttttgatttt tactttctgc aaaaatagta gcatttgcaa aatgcttttc   3840
atgatactta aagtgataag gttggtcttt tttctgacac tttttacact cttctacatt   3900
gtattgaaat tctaaataca tacccaataa taaaagcaca tcctcacact ttgtctctac   3960
tgcatactca gtaattaatc tccaagacac ctgctttgtt tcttcaggct cttctgggtt   4020
aaaatcatgc tccttttaagc ccccttgaat gctttcttct attgtatggt atggatctct   4080
agttaaggca ctatatagta agtattcctt attaacaccc ttacaaatta aaaaactaaa   4140
ggtacacagc ttttgacaga aattattaat tgcagaaact ctatgtctat gtggagttaa   4200
aaagaatata atattatgcc cagcacacat gtgtctacta atgaaagtta cagaatattt   4260
ttccataagt tttttataca gaatttgagc ttttttcttta gtagtataca cagcaaagca   4320
ggcaagggtt ctattactaa atacagcttg actaagaaac tggtgtagat cagagggaaa   4380
gtctttaggg tcttctacct ttctcttttt cttgggtggt gtggagtgtt gagaatctgc   4440
tgttgcttct tcatcactgg caaacatatc ttcatggcaa aataaatctt catcccattt   4500
ttcattaaag gagctccacc aggactccca ctcttctgtt ccataggttg cacctataa    4560 aaaaaataat tacttagggc ctttaaatat tttcttattt atctaaatat aagttagtta   4620
ccttaaagct ttagatctct gaagggagtt ctccaatta tttggaccca ccattgcaga    4680
gtttcttcag ttaggtctaa gccaaaccac tgtgtgaagc agtcaatgca gtagcaatct   4740
atccaaacca agggctcttt tcttaaaaat tttctattta aatgccttaa tctaagctga   4800
catagcatgc aagggcagtg cacagaaggc ttttggaac aaataggcca ttccttgcag    4860
tacagggtat ctgggcaaag aggaaaatca gcacaaacct ctgagctact ccaggttcca   4920
aaatcaggct gatgagctac ctttacatcc tgctccattt ttttatataa agtattcatt   4980
```

```
ctcttcattt tatcctcgtc gcccccttg tcagggcgaa attccttaca cttccttaaa      5040
taggcttttc tcattaaggg aaggtttccc caggcagctc tttcaaggcc taaaaggtcc      5100
atgagctcca tggattcttc cctgttaagc actttatcca t                        5141

<210> SEQ ID NO 24
<211> LENGTH: 5141
<212> TYPE: DNA
<213> ORGANISM: Human polyomavirus 1
<220> FEATURE:
<223> OTHER INFORMATION: Type BK virus

<400> SEQUENCE: 24
ttttgcaaaa attgcaaaag aatagggatt tccccaaata ttttgctag gcctcagaaa        60 aagcctccac acccttacta cttgagagaa agggtggagg cagaggcggc ctcggcctct     120
tatatattat aaaaaaaag gccacaggga ggagctgcta acccatggaa tgtagccaaa       180
ccatgacctc aggaaggaaa gtgcatgact gggcagccag ccgtggcag ttaatagtga      240 aaccccgccc ctaaaattct caaataaaca caagaggaag tggaaactgg ccaaaggagt     300
ggaaagcagc cagacagaca tgttttgcga gcctaggaat cttggccttg tccccagtta     360
aactggacaa aggccatggt tctgcgccag ctgtcacgac aagcttctgt gaaagttagt     420
aaaacctgga ctgaacaaa aaaagagct cagaggattt ttattttat tttagagctt       480 ttgctggaat tttgtagagg tgaagacagt gtagacggga aaaacaaaag taccactgct    540
ttacctgctg taaagactc tgtaaaagac tcctaggtaa gtaatccctt tttttttgta     600
tttccaggtt gatgggtgct gctctagcac ttttggggga cctagttgcc agtgtatctg     660
aggctgctgc tgccacagga ttttcagtgg ctgaaattgc tgctggggag gctgctgctg    720
ctatagaagt tcaaattgca tcccttgcta ctgtagaggg cataacaagt acctcagagg     780
ctatagctgc tataggccta actcctcaaa catatgctgt aattgctggt gctcctgggg     840
ctattgctgg gtttgctgct ttaattcaaa ctgttactgg tattagttcc ttggctcaag     900
tagggtatag gttttttagt gattgggatc acaaagtttc cactgtaggc ctctatcagc     960
aatcaggcat ggctttagaa ttgtttaacc cagatgagta ctatgatatt ttgtttcctg    1020
gtgtaaatac ttttgtaaat aatattcaat accttgatcc taggcattgg ggtccttcct    1080
tgtttgctac tatttcccag gctttgtggc atgttattag ggatgatata cctgctataa    1140
cctcacagga attgcaaaga agaacagaaa gatttttag agactccttg gctagatttt   1200
tggaggaaac tacctggaca attgtaaatg cccctatgaa cttttataat tatattcaag    1260
aatattattc tgatctttcc cctattaggc cctcaatggt cagacaagtg gctgaaaggg    1320 aagtacccg tgtacatttt ggccatactt atagtataga tgatgctgac agtatagaag    1380
aagttacaca aagaatggac ttaagaaatc aacaaactgt acattcagga gagtttatag    1440
aaaaaactat tgccccagga ggtgctaatc aaagaactgc tcctcaatgg atgttgcctt    1500
tacttctagg cctgtacggg actgtaacac ctgctcttga agcatatgaa gatggcccca    1560
accaaaagaa aaggagagtg tccaggggca gctcccaaaa agccaaagga acccgtgcaa    1620
gtgccaaaac tactaataaa aggaggagta gaagttctag aagttaaaac tggggtagat    1680
gctataacac aggtagaatg cttcctaaac ccagaaatgg gggatccaga tgaaaacctt    1740 agggggcttta gtctaaagct aagtgctgaa aatgacttta gcagtgatag cccagaaaga    1800
aaaatgcttc cctgttacag cacagcaaga attcccctcc ccaattaaa tgaggaccta     1860
```

```
acctgtggaa atctactgat gtgggaggct gtaactgtac aaacagaggt cattggaata    1920
actagcatgc ttaaccttca tgcagggtca caaaaagtgc atgagcatgg tggaggtaaa    1980
cctattcgag gcagtaattt ccacttcttt gctgttggtg gagacccctt ggaaatgcag    2040
ggagtgctaa tgaattacag gaccaagtac ccagaaggta ctataacccc aaaaaaccca    2100
acagcccagt cccaggtaat gaatactgac cataaggcct atttggacaa aaacaatgcc    2160
tatccagttg agtgctgggt tcctgatccc agtagaaatg aaaatactag gtattttggg    2220
actttcacag gaggggaaaa tgttccccca gtacttcatg tgaccaacac agctaccaca    2280
gtgttgctag atgaacaggg tgtggggcct ctttgtaaag ctgatagcct gtatgtttca    2340
gctgctgata tttgtggcct gtttactaac agctctggaa cacaacagtg gagaggcctt    2400
gcaagatatt ttaagatccg cctgagaaaa agatctgtaa aaaatcctta cccaatttcc    2460
ttttcgctaa gtgaccttat aaacaggaga acccagagag tggatgggca gcctatgtat    2520
ggtatggaat cccaggtaga agaggtcagg gtgtttgatg gcacagaaag acttccaggg    2580
gacccagata tgataagata tattgataaa caaggacaat tgcaaaccaa aatgctttaa    2640
acaggtgctt ttattgtaca tatacattta ataaatgctg cttttgtata agccactttt    2700
aagcttgtgt tattttgggg gtggtgtttt aggcctttta aaacattgaa agcctttaca    2760
caaatgcaac tcttcactat gggggtctga ccttttgggaa tcttcagcag gggctgaagt    2820
atctgagact tgggaagagc attgtgattg ggattcagtg cttgatccat gtccagagtc    2880
ttcagtttct gaatcttctt ctcttgtgat atcaagaata catttcccca tgcatatatt    2940
atatttcatc cttgaaaaag tatacatact tatctcagaa tccagccttt ccttccattc    3000
aacaattcta gattgtatat ctgttgcaaa atcagctaca ggcctaaacc aaattagcag    3060
tagcaacaag gtcattccac tttgtaaaat tcttttttca gtaagaact ctgagttttg    3120 taaggatttt cttaaatata ttttgggtct aaaatctatc tgtcttacaa atctagcctg    3180
cagggtttta ggaacaggat actcattcat tgtaaccagg cctggtggaa atatttgggt    3240 tctttgttt aaatgtttct ttctaaatt aaccttaaca cttccatcta ataatctct      3300 caaactgtct aaattgttta ttccatgtcc tgaaggcaaa tcctttgatt cagcccctgt    3360
tccttttaca tcttcaaaaa caaccatgta ctgatctata gctacaccta gttcaaaggt    3420 tagccttttcc atgggtaggt ttacatttaa ggctttacct ccacacaaat ctagtaaccc    3480
tgcagctagt gttgtttttc cactatcaat gggacccttta aataaccagt atcttctttt    3540
aggtacatta aaaacaatac agtgcaaaaa atcaaatata acagaatcca ttttaggtag    3600
caaacagtgc agccaggcaa cacctgccat atattgttcc agtacagcat ttccatgagc    3660
tccaaatatt aaatccattt tatctaatat atgattaaat ctttctgtta gcatttcttc    3720
tctggtcata tgaagggtat ctactctttt tttagctaaa actgtatcta ctgcttgctg    3780
acaaatactt ttttgatttt tactttctgc aaaaatagta gcatttgcaa aatgcttttc    3840
atgatactta aagtgataag gttggtcttt tttctgacac ttttttacact cttctacatt    3900 gtattgaaat tctaaataca tacccaataa taaaaacaca tcctcacact ttgtctctac    3960
tgcatactca gtaattaatt tccaagacac ctgctttgtt tcttcaggct cttctgggtt    4020
aaaatcatgc tcccttaagc ccccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaaagtta cagaatattt    4260
```

| | | | | |
|---|---|---|---|---|
| ttccataagt | ttttatacagaatttgagc | ttttcttta | gtagtataca | cagcaaagca | 4320 |
| ggcaagggtt | ctattactaa | atacagcttg | actaagaaac | tggtgtagat | cagaaggaaa | 4380 |
| gtctttaggg | tcttctacct | ttctcttttt | cttgggtggt | gtggagtgtt | gagaatctgc | 4440 |
| tgttgcttct | tcatcactgg | caaacatatc | ttcatggcaa | aataaatctt | catcccattt | 4500 |
| ttcattaaag | gagctccacc | aggactccca | ctcttctgtt | ccataggttg | gcacctataa | 4560 |
| aaaaaataat | tacttagggc | ctttaaatat | tttcttattt | atctaaatat | aagttagtta | 4620 |
| ccttaaagct | ttagatctct | gaagggagtt | tctccaatta | tttggaccca | ccattgcaga | 4680 |
| gtttcttcag | ttaggtctaa | gccaaaccac | tgtgtgaagc | agtcaatgca | gtagcaatct | 4740 |
| atccaaacca | agggctcttt | tcttaaaaat | tttctattta | aatgccttaa | tctaagctga | 4800 |
| catagcatgc | aagggcagtg | cacagaaggc | ttttggaac | aaataggcca | atccttgcag | 4860 |
| tacagggtat | ctgggcaaag | aggaaaatca | gcacaaacct | ctgagctact | ccaggttcca | 4920 |
| aaatcaggct | gatgagctac | ctttacatcc | tgctccattt | ttttatataa | agtattcatt | 4980 |
| ctcttcattt | tatcctcgtc | gcccccttg | tcagggtgaa | attccttaca | cttccttaaa | 5040 |
| taggcttttc | tcattaaggg | aaggttccc | caggcagctc | tttcaaggcc | taaaaggtcc | 5100 |
| atgagctcca | tggattcttc | cctgttaagc | actttatcca | t | 5141 |

<210> SEQ ID NO 25
<211> LENGTH: 5141
<212> TYPE: DNA
<213> ORGANISM: Human polyomavirus 1
<220> FEATURE:
<223> OTHER INFORMATION: Type BK virus

<400> SEQUENCE: 25

| | | | | | |
|---|---|---|---|---|---|
| ttttgcaaaa | attgcaaaag | aatagggatt | tccccaaata | ttttgctag | gcctcagaaa | 60 |
| aagcctccac | acccttacta | cttgagagaa | agggtggagg | cagaggcggc | ctcggcctct | 120 |
| tatatattat | aaaaaaaaag | gccacaggga | ggagctgcta | acccatggaa | tgtagccaaa | 180 |
| ccatgacctc | aggaaggaaa | gtgcatgact | gggcagccag | ccagtggcag | ttaatagtga | 240 |
| aaccccgccc | ctaaaattct | caaataaaca | caagaggaag | tggaaactgg | ccaaaggagt | 300 |
| ggaaagcagc | cagacagaca | tgttttgcga | gcctaggaat | cttggccttg | tcccagtta | 360 |
| aactggacaa | aggccatggt | tctgcgccag | ctgtcacgac | aagcttctgt | gaaagttagt | 420 |
| aaaacctgga | ctggaacaaa | aaaagagct | cagaggattt | ttatttttat | tttagagctt | 480 |
| ttgctggaat | tttgtagagg | tgaagacagt | gtagacggga | aaaacaaaag | taccactgct | 540 |
| ttacctgctg | taaaagactc | tgtaaaagac | tcctaggtaa | gtaatccctt | ttttttgta | 600 |
| tttccaggtt | gatgggtgct | gctctagcac | ttttggggga | cctagttgcc | agtgtatctg | 660 |
| aggctgctgc | tgccacagga | ttttcagtgg | ctgaaattgc | tgctggggag | ctgctgctg | 720 |
| ctatagaagt | tcaaattgca | tcccttgcta | ctgtagaggg | cataacaagt | acctcagagg | 780 |
| ctatagctgc | tataggccta | actcctcaaa | catatgctgt | aattgctggt | gctcctgggg | 840 |
| ctattgctgg | gtttgctgct | ttaattcaaa | ctgttactgg | tattagttcc | ttggctcaag | 900 |
| tagggtatag | gttttttagt | gattgggatc | acaaagtttc | cactgtaggc | ctctatcagc | 960 |
| aatcaggcat | ggctttggaa | ttgtttaacc | cagatgagta | ctatgatatt | tgtttcctg | 1020 |
| gtgtaaaatac | ttttgtaaat | aatattcaat | accttgatcc | taggcattgg | ggtccttcct | 1080 |
| tgtttgctac | tatttcccag | gctttgtggc | atgttattag | ggatgatata | cctgctataa | 1140 |

```
cctcacaaga attgcaaaga agaacagaaa gattttttag agactccttg gctagatttt   1200
tggaggaaac tacctggaca attgtaaatg cccctatgaa cttttataat tatattcaag   1260
aatattattc tgatctttcc cctattaggc cctcaatggt tagacaagtg gctgaaaggg   1320
aaggtacccg tgtacatttt ggccatactt atagtataga tgatgctgac agtatagaag   1380
aagttacaca agaatggac ttaagaaatc aacaaactgt acattcagga gagtttatag    1440
aaaaaactat tgccccagga ggtgctaatc aaagaactgc tcctcaatgg atgttgcctt   1500
tacttctagg cctgtacggg actgtaacac ctgctcttga agcatatgaa gatggcccca   1560
gccaaaagaa aaggagagtg tccaggggca gctcccaaaa agccaaagga acccgtgcaa   1620
gtgccaaaac tactaataaa aggaggagta gaagttctag aagttaaaac tggggtagat   1680
gctataacag aggtagaatg cttcctaaac ccagaaatgg gggatccaga tgaaaacctt   1740
aggggcttta gtctaaagct aagtgctgaa aatgacttta gcagtgatag cccagaaaga   1800
aaaatgcttc cctgttacag cacagcaaga attcccctcc ccaatttaaa tgaggaccta   1860
acctgtggaa atctactgat gtgggaggct gtaactgtac aaacagaggt cattggaata   1920
actagcatgc ttaaccttca tgcagggtca caaaaagtgc atgagcatgg tggaggtaaa   1980
cctattcaag gcagtaattt ccacttcttt gctgttggtg agacccctt ggaaatgcag    2040
ggagtgctaa tgaattacag gaccaagtac ccagatggta ctataacccc aaaaaaccca   2100
acagcccagt cccaggtaat gaatactgac cataaggcct atttggacaa aaacaatgct   2160
tatccagttg agtgctgggt tcctgatccc agtagaaatg aaaatactag gtattttgga   2220
actttcacag gaggggaaaa tgttccccca gtacttcatg tgaccaacac agctaccaca   2280
gtgttgctag atgaacaggg tgtggggcct cttgtaaag ctgatagcct gtatgtttca    2340
gctgctgata tttgtggcct gtttactaac agctctggaa cacaacagtg gagaggcctt   2400
gcaagatatt ttaggattcg cctgagaaaa agatctgtaa aaaatcctta cccaatttcc   2460
tttttgctga gtgaccttat aaacaggaga acccagagag tggatgggca gcctatgtat   2520
ggtatggaat cccaggtagg agaggtcagg gtgtttgatg gcacagaaag acttccaggg   2580
gacccagata tgataagata tattgataaa caaggacaat tgcaaaccaa aatgctttaa   2640
acaggtgctt ttattgtaca tatacattta ataaatgctg cttttgtata agccacttt    2700
aagcttgtgt tattttgggg gtggtgtttt aggccttta aaacattgaa agcctttaca    2760
caaatgcaac tcttgactat gggggtctga cctttgggaa tcttcagcag gggctgaagt   2820
atctgagact tgggaagagc attgtgattg ggattcagtg cttgatccat gtccagagtc   2880
ttcagtttct gaatcttctt ctcttgtgat atcaagaata catttcccca tgcatatatt   2940
atatttcatc cttgaaaaag tatacatact tatctcagaa tccagccttt ccttccattc   3000
aacaattcta gattgtatat ctgttgcaaa atcagctaca ggcctaaacc aaattagcag   3060
tagcaacaag gtcattccac tttgtaaaat tcttttttca agtaagaact ctgagttttg   3120
taaggatttt cttaaatata ttttgggtct aaaatctatc tgtcttacaa atctagcctg   3180
cagggtttta ggaacaggat actcattcat tgtaaccagg cctggtggaa atatttgggt   3240
tcttttgttt aaatgtttct tttctaaatt aaccttaaca cttccatcta ataatctct    3300
caaactgtct aaattgttta ttccatgtcc tgaaggcaaa tcctttgatt cagccccagt   3360
tccttttaca tcttcaaaaa caaccatgta ctgatctata gctacaccta gttcaaaggt   3420
tagccttttcc atgggtaggt ttacatttaa ggctttacct ccacacaaat ctaataaccc   3480
tgcagctagt gttgttttc cactatcaat gggacctta aataaccagt atcttctttt     3540
```

-continued

```
aggtacatta aaaacaatac agtgcaaaaa atcaaatata acagaatcca ttttaggtag      3600
caaacagtgc agccaagcaa cacctgccat atattgttcc agtacagcat ttccatgagc      3660
tccaaatatt aaatccattt tatctaatat atgattaaat ctttctgtta gcatttcttc      3720
tctggtcata tgaagggtat ctactctttt tttagctaaa actgtatcta ctgcttgctg      3780
acaaatactt ttttgatttt tactttctgc aaaaatagta gcatttgcaa aatgcttttc      3840
atgatactta aagtgataag gttggtcttt tttctgacac tttttacact cttctacatt      3900
gtattgaaat tctaaataca tacccaataa taaaaacaca tcctcacact ttgtctctac      3960
tgcatactca gtaattaatt tccaagacac ctgctttgtt tcttcaggct cttctgggtt      4020
aaaatcatgc tcctttaagc ccccttgaat gctttcttct attgtatggt atggatctct      4080
agttaaggca ctatatagta agtattcctt attaacaccc ttacaaatta aaaaactaaa      4140
ggtacacagc ttttgacaga aattattaat tgcagaaact ctatgtctat gtggagttaa      4200
aaagaatata atattatgcc cagcacacat gtgtctacta ataaaagtta cagaatattt      4260
ttccataagt tttttataca gaatttgagc ttttttcttta gtagtataca cagcaaagca      4320
ggcaagggtt ctattactaa atacagcttg actaagaaac tggtgtagat cagaaggaaa      4380
gtctttaggg tcttctacct ttctctttttt cttgggtggt gtggagtgtt gagaatctgc      4440
tgttgcttct tcatcactgg caaacatatc ttcatggcaa ataaatcttt catcccattt      4500
ttcattaaag gagctccacc aggactccca ctcttctgtt ccataggttg gcacctataa      4560
aaaaaataat tacttagggc ctttaaatat tttcttattt atctaaatat aagttagtta      4620
ccttaaagct ttagatctct gaagggagtt tctccaatta tttggaccca ccattgcaga      4680
gtttcttcag ttaggtctaa gccaaaccac tgtgtgaagc agtcaatgca gtagcaatct      4740
atccaaacca agggctcttt tcttaaaaat tttctattta aatgccttaa tctaagctga      4800
catagcatgc aagggcagtg cacagaaggc ttttttgaac aaataggcca atccttgcag      4860
tacagggtat ctgggcaaag aggaaaatca gcacaaacct ctgagctact ccaggttcca      4920
aaatcaggct gatgagctac ctttacatcc tgctccattt ttttatataa agtattcatt      4980
ctcttcattt tatcctcgtc gccccctttg tcagggtgaa attccttaca cttccttaaa      5040
taggcttttc tcattagggg aaggtttccc caggcagctc tttcaaggcc taaaaggtcc      5100
atgagctcca tggattcttc cctgttaagc actttatcca t                         5141
```

<210> SEQ ID NO 26
<211> LENGTH: 5141
<212> TYPE: DNA
<213> ORGANISM: Human polyomavirus 1
<220> FEATURE:
<223> OTHER INFORMATION: Type BK virus

<400> SEQUENCE: 26

```
ttttgcaaaa attgcaaaag aatagggatt tccccaaata tttttgctag gcctcagaaa        60
aagcctccac acccttacta cttgagagaa agggtggagg cagaggcggc ctcggcctct       120
tatatattat aaaaaaaaag gccacaggga ggagctgcta acccatggaa tgtagccaaa       180
ccatgaccct aggaaggaaa gtgcatgact gggcagccag ccagtggcag ttaatagtga       240
aaccccgccc ctaaaattct caaataaaca caagaggaag tggaaactgg ccaaaggagt       300
ggaaagcagc cagacagaca tgttttgcga gcctaggaat cttggccttg tcccagtta       360 aactggacaa aggccatggt tctgcgccag ctgtcacgac aagcttctgt gaaagttagt       420
```

```
aaaacctgga ctggaacaaa aaaaagagct cagaggattt ttattttat tttagagctt      480 ttgctggaat tttgtagagg tgaagacagt gtagacggga aaaacaaaag taccactgct      540
ttacctgctg taaaagactc tgtaaaagac tcctaggtaa gtaatcccttt tttttttgta     600 tttccaggtt gatgggtgct gctctagcac ttttggggga cctagttgcc agtgtatctg      660
aggctgctgc tgccacagga ttttcagtgg ctgaaattgc tgctgggag gctgctgctg       720 ctatagaagt tcaaattgca tcccttgcta ctgtagaggg cataacaagt acctcagagg      780
ctatagctgc tataggccta actcctcaaa catatgctgt aattgctggt gctcctgggg      840
ctattgctgg gtttgctgct ttaattcaaa ctgttactgg tattagttcc ttggctcaag      900
tagggtatag gttttttagt gattgggatc acaaagttc cactgtaggc ctctatcagc       960
aatcaggcat ggctttggaa ttgttaacc cagatgagta ctatgatatt ttgttcctg       1020 gtgtaaatac ttttgtaaat aatattcaat accttgatcc taggcattgg ggtccttcct     1080
tgtttgctac tatttcccag gctttgtggc atgttattag ggatgatata cctgctataa     1140
cctcacaaga attgcaaaga gaacagaaa gatttttag agactcctg gctagatttt        1200 tggaggaaac tacctggaca attgtaaatg cccctatgaa ctttttataat tatattcaag    1260 aatattattc tgatctttcc cctattaggc cctcaatggt tagacaagtg gctgaaaggg     1320
aaggtacccg tgtacatttt ggccatactt atagtataga tgatgctgac agtatagaag    1380
aagttacaca aagaatggac ttaagaaatc aacaaactgt acattcagga gagttttatag  1440 aaaaaactat tgccccagga ggtgctaatc aaagaactgc tcctcaatgg atgttgcctt    1500
tacttctagg cctgtacggg actgtaacac ctgctcttga agcatatgaa gatggccca     1560 accaaaagaa aaggagagtg tccagggca gctcccaaaa agccaaagga acccgtgcaa     1620 gtgccaaac tactaataaa aggaggagta gaagttctag aagttaaaac tggggtagat     1680
gctataacag aggtagaatg cttcctaaac ccagaaatgg gggatccaga tgaaaacctt    1740
aggggcttta gtctaaagct aagtgctgaa atgactttta gcagtgatag cccagaaaga    1800
aaaatgcttc cctgttacag cacagcaaga attccctcc ccaatttaaa tgaggaccta     1860
acctgtggaa atctactgat gtgggaggct gtaactgtac aaacagaggt cattggaata   1920
actagcatgc ttaaccttca tgcagggtca caaaaagtgc atgagcatgg tggaggtaaa   1980
cctattcaag gcagtaattt ccacttcttt gctgttggtg agaccccctt ggaaatgcag    2040
ggagtgctaa tgaattacag gaccaagtac ccagatggta ctataaccc aaaaaaccca    2100 acagcccagt cccaggtaat gaatactgac cataaggcct atttggacaa aaacaatgct   2160
tatccagttg agtgctgggt tcctgatccc agtagaaatg aaaatactag gtattttgga   2220
actttcacag gaggggaaaa tgttccccca gtacttcatg tgaccaacac agctaccaca   2280
gtgttgctag atgaacaggg tgtggggcct cttgtaaag ctgatagcct gtatgtttca    2340
gctgctgata tttgtggcct gtttactaac agctctggaa cacaacagtg gagaggcctt   2400
gcaagatatt ttaagattcg cctgagaaaa agatctgtaa aaaatcctta cccaatttcc   2460
tttttgctga gtgaccttat aaacaggaga acccagagag tggatgggca gcctatgtat    2520
ggtatggaat cccaggtaga gaggtcagg gtgtttgatg gcacagaaag acttccaggg    2580
gacccagata tgataagata tattgataaa caaggacaat gcaaaccaa aatgctttaa    2640 acaggtgctt ttattgtaca tatacattta ataaatgctg cttttgtata agccactttt    2700
aagcttgtgt tattttgggg gtggtgtttt aggcctttta aaacattgaa agcctttaca    2760
caaatgcaac tcttgactat gggggtctga cctttgggaa tcttcagcag gggctgaagt    2820
```

```
atctgagact tgggaagagc attgtgattg ggattcagtg cttgatccat gtccagagtc    2880
ttcagtttct gaatcttctt ctcttgtgat atcaagaata catttcccca tgcatatatt    2940
atatttcatc cttgaaaaag tatacatact tatctcagaa tccagccttt ccttccattc    3000
aacaattcta gattgtatat ctgttgcaaa atcagctaca ggcctagacc aaattagcag    3060
tagcaacaag gtcattccac tttgtaaaat tcttttttca agtaagaact ctgagttttg    3120
taaggatttt cttaaatata ttttgggtct aaaatctatc tgtcttacaa atctagcctg    3180
cagggtttta ggaacaggat actcattcat tgtaaccagg cctggtggaa atatttgggt    3240
tcttttgttt aaatgtttct tttctaaatt aaccttaaca cttccatcta ataatctct     3300 caaactgtct aaattgttta ttccatgtcc tgaaggcaaa tcctttgatt cagccccagt    3360
tccttttaca tcttcaaaaa caaccatgta ctgatctata gctacaccta gttcaaaggt    3420 tagccttttcc atgggtaggt ttacatttaa ggctttacct ccacacaaat ctaataaccc    3480
tgcagctagt gttgttttc cactatcaat gggacccttta aataaccagt atcttctttt     3540
aggtacatta aaacaatac agtgcaaaaa atcaaatata acagaatcca ttttaggtag     3600
caaacagtgc agccaagcaa cacctgccat atattgttcc agtacagcat ttccatgagc    3660
tccaaatatt aaatccattt tatctaatat atgattaaat ctttctgtta gcatttcttc    3720
tctggtcata tgaagggtat ctactctttt tttagctaaa actgtatcta ctgcttgctg    3780
acaaatactt ttttgatttt tactttctgc aaaaatagta gcatttgcaa aatgcttttc    3840
atgatactta aagtgataag gttggtcttt tttctgacac ttttacact cttctacatt     3900 gtattgaaat tctaaataca tacccaataa taaaaacaca tcctcacact ttgtctctac    3960
tgcatactca gtaattaatt tccaagacac ctgctttgtt tcttcaggct cttctgggtt    4020
aaaatcatgc tcctttaagc ccccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaaagtta cagaatattt    4260
ttccataagt tttttataca gaatttgagc ttttttcttta gtagtataca cagcaaagca    4320
ggcaagggtt ctattactaa atacagcttg actaagaaac tggtgtagat cagaaggaaa    4380
gtctttaggg tcttctacct ttctcttttt cttgggtggt gtggagtgtt gagaatctgc    4440
tgttgcttct tcatcactgg caaacatatc ttcatggcaa aataaatctt catcccattt    4500
ttcattaaag gagctccacc aggactccca ctcttctgtt ccataggttg gcacctataa    4560
aaaaaataat tacttagggc ctttaaatat tttcttattt atctaaatat aagttagtta    4620
ccttaaagct ttagatctct gaagggagtt tctccaatta tttggaccca ccattgcaga    4680
gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg cacagaaggc ttttggaac aaataggcca atccttgcag     4860
tacagggtat ctgggcaaag aggaaaatca gcacaaacct ctgagctact ccaggttcca    4920
aaatcaggct gatgagctac ctttacatcc tgccccattt ttttatataa agtattcatt    4980
ctcttcattt tatcctcgtc gccccctttg tcagggtgaa attccttaca cttccttaaa    5040
taggcttttc tcattaaggg aaggtttccc caggcagctc tttcaaggcc taaaaggtcc    5100
atgagctcca tggattcttc cctgttaagc actttatcca t                        5141
```

<210> SEQ ID NO 27
<211> LENGTH: 5141
<212> TYPE: DNA
<213> ORGANISM: Human polyomavirus 1
<220> FEATURE:
<223> OTHER INFORMATION: Type BK virus

<400> SEQUENCE: 27

| | | | | | |
|---|---|---|---|---|---|
| ttttgcaaaa | attgcaaaag | aatagggatt | tccccaaata | tttttgctag | gcctcagaaa | 60 |
| aagcctccac | acccttacta | cttgagagaa | agggtggagg | cagaggcggc | ctcggcctct | 120 |
| tatatattat | aaaaaaaaag | gccacaggga | ggagctgcta | acccatggaa | tgtagccaaa | 180 |
| ccatgacctc | aggaaggaaa | gtgcatgact | gggcagccag | ccagtggcag | ttaatagtga | 240 |
| aaccccgccc | ctaaaattct | caaataaaca | aagaggaag | tggaaactgg | ccaaaggagt | 300 |
| ggaaagcagc | cagacagaca | tgttttgcga | gcctaggaat | cttggccttg | tccccagtta | 360 |
| aactggacaa | aggccatggt | tctgcgccag | ctgtcacgac | atgcttctgt | gaaagttagt | 420 |
| aaaacctgga | ctggaacaaa | aaaagagct | cagaggattt | ttattttat | tttagagctt | 480 |
| ttgctggaat | tttgtagagg | tgaagacagt | gtagacggga | aaaacaaaag | taccactgct | 540 |
| ttacctgctg | taaaagactc | tgtaaaagac | tcctaggtaa | gtaatccctt | ttttttgta | 600 |
| tttccaggtt | gatgggtgct | gctctagcac | ttttggggga | cctagttgcc | agtgtatctg | 660 |
| aggctgctgc | tgccacagga | ttttcagtgg | ctgaaattgc | tgctggggag | gctgctgctg | 720 |
| ctatagaagt | tcaaattgca | tcccttgcta | ctgtagaggg | cataacaagt | acctcagagg | 780 |
| ctatagctgc | tataggccta | actcctcaaa | catatgctgt | aattgctggt | gctcctgggg | 840 |
| ctattgctgg | gtttgctgct | ttaattcaaa | ctgttactgg | tattagttcc | ttggctcaag | 900 |
| tagggtatag | gtttttagt | gattgggatc | acaaagtttc | cactgtaggc | ctctatcagc | 960 |
| aatcaggcat | ggctttggaa | ttgtttaacc | cagatgagta | ctatgatatt | ttgtttcctg | 1020 |
| gtgtaaatac | ttttgtaaat | aatattcaat | accttgatcc | taggcattgg | ggtccttcct | 1080 |
| tgtttgctac | tatttcccag | gctttgtggc | atgttattag | ggatgatata | cctgctataa | 1140 |
| cctcacaaga | attgcaaaga | gaacagaaa | gatttttag | agactccttg | gctagatttt | 1200 |
| tggaggaaac | tacctggaca | attgtaaatg | ccctatgaa | cttttataat | tatattcaag | 1260 |
| aatattattc | tgatctttcc | cctattaggc | cctcaatggt | tagacaagtg | gctgaaaggg | 1320 |
| aaggtacccg | tgtacatttt | ggccatactt | atagtataga | tgatgctgac | agtatagaag | 1380 |
| aagttacaca | aagaatggac | ttaagaaatc | aacaaactgt | acattcagga | gagtttatag | 1440 |
| aaaaaactat | tgccccagga | ggtgctaatc | aaagaactgc | tcctcaatgg | atgttgcctt | 1500 |
| tacttctagg | cctgtacggg | actgtaacac | ctgctcttga | agcatatgaa | gatggcccca | 1560 |
| accaaaagaa | aaggagagtg | tccagggca | gctcccaaaa | agccaaagga | acccgtgcaa | 1620 |
| gtgccaaaac | tactaataaa | aggaggagta | gaagttctag | aagttaaaac | tggggtagat | 1680 |
| gctataacag | aggtagaatg | cttcctaaac | ccagaaatgg | gggatccaga | tgaaaacctt | 1740 |
| aggggcttta | gtctaaagct | aagtgctgaa | aatgacttta | gcagtgatag | cccagaaaga | 1800 |
| aaaatgcttc | cctgttacag | cacagcaaga | attcccctcc | ccaatttaaa | tgaggaccta | 1860 |
| acctgtggga | atctactgat | gtgggaggct | gtaactgtac | aaacagaggt | cattggaata | 1920 |
| actagcatgc | ttaaccttca | tgcagggtca | caaaaagtgc | atgagcatgg | tggaggtaaa | 1980 |
| cctattcaag | gcagtaattt | ccacttcttt | gctgttggtg | gagacccctt | ggaaatgcag | 2040 |
| ggagtgctaa | tgaattacag | gaccaagtac | ccagatggta | ctataacccc | aaaaaaccca | 2100 |

```
acagcccagt cccaggtaat gaatactgac cataaggcct atttggacaa aaacaatgct    2160
tatccagttg agtgctgggt tcctgatccc agtagaaatg aaaatactag gtattttgga    2220
actttcacag gaggggaaaa tgttccccca gtacttcatg tgaccaacac agctaccaca    2280
gtgttgctag atgaacaggg tgtggggcct ctttgtaaag ctgatagcct gtatgtttca    2340
gctgctgata tttgtggcct gtttactaac agctctggaa cacaacagtg gagaggcctt    2400
gcaagatatt ttaagattcg cctgagaaaa agatctgtaa aaaatcctta cccaatttcc    2460
tttttgctga gtgaccttat aaacaggaga acccagagag tggatgggca gcctatgtat    2520
ggtatggaat cccaggtaga agaggtcagg gtgtttgatg gcacagaaag acttccaggg    2580
gacccagata tgataagata tattgataaa caaggacaat tgcaaaccaa aatgctttaa    2640
acaggtgctt ttattgtaca tatgcattta ataaatgctg cttttgtata agccactttt    2700
aagcttgtgt tattttgggg gtggtgtttt aggccttttta aaacattgaa agcctttaca    2760
caaatgcaac tcttgactat gggggtctga cctttgggaa tcttcagcag gggctgaagt    2820
atctgagact tgggaagagc attgtgattg ggattcagtg cttgatccat gtccagagtc    2880
ttcagtttct gaatcttctt ctcttgtgat atcaagaata catttcccca tgcatatatt    2940
atatttcatc cttgaaaaag tatacatact tatctcagaa tccagccttt ccttccattc    3000
aacaattcta gattgtatat ctgttgcaaa atcagctaca ggcctaaacc aaattagcag    3060
tagcaacaag gtcattccac tttgtaaaat tcttttttca agtaagaact ctgagttttg    3120
taaggatttt cttaaatata ttttgggtct aaaatctatc tgtcttacaa atctagcctg    3180
cagggtttta ggaacaggat actcattcat tgtaaccagg cctggtggaa atatttgggt    3240
tcttttgttt aaatgtttct tttctaaatt aaccttaaca cttccatcta aataatctct    3300
caaactgtct aaattgttta ttccatgtcc tgaaggcaaa tcctttgatt cagccccagt    3360
tccttttaca tcttcaaaaa caaccatgta ctgatctata gctacaccta gttcaaaggt    3420
tagcctttcc atgggtaggt ttacatttaa ggctttacct ccacacaaat ctaataaccc    3480
tgcagctagt gttgtttttc cactatcaat gggaccttta aataaccagt atcttctttt    3540
aggtacatta aaaacaatac agtgcaaaaa atcaaatata acagaatcca ttttaggtag    3600
caaacagtgc agccaagcaa cacctgccat atattgttcc agtacggcat tccatgagc    3660 tccaaatatt aaatccattt tatctaatat atgattaaat ctttctgtta gcatttcttc    3720
tctggtcata tgaagggtat ctactctttt tttagctaaa actgtatcta ctgcttgctg    3780
acaaatactt ttttgatttt tactttctgc aaaaatagta gcatttgcaa aatgcttttc    3840
atgatactta aagtgataag gttggtcttt tttctgacac ttttttacact cttctacatt    3900 gtattgaaat tctaaataca tacccaataa taaaaacaca tcctcacact ttgtctctac    3960
tgcatactca gtaattaatt tccaagacac ctgctttgtt tcttcaggct cttctgggtt    4020
aaaatcatgc tcctttaagc ccccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaaagtta cagaatattt    4260
ttccataagt ttttatatca gaatttgagc tttttcttta gtagtataca cagcaaagca    4320
ggcaagggtt ctattactaa atacagcttg actaagaaac tggtgtagat cagaaggaaa    4380
gtctttaggg tcttctacct ttctcttttt cttgggtggt gtggagtgtt gagaatctgc    4440
```

| | |
|---|---|
| tgttgcttct tcatcactgg caaacatatc ttcatggcaa ataaatcttc catcccattt | 4500 |
| ttcattaaag gagctccacc aggactccca ctcttctgtt ccataggttg cacctataa | 4560 |
| aaaaaataat tacttagggc cttttaaatat tttcttattt atctaaatat aagttagtta | 4620 |
| ccttaaagct ttagatctct gaagggagtt tctccaatta tttggaccca ccattgcaga | 4680 |
| gtttcttcag ttaggtctaa gccaaaccac tgtgtgaagc agtcaatgca gtagcaatct | 4740 |
| atccaaacca agggctcttt tcttaaaaat tttctattta aatgccttaa tctaagctga | 4800 |
| catagcatgc aagggcagtg cacagaaggc ttttttggaac aaataggcca atccttgcag | 4860 |
| tacagggtat ctgggcaaag aggaaaatca gcacaaacct ctgagctact ccaggttcca | 4920 |
| aaatcaggct gatgagctac ctttacatcc tgctccattt ttttatataa agtattcatt | 4980 |
| ctcttcattt tatcctcgtc gccccctttg tcagggtgaa attccttaca cttcctttaaa | 5040 |
| taggcttttc tcattaaggg aaggtttccc caggcagctc tttcaaggcc taaaaggtcc | 5100 |
| atgagctcca tggattcttc cctgttaagc actttatcca t | 5141 |

<210> SEQ ID NO 28
<211> LENGTH: 5141
<212> TYPE: DNA
<213> ORGANISM: Human polyomavirus 1
<220> FEATURE:
<223> OTHER INFORMATION: Type BK virus

<400> SEQUENCE: 28

| | |
|---|---|
| ttttgcaaaa attgcaaaag aatagggatt tccccaaata ttttgctag gcctcagaaa | 60 |
| aagcctccac acccttacta cttgagagaa agggtggagg cagaggcggc ctcggcctct | 120 |
| tatatattat aaaaaaaaag gccacaggga ggagctgcta acccatggaa tgtagccaaa | 180 |
| ccatgacctc aggaaggaaa gtgcatgact gggcagccag ccagtggcag ttaatagtga | 240 |
| aaccccgccc ctaaaattct caaataaaca caagaggaag tggaaactgg ccaaaggagt | 300 |
| ggaaagcagc cagacagaca tgttttgcga gcctaggaat cttggccttg tcccagtta | 360 |
| aactggacaa aggccatggt tctgcgccag ctgtcacgac aagcttctgt gaaagttagt | 420 |
| aaaacctgga ctggaacaaa aaaaagagct cagaggattt tattttttat tttagagctt | 480 |
| ttgctggaat tttgtagagg tgaagacagt gtagacggga aaaacaaaag taccactgct | 540 |
| ttacctgctg taaaagactc tgtaaaagac tcctaggtaa gtaatccctt ttttttttgta | 600 |
| tttccaggtt gatgggtgct gctctagcac tttttgggga cctagttgcc agtgtatctg | 660 |
| aggctgctgc tgccacagga ttttcagtgg ctgaaattgc tgctggggag gctgctgctg | 720 |
| ctatagaagt tcaaattgca tcccttgcta ctgtagaggg cataacaagt acctcagagg | 780 |
| ctatagctgc tataggccta actcctcaaa catatgctgt aattgctggt gctcctgggg | 840 |
| ctattgctgg gtttgctgct ttaattcaaa ctgttactgg tattagttcc ttggctcaag | 900 |
| tagggtatag gtttttttagt gattgggatc acaaagtttc cactgtaggc ctctatcagc | 960 |
| aatcaggcat ggctttggaa ttgttaacc cagatgagta ctatgatatt ttgtttcctg | 1020 |
| gtgtaaatac ttttgtaaat aatattcaat accttgatcc taggcattgg ggtccttcct | 1080 |
| tgtttgctac tatttcccag gctttgtggc atgttattag gatgatata cctgctataa | 1140 |
| cctcacaaga attgcaaaga agaacagaaa gatttttag agactccttg gctagatttt | 1200 |
| tggaggaaac tacctggaca attgtaaatg cccctatgaa cttttataat tatattcaag | 1260 |
| aatattattc tgatctttcc cctattaggc cctcaatggt tagacaagtg gctgaaaggg | 1320 |
| aaggtacccg tgtacatttt ggccatactt atagtataga tgatgctgac agtatagaag | 1380 |

```
aagttacaca aagaatggac ttaagaaatc aacaaactgt acattcagga gagtttatag    1440
aaaaaactat tgccccagga ggtgctaatc aaagaactgc tcctcaatgg atgttgcctt    1500
tacttctagg cctgtacggg actgtaacac ctgctcttga agcatatgaa gatggcccca    1560
accaaaagaa aaggagagtg tccaggggca gctcccaaaa agccaaagga acccgtgcaa    1620
gtgccaaaac tactaataaa aggaggagta gaagttctag aagttaaaac tggggtagat    1680
gctataacag aggtagaatg cttcctaaac ccagaaatgg gggatccaga tgaaaacctt    1740
aggggcttta gtctaaagct aagtgctgaa aatgacttta gcagtgatag cccagaaaga    1800
aaaatgcttc cctgttacag cacagcaaga attcccctcc ccaatttaaa tgaggaccta    1860
acctgtggaa atctactgat gtgggaggct gtaactgtac aaacagaggt cattggaata    1920
actagcatgc ttaaccttca tgcagggtca caaaaagtgc atgagcatgg tggaggtaaa    1980
cctattcaag gcagtaattt ccacttcttt gctgttggtg agacccctt ggaaatgcag     2040 ggagtgctaa tgaattacag gaccaagtac ccagatggta ctataacccc aaaaaaccca    2100
acagcccagt cccaggtaat gaatactgac cataaggcct atttggacaa aacaatgct    2160 tatccagttg agtgctgggt tcctgatccc agtagaaatg aaaatactag gtattttgga    2220
actttcacag gagggaaaa tgttccccca gtacttcatg tgaccaacac agctaccaca     2280
gtgttgctag atgaacaggg tgtggggcct ctttgtaaag ctgatagcct gtatgtttca    2340
gctgctgata tttgtggcct gtttactaac agctctggaa cacaacagtg gagaggcctt    2400
gcaagatatt ttaagattcg cctgagaaaa agatctgtaa aaaatcctta cccaatttcc    2460
tttttgctga gtgaccttat aaccaggaga acccagagag tggatgggca gcctatgtat    2520
ggtatggaat cccaggtaga agaggtcagg gtgtttgatg gcacagaaag acttccaggg    2580
gacccagata tgataagata tattgataaa caaggacaat gcaaaccaa atgctttaa     2640 acaggtgctt ttattgtaca tatacattta ataaatgctg cttttgtata agccactttt    2700
aagcttgtgt tattttgggg gtggtgtttt aggccttta aaacattgaa agcctttaca     2760
caaatgcaac tcttgactat gggggtctga ccttgggaa tcttcagcag gggctgaagt     2820
atctgagact tgggaagagc attgtgattg ggattcagtg cttgatccat gtccagagtc    2880
ttcagtttct gaatcttctt ctcttgtgat atcaagaata catttcccca tgcatatatt    2940
atatttcatc cttgaaaaag tatacatact tatctcagaa tccagccttt ccttccattc    3000
aacaattcta gattgtatat ctgttgcaaa atcagctaca ggcctaaacc aaattagcag    3060
tagcaacaag gtcattccac tttgtaaaat tcttttttca gtaagaact ctgagttttg     3120 taaggatttt cttaaatata ttttgggtct aaaatctatc tgtcttacaa atctagcctg    3180
cagggtttta ggaacaggat actcattcat tgtaaccagg cctggtggaa atatttgggt    3240
tcttttgttt aaatgtttct tttctaaatt aaccttaaca cttccatcta ataatctct    3300 caaactgtct aaattgttta ttccatgtcc tgaaggcaaa tcctttgatt cagccccagt    3360
tccttttaca tcttcaaaaa caaccatgta ctgatctata gctacaccta gttcaaaggt    3420 tagccttttcc atgggtaggt ttacatttaa ggctttacct ccacacaaat ctaataaccc    3480
tgcagctagt gttgttttc cactatcaat gggacccttta aataaccagt atcttctttt    3540
aggtacatta aaaacaatac agtgcaaaaa atcaaatata acagaatcca ttttaggtag    3600
caaacagtgc agccaagcaa cacctgccat atattgttcc agtacagcat tccatgagc    3660 tccaaatatt aaatccattt tatctaatat atgattaaat ctttctgtta gcatttcttc    3720
```

```
tctggtcata tgaagggtat ctactctttt tttagctaaa actgtatcta ctgcttgctg    3780
acaaatactt ttttgatctt tactttctgc aaaaatagta gcatttgcaa aatgcttttc    3840
atgatactta aagtgataag gttggtcttt tttctgacac tttttacact cttctacatt    3900
gtattgaaat tctaaataca tacccaataa taaaaacaca tcctcacact ttgtctctac    3960
tgcatactca gtaattaatt tccaagacac ctgctttgtt tcttcaggct cttctgggtt    4020
aaaatcatgc tcctttaagc ccccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaaagtta cagaatattt    4260
ttccataagt tttttataca gaatttgagc ttttttcttta gtagtataca cagcaaagca    4320
ggcaagggtt ctattactaa acacagcttg actaagaaac tggtgtagat cagaaggaaa    4380
gtctttaggg tcttctacct ttctcttttt cttgggtggt gtggagtgtt gagaatctgc    4440
tgttgcttct tcatcactgg caaacatatc ttcatggcaa aataaatctt catcccattt    4500
ttcattaaag gagctccacc aggactccca ctcttctgtt ccataggttg gcacctataa    4560
aaaaaataat tacttagggc cttttaaatat tttcttattt atctaaatat aagttagtta    4620
ccttaaagct ttagatctct gaagggagtt tctccaatta tttggaccca ccattgcaga    4680
gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg cacagaaggc ttttggaac aaataggcca atccttgcag    4860
tacagggtat ctgggcaaag aggaaaatca gcacaaacct ctgagctact ccaggttcca    4920
aaatcaggct gatgagctac ctttacatcc tgctccattt ttttatataa agtattcatt    4980
ctcttcattt tatcctcgtc gccccctttg tcagggtgaa attccttaca cttccttaaa    5040 taggctttc tcattaaggg aaggtttccc caggcagctc tttcaaggcc taaaaggtcc    5100
atgagctcca tggattcttc cctgttaagc actttatcca t                       5141
```

<210> SEQ ID NO 29
<211> LENGTH: 5141
<212> TYPE: DNA
<213> ORGANISM: Human polyomavirus 1
<220> FEATURE:
<223> OTHER INFORMATION: Type BK virus

<400> SEQUENCE: 29

```
ttttgcaaaa attgcaaaag aatagggatt tccccaaata ttttcgctag gcctcagaaa     60
aagcctccac acccttacta cttgagagaa agggtggagg cagaggcggc ctcggcctct    120
tatatattat aaaaaaaaag gccacaggga ggagctgcta acccatggaa tgtagccaaa    180
ccatgacctc aggaaggaaa gtgcatgact gggcagccag ccagtggcag ttaatagtga    240
aaccccgccc ctaaaattct caaataaaca caagaggaag tggaaactgg ccaaaggagt    300
ggaaagcagc cagacagaca tgttttgcga gcctaggaat cttggccttg tccccagtta    360
aactggacaa aggccatggt tctgcgccag ctgtcacgac aagcttctgt gaaagttagt    420
aaaacctgga ctgaacaaa aaaagagct cagaggattt ttatttttat tttagagctt    480
ttgctggaat tttgtagagg tgaagacagt gtagacggga aaaacaaaag taccactgct    540
ttacctgctg taaagactc tgtaaaagac tcctaggtaa gtaatccctt tttttttgta    600
tttccaggtt gatgggtgct gctctagcac tttttgggga cctagttgcc agtgtatctg    660
```

```
aggctgctgc tgccacaggg ttttcagtgg ctgaaattgc tgctgggag gctgctgctg    720 ctatagaagt tcaaattgca tcccttgcta ctgtagaggg cataacaagt acctcagagg    780
ctatagctgc tataggccta actcctcaaa catatgctgt aattgctggt gctcctgggg    840
ctattgctgg gtttgctgct ttaattcaaa ctgttactgg tattagttcc ttggctcaag    900
tagggtatag gttttttagt gattgggatc acaaagtttc cactgtaggc ctctatcagc    960
aatcaggcat ggctttggaa ttgtttaacc cagatgagta ctatgatatt ttgtttcctg   1020
gtgtaaatac ttttgtaaat aatattcaat accttgatcc taggcattgg ggtccttcct   1080
tgtttgctac tatttcccag gctttgtggc atgttattag ggatgatata cctgctataa   1140
cctcacaaga attgcaaaga agaacagaaa gattttttag agactccttg gctagatttt   1200
tggaggaaac tacctggaca attgtaaatg cccctatgaa cttttataat tatattcaag   1260
aatattattc tgatctttcc cctattaggc cctcaatggt tagacaagtg gctgaaaggg   1320
aaggtacccg tgtacatttt ggccatactt atagtataga tgatgctgac agtatagaag   1380
aagttacaca aagaatggac ttaagaaatc aacaaactgt acattcagga gagtttatag   1440
aaaaaactat tgccccagga ggtgctaatc aaagaactgc tcctcaatgg atgttgcctt   1500
tacttctagg cctgtacggg actgtaacac ctgctcttga agcatgaa gatggcccca   1560 accaaaagaa aaggagagtg tccaggggca gctcccaaaa agccaaagga acccgtgcaa   1620
gtgccaaaac tactaataaa aggaggagta gaagttctag aagttaaaac tggggtagat   1680
gctataacag aggtagaatg cttcctaaac ccagaaatgg gggatccaga tgaaaacctt   1740
aggggcttta gtctaaagct aagtgctgaa aatgacttta gcagtgatag cccagaaaga   1800
aaaatgcttc cctgttacag cacagcaaga attccctcc ccaatttaaa tgaggaccta   1860
acctgtggaa atctactgat gtgggaggct gtaactgtac aaacagaggt cattggaata   1920
actagcatgc ctaaccttca tgcagggtca caaaaagtgc atgagcatgg tggaggtaaa   1980
cctattcaag gcagtaattt ccacttcttt gctgttggtg gagacccctt ggaaatgcag   2040
ggagtgctaa tgaattacag gaccaagtac ccagatggta ctataacccc aaaaaaccca   2100
acagcccagt cccaggtaat gaatactgac cataaggcct atttggacaa aaacaatgct   2160
tatccagttg agtgctgggt tcctgatccc agtagaaatg aaaatactag gtattttgga   2220
actttcacag gaggggaaaa tgttcccca gtacttcatg tgaccaacac agctaccaca   2280
gtgttgctag atgaacaggg tgtggggcct cttgtaaag ctgatagcct gtatgtttca   2340
gctgctgata tttgtggcct gtttactaac agctctggaa cacaacagtg gagaggcctt   2400
gcaagatatt ttaagattcg cctgagaaaa agatctgtaa aaaatcctta cccaatttcc   2460
tttttgctga gtgaccttat aaacaggaga acccagagag tggatgggca gcctatgtat   2520
ggtatggaat cccaggtaga agaggtcagg gtgtttgatg gcacagaaag acttccaggg   2580
gacccagata tgataagata tattgataag caaggacaat tgcaaaccaa aatgctttaa   2640
acaggtgctt ttattgtaca tatacatta ataaatgctg cttttgtata agccacttttt   2700 aagcttgtgt tattttgggg gtggtgtttt aggccttta aaacattgaa agcctttaca   2760
caaatgcagc tcttgactat gggggtctga ccttttggaa tcttcagcag gggctgaagt   2820
atctgagact tgggaagagc attgtgattg ggattcagtg cttgatccat gtccagagtc   2880 ttcagttct gaatcttctt ctcttgtgat atcaagaata catttcccca tgcatatatt   2940
atatttcatc cttgaaaaag tatacatact tatctcagaa tccagccttt ccttccattc   3000
```

```
aacaattcta gattgtatat ctgttgcaaa atcagctaca ggcctaaacc aaattagcag    3060
tagcaacaag gtcattccac tttgtaaaat tcttttttca agtaagaact ctgagttttg    3120
taaggatttt cttaaatata ttttgggtct aaaatctatc tgtcttacaa atctagcctg    3180
cagggtttta ggaacaggat actcattcat tgtaaccagg cctggtggaa atatttgggt    3240
tcttttgttt aaatgtttct tttctaaatt aaccttaaca cttccatcta ataatctct     3300 caaactgtct aaattgttta ttccatgtcc tgaaggcaaa tcctttgatt cagccccagt    3360 tcctttaca tctccaaaaa caaccatgta ctgatctata gctacaccta gttcaaaggt    3420
tagcctttcc atgggtaggt ttacatttaa ggctttacct ccacacaaat ctaataaccc    3480
tgcagctagt gttgtttttc cactatcaat gggaccttta ataaccagt atcttctttt     3540 aggtacatta aaaacaatac agtgcaaaaa atcaaatata acagaatcca ttttaggtag    3600
caaacagtgc agccaagcaa cacctgccat atattgttcc agtacagcat ttccatgagc    3660
tccaaatatt aaatccattt tatctaatat atgattaaat ctttctgtta gcatttcttc    3720
tctggtcata tgaagggtat ctactctttt tttagctaaa actgtatcta ctgcttgctg    3780
acaaatactt ttttgatttt tactttctgc aaaaatagta gcatttgcaa aatgcttttc    3840
atgatactta aagtgataag gttggtcctt tttctgacac ttttttacact cttctacatt    3900 gtattgaaat tctaaataca tacccaataa taaaaacaca tcctcacact ttgtctctac    3960
tgcatactca gtaattaatt tccaagacac ctgctttgtt tcttcaggct cttctgggtt    4020
aaaatcatgc tcctttaagc cccctttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaaagtta cagaatattt    4260
ttccataagt ttttttataca ggatttgagc ttttttcttta gtagtataca cagcaaagca    4320
ggcaagggtt ctattactaa atacagcttg actaagaaac tggtgtagat cagaaggaaa    4380
gtctttaggg tcttctacct ttctcttttt cttgggtggt gtggagtgtt gagaatctgc    4440
tgttgcttct tcatcactgg caaacatatc ttcatggcaa aataaatctt catcccattt    4500
ttcattaaag gagctccacc aggactccca ctcttctgtt ccataggttg gcacctataa    4560
aaaaaataat tacttagggc ctttaaatat tttcttattt atctaaatat aagttagtta    4620
ccctaaagct ttagatctct gaagggagtt tctccaatta ttttggaccca ccattgcaga    4680 gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg cacagaaggc ttttttggaac aaataggcca atccttgcag    4860
tacagggtat ctgggcaaag aggaaaatca gcacaaacct ctgagctact ccaggttcca    4920
aaatcaggct gatgagctac ctttacatcc tgctccattt tttatataa agtattcatt    4980 ctcttcattt tatcctcgtc gcccccttg tcagggtgaa attccttaca cctccttaaa    5040
taggcttttc tcattaaggg aaggtttccc caggcagctc tttcaaggcc taaaaggtcc    5100
atgagctcca tggattcttc cctgttaagc actttatcca t                      5141
```

<210> SEQ ID NO 30
<211> LENGTH: 5141
<212> TYPE: DNA
<213> ORGANISM: Human polyomavirus 1
<220> FEATURE:
<223> OTHER INFORMATION: Type BK virus

<400> SEQUENCE: 30

```
ttttgcaaaa attgcaaaag aatagggatt tccccaaata ttttttgctag gcctcagaaa      60
aagcctccac acccttacta cttgagagaa agggtggagg cagaggcggc ctcggcctct     120
tatatattat aaaaaaaaag gccacaggga ggagctgcta acccatggaa tgtagccaaa     180
ccatgacctc aggaaggaaa gtgcatgact gggcagccag ccagtggcag ttaatagtga     240
aaccccgccc ctaaaattct caaataaaca caagaggaag tggaaactgg ccaaaggagt     300
ggaaagcagc cagacagaca tgttttgcga gcctaggaat cttggccttg tccccagtta     360
aactggacaa aggccatggt tctgcgccag ctgtcacgac aagcttctgt gaaagttagt     420
aaaacctgga ctggaacaaa aaaagagct cagaggattt ttatttttat tttagagctt     480
ttgctggaat tttgtagagg tgaagacagt gtagacggga aaaacaaaag taccactgct     540
ttacctgctg taaaagactc tgtaaaagac tcctaggtaa gtaatcccct ttttttttgta     600
tttccaggtt gatgggtgct gctctagcac ttttggggga cctagttgcc agtgtatctg     660
aggctgctgc tgccacagga ttttcagtgg ctgaaattgc tgctgggag ctgctgctg     720
ctatagaagt tcaaattgca tcccttgcta ctgcagaggg cataacaagt acctcagagg     780
ctatagctgc tataggccta actcctcaaa catatgctgt aattgctggt gctcctgggg     840
ctattgctgg gtttgctgct ttaattcaaa ctgttactgg tattagttcc ttggctcaag     900
tagggtatag gttttttagt gattgggatc acaaagtttc cactgtaggc ctctatcagc     960
aatcaggcat ggctttggaa ttgtttaacc cagatgagta ctatgatatt ttgttcctg    1020
gtgtaaatac ttttgtaaat aatattcaat accttgatcc taggcattgg ggtccttcct    1080
tgtttgctac tatttcccag gctttgtggc atgttattag ggatgatata cctgctataa    1140
cctcacaaga attgcaaaga agaacagaaa gatttttttag agactccttg gctagatttt    1200
tggaggaaac tacctggaca attgtaaatg cccctatgaa cttttataat tatattcaag    1260
aatattattc tgatcttttcc cctattaggc cctcaatggt tagacaagtg gctgaaaggg    1320
aaggtacccg tgtacatttt ggccatactt atagtataga tgatgctgac agtatagaag    1380
aagttacaca aagaatggac ttaagaaatc aacaaactgt acattcagga gagtttatag    1440
aaaaaactat tgccccagga ggtgctaatc aaagaactgc tcctcaatgg atgttgcctt    1500
tacttctagg cctgtacggg actgtaacac ctgctcttga agcatatgaa gatggcccca    1560
accaaaagaa aaggagagtg tccagggggca gctcccaaaa agccagagga acccgtgcaa    1620
gtgccaaaac tactaataaa aggaggagta gaagttctag aagttaaaac tggggtagat    1680
gctataacag aggtagaatg cttcctaaac ccagaaatgg gggatccaga tgaaaaccctt    1740
aggggcttta gtctaaagct aagtgctgaa atgactttta gcagtgatag cccagaaaga    1800
aaaatgcttc cctgttacag cacagcaaga attcccctcc ccaatttaaa tgaggaccta    1860
acctgtggaa atctactgat gtgggaggct gtaactgtac aaacagaggt cattggaata    1920
actagcatgc ttaaccttca tgcagggtca caaaaagtgc atgagcatgg tggaggtaaa    1980
cctattcaag gcagtaattt ccacttcttt gctgttggtg agacccctt ggaaatgcag    2040
ggagtgctaa tgaattacag gaccaagtac ccagatggta ctataacccc aaaaaaccca    2100
acagcccagt cccaggtaat gaatactgac cataaggcct atttggacaa aaacaatgct    2160
tatccagttg agtgctgggt tcctgatccc agtagaaatg aaaatactag gtatttgga    2220
actttcacag gaggggaaaa tgttcccccca gtacttcatg tgaccaacac agctaccaca    2280
```

-continued

```
gtgttgctag atgaacaggg tgtggggcct ctttgtaaag ctgatagcct gtatgtttca    2340
gctgctgata tttgtggcct gtttactaac agctctggaa cacaacagtg gagaggcctt    2400
gcaagatatt ttaagattcg cctgagaaaa agatctgtaa aaaatcctta cccaatttcc    2460
tttttgctga gtgaccttat aaacaggaga acccagagag tggatgggca gcctatgtat    2520
ggtatggaat cccaggtaga agaggtcagg gtgtttgatg gcacagaaag acttccaggg    2580
gacccagata tgataagata tattgataaa caaggacaat tgcaaaccaa atgctttaa     2640 acaggtgctt ttattgtaca tatacattta ataaatgctg cttttgtata agccacttt     2700 aagcttgtgt tattttgggg gtggtgtttt aggcctttta aaacattgaa agcctttaca    2760
caaatgcaac tcttgactat ggggtctga cctttgggaa tcttcagcag gggctgaagt     2820
atctgagact tgggaagagc attgtgattg ggattcagtg cttgatccat gtccagagtc    2880
ttcagtttct gaatcttctt ctcttgtgat atcaagaata catttcccca tgcatatatt    2940
atatttcatc cttgaaaaag tatacatact tatctcagaa tccagccttt ccttccattc    3000
aacaattcta gattgtatat ctgttgcaaa atcagctaca ggcctaaacc aaattagcag    3060
tagcaacaag gtcattccac tttgtaaaat tcttttttca agtaagaact ctgagttttg    3120
taaggatttt cttaaatata ttttgggtct aaaatctatc tgtcttacaa atctagcctg    3180
cagggtttta ggaacaggat actcattcat tgtaaccagg cctggtggaa atatttgggt    3240 cctttgttt aaatgtttct tttctaaatt aaccttaaca cttccatcta ataatctct      3300 caaactgtct aaattgttta ttccatgtcc tgaaggcaaa tcctttgatt cagccccagt    3360 tcctttaca tcttcaaaaa caaccatgta ctgatctata gctacaccta gttcaaaggt     3420
tagcctttcc atgggtaggt ttacatttaa ggctttacct ccacacaaat ctaataaccc    3480
tgcagctagt gttgtttttc cactatcaat gggacccttta ataaccagt atcttctttt    3540 aggtacatta aaacaatac agtgcaaaaa atcaaatata acagaatcca ttttaggtag    3600
caaacagtgc agccaagcaa cacctgccat atattgttcc agtacagcat ttccatgagc   3660
tccaaatatt aaatccattc tatctaatat atgattaaat cttttctgtta gcatttcttc   3720 tctggtcata tgaagggtat ctactctttt tttagctaaa actgtatcta ctgcttgctg   3780
acaaatactt ttttgatttt tactttctgc aaaaatagta gcatttgcaa aatgcttttc    3840
atgatactta aagtgataag gttggtcttt tttctgacac tttttacact cttctacatt    3900
gtattgaaat tctaaataca tacccaataa taaaaacaca tcctcacact ttgtctctac    3960
tgcatactca gtaattaatt tccaagacac ctgctttgtt tcttcaggct cttctgggtt    4020
aaaatcatgc tcctttaagc ccccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaaagtta caggatattt    4260
ttccataagt tttttataca gaatttgagc tttttcttta gtagtataca cagcaaagca    4320
ggcaagggtt ctattactaa atacagcttg actaagaaac tggtgtagat cagaaggaaa    4380
gtctttaggg tcttctacct ttctcttttt cttgggtggt gtggagtgtt gagaatctgc    4440
tgttgcttct tcatcactgg caaacatatc ttcatggcaa aataaatctt catcccattt    4500
ttcattaaag gagctccacc aggactccca ctcttctgtt ccataggttg gcacctataa    4560
aaaaaaaaat tacttagggc ctttaaatat tttcttattt atctaaatat aagttagtta    4620
ccttaaagct ttagatctct gaagggagtt tctccaatta tttggaccca ccattgcaga    4680
```

```
gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg acagaaggc ttttttggaac aaataggcca atccttgcag    4860
tacggggtat ctgggcaaag aggcaaatca gcacaaacct ctgagctact ccaggttcca    4920
aaatcaggct gatgagctac ctttacatcc tgctccattt ttttatataa agtattcatt    4980
ctcttcattt tatcctcgtc gccccctttg tcagggtgaa attccttaca cttccttaaa    5040
taggcttttc tcattaaggg aaggtttccc caggcagctc tttcaaggcc taaaaggtcc    5100
atgagctcca tggattcttc cctgttaagc actttatcca t                       5141

<210> SEQ ID NO 31
<211> LENGTH: 5141
<212> TYPE: DNA
<213> ORGANISM: Human polyomavirus 1
<220> FEATURE:
<223> OTHER INFORMATION: Type BK virus

<400> SEQUENCE: 31
ttttgcaaaa attgcaaaag aatagggatt tccccaaata ttttttgctag gcctcagaaa      60 aagcctccac acccttacta cttgagagaa agggtggagg cagaggcggc ctcggcctct     120
tatatattat aaaaaaaaag gccacaggga ggagctgcta acccatggaa tgtagccaaa     180
ccatgacctc aggaaggaaa gtgcatgact gggcagccag ccagtggcag ttaatagtga     240
aaccccgccc ctaaaattct caaataaaca caagagggag tggaaactgg ccaaaggagt     300
ggaaagcagc cagacagaca tgttttgcga gcctaggaat cttggccttg tccccagtta     360
aactggacaa aggccatggt tctgcgccag ctgtcacgac aagcttctgt gaaagttagt     420
aaaacctgga ctgaacaaa aaaaagagct cagaggattt ttatttttat tttagagctt     480
ttgctggaat tttgtagagg tgaagacagt gtagacggga aaaacaaaag taccactgct     540
ttacctgctg taaaagactc tgtaaaagac tcctaggtaa gtaatccctt ttttttttgta     600 tttccaggtt gatgggtgct gctctagcac ttttgggggga cctagttgcc agtgtatctg     660
aggctgctgc tgccacagga ttttcagtgg ctgaaattgc tgctggggag gctgctgctg     720
ctatagaagt tcaaattgca tcccttgcta ctgtagaggg cataacaagt acctcagagg     780
ctatagctgc tataggccta actcctcaaa catatgctgt aattgctggt gctcctgggg     840
ctattgctgg gtttgctgct ttaattcaaa ctgttactgg tattagttcc ttggctcaag     900
tagggtatag gttttttagt gattgggatc acaaagtttc cactgtaggc ctctatcagc     960
aatcaggcat ggctttggaa ttgtttaacc cagatgagta ctatgatatt ttgtttcctg    1020
gtgtaaatac ttttgtaaat aatattcaat accttgatcc taggcattgg ggtccttcct    1080
tgtttgctac tatttcccag gctttgtggc atgttattag ggatgatata cctgctataa    1140
cctcacaaga attgcaaaga agaacagaaa gattttttag agactccttg gctagatttt    1200
tggaggaaac tacctggaca attgtaaatg cccctatgaa cttttataat tatattcaag    1260
aatattattc tgatctttcc cctattaggc cctcaatggt tagacaagtg gctgaaaggg    1320
aaggtacccg tgtacatttt ggccatactt atagtataga tgatgctgac agtatagaag    1380
aagttacaca agaatggac ttaagaaatc aacaaactgt acattcagga gagtttatag    1440
aaaaaactat tgccccagga ggtgctaatc aaagaactgc tcctcaatgg atgttgcctt    1500
tacttctagg cctgtacggg actgtaacac ctgctcttga agcatatgaa gatggcccca    1560
```

```
accaaaagaa aaggagagtg tccaggggca gctcccaaaa agccaaagga acccgtgcaa    1620
gtgccaaaac tactaataaa aggaggagta gaagttctag aagttaaaac tggggtagat    1680
gctataacag aggtagaatg cttcctaaac ccagaaatgg gggatccaga tgaaaacctt    1740
aggggcttta gtctaaagct aagtgctgaa aatgacttta gcagtgatag cccagaaaga    1800
aaaatgcttc cctgttacag cacagcaaga attcccctcc ccaatttaaa tgaggaccta    1860
acctgtggaa atctactgat gtgggaggct gtaactgtac aaacagaggt cattggaata    1920
actagcatgc ttaaccttca tgcagggtca caaaaagtgc atgagcatgg tggaggtaaa    1980
cctattcaag gcagtaattt ccacttcttt gctgttggtg gagacccctt ggaaatgcag    2040
ggagtgctaa tgaattacag gaccaagtac ccagatggta ctataacccc aaaaaaccca    2100
acagcccagt cccaggtaat gaatactgac cataaggcct atttggacaa aaacaatgct    2160
tatccagttg agtgctgggt tcctgatccc agtagaaatg aaaatactag gtattttgga    2220
actttcacag gaggggaaaa tgttccccca gtacttcatg tgaccaacac agctaccaca    2280
gtgttgctag atgaacaggg tgtggggcct cttttgtaaag ctgatagcct gtatgtttca    2340
gctgctgata tttgtggcct gtttactaac agctctggaa cacaacagtg gagaggcctt    2400
gcaagatatt ttaagattcg cctgagaaaa agatctgtaa aaaatcctta cccaatttcc    2460
ttttttgctga gtgaccttat aaacaggaga acccagagag tggatgggca gcctatgtat    2520
ggtatggaat cccaggtaga agaggtcagg gtgtttgatg gcacagaaag acttccaggg    2580
gacccagata tgataagata tattgataaa caaggacaat gcaaaccaa aatgctttaa    2640
acaggtgctt ttattgtaca tatacattta ataaatgctg cttttgtata agccactttt    2700
aagcttgtgt tattttgggg gtggtgtttt aggcctttta aaacattgaa agcctttaca    2760
caaatgcaac tcttgactat gggggtctga cctttgggaa tcttcagcag gggctgaagt    2820
atctgagact tgggaagagc attgtgattg ggattcagtg cttgatccat gtccagagtc    2880
ttcagttttct gaatcttctt ctcttgtgat accaagaata catttcccca tgcatatatt    2940
atatttcatc cttgaaaaag tatacatact tatctcagaa tccagccttt ccttccattc    3000
aacaattcta gattgtatat ctgttgcaaa atcagctaca ggcctaaacc aaattagcag    3060
tagcaacaag gtcattccac tttgtagaat tcttttttca agtaagaact ctgagttttg    3120
taaggatttt cttaaatata ttttgggtct aaaatctatc tgtcttacaa atctagcctg    3180
cagggtttta ggaacaggat actcattcat tgtaaccagg cctggtggaa atatttgggt    3240
tcttttgttt aaatgtttct tttctaaatt aaccttaaca cttccatcta ataatctct    3300
caaactgtct aaattgttta ttccatgtcc tgaaggcaaa tcctttgatt cagccccagt    3360
tcctttaca tcttcaaaaa caaccatgta ctgatctata gctacaccta gttcaaaggt    3420
tagcctttcc atgggtaggt ttacatttaa ggctttacct ccacacaaat ctaataaccc    3480
tgcagctagt gttgtttttc cactatcaat gggaccttta aataaccagt atcttctttt    3540
aggtacatta aaaacaatac agtgcaaaaa atcaaatata acagaatcca ttttaggtag    3600
caaacagtgc agccaagcaa cacctgccat atattgttcc agtacagcat ttccatgagc    3660
tccaaatatc aaatccattt tatctaatat atgattaaat ctttctgtta gcatttcttc    3720
tctggtcata tgaagggtat ctactctttt tttagctaaa actgtatcta ctgcttgctg    3780
acaaatactt ttttgatttt tactttctgc aaaaatagta gcatttgcaa aatgcttttc    3840
atgatactta aagtgataag gttggtcttt tttctgacac ttttacact cttctacatt    3900
gtattgaaat tctaaataca tacccaataa taaaaacaca tcctcacact ttgtctctac    3960
```

```
tgcatactca gtaattaatt tccaagacac ctgctttgtt tcttcaggct cttctgggtt    4020
aaaatcatgc tcctttaagc ccccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaaagtta cagaatattt    4260
ttccataagt tttttataca gaatttgagc tttttcttta gtagtataca cagcaaagca    4320
ggcaagggtt ctattactaa atacagcttg actaagaaac tggtgtagat cagagggaaa    4380
gtctttaggg tcttctacct ttctcttttt cttgggtggt gtggagtgtt gagaatctgc    4440
tgttgcttct tcatcactgg caaacatatc ttcatggcaa ataaatcttt catcccattt    4500
ttcattaaag gagctccacc aggactccca ctcttctgtt ccataggttg cacctataa     4560 aaaaaataat tacttagggc ctttaaatat tttcttattt atctaaatat aagttagtta    4620
ccttaaagct ttagatctct gaagggagtt ctccaatta tttggaccca ccattgcaga     4680
gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg cacagaaggc ttttggaac aaataggcca atccttgcag     4860
tacagggtat ctgggcaaag aggaaaatca gcacaaacct ctgagctact ccaggttcca    4920
aaatcaggct gatgagctac ctttacatcc tgctccattt ttttatataa agtattcatt    4980
ctcttcattt tatcctcgtc gcccccttg tcagggtgaa attccttaca cttccttaaa     5040
taggcttttc tcattaaggg aaggtttccc caggcagctc tttcaaggcc taaaaggtcc    5100
atgagctcca tggattcttc cctgttaagc actttatcca t                       5141
```

<210> SEQ ID NO 32
<211> LENGTH: 5141
<212> TYPE: DNA
<213> ORGANISM: Human polyomavirus 1
<220> FEATURE:
<223> OTHER INFORMATION: Type BK virus

<400> SEQUENCE: 32

```
ttttgcaaaa attgcaaaag aatagggatt tccccaaata tttttgctag gcctcagaaa      60
aagcctccac acccttacta cttgagagaa agggtggagg cagaggcggc ctcggcctct     120
tatatattat aaaaaaaaag gccacaggga ggagctgcta acccatggaa tgtagccaaa     180
ccatgacctc aggaaggaaa gtgcatgact gggcagccag ccagtggcag ttaatagtga     240
aaccccgccc ctaaaattct caaataaaca caagaggaag tggaaactgg ccaaaggagt     300
ggaaagcagc cagacagaca tgttttgcga gcctaggaat cttggccttg tcccagtta     360 aactggacaa aggccatggt tctgcgccag ctgtcacgac aagcttctgt gaaagttagt     420
aaaacctgga ctggaacaaa aaaaagagct cagaggattt ttattttat tttagagctt     480 ttgctggaat tttgtagagg tgaagacagt gtagacggga aaaacaaaag taccactgct     540
ttacctgctg taaagactc tgtaaaagac tcctaggtaa gtaatccctt tttttttgta     600
tttccaggtt gatgggtgct gctctagcac ttttggggga cctagttgcc agtgtatctg     660
aggctgctgc tgccacagga ttttcagtgg ctgaaattgc tgctggggag gctgctgctg     720
ctatagaagt tcaaattgca tcccttgcta ctgtagaggg cataacaagt acctcagagg     780
ctatagctgc tataggccta actcctcaaa catatgctgt aattgctggt gctcctgggg     840
```

```
ctattgctgg gtttgctgct ttaattcaaa ctgttactgg tattagttcc ttggctcaag    900
tagggtatag gttttttagt gattgggatc acaaagtttc cactgtaggc ctctatcagc    960
aatcaggcat ggctttggaa ttgtttaacc cagatgagta ctatgatatt ttgtttcctg   1020
gtgtaaatac ttttgtaaat aatattcaat accttgatcc taggcattgg ggtccttcct   1080
tgtttgctac tatttcccag gctttgtggc atgttattag ggatgatata cctgctatga   1140
cctcacaaga attgcaaaga agaacagaaa gatttttttag agactccttg gctagatttt   1200
tggaggaaac tacctggaca attgtaaatg ccctatgaa cttttataat tatattcaag   1260
aatattattc tgatctttcc cctattaggc cctcaatggt tagacaagtg gctgaaaggg   1320
aaggtacccg tgtacatttt ggccatactt atagtataga tgatgctgac agtatagaag   1380
aagttacaca aagaatggac ttaagaaatc aacaaactgt acattcagga gagtttatag   1440
aaaaaactat tgccccagga ggtgctaatc aaagaactgc tcctcaatgg atgttgcctt   1500
tacttctagg cctgtacggg actgtaacac ctgctcttga agcatatgaa gatggcccca   1560
accaaaagaa aaggagagtg tccaggggca gctcccaaaa agccaaagga acccgtgcaa   1620
gtgccaaaac tactaataaa aggaggagta gaagttctag aagttaaaac tggggtagat   1680
gctataacag aggtagaatg cttcctaaac ccagaaatgg gggatccaga tgaaaacctt   1740
aggggcttta gtctaaagct aagtgctgaa aatgacttta gcagtgatag cccagaaaga   1800
aaaatgcttc cctgttacag cacagcaaga attcccctcc ccaatttaaa tgaggaccta   1860
acctgtggaa atctactgat gtgggaggct gtaactgtac aaacagaggt tactggaata   1920
actagcatgc ttaaccttca tgcagggtca caaaaagtgc atgagcatgg tggaggtaaa   1980
cctattcaag gcagtaattt ccacttcttt gctgttggtg agaccccctt ggaaatgcag   2040
ggagtgctaa tgaattacag gaccaagtac ccagatggta ctataacccc aaaaaaccca   2100
acagcccagt cccaggtaat gaatactgac cataaggcct atttggacaa aaacaatgct   2160
tatccagttg agtgctgggt tcctgatccc agtagaaatg aaaatactag gtattttgga   2220
actttcacag gaggggaaaa tgttcccca gtacttcatg tgaccaacac agctaccaca   2280
gtgttgctag atgaacaggg tgtggggcct ctttgtaaag ctgatggcct gtatgtttca   2340
gctgctgata tttgtggcct gtttactaac agctctggaa cacaacagtg gagaggcctt   2400
gcaagatatt ttaagactcg cctgagaaaa agatctgtaa aaaatcctta cccaatttcc   2460
tctttgctga gtgaccttat aaacaggaga acccagagag tggatgggca gcctatgtat   2520
ggtatggaat cccaggtaga agaggtcagg gtgtttgatg gcacagaaag acttccaggg   2580
gacccagata tgataagata tattgataaa caaggacaat gcaaaccaa atgctttaa   2640 acaggtgctt ttattgtaca tatacattta ataaatgctg cttttgtata agccactttt   2700
aagcttgtgt tattttgggg gtggtgtttt aggcctttta aaacattgaa agcctttaca   2760
caaatgcaac tcttgactat ggggtgtctga cctttgggaa tcttcagcag gggctgaagt   2820
atctgagact tgggaagagc attgtgattg ggattcagtg cttgatccat gtccagagtc   2880
ttcagtttct gaatcttctt ctcttgtgat atcaagaata catttcccca tgcatatatt   2940
atatttcatc cttgaaaaag tatacatact tatctcagaa tccagccttt tcttccattc   3000
aacaattcta gattgtatat ctgttgcaaa atcagctaca ggcctaaacc aaattagcag   3060
tagcaacaag gtcattccac tttgtaaaat tctttttttca agtaagaact ctgagttttg   3120
taaggatttt cttaaatata ttttgggtct aaaatctatc tgtcttacaa atctagcctg   3180
cagggtttta ggaacaggat actcattcat tgtaaccagg cctggtggaa atatttgggt   3240
```

```
tcttttgttt aaatgtttct tttctaaatt aaccttaaca cttccaccta aataatctct    3300
caaactgtct aaattgttta ttccatgtcc tgaaggcaaa tcctttgatt cagccccagt    3360
tccttttaca tcttcaaaaa caaccacgta ctgatctata gctacaccta gttcaaaggt    3420
tagcctttcc atgggtaggt ttacatttaa ggctttacct ccacacaaat ctaataaccc    3480
tgcagctagt gttgttttc cactatcagt gggacccttta aataaccagt atcttctttt    3540
aggtacatta aaaacaatac agtgcaaaaa atcaaatata acagaatcca ttttaggtag    3600
caaacagtgc agccaagcaa cacctgccat atattgttcc agtacagcat tccatgagc    3660 tccaaatatt aaatccattt tatctaatat atgattaaat ctttctgtta gcatttcttc    3720
tctggtcata tgaagggtat ctactctttt tttagctaaa actgtatcta ctgcttgctg    3780
acaaatactt ttttgatttt tactttctgc aaaaatagta gcatttgcaa aatgcttttc    3840
atgatactta aagtgataag gttggtcttt tttctgacac tttttgcact cttctacatt    3900
gtattgaaat ctaaataca tacccaataa taaaaacaca tcctcacact ttgtctctac    3960
tgcatactca gtaattaatt tccaagacac ctgctttgtt tcttcaggct cttctgggtt    4020
aaaatcatgc tccttaagc cccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaaagtta cagaatattt    4260
ttccataagt tttttataca gaatttgagc tttttcttta gtagtataca cagcaaagca    4320
ggcaagggtt ctattactaa atacagcttg actaagaaac tggtgtagat cagaaggaaa    4380
gtctttaggg tcttctacct ctctcttttt cttgggtggt gtggagtgtt gagaatctgc    4440
tgttgcttct tcatcactgg caaacatatc ttcatggcaa aataaatctt catcccattt    4500
ttcattaaag gagctccacc aggactccca ctcttctgtt ccataggttg gcacctataa    4560
aaaaaataat tacttagggc ctttaaatat tttcttattt atctaaatat aagttagtta    4620
ccttaaagct ttagatctct gaagggagtt tctccaatta tttggaccca ccattgcaga    4680
gtttcttcag ctaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg cacagaaggc ttttggaac aaataggcca ttccttgcag    4860
tacagggtat ctgggcaaag aggaaaatca gcacaaacct ctgagctact ccaggttcca    4920
aaatcaggct gatgagctac ctttacatcc tgctccattt ttatataa agtattcatt    4980 ctcttcattt tatcctcgtc gccccctttg tcagggtgaa attccttaca cttccttaaa    5040
taggcttttc tcattaaggg aaggtttccc caggcagctc tttcaaggcc taaaaggtcc    5100
atgagctcca tggattcttc cctgttaagc actttatcca t                        5141
```

<210> SEQ ID NO 33
<211> LENGTH: 5092
<212> TYPE: DNA
<213> ORGANISM: Human polyomavirus 1
<220> FEATURE:
<223> OTHER INFORMATION: Type BK virus

<400> SEQUENCE: 33

```
ttttgcaaaa attgcaaaag aataggatt tccccaaata gttttgctag gcctcagaaa      60
aagcctccac acccttacta cttgaaagaa agggtggagg cagaggcggc ctcggcctct    120
```

```
tatatattat aaaaaaaaag gccacaggga ggagctgctt acccatggaa tgcagccaaa      180
ccatgacctc aggaaggaaa gtgcatgact gggcagccag ccaagaggaa gtggaaactg      240
gccaaaggag tggaaagcag ccagacagac atgttttgcg ggcctaggaa tcttggcctt      300
gtccccagtt aaactggaca aaggccatgg ttctgcgcca gctgtcacga caagcttctg      360
tgaaacttgg taaaacctgg actggaacaa aaaaagagc tcagaggatt tttatttta      420 ttttagagct tttgctggaa ttttgtagag gtgaagacag tgtagacggg aaaaacaaaa      480
gtaccactgc tttacctgct gtaaaagact ctgtaaaaga ctcctaggta agtaatccct      540
ttttttttgt atttccaggt tgatgggtgc tgctctagca cttttggggg acctagttgc      600
cagtgtatct gaggctgctg ctgccacagg attttcagtg gctgaaattg ctgctgggga      660
ggctgctgct gctatagaag ttcaaattgc atcccttgct actgtagagg cataacaag      720 tacctcagag gctatagctg ctataggcct aactcctcaa acatatgctg taattgctgg      780
tgctcctggg gctattgctg ggtttgctgc tttaattcaa actgttactg gtattagttc      840
cttggctcaa gtagggtata ggttttttag tgattgggat cacaaagttt ccactgtagg      900
cctctatcag caatcaggca tggctttgga attgtttaac ccagatgagt actatgatat      960
attgttccct ggtgtaaata cttttgtaaa taatattcaa taccttgatc ctaggcattg     1020
gggtccttct ttgtttgcta ctatttctca ggctttgtgg catgttatta gggatgatat     1080
acctgctata acctcacaag aattgcaaag aagaacagaa agatttttta gagactcctt     1140
ggctagattt ttggaggaaa ctacctggac aattgtaaat gccctatga acttttataa     1200 ttatattcaa gaatattatt ctgatctttc ccctattagg cccttaatgg ttagacaagt     1260
agctgaaagg gaaggtaccc gtgtacattt tggccatact tatagtatag atgatgctga     1320
cagtatagaa gaagttacac aaagaatgga cttaagaaat caacaaactg tacattcagg     1380
agagtttata gaaaaaacta ttgccccagg aggtgctaat caaagaactg ctcctcaatg     1440
gatgttgcct ttacttctag gcctgtacgg gactgtaaca cctgctcttg aagcatatga     1500
agatggcccc aacaaaaaga aaaggagagt gtccaggggc agctcccaaa aagccaaagg     1560
aacccgtgca agtgccaaaa ctactaataa aaggaggagt agaagttcta gaagttaaaa     1620
ctgggctaga tgctataaca gaggtagaat gcttcctaaa cccagaaatg ggggatccag     1680
atgaaaacct tagggctttt agtctaaagc taagtgctga aaatgacttt agcagtgata     1740
gcccagaaag aaaaatgctt ccctgttaca gcacagcaag aattcccctc cccaatttaa     1800
atgaggacct aacctgtgga aatctactga tgtgggaggc tgtaacagta caaacagagg     1860
tcattggaat aactagcatg cttaaccttc atgcagggtc acaaaagtg catgagcatg      1920 gtggaggtaa acctattcaa ggcagtaatt tccactttt tgctgttggt ggagacccct     1980
tggaaatgca gggagtgcta atgaattaca ggacaaagta cccagaaggt actataaccc     2040 caaaaaccc aacagcccag tcccaagtaa tgaatactga ccataaggcc tatttggaca      2100
aaaacaatgc ttatccagtt gagtgctgga ttcctgatcc cagtagaaat gaaaatacta     2160
ggtattttgg gactttcaca ggaggggaaa atgttccccc agtacttcat gtgaccaaca     2220
cagctaccac agtgttgcta gatgaacagg gtgtggggcc tctttgtaaa gctgatagcc     2280
tgtatgtttc agctgctgat atttgtggcc tgtttactaa cagctctgga acacaacagt     2340
ggagaggcct tgcaagatat tttaagattc gcctgagaaa aagatctgta aaaaatcctt     2400
acccaatttc cttttttgcta agtgacctta taaacagggg aacccagaga gtggatgggc     2460
agcctatgta tggtatggaa tcccaggtag aagaggtcag ggtgtttgat ggcacagaaa     2520
```

```
gacttccagg ggacccagat atgataagat atattgacaa acaaggacaa ttgcaaacta    2580
aaatggttta aacaggtgct tttattgtac atatacattt aataaatgct gcttttgtat    2640
aagccagttc taagcttgtg ttattttggg ggtggtgttt taggccttttt aaaacactga   2700 aagcctttac acaaatgcaa ctcttgacta tgggggtctg acctttggga atcttcagca    2760
ggggctgaag tatctgagac ttgggaagag cattgtgatt gggattcagt gcttgatcca    2820
tgtccagagt cttcagtttc tgaatcttct tctcttgtga tatcaagaat acatttcccc    2880
atgcatatat tatatttcat ccttgaaaaa gtatacatac ttatctcaga atccagcctt    2940
tccttccatt caacaattct agattgtata tctgttgcaa atcagctac aggcctaaac     3000 caaattagca gtagcaacaa ggtcattcca ctttgtaaaa ttcttttttc aagtaagaac    3060
tctgagtttt gtaaggattt tcttaaatat attttgggcc taaaatctat ctgtcttaca    3120
aatctagcct gcagggtttt agggacagga tactcattca ttgtaaccag gcctggtgga    3180
aatatttggg ttcttttgtt taaatgtttc ttttctaaat taaccttaac acttccatct    3240
aaataatctc tcaaactgtc taaattgttt attccatgtc ctgaaggcaa atcctttgat    3300
tcagctcctg ttccttttac atcttcaaaa acaaccatgt actgatctat agctacacct    3360
agttcaaagg tcagccttc catgggtagg tttacattta aagctttacc tccacacaaa     3420
tctaataacc ctgcagctag tgttgttttt ccactatcaa tgggaccttt aaataaccag    3480
tatcttcttt taggtacatt aaaaacaata cagtgcaaaa aatcaaatat aacagaatcc    3540
attttaggta acaaacagtg cagccaagca acacctgcca tatattgttc taatacagca    3600
tttccatgag ccccaaatat taaatccatt ttatctaata tatgattaaa tctttctgtt    3660
agcatttctt ctctagtcat atggaggcta tctactcttt ttttagctaa aactgtatct    3720
actgcttgct gacaaatact ttttttgattt ttactttctg caaagatagt agcatttgca   3780
aaatgctttt catgatactt aaagtgataa ggttggtctt ttttctgaca cttttttacac   3840 tcctctacat tgtattgaaa ttctaaatac atacctaata ataaaaacac atcctcacac    3900
tttgtttcta ctgcatactc agtaattaat ttccaagaga cctgctttgt ttcttcaggc    3960
tcttctgggt taaaatcatg ctcctttaag ccccccttgaa tgcttcttc tattgtatgg    4020 tatggatctc tagttaaggc actatatagt aagtattcct tattaacacc cttacaaatt    4080
aaaaaactaa aggtacacag cttttgacag aaattattaa ttgcagaaac tctatgtcta    4140
tgtggagtta aaaagaatat aatattatgc ccagcacaca tgtgtctact aataaaagtt    4200
acagaatatt tttccataag ttttttatac agaatttgag cttttctttt agtagtatac    4260
acagcaaagc aggcaagggt tctattacta aatacagctt gactaagaaa ctggtgtaga    4320
tcacaaggaa agtctttagg gtcttctacc tttctttttt tcttgggtgg tgttgagtgt    4380
tgagaatctg ctgttgcttc ttcatcactg gcaaacatat cttcatggca aaataaatct    4440
tcatcccatt tttcattaaa ggagctccac caggactccc actcttctgt tccataggtt    4500
ggcacctata aaacaaataa ttacttaggg ccttttaaata ttttattatt tatttaaata    4560
taaggtagtt accttaaagc tttagatctc tgaagggagt ttctccaatt atttggaccc    4620
accattgcag agtttcttca gttaggtcta agccaaacca ctgtgtgaag cagtcaatgc    4680
agtagcaatc tatccaaacc aagggctctt ttcttaaaaa ttttctattt aaatgcctta    4740
atctaagctg acatagcatg caaggacagt gcacagaagg cttttggaa caaataggcc     4800 attccttgca gtacagggta tctgggcaaa gaggaaaatc agcacaaacc tctgagctac    4860
```

```
tccaggttcc aaaatcaggc tgatgagcta cctttacatc ttgctccatt ttttatata      4920 aagtattcat tctcttcatt ttatcctcgt cgcccccttt gtcagggtga aattccttac      4980
acttccttaa ataggctttt ctcattaagg aaaggtttcc ccaggcagct ctttcaaggc      5040
ccaaaaggtc catgagctcc atggattctt ccctgttaag cactttatcc at              5092
```

<210> SEQ ID NO 34
<211> LENGTH: 5141
<212> TYPE: DNA
<213> ORGANISM: Human polyomavirus 1
<220> FEATURE:
<223> OTHER INFORMATION: Type BK virus

<400> SEQUENCE: 34

```
ttttgcaaaa attgcaaaag aatagggatt tccccaaata gttttgctag gcctcagaaa        60
aagcctccac acccttacta cttgaaagaa agggtggagg cagaggcggc ctcggcctct       120
tatatattat aaaaaaaaag gccacaggga ggagctgctt acccatggaa tgcagccaaa       180
ccatgacctc aggaaggaaa gtgcatgact gggcagccag ccagtggcag ttaatagtga       240
aaccccgccc ctgaaattct caaataaaca caagaggaag tggaaactgg ccaaaggagt       300
ggaaagcagc cagacagaca tgttttgcgg gcctaggaat cttggccttg tccccagtta       360
aactggacaa aggccatggt tctgcgccag ctgtcacgac aagcttctgt gaaacttggt       420
aaaacctgga ctgaacaaa aaaagagct cagaggattt ttattttat tttagagctt         480 ttgctggaat tttgtagagg tgaagacagt gtagacggga aaaacaaaag taccactgct       540
ttacctgctg taaaagactc tgtaaaagac tcctaggtaa gtaatccctt ttttttgta        600 tttccaggtt gatgggtgct gctctagcac ttttggggga cctagttgcc agtgtatctg       660
aggctgctgc tgccacagga ttttcagtgg ctgaaattgc tgctggggag ctgctgctg        720 ctatagaagt tcaaattgca tcccttgcta ctgtagaggg cataacaagt acctcagagg       780
ctatagctgc tataggccta actcctcaaa catatgctgt aattgctggt gctcctgggg       840
ctattgctgg gtttgctgct ttaattcaaa ctgttactgg tattagttcc ttggctcaag       900
tagggtatag gttttttagt gattgggatc acaaagtttc cactgtaggc ctctatcagc       960
aatcaggcat ggctttggaa ttgtttaacc cagatgagta ctatgatata ttgtttcctg      1020 gtgtaaaatac ttttgtaaat aatattcaat accttgatcc taggcattgg ggtccttctt     1080
tgtttgctac tatttctcag gctttgtggc atgttattag ggatgatata cctgctataa      1140
cctcacaaga attgcaaaga agaacagaaa gattttttag agactccttg gctagatttt      1200
tggaggaaac tacctggaca attgtaaatg cccctatgaa cttttataat tatattcaag      1260
aatattattc tgatctttcc cctattaggc cctcaatggt tagacaagta gctgaaaggg      1320
aaggtacccg tgtacatttt ggccatactt atagtataga ttatgctgac agtatagaag      1380
aagttacaca aagaatggac ttaagaaatc aacaaactgt acattcagga gagtttatag      1440
aaaaaactat tgccccagga ggtgctaatc aaagaactgc tcctcaatgg atgttgcctt      1500
tacttctagg cctgtacggg actgtaacac ctgctcttga agcatatgaa gatggcccca      1560
acaaaaagaa aaggagagtg tccaggggca gctcccaaaa agccaaagga acccgtgcaa      1620
gtgccaaaac tactaataaa aggaggagta gaagttctag aagttaaaac tgggctagat      1680
gctataacag aggtagaatg cttcctaaac ccagaaatgg gggatccaga tgaaaacctt     1740 agggggcttta gtctaaagct aagtgctgaa atgactttta gcagtgatag cccagaaaga      1800
aaaatgcttc cctgttacag cacagcaaga attcccctcc ccaatttaaa tgaggaccta     1860
```

```
acctgtggaa atctactgat gtgggaggct gtaacagtac aaacagaggt cattggaata   1920
actagcatgc ttaaccttca tgcagggtca caaaaagtgc atgagcatgg tggaggtaaa   1980
cctattcaag gcagtaattt ccactttttt gctgttggtg gagacccctt ggaaatgcag   2040
ggagtgctaa tgaattacag gacaaagtac ccagaaggta ctataacccc aaaaaaccca   2100
acagcccagt cccaagtaat gaatactgac cataaggcct atttggacaa aaacaatgct   2160
tatccagttg agtgctggat tcctgatccc agtagaaatg aaaatactag gtattttggg   2220
actttcacag gaggggaaaa tgttcccccca gtacttcatg tgaccaacac agctaccaca   2280
gtgttgctag atgaacaggg tgtggggcct ctttgtaaag ctgatagcct gtatgtttca   2340
gctgctgata tttgtggcct gtttactaac agctctggaa cacaacagtg gagaggcctt   2400
gcaagatatt ttaagattcg cctgagaaaa agatctgtaa aaaatcctta cccaatttcc   2460
tttttgctaa gtgaccttat aaacaggaga acccagagag tggatgggca gcctatgtat   2520
ggtatggaat cccaggtaga agaggtcagg gtgtttgatg gcacagaaag acttccaggg   2580
gacccagata tgataagata tattgacaaa caaggacaat gcaaactaa aatggtttaa   2640 acaggtgctt ttattgtaca tatacattta ataaatgctg cttttgtata agccagttct   2700
aagcttgtgt tattttgggg gtggtgtttt aggcctttta aaacactgaa agcctttaca   2760
caaatgcaac tcttgactat ggggggtctga ccttttgggaa tcttcagcag gggctgaagt   2820
atctgagact tgggaagagc attgtgattg ggattcagtg cttgatccat gtccagagtc   2880 ttcagttct gaatcttctt ctcttgtgat atcaagaata catttcccca tgcatatatt   2940
atatttcatc cttgaaaaag tatacatact tatctcagaa tccagccttt ccttccattc   3000
aacaattcta gattgtatat ctgttgcaaa atcagctaca ggcctaaacc aaattagcag   3060
tagcaacaag gtcattccac tttgtaaaat tctttttca gtaagaact ctgagttttg   3120 taaggatttt cttaaatata ttttgggcct aaaatctatc tgtcttacaa atctagcctg   3180 cagggttttta gggacaggat actcattcat tgtaaccagg cctggtggaa atatttgggt   3240
tcttttgttt aaatgtttct tttctaaatt aaccttaaca cttccatcta aataatctct   3300
caaactgtct aaattgttta ttccatgtcc tgaaggcaaa tcctttgatt cagctcctgt   3360
tccttttaca tcttcaaaaa caaccatgta ctgatctata gctacaccta gttcaaaggt   3420 cagccttttcc atgggtaggt ttacatttaa agctttacct ccacacaaat ctaataaccc   3480
tgcagctagt gttgtttttc cactatcaat gggaccttta ataaccagt atcttctttt   3540 aggtacatta aaaacaatac agtgcaaaaa atcaaatata acagaatcca ttttaggtaa   3600
caaacagtgc agccaagcaa cacctgccat atattgttct aatacagcat ttccatgagc   3660
cccaaatatt aaatccattt tatctaatat atgattaaat ctttctgtta gcatttcttc   3720
tctagtcata tgaaggctat ctactctttt tttagctaaa actgtatcta ctgcttgctg   3780
acaaatactt ttttgatttt tactttctgc aaagatagta gcatttgcaa aatgcttttc   3840
atgatactta aagtgataag gttggtcttt tttctgacac ttttttacact cctctacatt   3900 gtattgaaat tctaaatcac tacctaataa taaaaacaca tcctcacact ttgtttctac   3960
tgcatactca gtaattaatt tccaagagac ctgctttgtt tcttcaggct cttctgggtt   4020
aaaatcatgc tccttaagc ccccttgaat gctttcttct attgtatggt atggatctct   4080
agttaaggca ctatatagta agtattcctt attaacaccc ttacaaatta aaaaactaaa   4140
ggtacacagc ttttgacaga aattattaat tgcagaaact ctatgtctat gtggagttaa   4200
```

```
aaagaatata atattatgcc cagcacacat gtgtctacta ataaaagtta cagaatattt    4260
ttccataagt ttttatacag aatttgagc tttttcttta gtagtataca cagcaaagca    4320
ggcaagggtt ctattactaa atacagcttg actaagaaac tggtgtagat cacaaggaaa    4380
gtctttaggg tcttctacct ttctttttt cttgggtggt gttgagtgtt gagaatctgc    4440
tgttgcttct tcatcactgg caaacatatc ttcatggcaa ataaatctt catcccattt    4500 ttcattaaag gagctccacc aggactccca ctcttctgtt ccataggttg gcacctataa    4560
aacaaataat tacttagggc ctttaaatat tttattattt atttaaatat aaggtagtta    4620
ccttaaagct ttagatctct gaagggagtt tctccaatta tttggaccca ccattgcaga    4680
gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg cacagaaggc ttttggaac aaataggcca ttccttgcag    4860
tacagggtat ctgggcaaag aggaaaatca gcacaaacct ctgagctact ccaggttcca    4920
aaatcaggct gatgagctac ctttacatct tgctccattt ttttatataa agtattcatt    4980
ctcttcattt tatcctcgtc gccccctttg tcagggtgaa attccttaca cttccttaaa    5040
taggcttttc tcattaagga aaggtttccc caggcagctc tttcaaggcc caaaaggtcc    5100
atgagctcca tggattcttc cctgttaagc actttatcca t                       5141

<210> SEQ ID NO 35
<211> LENGTH: 5141
<212> TYPE: DNA
<213> ORGANISM: Human polyomavirus 1
<220> FEATURE:
<223> OTHER INFORMATION: Type BK virus

<400> SEQUENCE: 35
ttttgcaaaa attgcaaaag aatagggatt tccccaaata gttttgctag gcctcagaaa      60
aagcctccac acccttacta cttgaaagaa agggtggagg cagaggcggc ctcggcctct     120
tatatattat aaaaaaaaag gccacaggga ggagctgctt acccatggaa tgcagccaaa     180
ccatgacctc aggaaggaaa gtgcatgact gggcagccag ccagtggcag ttaatagtga     240
aaccccgccc ctgaaattct caaataaaca caagaggaag tggaaactgg ccaaaggagt     300
ggaaagcagc cagacagaca tgttttgcgg gcctaggaat cttggccttg tcccagtta     360 aactggacaa aggccatggt tctgcgccag ctgtcacgac aggcttctgt gaaacttggt     420
aaaacctgga ctggaacaaa aaaagagct cagaggattt ttatttttat tttagagctt     480
ttgctggaat tttgtagagg tgaagacagt gtagacggga aaaacaaaag taccactgct     540
ttacctgctg taaagactc tgtaaaagac tcctaggtaa gtaatccctt ttttttttgta     600 tttccaggtt gatgggtgct gctctagcac ttttggggga cctagttgcc agtgtatctg     660
aggctgctgc tgccacagga ttttcagtgg ctgaaattgc tgctggggag ctgctgctg     720 ctatagaagt tcaaattgca tcccttgcta ctgtagaggg cataacaagt acctcagagg     780
ctatagctgc tataggccta actcctcaaa catatgctgt aattgctggt gctcctgggg     840
ctattgctgg gttgctgct ttaattcaaa ctgttactgg tattagttcc ttggctcaag     900
tagggtatag gttttttagt gattgggatc acaaagtttc cactgtaggc ctctatcagc     960
aatcaggcat ggctttggaa ttgtttaacc cagatgagta ctatgatata ttgtttcctg    1020
gtgtaaaatc ttttgtaaat aatattcaat accttgatcc taggcattgg ggtccttctt    1080
tgtttgctac tatttctcag gctttgtggc atgttattag ggatgataa cctgctataa    1140
```

```
cctcacaaga attgcaaaga agaacagaaa gattttttag agactccttg gctagatttt      1200
tggaggaaac tacctggaca attgtaaatg ccccctatgaa cttttataat tatattcaag     1260
aatattattc tgatctttcc cctattaggc ccttaatggt tagacaagta gctgaaaggg      1320
aaggtacccg tgtacatttt ggccatgctt atagtataga tgatgctgac agtatagaag     1380
aagttacaca aagaatggac ttaagaaatc aacaaactgt acattcagga gagtttatag     1440
aaaaaactat tgccccagga ggtgctaatc aaagaactgc tcctcaatgg atgttgcctt     1500
tacttctagg cctgtacggg actgtaacac ctgctcttga agcatatgaa gatggcccca    1560
acaaaaagaa aaggagagtg tccaggggca gctcccaaaa agccaaagga acccgtgcaa    1620
gtgccaaaac tactaataaa aggaggagta gaagttctag aagttaaaac tgggctagat   1680
gctataacag aggtagaatg cttcctaaac ccagaaatgg gggatccaga tgaaaacctt   1740
aggggcttta gtctaaagct aagtgctgaa aatgacttta gcagtgatag cccagaaaga   1800
aaaatgcttc cctgttacag cacagcaaga attcccctcc ccaatttaaa tgaggaccta   1860
acctgtggaa atctactgat gtgggaggct gtaacagtac aaacagaggt cattggaata   1920
actagcatgc ttaaccttca tgcagggtca caaaaagtgc atgagcatgg tggaggtaaa   1980
cctattcaag gcagtaattt ccactttttt gctgttggtg gagacccctt ggaaatgcag   2040
ggagtgctaa tgaattacag gacaaagtac ccagaaggta ctataacccc aaaaaaccca   2100
acagcccagt cccaagtaat gaatactgac cataaggcct atttggacaa aaacaatgct   2160
tatccagttg agtgctggat tcctgatccc agtagaaatg aaaatactag gtattttggg   2220
actttcacag gaggggaaaa tgttcccccca gtacttcatg tgaccaacac agctaccaca   2280
gtgttgctag atgaacaggg tgtgggggcct ctttgtaaag ctgatagcct gtatgtttca   2340
gctgctgata tttgtggcct gtttactaac agctctggaa cacaacagtg gagaggcctt    2400
gcaagatatt ttaagattcg cctgagaaaa agatctgtaa aaaatcctta cccaatttcc   2460 ttttttgctaa gtgaccttat aaacaggaga acccagagag tggatgggca gcctatgtat   2520
ggtatggaat cccaggtaga agaggtcagg gtgtttgatg gcacagaaag acttccaggg   2580
gacccagata tgataagata tattgacaaa caaggacaat gcaaactaa aatgggttaa    2640 acaggtgctt ttattgtaca tatacatttta ataaatgctg cttttgtata agccagttct   2700
aagcttgtgt tattttgggg gtggtgtttt aggccttta aaacactgaa agcctttaca   2760
caaatgcaac tcttgactat gggggtctga cctttgggaa tcttcagcag gggctgaagt   2820
atctgagact tgggaagagc attgtgattg ggattcagtg cttgatccat gtccagagtc   2880
ttcagtttct gaatcttctt ctcttgtgat atcaagaata catttccca tgcatatatt    2940 atatttcatc cttgaaaaag tatacatact tatctcagaa tccagccttt ccttccattc   3000
aacaattcta gattgtatat ctgttgcaaa atcagctaca ggcctaaacc aaattagcag   3060
tagcaacaag gtcattccac tttgtaaaat tcttttttca gtaagaaact ctgagttttg   3120
taaggatttt cttaaatata ttttgggcct aaaatctatc tgtcttacaa atctagcctg   3180
cagggtttta gggacaggat actcattcat tgtaaccagg cctggtggaa atatttgggt   3240 tctttttgttt aaatgtttct tttctaaatt aaccttaaca cttccatcta aataatctct   3300
caaactgtct aaattgttta ttccatgtcc tgaaggcaaa tcctttgatt cagctcctgt   3360
tccttttaca tcttcaaaaa caaccatgta ctgatctata gctacaccta gttcaaaggt   3420 cagccttttcc atgggtaggt ttacatttaa agctttacct ccacacaaat ctaataaccc   3480
```

```
tgcagctagt gttgtttttc cactatcaat gggacctttta ataaccagt atcttctttt    3540 aggtacatta aaaacaatac agtgcaaaaa atcaaatata acagaatcca ttttaggtaa    3600
caaacagtgc agccaagcaa cacctgccat atattgttct aatacagcat tccatgagc    3660 cccaaatatt aaatccattt tatctaatat atgattaaat ctttctgtta gcatttcttc    3720
tctagtcata tgaaggctat ctactctttt tttagctaaa actgtatcta ctgcttgctg    3780
acaaatgctt ttttgatttt tactttctgc aaagatagta gcatttgcac aatgcttttc    3840
atgatactta aagtgataag gttggtcttt tttctgacac ttttacact cctctacatt    3900 gtattgaaat tctaaataca tacctaataa taaaaacaca tcctcacact tgtttctac    3960 tgcatactca gtaattaatt tccaagagac ctgctttgct tcttcaggct cttctgggtt    4020
aaaatcatgc tcctttaagc ccccttgaat gctttcttct attgtatggt atggatctct    4080
agttaaggca ctatatagta agtattcctt attaacaccc ttacaaatta aaaaactaaa    4140
ggtacacagc ttttgacaga aattattaat tgcagaaact ctatgtctat gtggagttaa    4200
aaagaatata atattatgcc cagcacacat gtgtctacta ataaaagtta cagaatattt    4260
ttccataagt tttttataca gaatttgagc ttttttcttta gtagtataca cagcaaagca    4320
ggcaagggtt ctattactaa atacagcttg actaagaaac tggtgtagat cacaaggaaa    4380
gtctttaggg tcttctacct ttcttttttt cttgggtggt gttgagtgtt gagaatctgc    4440
tgttgcttct tcatcactgg caaacatatc ttcatggcaa aataaatctt catcccattt    4500
ttcattaaag gagctccacc aggactccca ctcttctgtt ccataggttg cacctataa    4560 aacaaataat tacttagggc ctttaaatat tttattattt atttaaatat aaggtagtta    4620
ccttaaagct ttagatctct gaagggagtt tctccaatta tttggaccca ccattgcaga    4680
gtttcttcag ttaggtctaa gccaaaccac tgtgtgaagc agtcaatgca gtagcaatct    4740
atccaaacca agggctcttt tcttaaaaat tttctattta aatgccttaa tctaagctga    4800
catagcatgc aagggcagtg cacagaaggc tttttggaac aaataggcca ttccttgcag    4860
tacagggtat ctgggcaaag aggaaaatca gcacaaacct ctgagctact ccaggttcca    4920
aaatcaggct gatgagctac ctttacatct tgctccattt ttttatataa agtattcatt    4980
ctcttcattt tatcctcgtc gcccccttttg tcagggtgaa attccttaca cttccttaaa    5040
taggcttttc tcattaagga aaggtttccc caggcagctc tttcaaggcc caaaaggtcc    5100
atgagctcca tggattcttc cctgttaagc actttatcca t                        5141
```

<210> SEQ ID NO 36  
<211> LENGTH: 5129  
<212> TYPE: DNA  
<213> ORGANISM: Human polyomavirus 1  
<220> FEATURE:  
<223> OTHER INFORMATION: Type BK virus

<400> SEQUENCE: 36

```
ttttgcaaaa attgcaaaag aataggatt tccccaaata tttttgctag gcctcagaaa      60
aagcctccac acccttacta cttgagagaa agggtggagg cagaggcggc ctcggcctct    120
tatatattat aaaaaaaaag gccacaggga ggagctgcta acccatggaa tgtagccaaa    180
ccatgacctc aggaaggaaa gtgcatgact gggcagccag ccagtggcag ttaatagtga    240
aaccccgccc ctaaaattct caaataaaca caagagggag tggaaactgg ccaaaggagt    300
ggaaagcagc cagacagaca tgttttgcga gcctaggaat cttggccttg tcccagtta     360 aactggacaa aggccatggt tctgcgccag ctgtcacgga aagttagtaa aacctggact    420
```

```
ggaacaaaaa aaagagctca gaggattttt attttttattt tagagcttttt gctggaattt      480 tgtagaggtg aagacagtgt agacgggaaa aacaaaagta ccactgcttt acctgctgta      540
aaagactctg taaaagactc ctaggtaagt aatccctttt tttttgtatt tccaggttga      600
tgggtgctgc tctagcactt tgggggacc tagttgccag tgtatctgag gctgctgctg       660
ccacaggatt ttcagtggct gaaattgctg ctggggaggc tgctgctgct atagaagttc      720
aaattgcatc ccttgctact gtagagggca taacaagtac ctcagaggct atagctgcta     780
taggcctaac tcctcaaaca tatgctgtaa ttgctggtgc tcctggggct attgctgggt      840
ttgctgcttt aattcaaact gttactggta ttagttcctt ggctcaagta gggtataggt      900
tttttagtga ttgggatcac aaagtttcca ctgtaggcct ctatcagcaa tcaggcatgg     960
ctttggaatt gttaacccca gatgagtact acgatatttt gtttcctggt gtaaatactt     1020
ttgtaaataa tattcaatac cttgatccta ggcattgggg tccttccttg tttgctacta    1080
tttcccaggc tttgtggcat gttattaggg atgatatacc tgctataacc tcacaggaat   1140
tgcaaagaag aacagaaaga tttttttagag actccttggc tagattttttg gaggaaacta   1200 cctggacaat tgtaaatgcc cctatgaact tttataatta tattcaagaa tattattctg    1260
atctttcccc tattaggccc tcaatggtca gacaagtggc tgaaagggaa ggtacccgtg    1320
tacattttgg ccatacttat agtatagatg atgctgacag tatagaagaa gttacacaaa    1380
gaatggactt aagaaatcaa caaactgtac attcaggaga gtttatagaa aaaactattg    1440
ccccaggagg tgctaatcaa agaactgctc ctcaatggat gttgccttta cttctaggcc    1500
tgtacgggac tgtaacacct gctcttgaag catatgaaga tggccccaac caaagaaaa    1560 ggagagtgtc caggggcagc tcccaaaaag ccaaaggaac ccgtgcaagt gccaaaacta    1620
ctaataaaag gaggagtaga agttctagaa gttaaaactg gggtagatgc tataacagag   1680
gtagaatgct tcctaaaccc agaaatgggg gatccagatg aaaaccttag ggctttagt    1740 ctaaagctaa gtgctcaaaa tgactttagc agtgatagcc cagaaagaaa aatgcttccc   1800
tgttacagca cagcaagaat tcccctcccc aatttaaatg aggacctaac ctgtggaaat   1860
ctactgatgt gggaggctgt aactgtacaa acagaggtca ttggaataac tagcatgctt   1920
aaccttcatg cagggtcaca aaaagtgcat gagcatggtg gaggtaaacc tattcaaggc    1980 agtaattttcc acttctttgc tgttggtgga gatcccttgg aaatgcaggg agtgctaatg    2040
aattacagga ccaagtaccc agaaggtact ataaccccaa aaacccaac agcccagtcc     2100 caggtaatga atactgacca taaggcctat ttggacaaaa acaatgccta tccagttgag   2160
tgctgggttc ctgatcccag tagaaatgaa aatactaggt attttgggac tttcacagga    2220
ggggaaaatg ttcccccagt acttcatgtg accaacacag ctaccacagt gttgctagat    2280
gaacagggtg tggggcctct ttgtaaagct gatagcctgt atgtttcagc tgctgatatt     2340
tgtggcctgt ttactaacag ctctggaaca caacagtgga gaggccttgc aagatatttt    2400
aagatccgcc tgagaaaaag atctgtaaaa aatccttacc caatttcctt tttgctaagt    2460
gaccttataa acaggagaac ccagagagtg atgggcagc ctatgtatgg tatggaatcc    2520
caggtagaag aggtcagggt gtttgatggc acagaaagac ttccagggga cccagatatg    2580
ataagatata ttgataaaca aggacaattg caaaccaaaa tgctttaaac aggtgctttt    2640
attgtacata tacattttaat aaatgctgct tttgtataag ccacttttaa gcttgtgtta    2700
ttttgggggt ggtgttttag gccttttaaa acattgaaag cctttacaca aatgcaactc    2760
```

```
ttcactatgg gggtctgacc tttgggaatc ttcagcaggg gctgaagtat ctgagacttg    2820
ggaagagcat tgtgattggg attcagtgct tgatccatgt ccagagtctt cagtttctga    2880
atcttcttct cttgtgatat caagaataca tttccccatg catatattat atttcatcct    2940
tgaaaaagta tacatactta tctcagaatc cagcctttcc ttccattcaa caattctaga    3000
ttgtatatct gttgcaaaat cagctacagg cctaaaccaa attagcagta gcaacaaggt    3060
cattccactt tgtaaaattc ttttttcaag taagaactct gagttttgta aggattttct    3120
taaatatatt ttgggtctaa atctatctg tcttacaaat ctagcctgca gggttttagg    3180
aacaggatac tcattcattg taaccaggcc tggtggaaat atttgggttc ttttgtttaa    3240
atgtttcttt tctaaattaa ccttaacact tccatctaaa taatctctca aactgtctaa    3300
attgtttatt ccatgtcctg aaggcaaatc ctttgattca gcccctgttc cttttacatc    3360
ttcaaaaaca accatgtact gatctatagc tacacctagt tcaaaggtta gcctttccat    3420
gggtaggttt acatttaagg ctttacctcc acacaaatct agtaaccctg cagctagtgt    3480 tgttttttcca ctatcaatgg gacctttaaa taaccagtat cttcttttag gtacattaaa    3540
aacaatacag tgcaaaaaat caaatataac agaatccatt ttaggtagca aacagtgcag    3600
ccaggcaaca cctgccatat attgttccag tacagcattt ccatgagctc caaatattaa    3660
atccatttta tctaatatat gattaaatct ttctgttagc atttcttctc tggtcatatg    3720
aagggtatct actctttttt tagctaaaac tgtatctact gcttgctgac aaatactttt    3780
ttgattttta ctttctgcaa aaatagtagc atttgcaaaa tgcttttcat gatacttaaa    3840
gtgataaggt tggtcttttt tctgacactt tttacactct tctacattgt attgaaattc    3900
taaatacata cccaataata aaaacacatc ctcacacttt gtctctactg catactcagt    3960
aattaatttc caagacacct gctttgtttc ttcaggctct tctgggttaa aatcatgctc    4020
ctttaagccc ccttgaatgc tttcttctat tgtatggtat ggatctctag ttaaggcact    4080
atatagtaag tattccttat taacacccctt acaaattaaa aaactaaagg tacacagctt    4140
ttgacagaaa ttattaattg cagaaactct atgtctatgt ggagttaaaa agaatataat    4200
attatgccca gcacacatgt gtctactaat aaaagttaca gaatattttt ccataagttt    4260
tttatacaga atttgagctt tttctttagt agtatacaca gcaaagcagg caagggttct    4320
attactaaat acagcttgac taagaaactg gtgtagatca gaaggaaagt ctttagggtc    4380
ttctaccttt ctctttttct tgggtggtgt ggagtgttga gaatctgctg ttgcttcttc    4440
atcactggca aacatatctt catggcaaaa taaatcttca tcccattttt cattaaagga    4500
gctccaccag gactcccact cttctgttcc ataggttggc acctataaaa aaaataatta    4560
cttagggcct ttaaatattt tcttatttat ctaaatataa gttagttacc ttaaagcttt    4620
agatctctga agggagtttc tccaattatt tggacccacc attgcagagt tcttcagtt    4680 aggtctaagc caaccactg tgtgaagcag tcaatgcagt agcaatctat ccaaaccaag    4740
ggctcttttc ttaaaaattt tctatttaaa tgccttaatc taagctgaca tagcatgcaa    4800
gggcagtgca cagaaggctt tttggaacaa ataggccaat ccttgcagta cagggtatct    4860
gggcaaagag gaaaatcagc acaaacctct gagctactcc aggttccaaa atcaggctga    4920
tgagctacct ttacatcctg ctccattttt ttatataaag tattcattct cttcatttta    4980
tcctcgtcgc ccccttttgtc agggtgaaat tccttacact tccttaaata ggcttttctc    5040
attaagggaa ggtttcccca ggcagctctt ccaaggccta aaggtccat gagctccatg    5100 gattcttccc tgttaagcac tttatccat                                    5129
```

<210> SEQ ID NO 37
<211> LENGTH: 5132
<212> TYPE: DNA
<213> ORGANISM: Human polyomavirus 1
<220> FEATURE:
<223> OTHER INFORMATION: Type BK virus

<400> SEQUENCE: 37

| | | | | | |
|---|---|---|---|---|---|
| ttttgcaaaa | attgcaaaag | aatagggatt | tccccaaata | ttttttgctag | gcctcagaaa | 60 |
| aagcctccac | acccttacta | cttgagagaa | agggtggagg | cagaggcggc | ctcggcctct | 120 |
| tatatattat | aaaaaaaaag | gccacaggga | ggagctgcta | acccatggaa | tgtagccaaa | 180 |
| caggaaggaa | agtgcatgac | tgggcagcca | gccagtggca | gttaatagtg | aaaccccgcc | 240 |
| cctaaaattc | tcaaataaac | acaagaggga | gtggaaactg | gccaaaggag | tggaaagcag | 300 |
| ccagacagac | atgttttgcg | agcctaggaa | tcttggcctt | gtccccagtt | aaactggaca | 360 |
| aaggccatgg | ttctgcgcca | gctgtcacga | caagcttctg | tgaaagttag | taaaacctgg | 420 |
| actggaacaa | aaaaagagc | tcagaggatt | tttatttta | ttttagagct | tttgctggaa | 480 |
| ttttgtagag | gtgaagacag | tgtagacggg | aaaaacaaaa | gtaccactgc | tttacctgct | 540 |
| gtaaaagact | ctgtaaaaga | ctcctaggta | agtaatccct | ttttttttgt | atttccaggt | 600 |
| tgatgggtgc | tgctctagca | cttttggggg | acctagttgc | cagtgtatct | gaggctgctg | 660 |
| ctgccacagg | attttcggtg | gctgaaattg | ctgctgggga | ggctgctgct | gctatagaag | 720 |
| ttcaaattgc | atcccttgct | actgtagagg | gcataacaag | tacctcagag | gctatagctg | 780 |
| ctataggcct | aactcctcaa | acatatgctg | taattgctgg | tgctcctggg | gctattgctg | 840 |
| ggtttgctgc | tttaattcaa | actgttactg | gtattagttc | cttggctcaa | gtagggtaca | 900 |
| ggtttttttag | tgattgggat | cacaaagttt | ccactgtagg | cctctatcag | caatcaggca | 960 |
| tggctttgga | attgtttaac | ccagatgagt | actatgatat | tttgttcct | ggtgtaaata | 1020 |
| cttttgtaaa | taatattcaa | taccttgatc | ctaggcattg | gggtccttcc | ttgtttgcta | 1080 |
| ctatttccca | ggctttgtgg | catgttatta | gggatgatat | acctgctata | acctcacagg | 1140 |
| aattgcaaag | aagaacagaa | agatttttta | gagactcctt | ggctagattt | ttggaggaaa | 1200 |
| ctacctggac | aattgtaaat | gcccctatga | acttttataa | ttatattcaa | gaatattatt | 1260 |
| ctgatctttc | ccctattagg | ccctcaatgg | tcagacaagt | ggctgaaagg | gaaggtaccc | 1320 |
| gtgtacattt | tggccatact | tatagtatag | atgatgctga | cagtatagaa | gaagttacac | 1380 |
| aaagaatgga | cttaagaaat | caacaaactg | tacattcagg | agagtttata | gaaaaaacta | 1440 |
| ttgccccagg | aggtgctaat | caaagaactg | ctcctcaatg | gatgttgcct | ttacttctag | 1500 |
| gcctgtacgg | gactgtaaca | cctgctcttg | aagcatatga | agatggcccc | aaccaaaaga | 1560 |
| aaaggagagt | gtccaggggc | agctcccaaa | aagccaaagg | aacccgtgca | agtgccaaaa | 1620 |
| ctactaataa | aaggaggagt | agaagttcta | gaagttaaaa | ctgggtaga | tgctataaca | 1680 |
| gaggtagaat | gcttcctaaa | cccagaaatg | ggggatccag | atgaaaacct | taggggcttt | 1740 |
| agtctaaagc | taagtgctca | aaatgacttt | agcagtgata | gcccagaaag | aaaaatgctt | 1800 |
| ccctgttaca | gcacagcaag | aattcccctc | cccaatttaa | atgaggacct | aacctgtgga | 1860 |
| aatctactga | tgtgggaggc | tgtaactgta | caaacagagg | tcattggaat | aactagcatg | 1920 |
| cttaaccttc | atgcagggtc | acaaaaagtg | catgagcatg | gtgaggtaa | acctattcaa | 1980 |
| ggcagtaatt | tccacttctt | tgctgttggt | ggagacccct | tggaaatgca | gggagtgcta | 2040 |

```
atgaattact ggaccaagta cccagaaggt actataaccc caaaaaaccc aacagcccag    2100
tcccaggtaa tgaatactga ccataaggcc tatttggaca aaaacaatgc ctatccagtt    2160
gagtgctggg ttcctgatcc cagtagaaat gaaaatacta ggtattttgg gactttcaca    2220
ggaggggaaa atgttccccc agtacttcat gtgaccaaca cagctaccac agtgttgcta    2280
gatgaacagg gtgtggggcc tctttgtaaa gctgatagcc tgtatgtttc agctgctgat    2340
atttgtggcc tgtttactaa cagctctgga acacaacagt ggagaggcct tgcaagatat    2400
tttaagatcc gcctgagaaa aagatctgta aaaaatcctt acccaatttc cttttttgcta   2460 agtgaccctta taaacaggag aacccagaga gtggatgggc agcctatgta tggtatggaa    2520
tcccaggtag aagaggtcag ggtgtttgat ggcacagaaa gacttccagg ggacccagat    2580
atgataagat atattgataa acaaggacaa ttgcaaacca aatgcttta aacaggtgct     2640 tttattgtac atatacattt aataaatgct gcttttgtat aagccacttt taagcttgtg    2700
ttattttggg ggtggtgttt taggcctttt aaaacattga aagcctttac acaaatgcaa    2760
ctcttcacta tgggggtctg accttttggga atcttcagca ggggctgaag tatctgagac   2820
ttgggaagag cattgtgatt gggattcagt gcttgatcca tgtccagagt cttcagtttc    2880
tgaatcttct tctcttgtga tatcaagaat acatttcccc atgcatatat tatatttcat    2940
ccttgaaaaa gtatacatac ttatctcaga atccagcctt tccttccatt caacaattct    3000
agattgtata tctgttgcaa aatcagctac aggcctaaac caaattagca gtagcaacaa    3060
ggtcattcca ctttgtaaaa ttctttttc aagtaagaac tctgagtttt gtaaggattt     3120
tcttaaatat attttgggtc taaaatctat ctgtcttaca aatctagcct gcagggtttt    3180
aggaacagga tactcattca ttgtaaccag gcctggtgga atatttgggg ttcttttgtt    3240
taaatgtttc ttttctaaat taaccttaac acttccatct aaataatctc tcaaactgtc    3300
taaattgttt attccatgtc ctgaaggcaa atcctttgat tcagcccctg ttccttttac    3360
atcttcaaaa acaaccatgt actgatctat agctacacct agttcaaagg ttagcctttc    3420
catgggtagg tttacattta aggctttacc tccacacaaa tctagtaacc ctgcagctag    3480
tgttgttttt ccactatcaa tgggaccttt aaataaccag tatcttcttt taggtacatt    3540
aaaaacaata cagtgcaaaa aatcaaatat aacagaatcc attttaggta gcaaacagtg    3600
cagccaggca acacctgcca tatattgttc cagtacagca tttccatgag ctccaaatat    3660
taaatccatt ttatctaata tatgattaaa tcttttctgtt agcatttctt ctctggtcat    3720
atgaagggta tctactcttt ttttagctaa aactgtatct actgcttgct gacaaatact    3780
tttttgattt ttactttctg caaaaatagt agcatttgca aaatgctttt catgatactt    3840
aaagtgataa ggttggtctt ttttctgaca cttttttacac tcttctacat tgtattgaaa   3900
ttctaaatac atacccaata ataaaaacac atcctcacac tttgtctcta ctgcatactc    3960
agtaattaat ttccaagaca cctgcttttgt tccttcaggc tcttctgggt taaaatcatg   4020
ctcctttaag ccccccttgaa tgctttcttc tattgtatgg tatggatctc tagttaaggc   4080
actatatagt aagtattcct tattaacacc cttacaaatt aaaaaactaa aggtacacag    4140
cttttgacag aaattattaa ttgcagaaac tctatgtcta tgtggagtta aaagaatat     4200 aatattatgc ccagcacaca tgtgtctact aataaaagtt acagaatatt tttccataag    4260
ttttttatac agaatttgag ctttttcttt agtagtatac acagcaaagc aggcaagggt    4320
tctattacta aatacagctt gactaagaaa ctggtgtaga tcagaaggaa agtctttagg    4380
gtcttctacc tttctctttt tcttgggtgg tgtggagtgt tgagaatctg ctgttgcttc    4440
```

```
ttcatcactg gcaaacatat cttcatggca aaataaatct tcatcccatt tttcattaaa        4500
ggagctccac caggactccc actcttctgt tccataggtt ggcacctata aaaaaaataa        4560
ttacttaggg cctttaaata ttttcttatt tatctaaata taagttagtt accttaaagc        4620
tttagatctc tgaagggagt ttctccaatt atttggaccc accattgcag agtttcttca        4680
gttaggtcta agccaaacca ctgtgtgaag cagtcaatgc agtagcaatc tatccaaacc        4740
aagggctctt ttcttaaaaa ttttctattt aaatgcctta atctaagctg acatagcatg        4800
caagggcagt gcacagaagg cttttggaa  caaataggcc aatccttgca gtacagggta        4860
tctgggcaaa gaggaaaatc agcacaaacc tctgagctac tccaggttcc aaaatcaggc        4920
tgatgagcta cctttacatc ctgctccatt ttttatata  aagtattcat tctcttcatt        4980
ttatcctcgt cgccccc ttt gtcagggtga aattccttac acttccttaa ataggctttt        5040
ctcattaagg gaaggtttcc ccaggcagct ctttcaaggc ctaaaaggtc catgagctcc        5100
atggattctt ccctgttaag cactttatcc at                                     5132
```

<210> SEQ ID NO 38
<211> LENGTH: 5098
<212> TYPE: DNA
<213> ORGANISM: Human polyomavirus 1
<220> FEATURE:
<223> OTHER INFORMATION: Type BK virus

<400> SEQUENCE: 38

```
ttttgcaaaa aattgcaaaa gaatagggat ttccccaaat agttttgcta ggcctcagaa          60
aaagcctcca caccttact  acttcagaga aagggtggag gcagaggcgg cctcggcctc         120
ttatatatta taaaaaaaaa ggccacaggg aggagctgct tacccatgga atgcagccaa         180
accatgacct caagaagcaa gtgcatgact gggcagccag ccagtggcag ttaatagtga         240
aaccccgccc ctaacattct caaataaaca caagaggaag tggaaactgt ccaaaggagt         300
ggaaagcagc cagacagaca tgttttgcga gcctaagaat cttgtggttt tgcgccagct         360
gtcacgacaa gcttcagtga agttggtaa  aacctggact ggaactaaaa aaagagctca         420
gaggattttt attttattt  tagagctttt gctggaattt tgtagaggtg aagacagtgt         480
agacgggaaa acaaaagta  ccactgcttt acctgctgta aaagactctg taaaagactc         540
ctaggtaagt aatgcttttt ttttgtattt tcaggttgat gggtgctgct ctagcacttt         600
tgggggacct agttgccagt gtatctgagg ctgctgctgc cacaggattt tcagtggctg         660
aaattgctgc tgggggaggct gctgctgcca tagaagttca aattgcatcc cttgctactg         720
tagagggcat aacaactacc tcagaggcta tagctgctat aggcctaaca cctcaaacat         780
atgctgtaat tgctggtgct ccaggggcta ttgctgggtt tgctgcttta attcaaactg         840
ttactggtat tagttctttg gctcaagtag ggtataggtt ttttagtgat tgggatcaca         900
aagtttccac tgtaggcctt tatcagcaat caggcatggc tttggaattg tttaacccag         960
atgagtacta tgatatttg  tttcctggtg taaatacttt tgttaataat attcaatatc        1020
tagatcctag gcattgggt  ccttctttgt ttgctactat ttcccaggct ttgtggcatg        1080
ttattagaga tgatatacct gctataactt cacaagaatt gcaaggaga  acagagagat        1140 ttttaggga  ctctttggct agattttgg  aagaaccac  ctggacaatt gtaaatgccc        1200
ccataaactt ttataattat attcaggatt attattctaa tttgtcccct attaggcctt        1260
caatggttag gcaagtagct gaaagggaag gtacccatgt aaatttggc  catacctaca        1320
```

```
gcatagataa tgctgacagt atagaagaag ttacccaaag aatggattta agaaataagg    1380
aaagtgtaca ttcaggagag tttatagaaa aaactattgc cccaggaggt gctaatcaaa    1440
gaactgctcc tcaatggatg ttgcctttgc ttctaggcct gtacgggact gtaacacctg    1500
ctcttgaagc atatgaagat ggccccaacc aaaagaaaag gagagtgtcc aggggcagct    1560
cccaaaaagc caaggaacc cgtgcaagtg ccaaaactac taataaaagg aggagtagaa    1620
gttctagaag ttaaaactgg ggtagatgct ataacagagg tagaatgctt tctaaaccca    1680
gaaatggggg atccagatga taaccttagg ggctatagtc agcacctaag tgctgaaaat    1740
gcctttgaga gtgatagccc agacagaaaa atgcttcctt gttacagtac agcaagaatt    1800
ccactgccca acctaaatga ggacctaacc tgtggaaatc tactaatgtg ggaggctgta    1860
actgtaaaaa cagaggttat tggaataact agcatgctta accttcatgc agggtcccaa    1920
aaagttcatg agaatggtgg aggtaaacct gtccaaggca gtaatttcca cttttttgct    1980
gtgggtggag accccttgga aatgcaggga gtgctaatga attacagaac aaagtaccca    2040
caaggtacta taaccccctaa aaaccctaca gctcagtccc aggtaatgaa tactgatcat    2100
aaggcctatt tggacaaaaa caatgcttat ccagttgagt gctggattcc tgatcctagt    2160
agaaatgaaa atactaggta ttttggaact tacacaggag gggaaaatgt tcctccagta    2220
cttcatgtta ccaacacagc taccacagtg ttgctggatg aacagggtgt ggggcctctg    2280
tgtaaagcta tagcctgta tgtttcagct gctgatattt gtgggctgtt tactaacagc    2340
tctgggacac aacagtggag aggccttgca agatatttta agattcgcct gagaaaaaga    2400
tctgtgaaga atccttaccc aatttccttt ttgctaagtg accttataaa caggagaacc    2460
caaaaagtgg atgggcagcc tatgtatggt atggaatctc aggttgagga ggtaagggtg    2520
tttgatggca cagaacagct tccaggggac ccagatatga taagatatat tgacagacaa    2580
ggacaattgc aaacaaaaat ggtttaaaca ggtgctttat tgtacatata tatgcttaat    2640
aaatgctgct tttgtataac acagttgaag cttctgttat tttggggtg gtgttttagg    2700 ccttttaaaa cactgaaagc ctttacacaa atgtaactct tggctgtgag ggttttctga    2760
atcaggggct gaagtatctg agacttggga agagcattgt gattgggatt cagtgcttga    2820
tccatgtcca gagtcttcag tttctgaatc ttcttctctt gtaatatcaa gaatacattt    2880
tcccatgcat atattatatt tcatccttga aaaagtatac atacttatct cagaatccag    2940
cctttccttc cattcaacaa ttctagactg tatatctttt gaaaaatcag ctacaggcct    3000
aaaccaaatt agtagtagca aagggtcat tccactttgt aatattcttt ttcaagtaa    3060 aaactcagag ttttgcaggg actttcttaa atatattttg ggtctaaaat ctatctgtct    3120
tacaaatcta gcctgaagag ttttagggac aggatactca ttcattgtaa ctaaccctgg    3180
tggaaatatt tgtgttcttt tgtttaaatg tttctttct aaattaacct taacacttcc    3240
atctagataa tccctcaaac tgtctaaatt gtttattcca tgtcctgaag gcaaatcctt    3300
tgattcagct cctgtccctt ttacatcttc aaaaacaacc atgtactgat caatagccac    3360
acccagttca aaagttagcc tttccatggg taaatttaca tttaaagctt tacctccaca    3420
taagtctaat aaccctgcag ctaaggttgt tttgccacta tcaattggac ctttaaataa    3480
ccagtatctt cttttaggta cattaaaaac aacacagtga agaaaatcaa aataacaga    3540 atccattta ggtagcaaac aatgtagcca agcaacccct gccatatatt gttctagtac    3600
agcatttcca tgagctccaa atattaaatc catttatct aatatatgat taaatctttc    3660
tgttagcatt tcttccctgg tcatatgaag ggtatctact ctttttttag ctaatactgt    3720
```

```
atctactgct tgctgacaaa tactttttg attttactt tctgcaaaaa taatagcatt    3780
tgcaaaatgc ttttcatgat acttaaagtg gtaaggttga tctttttttt gacactttt    3840 acactcctct acattgtatt gaaattctaa atacataccc aataataaaa acacatcctc   3900
acactttgtt tctactgcat attcagtaat taatttccaa dacacctgct tgtttcttc    3960 aggctcctct gggttaaagt catgctcctt taagcccccct tgaatgcttt cctctattat   4020
atggtatgga tccctagtta aggcactgta tagtaagtat tccttattaa cacccttaca   4080
aattaaaaaa ctaaaagtac acagcttttg acagaaatta ttaattgcag aaactctatg   4140
tctatgtgga gttaaaaaga atataatatt atgaccagca cacatgtgtc tactgataaa   4200
agttacagaa tatttttcca taagttttt atacagaatt tgagcttttt ctttagtggt    4260
atacacagca aaacaggcaa gtgttctatt actaaataca gcttgactaa gaaactggtg   4320
tagatcagag ggaaagtctt tagggtcttc tacctttctt tttttttttgg gtggtgttga   4380 gtgttgggaa tctgctgttg cttcttcatc actggcaaac atatcctcat ggcagaataa   4440
atcttcatcc cattttcat taaggagct ccaccaggac tcccactctt ctgttccata    4500
ggttggcacc tataaaaaaa aataattac ttagggtctt cttttaattt actactttc    4560 taaatataaa ttagttacct taaagcttta gatctctgaa gggagttct ccaattattt    4620 ggacccacca ttgcagggtt tcttcagtga ggtctaagcc aaaccactgt gtgaagcaat   4680
caatgcagta gcaatctatc caaccaatg gctctttct taaaaatttt ctatttaaat    4740
gccttaatct tagctgacat agcatgcaag ggcaatgcac tgaaggcttt ttggaacaaa   4800
taggccattc cttgcagtac aaagtatctg ggcaaagagg aaaatcagca caaacctctg   4860
agctattcca ggttccaaaa tcaggctgat gagctacct tacatcctgc tccattttt    4920 tatataaagt attcattctc ttcattttat cctcgtcgcc cctttgtca gggtgaaatt    4980 ccttacactt ttttaaatag ctttctctca ttaagggaag gtttccccag gcagctcttt   5040
caaggcctaa aaggtccatg agctccatgg attcttccct gtttaagact ttatccat     5098
```

<210> SEQ ID NO 39
<211> LENGTH: 5153
<212> TYPE: DNA
<213> ORGANISM: Human polyomavirus 1
<220> FEATURE:
<223> OTHER INFORMATION: Type BK virus

<400> SEQUENCE: 39

```
ttttgcaaaa attgcaaaag aatagggatt tccccaaata gttttgctag gcctcagaaa     60
aagcctccac acccttacta cttgagagaa agggtggagg cagaggcggc ctcggcctct    120
tatatattat aaaaaaaaag gccacaggga ggagctgctt acccatggaa tgcagccaaa    180 ccatgaccctc aggaaggaaa gtgcatgact cacagggaa tgcagccaaa ccatgacctc    240
aggaaggaaa gtgcatgact cacagggagg agctgcttac ccatggaatg cagccaaacc    300
atgacctcag gaaggaaagt gcatgacaga catgttttgc gagcctagga atcttggcct    360
tgtccccagt taaactggac aaaggccatg gttctgcgcc agctgtcacg acaagcttca    420
gtgaaagttg gtaaaacctg gactggaaca aaaaaaagag ctcagaggat tttatttt     480 atttagagc ttttgctgga atttgtaga ggtgaagaca gtgtagacgg gaaaaacaaa     540
agtaccactg ctttacctgc tgtaaaagac tctgtaaaag actcctaggt aagtaatccc    600 ttttttttg tatttccagg ttcatgggtg ctgctctagc acttttgggg gacctagttg     660
```

```
ccagtgtatc tgaggctgct gctgccacag gattttcagt ggctgaaatt gctgctgggg    720
aggctgctgc tgctatagaa gttcaaattg catcccttgc tactgtagag ggcataacaa    780
gtacctcaga ggctatagct gctataggcc taactcctca acatatgct gtaattgctg     840 gtgctcctgg ggctattgct gggtttgctg cttttaattca aactgttagt ggtattagtt   900
ccttagctca agtagggtat aagttctttg atgattggga tcacaaagtt tccactgtag    960
gcctctatca gcaatcaggc atggctttgg aattgtttaa cccagatgag tactatgata   1020
ttctgtttcc tggtgtaaat acttttgtta ataatattca ataccttgat cctaggcatt   1080
ggggtccttc tttgtttgct actatttccc aggctttgtg gcatgttatt agggatgata   1140
taccttctat aacctcacag gaattgcaga gaagaacaga aagatttttt agagactcct   1200
tggctagatt tttggaggaa actacctgga caattgtaaa tgcccctata aactttttata  1260 attatattca acaatattat tctgatcttt cccctattag gccctcaatg gttagacaag   1320
tagctgaaag ggaaggtacc cgtgtacatt ttggccatac ttatagtata gatgatgctg   1380
acagtataga agaagttaca caaagaatgg acttaagaaa tcaacaaagt gtacattcag   1440
gagagtttat agaaaaaact attgccccag gaggtgctaa tcaaagaact gctcctcaat   1500
ggatgttgcc tttacttcta ggcctgtacg ggactgtaac acctgctctt gaagcatatg   1560
aagatggccc caaccaaaag aaaaggagag tgtccagggg cagctcccaa aaagccaaag   1620
gaacccgtgc aagtgccaaa actactaata aaaggaggag tagaagttct agaagttaaa   1680
actggggtag atgctattac agaggtagaa tgcttcctaa acccagaaat gggggatcca   1740
gatgaaaacc ttagggggctt tagtctaaag ctaagtgctg aaaatgactt tagcagtgat   1800
agcccagaga gaaaaatgct tccctgttac agcacagcaa gaattcccct ccccaattta   1860
aatgaggacc taacctgtgg aaatctactg atgtgggagg ctgtaactgt acaaacagag   1920
gttattggaa taactagcat gcttaacctt catgcagggt cacaaaaagt gcatgagcat   1980 ggtgaggaa aacctattca aggcagtaat ttccacttct ttgctgtagg tggagaaccc   2040
ttggaaatgc agggagtgct aatgaattac aggtcaaagt accctgatgg tactataacc   2100
cctaaaaacc caacagccca gtcccaggta atgaatactg accataaggc ctatttggac   2160
aaaaacaatg cttatccagt tgagtgctgg gtacctgatc ccagtagaaa tgaaaatgct   2220
aggtattttg ggactttcac aggaggggaa aatgttcccc cagtacttca tgtgaccaac   2280
acagctacca cagtgttgct agatgaacag ggtgtggggc ctcttgtaa agctgatagc   2340 ctgtatgttt cagctgctga tatttgtggc ctgtttacta acagtctgg aacacaacag   2400 tggagaggcc ttgcaagata ttttaagatc cgcctgagaa aaagatctgt aaagaatcct   2460
tacccaattt cctttttgct aagtgaccttt ataaacagga gaaccagag agtggatggg   2520 cagcctatgt atggtatgga atcccaggta gaagaggtta gggtgtttga tggcacagaa   2580
agacttccag gggacccaga tatgataaga tatattgaca acagggaca attgcaaacc   2640 aaaatgcttt aaacaggtgc ttttattgta catatacatt taataaatgc tgcttttgta   2700
taagccactt ttaagcttgt gttattttgg gggtggtgtt ttaggccttt taaaacactg   2760
aaagccttta cacaaatgca actcttgact atggggtct gacctttggg aatcttcagc    2820 agggctgaa gtatctgaga cttgggaaga gcattgtgat tgggattcag tgcttgatcc   2880
atgtccagag tcttcagttt ctgaatcctc ttctcttgta atatcaagaa tacatttccc   2940
catgcatata ttatatttca tccttgaaaa agtatacata cttatctcag aatccagcct   3000
ttccttccat tcaacaattc tagattgtat atcagttgca aaatcagcta caggcctaaa   3060
```

```
ccaaattagc agtagcaaca aggtcattcc actttgtaaa attctttttt caagtaagaa    3120
ctctgagttt tgtaaggatt ttcttaaata tattttgggc ctaaaatcta tttgtcttac    3180
aaatctagct tgcagggttt tagggacagg atactcattc attgtaacca agcctggtgg    3240
aaatatttgg gttcttttgt ttaaatgttt cttttctaaa tttaccttaa cacttccatc    3300
taaataatct ctcaaactgt ctaaattgtt tattccatgt cctgaaggca atcctttga    3360 ttcagctcct gtccctttta catcttcaaa acaaccatg tactgatcta tagctacacc    3420
tagctcaaag gttagccttt ccatgggtag gtttacattt aaggctttac caccacacaa    3480
atctaataac cctgcagcta gtgttgtttt tccactatca atgggacctt taaataacca    3540
gtatcttctt ttaggtacat tgaaaacaat acagtgcaaa aaatcaaata ttacagaatc    3600
cattttaggt agcaaacagt gcagccaagc aacacctgcc atatattgtt ctagtacagc    3660
atttccatga gctccaaata ttaaatccat tttatctaat atatgattga atctttctgt    3720
tagcatttct tccctggtca tatgaagggt atctactctt ttttttagcta aaactgtatc    3780 tactgcttgc tgacaaatac ttttttgatt tttactttct gcaaaaataa tagcatttgc    3840
aaagtgcttt tcatgatact taaagtgata aggctggtct ttttttctgac acttttaca    3900 ctcctctaca ttgtattgaa attctaaata catacctaat aataaaaaca catcctcaca    3960
ctttgtctct actgcatact cagtaattaa tttccaagac acctgctttg tttcttcagg    4020
ctcttctggg ctaaaatcat gctcctttaa gcccccttga atgctttctt ctatagtatg    4080
gtatggatct ctagttaagg cactatatag taagtattcc ttattaacac ccttacaaat    4140
taaaaaacta aaggtacaca gcttttgaca gaaattatta attgcagaaa ctctatgtct    4200
atgtggagtt aaaaagaata taatattatg cccagcacac atgtgtctac taataaaagt    4260
tacagaatat ttttccataa gttttttata cagaatttga gcttttctt tagtagtata    4320 cacagcaaag caggcaaggg ttctattact aaatacagct tgactaagaa actggtgtag    4380
atcagaggga aagtctttag ggtcttctac ctttcttttt ttttggggtg gtgttgagtg    4440
ttgagaatct gctgttgctt cttcatcact ggcaaacata tcttcatggc aaaataaatc    4500
ttcatcccat ttttcattaa aggaactcca ccaggactcc cactcttctg ttccataggt    4560
tggcacctat aaaaaaaata attacttagg gcctttaat attttattat ttatctaaat    4620
ataagttagt taccttaaag ctttagatct ctgaagggag tttctccaat tatttggacc    4680
caccattgca gagttcttc agttaggtct aagccaaacc actgtgtgaa gcagtcaatg    4740
cagtagcaat ctatccaaac caagggctct tttcttaaaa attttctatt taaatgcctt    4800
aatctaagct gacatagcat gcaagggcag tgcacagaag gcttttgga acaaataggc    4860 cattccttgc agtacagggt atctgggcaa agaggaaaat cagcacaaac ctctgagcta    4920
ctccaggttc caaaatcagg ctgatgagct acctttacat cctgctccat tttttatac     4980 aaagtattca ttctcttcat tttatcctcg tcgccccctt tgtcagggtg aaattccta    5040 cacttcctta aataagcttt tctcattaag ggaagatttc cccaggcagc ctttcaagg     5100 cctaaaaggt ccatgagctc catggattct tccctgttaa gaactttatc cat          5153
```

<210> SEQ ID NO 40
<211> LENGTH: 5153
<212> TYPE: DNA
<213> ORGANISM: Human polyomavirus 1
<220> FEATURE:
<223> OTHER INFORMATION: Type BK virus

```
<400> SEQUENCE: 40
ttttgcaaaa attgcaaaag aatagggatt tccccaaata gttttgctag gcctcagaaa        60
aagcctccac acccttacta cttgagagaa agggtggagg cagaggcggc ctcggcctct       120
tatatattat aaaaaaaaag gccacaggga ggagctgctt acccatggaa tgcagccaaa       180
ccatgacctc aggaaggaaa gtgcatgact cacagggaa tgcagccaaa ccatgacctc        240
aggaaggaaa gtgcatgact cacagggagg agctgcttac ccatggaatg cagccaaacc       300
atgacctcag gaaggaaagt gcatgacaga catgttttgc gagcctagga atcttggcct       360
tgtccccagt taaactggac aaaggccatg gttctgcgcc agctgtcacg acaagcttca       420
gtgaaagttg gtaaaacctg gactggaaca aaaaaaagag ctcagaggat ttttattttt       480
attttagagc ttttgctgga attttgtaga ggtgaagaca gtgtagacgg aaaaacaaa        540
agtaccactg ctttacctgc tgtaaaagac tctgtaaaag actcctaggt aagtaatccc       600
ttttttttg tatttccagg ttcatgggtg ctgctctagc acttttgggg gacctagttg        660
ccagtgtatc tgaggctgct gctgccacag gattttcagt ggctgaaatt gctgctgggg       720
aggctgctgc tgctatagaa gttcaaattg catcccttgc tactgtagag ggcataacaa       780
gtacctcaga ggctatagct gctataggcc taactcctca aacatatgct gtaattgctg       840
gtgctcctgg ggctattgct gggtttgctg ctttaattca aactgttagt ggtattagtt       900
ccttagctca gtagggtat aagttctttg atgattggga tcacaaagtt tccactgtag        960
gcctctatca gcaatcaggc atggctttgg aattgtttaa cccagatgag tactatgata      1020
ttctgttttcc tggtgtaaat acttttgtta ataatattca ataccttgat cctaggcatt      1080
ggggtccttc tttgtttgct actatttccc aggctttgtg gcatgttatt agggatgata      1140
taccttctat aacctcacag gaattgcaga gaagaacaga aagatttttt agagactcct      1200
tggctagatt tttggaggaa actacctgga caattgtaaa tgcccctata aactttttata     1260
attatattca acaatattat tctgatcttt cccctattag gccctcaatg gttagacaag      1320
tagctgaaag ggaaggtacc cgtgtacatt ttggccatac ttatagtata gatgatgctg      1380
acagtataga agaagttaca caaagaatgg acttaagaaa tcaacaaagt gtacattcag      1440
gagagtttat agaaaaaact attgccccag gaggtgctaa tcaagaact gctcctcaat       1500
ggatgttgcc tttacttcta ggcctgtacg ggactgtaac acctgctctt gaagcatatg      1560
aagatggccc caaccaaaag aaaaggagag tgtccagggg cagctcccaa aaagccaaag      1620
gaacccgtgc aagtgccaaa actactaata aaaggaggag tagaagttct agaagttaaa      1680
actggggtag atgctattac agaggtagaa tgcttcctaa acccagaaat gggggatcca      1740
gatgaaaacc ttaggggctt tagtctaaag ctaagtgctg aaaatgactt tagcagtgat      1800
agcccagaga gaaaaatgct tccctgttac agcacagcaa gaattcccct ccccaattta      1860
aatgaggacc taacctgtgg aaatctactg atgtgggagg ctgtaactgt acaaacagag      1920
gttattggaa taactagcat gcttaacctt catgcagggt cacaaaaagt gcatgagcat      1980
ggtggaggaa aacctattca aggcagtaat ttccacttct ttgctgtagg tggagaaccc      2040
ttggaaatgc agggagtgct aatgaattac aggtcaaagt accctgatgg tactataacc      2100
cctaaaaacc caacagccca gtcccaggta atgaatactg accataaggc ctatttggac      2160
aaaaacaatg cttatccagt tgagtgctgg gtacctgatc ccagtagaaa tgaaaatgct      2220
aggtattttg ggacttteac aggaggggaa aatgttcccc cagtacttca tgtgaccaac      2280
acagctacca cagtgttgct agatgaacag ggtgtggggc ctctttgtaa agctgatagc      2340
```

```
ctgtatgttt cagctgctga tatttgtggc ctgtttacta acagctctgg aacacaacag    2400
tggagaggcc ttgcaagata ttttaagatc cgcctgagaa aaagatctgt aaagaatcct    2460
tacccaattt ccttttttgct aagtgacctt ataaacagga gaacccagag agtggatggg    2520
cagcctatgt atggtatgga atcccaggta gaagaggtta gggtgtttga tggcacagaa    2580
agacttccag gggacccaga tatgataaga tatattgaca aacagggaca attgcaaacc    2640
aaaatgcttt aaacaggtgc ttttattgta catatacatt taataaatgc tgcttttgta    2700
taagccactt ttaagcttgt gttattttgg gggtggtgtt ttaggccttt taaaacactg    2760
aaagccttta cacaaatgca actcttgact atgggggtct gacctttggg aatcttcagc    2820
aggggctgaa gtatctgaga cttgggaaga gcattgtgat tgggattcag tgcttgatcc    2880
atgtccagag tcttcagttt ctgaatcctc ttctcttgta atatcaagaa tacatttccc    2940
catgcatata ttatatttca tccttgaaaa agtatacata cttatctcag aatccagcct    3000
ttccttccat tcaacaattc tagattgtat atcagttgca aaatcagcta caggcctaaa    3060
ccaaattagc agtagcaaca aggtcattcc actttgtaaa attctttttt caagtaagaa    3120
ctctgagttt tgtaaggatt tcttaaata tattttgggc ctaaaatcta tttgtcttac    3180
aaatctagct tgcagggttt tagggacagg atactcattc attgtaacca agcctggtgg    3240
aaatatttgg gttcttttgt ttaaatgttt cttttctaaa tttaccttaa cacttccatc    3300
taaataatct ctcaaactgt ctaaattgtt tattccatgt cctgaaggca aatcctttga    3360
ttcagctcct gtcccttta catcttcaaa acaaccatg tactgatcta tagctacacc    3420
tagctcaaag gttagccttt ccatgggtag gtttacattt aaggctttac caccacacaa    3480
atctaataac cctgcagcta gtgttgtttt tccactatca atgggacctt taaataacca    3540
gtatcttctt ttaggtacat tgaaaacaat acagtgcaaa aatcaaata ttacagaatc    3600 cattttaggt agcaaacagt gcagccaagc aacacctgcc atatattgtt ctagtacagc    3660
atttccatga gctccaaata ttaaatccat tttatctaat atatgattga atctttctgt    3720
tagcatttct tccctggtca tatgaagggt atctactctt ttttttagcta aaactgtatc    3780 tactgcttgc tgacaaatac tttttttgatt tttacttct gcaaaaataa tagcatttgc    3840
aaagtgcttt tcatgatact taaagtgata aggctggtct tttttctgac acttttaca    3900 ctcctctaca ttgtattgaa attctaaata catacctaat aataaaaaca catcctcaca    3960
ctttgtctct actgcatact cagtaattaa tttccaagac acctgctttg tttcttcagg    4020
ctcttctggg ctaaaatcat gctcctttaa gccccccttga atgctttctt ctatagtatg    4080
gtatggatct ctagttaagg cactatatag taagtattcc ttattaacac ccttacaaat    4140
taaaaaacta aagtacaca gcttttgaca gaaattatta attgcagaaa ctctatgtct    4200
atgtggagtt aaaaagaata taatattatg cccagcacac atgtgtctac taataaaagt    4260
tacagaatat ttttccataa gttttttata cagaatttga gcttttctt tagtagtata    4320 cacagcaaag caggcaaggg ttctattact aaatacagct tgactaagaa actggtgtag    4380
atcagaggga aagtctttag ggtcttctac ctttctttt tttttgggtg gtgttgagtg    4440
ttgagaatct gctgttgctt cttcatcact ggcaaacata tcttcatggc aaaataaatc    4500
ttcatcccat ttttcattaa aggaactcca ccaggactcc cactcttctg ttccataggt    4560
tggcacctat aaaaaaaata attacttagg gccttttaat attttattat ttatctaaat    4620
ataagttagt taccttaaag ctttagatct ctgaagggag tttctccaat tatttggacc    4680
```

| | |
|---|---|
| caccattgca gagtttcttc agttaggtct aagccaaacc actgtgtgaa gcagtcaatg | 4740 |
| cagtagcaat ctatccaaac caagggctct tttcttaaaa attttctatt taaatgcctt | 4800 |
| aatctaagct gacatagcat gcaagggcag tgcacagaag gcttttttgga acaaataggc | 4860 |
| cattccttgc agtacagggt atctgggcaa agaggaaaat cagcacaaac ctctgagcta | 4920 |
| ctccaggttc caaaatcagg ctgatgagct acctttacat cctgctccat ttttttatac | 4980 |
| aaagtattca ttctcttcat tttatcctcg tcgccccctt tgtcagggtg aaattcctta | 5040 |
| cacttcctta aataagcttt tctcattaag ggaagatttc cccaggcagc tctttcaagg | 5100 |
| cctaaaaggt ccatgagctc catggattct tccctgttaa gaactttatc cat | 5153 |

<210> SEQ ID NO 41
<211> LENGTH: 4963
<212> TYPE: DNA
<213> ORGANISM: Human polyomavirus 1
<220> FEATURE:
<223> OTHER INFORMATION: Type BK virus

<400> SEQUENCE: 41

| | |
|---|---|
| accatgacct caggaaggaa agtgcatgac tgggcagcca gccagtggca gttaatagtg | 60 |
| aaaccatgcc aaaccatgac ctcaggaagg aaagtgcatg actgggcagc cagccagtgg | 120 |
| cagttaattt gcgagcctag gaatcttggc cttgtcccca gttaaactgg acaaaggcca | 180 |
| tggttctgcg ccagctgtca cgacaagctt cagtgaaagt tggtaaaacc tggactggaa | 240 |
| caaaaaaaag agctcagagg atttttattt ttattttaga gcttttgctg gaattttgta | 300 |
| gaggtgaaga cagtgtagac gggaaaaaca aaagtaccac tgctttacct gctgtaaaag | 360 |
| actctgtaaa agactcctag gtaagtaatc cttttttttt tgtatttcca ggttcatggg | 420 |
| tgctgctcta gcacttttgg gggacctagt tgccagtgta tctgaggctg ctgctgccac | 480 |
| aggattttca gtggctgaaa ttgctgctgg ggaggctgct gctgctatag aagttcaaat | 540 |
| tgcatccctt gctactgtag agggcataac aagtacctca gaggctatag ctgctatagg | 600 |
| cctaactcct caaacatatg ctgtaattgc tggtgctcct ggggctattg ctgggtttgc | 660 |
| tgctttaatt caaactgtta gtggtattag ttccttggct caagtagggt ataggttctt | 720 |
| tagtgattgg gatcacaaag tttccactgt aggcctctat cagcaatcag gcatggcttt | 780 |
| ggaattgttt aacccagatg agtactatga tattctgttt cctggtgtaa atactttgt | 840 |
| taataatatt caataccttg atcctaggca ttggggtcct tctttgtttg ctactatttc | 900 |
| ccaggctttg tggcatgtta ttagggatga tatccttct ataacctcac aggaattgca | 960 |
| gagaagaaca gaaagatttt ttagagactc cttggctaga ttttttggagg aaactacctg | 1020 |
| gacaattgta aatgccccta taaactttta taattatatt caacaatatt attctgatct | 1080 |
| ttcccctatt aggccctcaa tggttagaca agtagctgaa agggaaggta cccgtgtaca | 1140 |
| ttttggccat acttatagta tagatgatgc tgacagtata gaagaagtta cacaaagaat | 1200 |
| ggactttaaga aatcaacaaa gtgtacattc aggagagttt atagaaaaaa ctattgcccc | 1260 |
| aggaggtgct aatcaaagaa ctgctcctca atggatgttg ccttacttc taggcctgta | 1320 |
| cgggactgta acacctgctc ttgaagcatg tgaagatggc cccaaccaaa agaaaaggag | 1380 |
| agtgtccagg ggcagctccc aaaaagccaa aggaacccgt gcaagtgcca aaactactaa | 1440 |
| taaaaggagg agtagaagtt ctagaagtta aaactgggggt agatgctatt acagaggtag | 1500 |
| aatgcttcct aaacccagaa atgggggatc cagatgaaaa ccttagggggc tttagtctaa | 1560 |
| agctaagtgc tgaaaatgac tttagcagtg atagcccaga gagaaaaatg cttccctgtt | 1620 |

```
acagcacagc aagaattccc ctccccaatt taaatgagga cctaacctgt ggaaatctac    1680
tgatgtggga ggctgtaact gtacaaacag aggttattgg aataactagc atgcttaacc    1740
ttcatgcagg gtcacaaaaa gtgcatgagc atggtggagg aaaacctatt caaggcagta    1800
atttccactt ctttgctgtt ggtggagacc ccttggaaat gcagggagtg ctaatgaatt    1860
acaggacaaa gtacccagat ggtactataa cccctaaaaa cccaacagcc cagtcccagg    1920
taatgaatac tgaccataag gcctatttgg acaaaaacaa tgcttatcca gttgagtgct    1980
gggttcctga tcctagtaga aatgaaaata ctaggtattt tgggactttc acaggagggg    2040
aaaatgttcc cccagtactt catgtgacca acacagctac cacagtgttg ctagatgaac    2100
agggtgtggg gcctctttgt aaagctgata gcctgtatgt tcagctgct gatatttgtg     2160 gcctgtttac taacagctct ggaacacaac agtggagagg ccttgcaaga tattttaaga    2220
tccgcctgag aaaaagatct gtaaagaatc cttacctaat ttcctttttg ctaagtgacc    2280
ttataaacag gagaacccag agagtggatg ggcagcctat gtatggtatg gaatcccagg    2340
tagaagaggt tagggtgttt gatggcacag aaagacttcc aggggaccca gatatgataa    2400
gatatattga caaacaggga caattgcaaa ccaaaatgct ttaaacaggt gcttttattg    2460
tacatataca tttaataaat gctgcttttg tataagccac ttttaagctt gtgttatttt    2520
gggggtggtg tttaggcct tttaaaacac tgaaagcctt tacacaaatg caactcttga     2580 ctatggggt ctgacctttg gaatcttca gcagggctg aagtatctga acttgggaa        2640 gagcattgtg attgggattc agtgcttgat ccatgtccag agtcttcagt ttctgaatcc    2700
tcttctcttg taatatcaag aatacatttc cccatgcata tattatattt catccttgaa    2760
aaagtataca tacttatctc agaatccagc ctttccttcc attcaacaat tctagattgt    2820
atatcagttg caaaatcagc tacaggccta aaccaaatta gcagtagcaa caaggtcatt    2880
ccactttgta aaattctttt ttcaagtaag aactctgagt tttgtaagga ttttcttaaa    2940
tatattttgg gcctaaaatc tatttgtctt acaaatctag cttgcagggt tttagggaca    3000
ggatactcat tcattgtaac caagcctggt ggaaatattt gggttctttt gtttaaatgt    3060
ttcttttcta aatttacctt aacacttcca tctaaataat ctctcaaact gtctaaattg    3120
tttattccat gtcctgaagg caaatccttt gattcagctc ctgtcccttt tacatcttca    3180
aaaacaacca tgtactgatc tatagctaca cctagctcaa aggttagcct ttccatgggt    3240
aggtttacat ttaaggcttt acctctacac aaatctaaca accctgcagc tagtgttgtt    3300
tttccactat caatgggacc tttaaataac cagtatcttc ttttaggtac attgaaaaca    3360
atacagtgca aaaatcaaa tattacagaa tccattttag gtagcaaaca gtgcagccaa     3420
gcaacacctg ccatatattg ttctagtaca gcatttccat gagctccaaa tattaaatcc    3480
attttatcta atatatgatt gaatctttct gttagcattt cttccctggt catatgaagg    3540
gtatctactc ttttttagc taaaactgta tctactgctt gctgacaaat aacttttttg     3600
tttttacttt ctgcaaaaat aatagcattt gcaaagtgct tttcatgata cttaaagtga    3660
taaggctggt ctttttcctg acactttta cactcctcta cattgtattg aaattctaaa     3720
tacataccta ataataaaaa cacatcctca cactttgtct ctactgcata ctcagtaatt    3780
aatttccaag acacctgctt tgtttcttca ggctcttctg ggttaaaatc atgctccttt    3840
aagccccctt gaatgctttc ttctatagta tggtatggat ctctagttaa ggcactatat    3900
agtaagtatt ccttattaac acccttacaa attaaaaaac taaaggtaca cagcttttga    3960
```

```
cagaaattat taattgcaga aactctatgt ctatgtggag ttaaaaagaa tataatatta    4020
tgcccagcac acatgtgtct actaataaaa gttacagaat attttccat aagttttta      4080 tacagaattt gagcttttc tttagtagta tacacagcaa agcaggcaag ggttctatta    4140
ctaaatacag cttgactaag aaactggtgt agatcagagg gaaagtcttt agggtcttct    4200
acctttcttt tttttttggg tggtgttgag tgttgagaat ctgctgttgc ttcttcatca    4260
ctggcaaaca tatcttcatg gcaaaataaa tcttcatccc atttttcatt aaaggaactc    4320
caccaggact cccactcttc tgttccatag gttggcacct ataaaaaaa taattactta    4380 gggcataggc cattccttgc agtacagggg atctgggcaa agaggaaaat cagcacaaac    4440
ctctgagcta ctccaggttc caaatcagg ctgatgagct acctttacat cctgctccat     4500 tttttatac aaagtattca ttctcttcat tttatcctcg tcgccccctt tgtcaggtg      4560 aaattcctta cacttcctta aagcttttct cattaaggga gatttcccc aggcagctct    4620 ttcaaggcct aaaaggtcca tgagctccat ggattcttcc ctgttaagaa ctttatccat    4680
ttttgcaaaa attgcaaaag aatagggatt tccccaaata gttttgctag gcctcagaaa    4740
aagcctccac acccttacta cttgagagaa agggtggagg cagaggcggc ctcggcctct    4800
tatatattat aaaaaaaaag gccacaggga ggagctgctt acccatggaa tgcagccaaa    4860
ccatgacctc aggaaggaaa gtgcatgact gggcagccag ccagtggcag ttaatagtga    4920
aaccccgccc ctaaaatctc tcttacccat ggaatgcagc caa                      4963

<210> SEQ ID NO 42
<211> LENGTH: 5147
<212> TYPE: DNA
<213> ORGANISM: Human polyomavirus 1
<220> FEATURE:
<223> OTHER INFORMATION: Type BK virus

<400> SEQUENCE: 42
ttttgcaaaa attgcaaaag aatagggatt tccccaaata gttttgctag gcctcagaaa      60
aagcctccac acccttacta cttgagagaa agggtggagg cagaggcggc ctcggcctct     120
tatatattat aaaaaaaaag gccacaggga ggagctgctt acccatggaa tgcagccaaa     180
ccatgacctc aggaaggaaa gtgcatgact gggcagccag ccagtggcag ttaatagtga     240
aaccccgccc ctaaaattct caaataaaca caagaggaag tggaaactgg ccaaggagt     300 ggaaagcagc cagacagaca tgttttgcga gcctaggaat cttggccttg tccccagtta     360
aactggacaa aggccatggt tctgcgccag ctgtcacgac aagcttctgt gaaagttggt     420
aaaacctgga ctgaacaaa aaaagagct cagaggattt ttattttat tttagagctt       480 ttgctggaat tttgtagagg tgaagacagt gtagacggga aaacaaaag taccactgct     540 ttacctgctg taaagactc tgtaaaagac tcctaggtaa gtaatccctt ttttttgta      600 tttccaggtt catgggtgct gctctagcac tttgggga cctagttgcc agtgtatctg       660
aggctgctgc tgccacagga ttttcagtgg ctgaaattgc tgctgggag ctgctgctg       720 ctatagaagt tcaaattgca tcccttgcta ctgtagggg cataacaagt acctcagagg      780
ctatagctgc tataggccta actcctcaaa catatgctgt aattgctggt gctcctgggg    840
ctattgctgg gtttgctgct ttaattcaaa ctgttagtgg tattagttcc ttggctcaag    900
tagggtatag gttctttagt gattgggatc acaaagttc cactgtaggc ctctatcagc     960
aatcaggcat ggctttggaa ttgtttaacc cagatgagta ctatgatatt ctgtttcctg    1020
gtgtaaatac ttttgttaat aatattcaat accttgatcc taggcattgg ggtccttctt    1080
```

```
tgtttgctac tatttcccag gctttgtggc atgttattag ggatgatata ccttctataa    1140
cctcacagga attgcagaga agaacagaaa gattttttag agactccttg gctagatttt    1200
tggaggaaac tacctggacc attgtaaatg cccctataaa cttttataat tatattcaac    1260
aatattattc tgatctgtcc cctattaggc cctcaatggt tagacaagta gctgaaaggg    1320
aaggtacccg tgtacatttt ggccatactt atagtataga tgatgctgac agtatagaag    1380
aagttacaca aagaatggat ttaagaaatc aacaaagtgt acattcagga gagtttatag    1440
aaaaaactat tgccccagga ggtgctaatc aaagaactgc tcctcaatgg atgttgcctt    1500
tacttctagg cctgtacggg actgtaacac ctgctcttga agcatatgaa gatggcccca    1560
accaaaagaa aaggagagtg tccaggggca gctcccaaaa agccaaagga acccgtgcaa    1620
gtgccaaaac tactaataaa aggaggagta gaagttctag aagttaaaac tggggtagat    1680
gctattacag aggtagaatg cttcctaaac ccagaaatgg gggatccgga tccagatgaa    1740
aaccttaggg gctttagtct aaagctaagt gctgaaaatg actttagcag tgatagccca    1800
gagagaaaaa tgcttcccctg ttacagcaca gcaagaattc ccctcccccaa tttaaatgag    1860 gacctaacct gtggaaatct actgatgtgg gaggctgtaa ctgtacaaac agaggttatt    1920
ggataaacta gcatgcttaa ccttcatgca gggtcacaaa aagtgcatga gcatggtgga    1980
ggaaaaccta ttcaaggcag taatttccac ttctttgctg ttggtggaga ccccttggaa    2040
atgcagggag tgctaatgaa ttacaggaca aagtacccag atggtactat aacccctaaa    2100
aacccaacag cccagtccca ggtaatgaat actgaccata aggcctattt ggacaaaaac    2160
aatgcttatc cagttgagtg ctgggttcct gatcccagta gaaatgaaaa tactaggtat    2220
tttgggactt tcacaggagg ggaaaatgtt cccccagtac ttcatgtgac caacacagct    2280
accacagtgt tgctagatga acagggtgtg gggcctcttt gtaaagctga tagcctgtat    2340
gtttcagctg ctgatatttg tggcctgttt actaacagct ctggaacaca acagtggaga    2400
ggccttgcaa gatattttaa gatccgcctg agaaaaagat ctgtaaagaa tccttaccca    2460
atttcctttt tgctaagtga cctcataaac aggagaaccc agagagtgga tgggcagcct    2520
atgtatggta tggaatccca ggtagaagag gttagggtgt ttgatggcac agaaagactt    2580 ccagggggacc cagatatgat aagatatatt gacaaacagg gacaattgca aaccaaaatg    2640
ctttaaacag gtgcttttat tgtacatata catttaataa atgctgcttt tgtataagcc    2700
acttttaacc ttgtgttatt ttggggggtgg tgttttaggc cttttaaaac actgaaagcc    2760
tttacacaaa tgtaactctt gactatgggg gtctgacctt tgggaatctt cagcagggc    2820 tgaagtatct gagacttggg aagagcattg tgattgggat tcagtgcttg atccatgtcc    2880
agagtcttca gtttctgaat cctcttctct tgtgatatca agaatacatt tccccatgca    2940
tatattatat ttcatccttg aaaaagtata catacttatc tcagaatcca gcctttcctt    3000
ccattcaaca attctagatt gtatatctgt tgcaaaatca gctacaggcc taaaccaaat    3060
tagcagtagc aacaaggtca ttccactttg taaaattctt ttttcaagta agaactctga    3120
gttttgtaag gattttctta aatatatttt gggcctaaaa tctatttgtc ttacaaatct    3180
agcttgcagg gttttaggga caggatactc attcattgta accaagcctg gtggaaatat    3240
ttgggttctt ttgtttaaat gttttttttc taaatttacc ttaacacttc catctaaata    3300
atctcttaaa ctgtctaaat tgtttattcc atgtcctgaa ggcaaatcct ttgattcagc    3360
ccctgtccct tttacatctt caaaaacaac catgtactga tctatagcta cacctagctc    3420
```

-continued

```
aaaggttagc ctttccatgg gtaggtttac atttaaggct ttacctccac acaaatctaa    3480
taaccctgca gctagtgttg ttttttccact atcaatggga cctttaaata accagtatct    3540
tcttttaggt acattgaaaa caatacagtg caaaaaatca aatataacag aatccatttt    3600
aggtagcaaa cagtgcagcc aagcaacacc tgccatatat tgttctagta cagcatttcc    3660
atgagctcca aatattaaat ccattttatc taatatatga ttgaatcttt ctgttagcat    3720
ttcttccctg gtcatatgaa gggtatctac tctttttta gctaaaactg tatctactgc    3780
ttgctgacaa atactttttt gattttact ttctgcaaag ataatagcat ttgcaaagtg    3840
cttttcatga tacttaaagt gataaggttg gtctttttc tgacactttt tacactcctc    3900
tacattgtat tgaaattcta aatacatacc taataataaa aacacatcct cacactttgt    3960
ctctactgca tactcagtaa ttaatttcca agacacctgc tttgtttctt caggctcttc    4020
tgggttaaaa tcatgctcct ttaagccccc ttgaatgctt tcttctatag tatggtatgg    4080
ctctctagtt aaggcactat atagtaagta ttccttatta acacccttac aaattaaaaa    4140
actaaaggta cacagctttt gacagaagtt attaattgca gaaactctat gtctatgtgg    4200
agttaaaaag aatataatat tatgcccagc acacatgtgt ctactaataa aagttacaga    4260
atattttcc ataagttttt tatacagaat ttgagcttt tctttagtag tatacacagc     4320
aaagcaggca agggttctat tactaaatac agcttgacta agaaactggt gtagatcaga    4380
gggaaagtct ttagggtctt ctacctttct tttttcttg ggtggtgttg agtgttgaga    4440
atctgctgtt gcttcttcat cactggcaaa catatcttca tggcaaaata agtcttcatc    4500
ccattttca ttaaaggaac tccaccagga ctcccactct tctgttccat aggttggcac     4560
ctataaaaaa ataattact tagggccttt taatatttta ttatttatct aaatataagt    4620
tagttacctt aaagctttag atctctgaag ggagtttctc caattatttg gacccaccat    4680
tgcagagttt cttcagttag gtctaagcca aaccactgtg tgaagcagtc aatgcagtag    4740
caatctatcc aaaccaaggg ctcttttctt aaaaattttc tatttaaatg ccttaatcta    4800
agctgacata gcatgcaagg gcagtgcaca gaaggctttt tggaacaaat aggccattcc    4860
ttgcagtaca gggtatctgg gcaaagagga aaatcagcac aaacctctga gctactccag    4920
gttccaaaat caggctgatg agctaccttt acatcctgct ccattttttt atataaagta    4980
ttcattctct tcattttatc ctcgtcgccc cctttgtcag ggtgaaattc cttcacttc     5040
cttaaataag ctttttctcat taagggaaga tttccccagg cagctctttc aaggcctaaa    5100
aggtccatga gctccatgga ttcttccctg ttaagcactt tatccat                  5147
```

<210> SEQ ID NO 43
<211> LENGTH: 5147
<212> TYPE: DNA
<213> ORGANISM: Human polyomavirus 1
<220> FEATURE:
<223> OTHER INFORMATION: Type BK virus

<400> SEQUENCE: 43

```
ttttgcaaaa attgcaaaag aatagggatt tccccaaata gttttgctag gcctcagaaa      60
aagcctccac acccttacta cttgagagaa agggtggagg cagaggcggc ctcggcctct     120
tatatattat aaaaaaaaag gccacaggga ggagctgctt acccatggaa tgcagccaaa     180
ccatgacctc aggaaggaaa gtgcatgact gggcagccag ccagtggcag ttaatagtga     240
aaccccgccc ctgaaattct caaataaaca caagaggaag tggaaactgg ccaaaggagt     300
ggaaagcagc cagacagaca tgttttgcgg gcctaggaat cttggccttg tccccagtta     360
```

```
aactggacaa aggccatggt tctgcgccag ctgtcacgac aagcttctgt gaaacttggt      420
aaaacctgga ctggaacaaa aaaaagagct cagaggattt ttatttttat tttagagctt      480
ttgctggaat tttgtagagg tgaagacagt gtagacggga aaaacaaaag taccactgct      540
ttacctgctg taaaagactc tgtaaaagac tcctaggtaa gtaatccctt tttttttgta      600
tttccaggtt gatgggtgct gctctagcac ttttggggga cctagttgcc agtgtatctg      660
aggctgctgc tgccacagga ttttcagtgg ctgaaattgc tgctgggag gctgctgctg      720 ctatagaagt tcaaattgca tcccttgcta ctgtagaggg cataacaagt acctcagagg      780
ctatagctgc tataggccta actcctcaaa catatgctgt aattgctggt gctcctgggg      840
ctattgctgg gtttgctgct ttaattcaaa ctgttactgg tattagttcc ttggctcaag      900
tagggtatag gttttttagt gattgggatc acaaagtttc cactgtaggc ctctatcagc      960
aatcaggcat ggctttggaa ttgtttaacc cagatgagta ctatgatata ttgtttcctg     1020
gtgtaaatac ttttgtaaat aatattcaat accttgatcc taggcattgg ggtccttctt     1080
tgtttgctac tatttctcag gctttgtggc atgttattag ggatgatata cctgctataa     1140
cctcacaaga attgcaaaga agaacagaaa gattttttag agactccttg gctagatttt     1200
tggaggaaac tacctggaca attgtaaatg cccctataaa cttttataat tatattcaag     1260
aatattattc tgatctttcc cctattaggc cctcaatggt tagacaagta gctgaagggg     1320
aaggtacccg tgtacatttt ggccatactt atagtataga tgatgctgac agtatagaag     1380
aagttacaca aagaatggac ttaagaaatc aacaaactgt acattcagga gagtttatag     1440
aaaaaactat tgccccagga ggtgctaatc aaagaactgc tcctcaatgg atgttgcctt     1500
tacttctagg cctgtacggg actgtaacac ctgctcttga agcatatgaa gatggcccca     1560
acaaaaagaa aaggagagtg tccaggggca gctcccaaaa agccaaagga acccgtgcaa     1620
gtgccaaaac tactaataaa aggaggagta gaagttctag aagttaaaac tgggctagat     1680
gctataacag aggtagaatg cttcctaaac ccagaaatgg gggatccgga tccagatgaa     1740
aaccttaggg gctttagtct aaagctaagt gctgaaaatg actttagcag tgatagccca     1800
gaaagaaaaa tgcttccctg ttacagcaca gcaagaattc ccctcccccaa tttaaatgag     1860 gacctaacct gtggaaatct actgatgtgg gaggctgtaa cagtacaaac agaggtcatt     1920
ggaataacta gcatgcttaa ccttcatgca gggtcacaaa aagtgcatga gcatggtgga     1980
ggtaaaccta ttcaaggcag taatttccac tttttttgctg ttggtggaga ccccttggaa     2040
atgcagggag tgctaatgaa ttacaggaca aagtacccag aagtactat aaccccaaaa     2100 aacccaacag cccagtccca agtaatgaat actgaccata aggcctattt ggacaaaaac     2160
aatgcttatc cagttgagtg ctggattcct gatcccagta gaaatgaaaa tactaggtat     2220
tttgggactt tcacaggagg ggaaaatgtt cccccagtac ttcatgtgac caacacagct     2280
accacagtgt tgctagatga acagggtgtg gggcctcttt gtaaagctga tagcctgtat     2340
gtttcagctg ctgatatttg tggcctgtttt actaacagct ctggaacaca acagtggaga     2400
ggccttgcaa gatattttaa gattcgcctg agaaaaagat ctgtaaaaaa tccttaccca     2460
atttcctttt tgctaagtga cccttataaac aggaacccc agagagtgga tgggcagcct     2520
atgtatggta tggaatccca ggtagaagag gttagggtgt tgatggcac agaaagactt     2580 ccaggggacc cagatatgat aagatatatt gacaaacaag gacaattgca aactaaaatg     2640
gtttaaacag gtgcttttat tgttgatata catttaataa atgctgcttt tgtataagcc     2700
```

```
agttttaagc ttgtgttatt ttggggggtgg tgttttaggc cttttaaaac actgaaagcc    2760
tttacacaaa tgcaactctt gactatgggg gtctgacctt tgggaatctt cagcaggggc    2820
tgaagtatct gagacttggg aagagcattg tgattgggat tcagtgcttg atccatgtcc    2880
agagtcttca gtttctgaat cttcttctct tgtgatatca agaatacatt ttcccatgca    2940
tatattatat ttcatccttg aaaaagtata catacttatc tcagaatcca gcctttcctt    3000
ccattcaaca attctagatt gtatatctgt tgcaaaatca gctacaggcc taaaccaaat    3060
tagcagtagc aacaaggtca ttccactttg tagaattctt ttttcaagta agaactctga    3120
gttttgtaag gatttttctta aatatatttt gggcctaaaa tctatctgtc ttacaaatct    3180
agcctgcagg gttttaggga caggatactc attcattgta accaggcctg gtggaaatat    3240
ttgggttctt ttgtttaaat gtttcttttc taaattaacc ttaacacttc catctaaata    3300
atctctcaaa ctgtctaaat tgtttattcc atgtcctgaa ggcaaatcct ttgattcagc    3360
tcctgttcct tttacatctt caaaaacaac catgtactga tctatagcta cacctagttc    3420
aaaggtcagc ctttccatgg gtaggtttac atttaaagct ttacctccac acaaatctaa    3480
taaccctgca gctagtgttg tttttccact atcaatggga cctttaaata accagtatct    3540
tcttttaggt acattaaaaa caatacagtg caaaaaatca aatataacag aatccatttt    3600
aggtaacaaa cagtgcagcc aagcaacacc tgccatatat tgttctaata cagcatttcc    3660
atgagcccca aatattaaat ccattttatc taatatatga ttaaatcttt ctgttagcat    3720
ttcttctcta gtcatatgaa ggctatctac tcttttttta gctaaaactg tatctactgc    3780
ttgctgacaa atacttttttt gattttact ttctgcaaag atagtagcat ttgcaaaatg    3840
cttttcatga tacttaaagt gataaggttg gtcttttttc tgacactttt tacactcctc    3900
tacattgtat tgaaattcta aatacatacc taataataaa aacacatcct cacactttgt    3960
ttctactgca tactcagtaa ttaatttcca agagacctgc tttgtttctt caggctcttc    4020
tgggttaaaa tcatgctcct ttaagccccc ttgaatgctt tcttctattg tatggtatgg    4080
atctctagtt aaggcactat atagtaagta ttccttatta acacccttac aaattaaaaa    4140
actaaaggta cacagctttt gacagaaatt attaattgca gaaactctat gtctatgtgg    4200
agttaaaaag aatataatat tatgcccagc atacatgtgt ctactaataa aagttacaga    4260 atattttttcc ataagttttt tatacagaat ttgagctttt tctttagtag tatacacagc    4320
aaagcaggca agggttctat tactaaatac agcttgacta agaaactggt gtagatcaga    4380
aggaaagtct ttagggtctt ctaccttttct tttttttcttg ggtggtgttg agtgttgaga    4440
atctgctgtt gcttcttcat cactggcaaa catatcttca tggcaaaata aatcttcatc    4500
ccatttttca ttaaaggaac tccaccagga ctcccactct tctgttccat aggttggcac    4560
ctataaaaca ataattact tagggccttt aaatatttta ttatttatct aaatataagg    4620
tagttacctt aaagctttag atctctgaag ggagtttctc caattatttg gacccaccat    4680
tgcagagttt cttcagttag gtctaagcca aaccactgtg tgaagcagtc aatgcagtag    4740
caatctatcc aaaccaaggg ctctttttctt aaaaattttc tatttaaatg ccttaatcta    4800
agctgacata gcatgcaagg gcagtgcaca gaaggctttt tggaacaaat aggccattcc    4860
ttgcagtaca gggtatctgg gcaaagagga aaatcagcac aaacctctga gctactccag    4920
gttccaaaat caggctgatg agctaccttt acatcttgct ccatttttttt atataaagta    4980 ttcattctct tcatttttatc ctcgtcgccc cctttgtcag ggtgaaattc cttacacttc    5040
cttaaatagg cttttctcat taagggaagg tttccccagg cagctctttc aaggcccaaa    5100
```
aggtccatga gctccatgga ttcttccctg ttaagcactt tatccat                5147

<210> SEQ ID NO 44
<211> LENGTH: 5196
<212> TYPE: DNA
<213> ORGANISM: Human polyomavirus 1
<220> FEATURE:
<223> OTHER INFORMATION: Type BK virus

<400> SEQUENCE: 44

| | | | | | |
|---|---|---|---|---|---|
| ttttgcaaaa | attgcaaaag | aatagggatt | tccccaaata | gttttgctag | gcctcagaaa     60 |
| aagcctccac | acccttacta | cttgagagaa | agggtggagg | ccgaggcggc | ctcggcctct    120 |
| tatatattat | aaaaaaaaag | gccacaggga | ggagctgctt | acccatggaa | tgcagccaaa    180 |
| ccatgacctc | aggaaggaaa | gtgcatgact | cacaggggaa | tgcagccaaa | ccatgacctc    240 |
| aggaaggaaa | gtgcatgact | gggcagccag | ccagtggcag | ttaatagtga | accccgccc     300 |
| ctgaaattct | caaataaaca | aagaggaag | tggaaactgg | ccaaaggagt | ggaaagcgcc    360 |
| agacagacat | gttttgcggg | cctaggaatc | ttggccttgt | ccccagttaa | actggacaaa    420 |
| ggccatggtt | ctgcgccagc | tgtcacgaca | agcttctgtg | aaacttggta | aaacctggac    480 |
| tggaacaaaa | aaaagagctc | agaggatttt | tatttttatt | ttagagcttt | tgctggaatt    540 |
| ttgtagaggt | gaagacagtg | tagacgggaa | aaacaaaagt | accactgctt | tacctgctgt    600 |
| aaaagactct | gtaaaagact | cctaggtaag | taatccctt | ttttttgtat | ttccaggttg    660 |
| atgggtgctg | ctctagcact | tttggggac | ctagttgcca | gtgtatctga | ggctgctgct    720 |
| gccacaggat | tttcagtggc | tgaaattgct | gctggggagg | ctgctgctgc | tatagaagtt    780 |
| caaattgcat | cccttgctac | tgtagagggc | ataacaagta | cctcagaggc | tatagctgct    840 |
| ataggcctaa | ctcctcaaac | atatgctgta | attgctggtg | ctcctggggc | tattgctggg    900 |
| tttgctgctt | taattcaaac | tgttactggt | attagttcct | tggctcaagt | agggtatagg    960 |
| ttttttagtg | attgggatca | caaagtttcc | actgtaggcc | tctatcagca | atcaggcatg   1020 |
| gctttggaat | tgtttaaccc | agatgagtac | tatgatatat | tgtttcctgg | tgtaaatact   1080 |
| tttgtaaata | atattcaata | ccttgatcct | aggcattggg | gtccttcttt | gtttgctact   1140 |
| atttctcagg | ctttgtgca | tgttattagg | gatgatatac | ctgctataac | ctcacaagaa   1200 |
| ttgcaaagaa | gaacagaaag | attttttaga | gactccttgg | ctagattttt | ggaggaaact   1260 |
| acctggacaa | ttgtaaatgc | ccctataaac | ttttataatt | atattcaaga | atattattct   1320 |
| gatctttccc | ctattaggcc | ctcaatggtt | agacaagtag | ctgaaaggga | aggtacccgt   1380 |
| gtacattttg | gccatactta | tagtatagat | gatgctgaca | gtatagaaga | agttacacaa   1440 |
| agaatggact | aagaaatca | acaaactgta | cattcaggag | agtttataga | aaaaactatt   1500 |
| gccccaggag | gtgctaatca | aagaactgct | cctcaatgga | tgttgccttt | acttctaggc   1560 |
| ctgtacggga | ctgtaacacc | tgctcttgaa | gcatatgaag | atggccccaa | caaaagaaa    1620 |
| aggagagtgt | ccaggggcag | ctcccaaaaa | gccaaaggaa | cccgtgcaag | tgccaaaact   1680 |
| actaataaaa | ggaggagtag | aagttctaga | agttaaaact | ggggtagatg | ctattacaga   1740 |
| ggtagaatgc | ttcctaaacc | cagaaatggg | ggatccggat | ccagatgaaa | accttagggg   1800 |
| ctttagtcta | aagctaagtg | ctgaaaatga | ctttagcagt | gatagcccag | acagaaaaat   1860 |
| gcttccctgt | tacagcacag | caagaattcc | cctcccaat | ttaaatgagg | acctaacctg    1920 |
| tggaaatcta | ctgatgtggg | aggctgtaac | agtacaaaca | gaggtcattg | gaataactag   1980 |

```
catgcttaac cttcatgcag ggtcacaaaa agtgcatgag catggtggag gtaaacctat      2040
tcaaggcagt aatttccact tttttgctgt tggtggagac cccttggaaa tgcagggagt      2100
gctaatgaat tacaggacaa agtacccaga aggtactata accccaaaaa acccaacagc      2160
ccagtcccaa gtaatgaata ctgaccataa ggcctatttg dacaaaaaca atgcttatcc      2220
agttgagtgc tggattcctg atcccagtag aaatgaaaat actaggtatt ttgggacttt      2280
cacaggaggg gaaaatgttc ccccagtact tcatgtgacc aacacagcta ccacagtgtt      2340
gctagatgaa cagggtgtgg ggcctctttg taaagctgat agcctgtatg tttcagctgc      2400
tgatatttgt ggcctgttta ctaacagctc tggaacacaa cagtggagag gccttgcaag      2460
atattttaag attcgcctga gaaaaagatc tgtaaaaaat ccttacccaa tttccttttt      2520
gctaagtgac cttataaaca ggagaaccca gagagtggag gggcagccta tgtatggtat      2580
ggaatcccag gtagaagagg ttagggtgtt tgatggcaca gaaagacttc caggggaccc      2640
agatatgata agatatattg acaaacaagg acaattgcaa accaaaatgc tttaaacagg      2700
tgcttttatt gttgatatac atttaataaa tgctgctttt gtataagcca gttttaagct      2760
tgtgttattt tgggggtggt gttttaggcc ttttaaaaca ctgaaagcct ttacacaaat      2820
gcaactcttg actatggggg tctgaccttt gggaatcttc agcaggggct gaagtatctg      2880
agacttggga agagcattgt gattgggatt cagtgcttga tccatgtcca gagtcttcag      2940
tttctgaatc ttcttctctt gtaatatcaa gaatacattt tcccatgcat atattatatt      3000
tcatccttga aaaagtatac atacttatct cagaatccag cctttccttc cattcaacaa      3060
ttctagattg tatatctgtt gcaaaatcag ctacaggcct aaaccaaatt agcagtagca      3120
acaaggtcat tccactttgt agaattcttt tttcaagtaa gaactctgag tttggtaagg      3180
attttcttaa atatattttg ggcctaaaat ctatctgtct tacaaatcta gcctgcaggg      3240
ttttagggac aggatactca ttcattgtaa ccaggcctgg tggaaatatt tgggttcttt      3300
tgtttaaatg tttctttttct aaattaacct taacacttcc atctaaataa tctctcaaac      3360
tgtctaaatt gtttattcca tgtcctgaag gcaaatcctt tgattcagct cctgttcctt      3420
ttacatcttc aaaaacaacc atgtactgat ctatagctac acctagttca aaggttagcc      3480
tttccatggg taggtttaca tttaaagctt tacctccaca caaatctaat aaccctgcag      3540
ctagtgttgt ttttccacta tcaatgggac ctttaaataa ccagtatctt ctttttaggta      3600 cattaaaaac aatacagtgc aaaaaatcaa atataacaga atccatttta ggtagcaaac      3660
agtgcagcca agcaacacct gccatatatt gttctaatac agcatttcca tgagccccaa      3720
atattaaatc cattttatct aatatatgat taaatctttc tgttagcatt tcttctctag      3780
tcatatgaag gctatctact ctttttttag ctaaaactgt atctactgct tgctgacaaa      3840
tacttttttg attttactt tctgcaaata tagtagcatt tgcaaaatgc ttttcatgat      3900
acttaaagtg ataaggttgg tcttttttct gacactttt acactcctct acattgtatt      3960
gaaattctaa atacatacct aataataaaa acacatcctc acactttgtt tctactgcat      4020
actcagtaat taatttccaa gagacctgct tgtttcttc aggctcttct gggttaaaat      4080
catgctcctt taagccccct tgaatgcttt cttctattgt atggtatgga tctcagtta      4140 aggcactata tagtaagtat tccttattaa caccccttaca aattaaaaaa ctaaaggtac      4200
acagcttttg acagaaatta ttaattgcag aaactctatg tctatgtgga gttaaaaga      4260 atataatatt atgcccagca cacatgtgtc tactaataaa agttacagaa tattttttcca      4320 taagttttt atacagaatt tgagcttttt ctttagtagt atacacagca aagcaggcaa      4380
```

```
gggttctatt actaaataca gcttgactaa gaaactggtg tagatcagaa ggaaagtctt   4440
tagggtcttc taccttttctt ttttttcttgg gtggtgttga gtgttgagaa tctgctgttg   4500
cttcttcatc actggcaaac atatcttcat ggcaaaataa atcttcatcc cattttttcat   4560 taaaggaact ccaccaggac tcccactctt ctgttccata ggttggcacc tataaaacaa   4620
ataattactt agggccttta aatatttat tatttatcta aatataaggt agttaccta   4680 aagctttaga tctctgaagg gagtttctcc aattatttgg acccaccatt gcagagtttc   4740
ttcagttagg tctaagccaa accactgtgt gaagcagtca atgcagtagc aatctatcca   4800
aaccaagggc tcttttctta aaaattttct atttaaatgc cttaatctaa gctgacatag   4860
catgcaaggg cagtgcacag aaggcttttt ggaacaaata ggccattcct tgcagtacag   4920
ggtatctggg caaagaggaa aatcagcaca aacctctgag ctactccagg ttccaaaatc   4980
aggctgatga gctacctta catcttgctc cattttttta tataaagtat tcattctctt   5040
cattttatcc tcgtcgcccc cttttgtcagg gtgaaattcc ttacacttcc ttaaataggc   5100
ttttctcatt aagggaaggt tcccccaggc agctctttct aggcccaaaa ggtccatgag   5160
ctccatggat tcttccctgt taagcacttt atccat                              5196

<210> SEQ ID NO 45
<211> LENGTH: 5154
<212> TYPE: DNA
<213> ORGANISM: Human polyomavirus 1
<220> FEATURE:
<223> OTHER INFORMATION: Type BK virus

<400> SEQUENCE: 45
ttttgcaaaa aattgcaaaa gaatagggat tcccccaaat agtttgtgcta ggcctcagaa     60 aaagcctcca caccccttact acttgagaga aagggtggag gcagaggcgg cctcggcctc    120
ttatatatta taaaaaaaaa ggccacaggg aggagctgct ttcccatgga atgcagccaa    180
accatgacct caggaaggaa agtgcatgac tgggcagcca gccagtggca gttaatagtg    240
aaaccccgcc cctagaatgc tcaaataaac acaagaggaa gtggaaagta gccaaaggag    300
tggaaagcag ccagacagac atgttttgcg agccgaggaa tcttggcctt gtccccagtt    360
aatactggac aaaggccatg gttctgcgcc agctgtcacg acaagcttct gtgaaagtta    420
gtaaaacctg gactggaact aaaaaaagag ctcagaggat tcttattttt attttagagc    480
ttttgctgga atttttgtaga ggtgaagaca gtgtagacgg gaaaaacaaa agtaccactg    540
ctttacctgc tgtaaaagac tctgtaaaag actcctaggt aagtaatccc ttttttttttg    600 tatttccagg ttcatggggtg ctgctctagc acttttgggg gacctagttg ccagtgtatc    660
tgaggctgct gctgccacag gattttcagt ggctgaaatt gctgctgggg aggctgctgc    720
tgctatagaa gttcaaattg catccccttgc tactgtagag ggcataacaa gtacctcaga    780
ggctatagct gctataggcc taactcctca aacatatgct gtaattgctg gtgctccagg    840
ggctattgct gggtttgctg ctttaattca aactgttact ggtattagtt ctttggctca    900
agtagggtat aggttttttta gtgattggga tcacaaagtt tccactgtag gcctttatca    960
gcaatcaggc atggcattgg aattgtttaa cccagatgaa tactatgata ttttgttcc   1020 tggtgtaaat acttttgtaa ataatattca ataccctagat cctaggcatt ggggtcctttc   1080 tttgtttgct actattccc aggctttgtg gcatgttatt agggatgata tacctgctat   1140
aacttcacaa gaattgcaaa gaagaacaga gagattctttt agagactcct tggctagatt   1200
```

-continued

```
tttggaagaa actacctgga caattgtaaa tgccctgta aacttttata attatattca    1260
ggattattat tctaatttgt ccctattag gccttcaatg gttaggcaag ttgctgaaag    1320
ggaaggaacc caggtaaatt ttggccatac ctacagaata gatgatgctg acagtataca    1380
agaagttacc caaagaatgg agttaagaaa taaagagaat gtacattcag gagagtttat    1440
agaaaaaact attgccccag gaggtgctaa tcaaagaact gctcctcaat ggatgttgcc    1500
tttgcttcta ggcctgtacg ggactgtaac acctgctctt gaagcatatg aagatggccc    1560
caaccaaaag aaaaggagag tgtccagggg cagctcccaa aaagccaaag gaacccgtgc    1620
aagtgccaaa actactaata aaaggaggag tagaagttct agaagttaaa actggggtag    1680
atgctataac agaagtagaa tgcttcctaa acccagaaat gggggatccg gatccagatg    1740
aaaaccttag gggctttagt ctaagactaa ctgctgaaac tgcctttgac agtgatagcc    1800
cagacagaaa aatgcttccc tgttacagca cagcaagaat tccactacct aatttgaatg    1860
aggatctaac ctgtggaaat ctactaatgt gggaggctgt gactgtaaaa acagaggtta    1920
ttggaataac tagtatgctt aaccttcatg cagggtcaca gaaagtacat gaaaatggtg    1980
gaggcaaacc tattcaaggc agcaattttc acttttttgc tgtgggtggg gacccttgg     2040 aaatgcaggg agtacttatg aactacagaa caaagtaccc agaaggtact gtcaccccaa    2100
aaaatcccac agctcagtcc caggtaatga atactgacca taaggcctac ttggacaaaa    2160
acaatgctta tccagttgaa tgctggattc ctgaccctag tagaaatgaa atactaggt     2220 attttggaac atacacagga ggggaaaatg ttcccccagt acttcatgta accaacacag    2280
ctaccacagt gttgctggat gaacagggtg tggggcctct gtgtaaagct gatagcctgt    2340
atgtttcagc tgctgatatt tgtggactgt ttactaacag gtctggaaca caacagtgga    2400
ggggccttcc aagatatttt aagattcgcc tgagaaaaag atctgtaaag aacccttacc    2460
caatttcctt tttgcttagt gaccttataa acaggagaac ccagagagtg gatgggcagc    2520
ctatgtatgg tatggagtct caggtggagg aggtcagggt gtttgatggc acagaacagc    2580 ttccaggga cccagatatg ataagatata ttgacagaca gggacaattg caaacaaaaa    2640
tggtttaaac aaggtgcttt tattgtacat atacatgctt aataaatgct gcttttatat    2700
tacacacttt taatcttgtg ttattttggg ggtggtgttt taggccttttt aaaacactga    2760 aagcctttac acaaatgtaa ctcttcacta tggggtcta gcctttggga atcttcagca    2820
ggggctgaag tatctgagac ttgggaagag cattgtgatt gggattcagt gcttgatcca    2880
tgtccagagt cttcagtttc tgaatcttct tctcttgtta tatcaagaat acatttcccc    2940
atgcatatat tatatttcat ccttgaaaaa gtatacatac ttatctcaga atccagcctt    3000
tccttccatt caacaattct agactgtata tcttgtgcaa aatcagctac aggcctgaac    3060
caaattagca gtagcaacaa ggtcattcca ctttgtaata ttcttttttc aagtaaaaat    3120
tctgagtttt gcagggattt tcttaaataa attttaggtc taaatctat ctgtcttaca     3180 aatctagcct gcaaggtttt ggggacagga tactcattca ttgtaactaa acctggtgga    3240
aatatttggg ttcttttgtt taagtgtttc ttttctaaat taactttgac acttccatct    3300
aaataatccc ttaaactgtc taaattgttt attccatgtc ctgaaggcaa atcctttgat    3360
tcagctcctg ttcccttcac atcttcaaaa acaaccatat actgatctat agccacaccc    3420
agttcaaaag taagcctctc catgggtaaa ttcacattta aagctttgcc tccacataaa    3480
tctaataacc ctgcagctag tgttgttttt ccactatcaa ttggaccttt gaataaccag    3540
tatcttcttt taggtacatt aaaaacaata cagtgcagga aatcaaatat aacagaatcc    3600
```

```
atttaggta gcaaacagtg cagccaggca actcctgcca tatattgttc tagtacagca    3660
tttccatgag ctccaaatat taaatccatt ttatctaata tatgattaaa tctgtctgtt    3720
agcatttctt ctctggtcat atggagggta tctacccttt ttttagctaa cactgtatcc    3780
actgcttgct gacaaatact ttttttgattt ttactttctg caaaaatggt agcatttgca    3840
aaatgctttt catgatattt aaagtggtag ggttggtctt tttttttgaca ctttttacac    3900 tcctctacat tgtactgaaa ttctaaatac atacccaata gtagaaacac atcttcacac    3960
tttgtttcta ctgcatattc agttattaat ttccaggaca cctgctttgt ttcttcaggt    4020
tcctctgggt taaaatcatg ctcctttagg cccccttgaa tactttcctc tattatataa    4080
tatggatctc tagttaaggc actgtatagt aagtattcct tattaacacc cttacaaatt    4140
aaaaaactaa aagtacacag cttttgacag aaattattaa ttgcagaaac tctatgtcta    4200
tgtggagtta aaagaatat aatattatga ccagcacaca tgtgtctact aataaaagtt    4260
acagaatatt tttccataag ttttttatac agaattaaag cttttttcttt agtagtatac    4320 acagcaaagc aggcaagagt tctattacta aatacagctt gactaagaaa ctggtgtaga    4380
tcagaaggaa agtctttagg gtcttctacc tttcttttttt ttttgggtgg tgttgagtgt    4440
tgagaatctg ctgttgcctc ctcatcactg gcaaacatat cttcatggca aaataaatct    4500
tcatcccatt tttcattaaa ggacctccac caggactccc actcttctgt tccataggtt    4560
ggcacctata aaaaaaacat aattacttag ggccttccta taatttacta tttatctaaa    4620
gataaattag ttaccttaaa gctttagatc tctgaaggga gtctctccaa ttatttggac    4680
ccaccattgc agagtttctt cagttaggtc taagccaaac cactgtgtga agcagtcaat    4740
gcagtagcaa tctatccaaa ccaagggctc ttttcttaaa aattttctat ttaaatgtct    4800
taatcttagc tgacacagca tgcaagggca gtgcactgaa ggcttttttgg aacaaatagg    4860 ccattccttg cagtacaggg tatctgggca aagaggaaaa tcagcacaaa cctctgagct    4920
actccaggtt ccaaaatcag gctggtgagc tacctttaca tcctgctcca ttttttttata    4980 taaagtattc attctcttca ttttatcctc gtcgccccct ttgtcagggt gaaattcctt    5040
acactttctt aaataggctt tcctcattaa gggaaggttc cccaggcag ctctttcaag    5100 gcctaaaagg tccatgagct ccatggattc ctccctgttt agaactttat ccat          5154
```

<210> SEQ ID NO 46
<211> LENGTH: 5149
<212> TYPE: DNA
<213> ORGANISM: Human polyomavirus 1
<220> FEATURE:
<223> OTHER INFORMATION: Type BK virus

<400> SEQUENCE: 46

```
ttttgcaaaa attgcaaaag aatagggatt tcccccaaat agtttgtcta ggcctcagaa      60
aaagcctcca caccttact acttgagaga aaggtggag gcagaggcgg cctcggcctc       120
ttatatatta taaaaaaaaa ggccacaggg aggagctgct tacccatgga atgcagccaa     180
accatgacct caggaaggaa agtgcatgac tgggcagcca gccagtggca gttaatagtg     240
aaaccccgcc cctgaaattc tcaaataaac acaagaggga gtgaaactg gccaaaggag     300 tggaaagcag ccagacagac atgtttgcgg gcctaggaa tcttggcctt gtccccagtt     360
aaactggaca aaggccatgg ttctgcgcca gctgtcacga caagcttctg tgaaacttgg    420
taaaacctgg actggaacaa aaaaaagagc tcagaggatt tttatttta ttttagagct    480
```

```
tttgctggaa ttttgtagag gtgaagacag tgtagacggg aaaaacaaaa gtaccactgc    540
tttacctgct gtaaaagact ctgtaaaaga ctcctaggta agtaatccct ttttttttgt    600
atttccaggt tgatgggtgc tgctctagca cttttggggg acctagttgc cagtgtatct    660
gaggctgctg ctgccacagg attttcagtg gctgaaattg ctgctgggga ggctgctgct    720
gctatagaag ttcaaattgc atcccttgct actgtagagg cataacaag tacctcagag    780 gctatagctg ctataggcct aactcctcaa acatatgctg taattgctgg tgctcctggg    840
gctattgctg ggtttgctgc tttaattcaa actgttactg gtattagttc cttggctcaa    900
gtagggtata ggttttttag tgattgggat cacaaagttt ccactgtagg cctctatcag    960
caatcaggca tggctttgga attgtttaac ccagatgagt actatgatat attgtttcct   1020
ggtgtaaata cttttgtaaa taatattcaa taccttgatc ctaggcattg gggtccttct   1080
ttgtttgcta ctatttctca ggctttgtgg catgttatta gggatgatat acctgctata   1140
acctcacaag aattgcaaag aagaacagaa agatttttta gagactccct ggctagattt   1200
ttggaggaaa ctacctggac aattgtaaat gcccctataa acttttataa ttatattcaa   1260
gaatattatt ctgatctttc ccctattagg ccctcaatgg ttagacaagt agctgaaagg   1320
gaaggtaccc gtgtacattt tggccatact tatagtatag atgatgctga cagtatagaa   1380
gaagttacac aaagaatgga cttaagaaat caacaaactg tacattcagg agagtttata   1440
gaaaaaacta ttgccccagg aggtgctaat caaagaactg ctcctcaatg gatgttgcct   1500
ttacttctag gcctgtacgg gactgtaaca cctgctcttg aagcatatga agatggcccc   1560
aacaaaaaga aaaggagagt gtccaggggc agctcccaaa aagccaaagg aacccgtgca   1620
agtgccaaaa ctgctaataa aaggaggagt agaagttcta gaagttaaaa ctgggctaga   1680
tgctataaca gaggtagaat gcttcctaaa cccagaaatg ggggatccag gatccagatg   1740
aaaaccttag gggctttagt ctaaagctaa gtgctgaaaa tgactttagc agtgatagcc   1800
cagaaagaaa aatgcttccc tgttacagca cagcaagaat tcccctcccc aatttaaatg   1860
aggacctaac ctgtggaaat ctactgatgt gggaggctgt aacagtacaa acagaggtca   1920
ttggaataac tagcatgctt aaccttcatg cagggtcaca aaaagtgcat gagcatggtg   1980
gaggtaaacc tattcaaggc agtaatttcc acttttttgc tgttggtgga gacccccttgg   2040 aaatgcaggg agtgctaatg aattacagga caaagtaccc agaaggtact ataaccccaa   2100
aaaacccaac agcccagtcc caagtaatga atactgacca taaggcctat ttggacaaaa   2160
acaatgctta tccagttgag tgctggattc ctgatcccag tagaaatgaa aatactaggt   2220
attttgggac tttcacagga ggggaaaatg ttcccccagt acttcatgtg accaacacag   2280
ctaccacagt gttgctagat gaacagggtg tggggcctct ttgtaaagct gatagcctgt   2340
atgtttcagc tgctgatatt tgtggcctgt ttactaacag ctctggaaca caacagtgga   2400
gaggccttgc aagatatttt aagattcgcc tgagaaaaag atctgtaaaa aatccttacc   2460
caatttcctt tttgctaagt gaccttataa acaggagaac ccagagagtg gatgggcagc   2520
ctatgtatgg tatggaatcc caggtagaag aggttagggt gtttgatggc acagaaaaac   2580
ttccagggga cccagatatg ataagatata ttgacaaaca aggacaattg caaaccaaaa   2640
tgctttaaac aggtgctttt attgttgata tacatttaat aaatgctgct tttgtataag   2700
ccagttttaa gcttgtgtta ttttgggggt ggtgttttag gccttttaaa acactgaaag   2760
cctttacaca aatgcaactc ttgactatgg gggtctgacc tttgggaatc ttcagcaggg   2820
gctgaagtat ctgagacttg ggaagagcat tgtgattggg attcagtgct tgatccatgt   2880
```

```
ccagagtctt cagtttctga atcttcttct cttgtgatat caagaataca ttttcccatg   2940
catatattat atttcatcct tgaaaaagta tacatactta tctcagaatc cagcctttcc   3000
ttccattcaa caattctaga ttgtatatct gttgcaaaat cagctacagg cctaaaccaa   3060
attagcagta gcaacaaggt cattccactt tgtaaaattc ttttttcaag taagaactct   3120
gagttttgta aggattttct taaatatatt ttgggcctaa aatctatctg tcttacaaat   3180
ctagcctgca gggttttagg dacaggatac tcattcattg taaccaggcc tggtggaaat   3240
atttgggttc ttttgtttaa atgtttcttt tctaaattaa ccttaacact tccatctaaa   3300
taatctctca aactgtctaa attgtttatt ccatgtcctg aaggcaaatc ctttgattca   3360
gctcctgttc cttttacatc ttcaaaaaca accatgtact gatctatagc tacacctagt   3420
tcaaaggtta gcctttccat gggtaggttt acatttaaag ctttacctcc acacaaatct   3480
aataaccctg cagctagtgt tgttttccca ctatcaatgg gacctttaaa taaccagtat   3540
cttcttttag gtacattaaa aacaatacag tgcaaaaaat caaatataac agaatccatt   3600
ttaggtagca aacagtgcag ccaagcaaca cctgccatat attgttctaa tacagcattt   3660
ccatgagccc caaatattaa atccatttta tctaatatat gattaaatct ttctgttagc   3720
atttcttctc tagtcatatg aaggctatct actcttttt tagctaaaac tgtatctact   3780
gcttgctgac aaatactttt ttgattttta ctttctgcaa agatagtagc atttgcaaaa   3840
tgcttttcat gatacttaaa gtgataaggt tggtcttttt tctgacactt tttacactcc   3900
tctacattgt attgaaattc taaatacata cctaataata aaaacacatc ctcacacttt   3960
gtttctactg catactcagt aattaatttc caagagacct gctttgtttc ttcaggctct   4020
tctgggttaa aatcatgctc ctttaagccc ccttgaatgc tttcttctat tgtatggtat   4080
ggatctctag ttaaggcact atatagtaag tattccttat taacacccctt acaaattaaa   4140 aaactaaagg tacacagctt ttgacagaaa ttattaattg cagaaactct atgtctatgt   4200
ggagttaaaa agaatataat attatgccca gcacacatgg gtctactaat aaaagttaca   4260 gaatatttt ccataagttt tttatacaga atttgagctt tttctttagt agtatacaca   4320
gcaaagcagg cgagggttct attactaaat acagcttgac taagaaactg gtgtagatca   4380
gaaggaaagt ctttagggtc ttctaccttt cttttttttct tgggtggtgt tgagtgttga   4440
gaatctgctg ttgcttcttc atcactggca aacatatctt catggcaaaa taatctttca   4500
tcccattttt cattaaagga actccaccaa gactcccact cttctgttcc ataggttggc   4560
acctataaaa caataatta cttagggcct ttaaatatttt tattatttat ctaaatataa   4620
ggtagttacc ttaaagcttt agatctctga agggagtttc tccaattatt tggacccacc   4680
attgcagagt ttcttcagtt aggtctaagc caaaccactg tgtgaagcag tcaatgcagt   4740
agcaatctat ccaaaccaag ggctcttttc ttaaaaattt tctatttaaa tgccttaatc   4800
taagctgaca tagcatgcaa gggcagtgca cagaaggctt tttggaacaa ataggccatt   4860
ccttgcagta cagggtatct gggcaaagag gaaaatcagc acaaacctct gagctactcc   4920
aggttccaaa atcaggctga tgagctacct ttacatcttg ctccattttt ttatataaag   4980
tattcattct cttcattta tcctcgtcgc ccccttttgtc agggtgaaat tccttacact   5040
tccttaaata ggcttttctc attaagggaa ggtttcccca ggcagctctt tcaaggccca   5100
aaaggtccat gagctccatg gattcttccc tgttaagcac tttatccat              5149
```

<210> SEQ ID NO 47

<211> LENGTH: 5146
<212> TYPE: DNA
<213> ORGANISM: Human polyomavirus 1
<220> FEATURE:
<223> OTHER INFORMATION: Type BK virus

<400> SEQUENCE: 47

| | | | | | |
|---|---|---|---|---|---|
| ttttgcaaaa | attgcaaaag | aatagggatt | tccccaaata | gttttgctag | gcctcagaaa | 60 |
| aagcctccac | acccttacta | cttgagagaa | agggtggagg | cagaggcggc | ctcggcctct | 120 |
| tatatattat | aaaaaaaaag | gccacaggga | ggagctgctt | acccatggaa | tgcagccaaa | 180 |
| ccatgacctc | aggaaggaaa | gtgcatgact | gggcagccag | ccagtggcag | ttaatagtga | 240 |
| aaccccgccc | ctgaaattct | caaataaaca | caagaggaag | tggaaactgg | ccaaaggagt | 300 |
| ggaaagcagc | cagacagaca | tgttttgcgg | gcctaggaat | cttggccttg | tccccagtta | 360 |
| aactggacaa | aggccatggt | tctgcgccag | ctgtcacgac | aagcttctgt | gaaacttggt | 420 |
| aaaacctgga | ctggaacaaa | aaaagagct | cagaggattt | ttattttat | tttagagctt | 480 |
| ttgctggaat | tttgtagagg | tgaagacagt | gtagacggga | aaaacaaaag | taccactgct | 540 |
| ttacctgctg | taaagactc | tgtaaaagac | tcctaggtaa | gtaatcccctt | ttttttgta | 600 |
| tttccaggtt | gatgggtgct | gctctagcac | ttttggggga | cctagttgcc | agtgtatctg | 660 |
| aggctgctgc | tgccacagga | ttttcagtgg | ctgaaattgc | tgctggggag | gctgctgctg | 720 |
| ctatagaagt | tcaaattgca | tcccttgcta | ctgtagaggg | cataacaagt | acctcagagg | 780 |
| ctatagctgc | tataggccta | actcctcaaa | catatgctgt | aattgctggt | gctcctgggg | 840 |
| ctattgctgg | gtttgctgct | ttattcaaac | tgttactggt | attagttcct | tggctcaagt | 900 |
| agggtatagg | ttttttagtg | attgggatca | caaagtttcc | actgtaggcc | tctatcagca | 960 |
| atcaggcatg | gctttggaat | tgtttaaccc | agatgagtac | tatgatatat | tgtttcctgg | 1020 |
| tgtaaatact | tttgtaaata | atattcaata | ccttgatcct | aggcattggg | gtccttcttt | 1080 |
| gtttgctact | atttctcagg | ctttgtggca | tgttattagg | gatgatatac | ctgctataac | 1140 |
| ctcacaagaa | ttgcaaagaa | gaacagaaag | atttttaga | gactccttgg | ctagattttt | 1200 |
| ggaggaaact | acctggacaa | ttgtaaatgc | ccctataaac | ttttataatt | atattcaaga | 1260 |
| atattattct | gatctttccc | ctattaggcc | ctcaatggtt | agacaagtag | ctgaaaggga | 1320 |
| aggtacccgt | gtacattttg | gccatactta | tagtatagat | gatgctgaca | gtatagaaga | 1380 |
| agttacacaa | agaatggact | taagaaatca | acaaactgta | cattcaggag | agtttataga | 1440 |
| aaaaactatt | gccccaggag | gtgctaatca | agaactgct | cctcaatgga | tgttgccttt | 1500 |
| acttctaggc | ctgtacggga | ctgtaacacc | tgctcttgaa | gcatatgaag | atggccccaa | 1560 |
| caaaaagaaa | aggagagtgt | ccaggggcag | ctcccaaaaa | gccaaaggaa | cccgtgcaag | 1620 |
| tgccaaaact | actaataaaa | ggaggagtag | aagttctaga | agttaaaact | gggctagatg | 1680 |
| ctataacaga | ggtagaatgc | ttcctaaacc | cagaaatggg | ggatccggat | ccagatgaaa | 1740 |
| accttagggg | ctttagtcta | aagctaagtg | ctgaaaatga | ctttagcagt | gatagcccag | 1800 |
| aaagaaaaat | gcttcccctgt | tacagcacag | caagaattcc | cctcccccat | ttaaatgagg | 1860 |
| acctaacctg | tggaaatcta | ctgatgtggg | aggctgtaac | agtacaaaca | gaggtcattg | 1920 |
| gaataactag | catgcttaac | cttcatgcag | ggtcacaaaa | agtgcatgag | catggtggag | 1980 |
| gtaaacctat | tcaaggcagt | aatttccact | ttttgctgt | tggtggagac | cccttggaaa | 2040 |
| tgcagggagt | gctaatgaat | tacaggacaa | agtacccaga | aggtactata | accccaaaaa | 2100 |
| acccaacagc | ccagtcccaa | gtaatgaata | ctgaccataa | ggcctatttg | gacaaaaaca | 2160 |

```
atgcttatcc agttgagtgc tggattcctg atcccagtag aaatgaaaat actaggtatt    2220
ttgggacttt cacaggaggg gaaaatgttc ccccagtact tcatgtgacc aacacagcta    2280
ccacagtgtt gctagatgaa cagggtgtgg ggcctctttg taaagctgat agcctgtatg    2340
tttcagctgc tgatatttgt ggcctgttta ctaacagctc tggaacacaa cagtggagag    2400
gccttgcaag atattttaag attcgcctga gaaaagatc tgtaaaaaat ccttacccaa     2460
tttcctttt gctaagtgac cttataaaca ggagaaccca gagagtggat gggcagccta    2520
tgtatggtat ggaatcccag gtagaagagg ttagggtgtt tgatggcaca gaaagacttc    2580
caggggaccc agatatgata agatatattg acaaacaagg acaattgcaa actaaaatgg    2640
tttaaacagg tgcttttatt gttgatatac atttaataaa tgctgctttt gtataagcca    2700
gttttaagct tgtgttattt tgggggtggt gttttaggcc ttttaaaaca ctgaaagcct    2760
ttacacaaat gcaactcttg actatggggg tctgaccttt gggaatcttc agcagggggct   2820
gaagtatctg agacttggga agagcattgt gattgggatt cagtgcttga tccatgtcca    2880
gagtcttcag tttctgaatc ttcttctctt gtgatatcaa gaatacatttt tcccatgcat   2940
atattatatt tcatccttga aaagtatac atacttatct cagaatccag cctttccttc    3000
cattcaacaa ttctagattg tatatctgtt gcaaaatcag ctacaggcct aaaccaaatt    3060
agcagtagca acaaggtcat tccactttgt agaattcttt tttcaagtaa gaactctgag    3120
ttttgtaagg atttttcttaa atatattttg ggcctaaaat ctatctgtct tacaaatcta  3180
gcctgcaggg ttttagggac aggatactca ttcattgtaa ccaggcctgg tggaaatatt    3240
tgggttcttt tgtttaaatg tttctttttct aaattaacct taacacttcc atctaaataa  3300
tctctcaaac tgtctaaatt gtttattcca tgtcctgaag gcaaatcctt tgattcagct    3360
cctgttcctt ttacatcttc aaaaacaacc atgtactgat ctatagctac acctagttca    3420
aaggtcagcc tttccatggg taggtttaca tttaaagctt tacctccaca caaatctaat    3480
aaccctgcag ctagtgttgt ttttccacta tcaatgggac ctttaaataa ccagtatctt    3540
cttttaggta cattaaaaac aatacagtgc aaaaaatcaa atataacaga atccatttta    3600
ggtaacaaac agtgcagcca agcaacacct gccatatatt gttctaatac agcatttcca    3660
tgagccccaa atattaaatc cattttatct aatatatgat taaatctttc tgttagcatt    3720
tcttctctag tcatatgaag gctatctact ctttttttag ctaaaactgt atctactgct    3780
tgctgacaaa tacttttttg attttttactt tctgcaaaga tagtagcatt tgcaaaatgc    3840
ttttcatgat acttaaagtg ataaggttgg tcttttttct gacactttttt acactcctct    3900
acattgtatt gaaattctaa atacatacct aataataaaa acacatcctc acactttgtt    3960
tctactgcat actcagtaat taatttccaa gagacctgct tgtttcttc aggctcttct     4020
gggttaaaat catgctcctt taagccccct tgaatgcttt cttctattgt atggtatgga    4080
tctctagtta aggcactata tagtaagtat tccttattaa cacccttaca aattaaaaaa    4140
ctaaaggtac acagcttttg acagaaatta ttaattgcag aaactctatg tctatgtgga    4200
gttaaaaaga atataatatt atgcccagca cacatgtgtc tactaataaa agttacagaa    4260
tatttttcca taagtttttt atacagaatt tgagcttttt ctttagtagt atacacagca    4320
aagcaggcaa gggttctatt actaaataca gcttgactaa gaaactggtg tagatcagaa    4380
ggaaagtctt tagggtcttc taccttcttt ttttcttgg gtggtgttga gtgttgagaa     4440
tctgctgttg cttcttcatc actggcaaac atatcttcat ggcaaaataa atcttcatcc    4500
```

```
cattttttcat taaaggaact ccaccaggac tcccactctt ctgttccata ggttggcacc    4560
tataaaacaa ataattactt agggccttta aatattttat tatttatcta aatataaggt    4620 agttaccttta aagctttaga tctctgaagg gagtttctcc aattatttgg acccaccatt    4680
gcagagtttc ttcagttagg tctaagccaa accactgtgt gaagcagtca atgcagtagc    4740
aatctatcca aaccaagggc tcttttctta aaaattttct atttaaatgc cttaatctaa    4800
gctgacatag catgcaaggg cagtgcacag aaggcttttt ggaacaaata ggccattcct    4860
tgcagtacag ggtatctggg caaagaggaa aatcagcaca aacctctgag ctactccagg    4920
ttccaaaatc aggctgatga gctaccttta catcttgctc catttttta tataaagtat    4980 tcattctctt catttttatcc tcgtcgcccc ctttgtcagg gtgaaattcc ttacacttcc    5040
ttaaataggc ttttctcatt aagggaaggt tccccaggc agctctttca aggcccaaaa    5100
ggtccatgag ctccatggat tcttccctgt taagcacttt atccat               5146
```

<210> SEQ ID NO 48
<211> LENGTH: 5153
<212> TYPE: DNA
<213> ORGANISM: Human polyomavirus 1
<220> FEATURE:
<223> OTHER INFORMATION: Type BK virus

<400> SEQUENCE: 48

```
ttttgcaaaa aattgcaaaa gaatagggat ttccccaaat agttttgcta ggcctcagaa      60
aaagcctcca caccctact acttgagaga aagggtggag gcagaggcgg cctcggcctc     120
ttatatatta taaaaaaaaa ggccacaggg aggagctgct ttcccatgga atgcagccaa     180
accatgacct caggaaggaa agtgcatgac tgggcagcca gccagtggca gttaatagtg     240
aaaccccgcc cctagaattc tcaaataaac acaagaggaa gtggaaagta gccaaaggag     300
tggaaagcag ccagacagac atgttttgcg agccgaggaa tcttggcctt gtccccagtt     360
aatactggac aaaggccatg gttctacgcc agctgtcacg acaagcttct gtgaaagtta     420
gtaaaacctg gactggaact aaaaaaagag ctcagaggat tcttattttt attttagagc     480
ttttgctgga atttttgtaga ggtgaagaca gtgtagacgg gaaaaacaaa agtaccactg     540
ctttacctgc tgtaaaagac tctgtaaaag actcctaggt aagtaatccc ttttttttg     600 tatttccagg ttcatgggtg ctgctctagc acttttgggg gacctagttg ccagtgtatc     660
tgaggctgct gctgccacag gattttcagt ggctgaaatt gctgctgggg aggctgctgc     720
tgctatagaa gttcaaattg catcccttgc tactgtagag ggcataacaa gtacctcaga     780
ggctatagct gctataggcc taactcctca acatatgct gtaattgctg gtgctccagg     840
ggctattgct gggtttgctg ctttaattca aactgttact ggtattagtt ctttggctca     900
agtagggtat aggttttta gtgattggga tcacaaagtt tccactgtag gcctttatca     960
gcaatcaggc atggcattgg aattgtttaa cccagatgag tactatgata ttttgttcc    1020 tggtgtaaat actttttgtaa ataatattca ataccctagat cctaggcatt ggggtccttc    1080
tttgtttgct actatttccc aggctttgtg gcatgttatt agggatgata tacctgctat    1140
aacttcacaa gaattgcaaa gaagaacaga gagattcttt agagactcct ggctagatt    1200 tttggaagaa actacctgga caattgtaaa tgcccctgta aactttata attatattca    1260 ggattattat tctaatttgt cccctattag gccttcaatg gttaggcaag ttgctgaaag    1320
ggaaggaacc caggtaaatt ttggccatac ctacagaata gatgatgctg acagtataca    1380
agaagttacc caaagaatgg agttaagaaa taaagagaat gtacattcag gagagtttat    1440
```

-continued

```
agaaaaaact attgccccag gaggtgctaa tcaaagaact gctcctcaat ggatgttgcc    1500
tttgcttcta ggcctgtacg ggactgtaac acctgctctt gaagcatatg aagatggccc    1560
caaccaaaag aaaaggagag tgtccagggg cagctcccaa aaagccaaag gaatccgtgc    1620
aagtgccaaa actactaata aaaggaggag tagaagttct agaagttaaa acttgggtag    1680
atgctataac agaggtagaa tgcttcctaa acccagaaat gggggatccg gatccagatg    1740
aaaaccttag gggctttagt ctaagactaa ctgctgaaac tgcctttgac agtgatagcc    1800
cagacagaaa aatgcttccc tgttacagca cagcaagaat tccactacct aatttgaatg    1860
aggatctaac ctgtggaaat ctactaatgt gggaggctgt gactgtaaaa acagaggtta    1920
ttggaataac tagtatgctt aaccttcatg cagggtcaca gaaagtacat gaaaatggtg    1980
gaggcaaacc tattcaaggc agcaattttc acttttttgc tgtgggtggg gaccccttgg    2040
aaatgcaggg agtacttatg aactacagaa caaagtaccc agaaggtact gtcaccccaa    2100
aaaatcccac agctcagtcc caggtaatga atactgacca taaggcctac ttggacaaaa    2160
acaatgctta tccagttgaa tgctggattc ctgaccctag tagaaatgaa aatactaggt    2220
attttggaac atacacagga ggggaaaatg ttcccccagt acttcatgta accaacacag    2280
ctaccacagt gttgctggat gaacagggtg tggggcctct gtgtaaagct gatagcctgt    2340
atgtttcagc tgctgatatt tgtggactgt ttactaacag ctctggaaca caacagtgga    2400
ggggccttcc aagatatttt aagattcgcc tgagaaaaag atctgtaaag aacccttacc    2460
caatttcctt tttgcttagt gaccttataa acaggagaac ccagagagtg gatgggcagc    2520
ctatgtatgg tatggagtct cacgtggagg aggtcagggt gtttgatggc acagaaacag    2580
cttccagggg acccagatat gataagatat attgacagac agggacaatt gcaaacaaaa    2640
atggtttaaa caaggtgctt ttattgtaca tatacatgct taataaatgc tgcttttata    2700
ttacacactt ttaatcttgt gttatttttgg gggtggtgtt ttaggccttt taaaacactg    2760
aaagccttta cacaaatgta actcttcact atgggggtct gacctttggg aatcttcagc    2820
aggggctgaa gtatctgaga cttgggaaga gcattgtgat tgggattcag tgcttgatcc    2880
atgtccagag tcttcagttt ctgaatcttc ttctcttgtt atatcaagaa tacatttccc    2940
catgcatata ttatatttca tccttgaaaa agtatacata cttatctcag aatccagcct    3000
ttccttccat tcaacaattc tagattgtat atcagttgca aaatcagcta caggcctaaa    3060
ccaaattagc agtagcaaca aggtcattcc actttgtaaa attctttttt caagtaagaa    3120
ctctgagttt tgtaaggatt tcttaaata aatttttaggt ctaaaatcta tctgtcttac    3180
aaatctagcc tgcaaggttt tggggacagg atactcattc attgtaacta aacctggtgg    3240
aaatatttgg gttcttttgt ttaaatgttt cttttctaaa tttaccttga cacttccatc    3300
taaataatcc cttaaactgt ctaaattgtt tattccatgt cctgaaggca aatcctttga    3360
ttcagctcct gttcccttca catcttcaaa aacaaccata tactgatcta tagccacacc    3420
cagttcaaaa gtaagccttt ccatgggtaa attcacattt aaagctttgc ctccacataa    3480
atctaataac cctgcagcta gtgttgtttt tccactatca attggacctt tgaataacca    3540
gtatcttctt ttaggtacat taaaaacaat acagtgcagg aaatcaaata taacagaatc    3600
cattttaggt agcaaacagt gcagccaggc aactcctgcc atatattgtt ctagtacagc    3660
atttccatga gctccaaata ttaaatccat tttatctaat atatgattaa atctgtctgt    3720
tagcatttct tctctggtca tatggagggt atctacccct tttttagcta acactgtatc    3780
```

```
cactgcttgc tgacaaatac ttttttgatt tttactttct gcaaaaatgg tagcatttgc   3840
aaaatgcttt tcatgatatt taaagtggta gggttggtct ttttttttgac acttttttaca  3900
```
<br>


```
cactgcttgc tgacaaatac ttttttgatt tttactttct gcaaaaatgg tagcatttgc   3840
aaaatgcttt tcatgatatt taaagtggta gggttggtct ttttttttgac acttttttaca  3900
```

```
cactgcttgc tgacaaatac ttttttgatt tttactttct gcaaaaatgg tagcatttgc   3840
aaaatgcttt tcatgatatt taaagtggta gggttggtct ttttttgac  acttttttaca  3900 ctcctctaca ttgtactgaa attctaaata catacccaat agtagaaaca catcttcaca   3960
ctttgtttct actgcatatt cagttattaa tttccaggac acctgctttg tttcttcagg   4020
ttcctctggg ttaaaatcat gctcctttag gccccttga  atactttcct ctattatata   4080
atatggatct ctagttaagg cactgtatag taagtattcc ttattaacac ccttacaaat   4140
taaaaaacta aaagtacaca gcttttgaca gaaattatta attgcagaaa ctctatgtct   4200
atgtggagtt aaaaagaata taatattatg accagcacac atgtgtctac taataaaagt   4260
tacagaatat ttttccataa gttttttata cagaattaaa gcttttttctt tagtagtata   4320 cacagcaaag caggcaagag ttctattact aaatacagct tgactaagaa actggtgtag   4380
atcagaagga aagtctttag ggtcttctac ctttctttttt ttttgggtg gtgttgagtg   4440 ttgggaatct gctgttgcct cctcatcact ggcaaacata tcttcatggc aaaataaatc   4500
ttcatcccat ttttcattaa aggacctcca ccaggactcc cactcttctg ttccataggt   4560
tggcacctat aaaaaaaata attacttagg gccttttaat aatttactat ttatctaaag   4620
ataaattagt taccttaaag ctttagatct ctgaagggag tctctccaat tatttggacc   4680
caccattgca gagtttcttc agttaggtct aagccaaacc actgtgtgaa gcagtcaatg   4740
cagtagcaat ctatccaaac caagggctct tttcttaaaa attttctatt taaatgtctt   4800
aatcttagct gacacagcat gcaagggcag tgcactgaag cttttttgga acaaataggc   4860
cattccttgc agtacagggt atctgggcaa agaggaaaat cagcacaaac ctctgagcta   4920
ctccaggttc caaaatcagg ctggtgagct accttttacat cctgctccat ttttttatat   4980
aaagtattca ttctcttcat tttatcctcg tcgccccctt tgtcagggtg aaattcctta   5040
cactttctta aataggcttt cctcattaag ggaaggtttc cccaggcagc tctttcaagg   5100
cctaaaaggt ccatgagctc catggattcc tccctgttta gcactttatc cat          5153
```

<210> SEQ ID NO 49
<211> LENGTH: 5147
<212> TYPE: DNA
<213> ORGANISM: Human polyomavirus 1
<220> FEATURE:
<223> OTHER INFORMATION: Type BK virus

<400> SEQUENCE: 49

```
ttttgcaaaa attgcaaaag aatagggatt tccccaaata ttttttgctag gcctcagaaa    60 aagcctccac acccttacta cttgagagaa agggtggagg cagaggcggc ctcggcctct   120
tatatattat aaaaaaaaag gccacaggga ggagctgcta acccatggaa tgtagccaaa   180 ccatgaccctc aggaaggaaa gtgcatgact gggcagccag ccagtggcag ttaatagtga   240
aaccccgccc ctaaaattct caaataaaca caagaggaag tggaaactgg ccaaaggagt   300
ggaaagcagc cagacagaca tgttttgcga gcctaggaat cttggccttg tccccagtta   360
aactggacaa aggccatggt tctgcgccag ctgtcacgac aagcttctgt gaaagttagt   420
aaaacctgga ctggaacaaa aaaaagggct cagaggattt ttatttttat ttagagcttt   480
ttgctggaat tttgtagagg tgaagacagt gtagacggga aaaacaaaag taccactgct   540
ttacctgctg taaagactct ctgtaaaagac tcctaggtaa gtaatccctt ttttttttgta   600 tttcaggtt  gatgggtgct gctctagcac ttttggggga cctagttgcc agtgtatctg   660
aggctgctgc tgccacagga ttttcagtgg ctgaaattgc tgctggggag gctgctgctg   720
```

```
ctatagaagt tcaaattgca tcccttgcta ctgtagaggg cataacaagt acctcagagg      780
ctatagctgc tataggccta actcctcaaa catatgctgt aattgctggt gctcctgggg      840
ctattgctgg gtttgctgct ttaattcaaa ctgttactgg tattagttcc ttggctcaag      900
tagggtatag gtttttagt gattgggatc acaaagtttc cactgtaggc ctctatcagc      960
aatcaggcat ggctttggaa ttgtttaacc cagatgagta ctatgatatt ttgtttcctg     1020
gtgtaaatac ttttgtaaat aatattcaat accttgatcc taggcattgg ggtccttcct     1080
tgtttgctac tatttcccag gctttgtggc atgttattag ggatgatata cctgctataa     1140
cctcacaaga attgcaaaga agaacagaaa gattttttag agactccttg gctagatttt     1200
tggaggaaac tacctggaca attgtaaatg cccctataaa cttttataat tatattcaag     1260
aatattattc tgatctttcc cctattaggc cctcaatggt tagacaagtg gctgaaaggg     1320
aaggtacccg tgtacatttt ggccatactt atagtataga tgatgctgac agtatagaag     1380
aagttacaca agaatggac ttaagaaatc aacaaactgt acattcagga gagtttatag     1440
aaaaaactat tgccccagga ggtgctaatc aaagaactgc tcctcaatgg atgttgcctt     1500
tacttctagg cctgtacggg actgtaacac ctgctcttga agcatatgaa gatggccca      1560 accaaaagaa aaggagagtg tccaggggca gctcccaaaa agccaaagga acccgtgcaa     1620
gtgccaaaac tactaataaa aggaggagta gaagttctag aagttaaaac tggggtagat     1680
gctataacag aggtagaatg cttcctaaac ccagaaatgg gggatccgga tccagatgaa     1740
aaccttaggg gctttagtct aaagctaagt gctgaaaatg actttagcag tgatagccca     1800
gaaagaaaaa tgcttccctg ttacagcaca gcaagaattc ccctccccaa tttaaatgag     1860
gacctaacct gtggaaatct actgatgtgg gaggctgtaa ctgtacaaac agaggtcatt     1920
ggaataacta gcatgcttaa ccttcatgca gggtcacaaa aagtgcatga gcatggtgga     1980
ggtaaaccta ttcaaggcag taatttccac ttctttgctg ttggtggaga ccccttggaa     2040
atgcagggag tgctaatgaa ttacaggacc aagtacccag atggtactat aaccccaaaa     2100
aacccaacag cccagtccca ggtaatgaat actgaccata aggcctattt ggacaaaaac     2160
aatgcttatc cagttgagtg ctgggttcct gatcctagta gaaatgaaaa tactaggtat     2220
tttgggactt tcacaggagg ggaaaatgtt cccccagtac ttcatgtgac caacacagct     2280
accacagtgt tgctagatga acagggtgtg gggcctcttt gtaaagctga tagcctgtat     2340
gtttcagctg ctgatatttg tggcctgttt actaacagct ctggaacaca acagtggaga     2400
ggccttgcaa gatattttaa gattcgcctg agaaaagat ctgtaaaaaa tccttaccca     2460
atttcctttt tgctaagtga ccttataaac aggagaaccc agagagtgga tgggcagcct     2520
atgtatggta tggaatccca ggtagaagag ttagggtgt tgatggcac agaaagactt     2580 ccagggacc cagatatgat aagatatatt gataaacaag acaattgcaa aaccaaaatg     2640
ctttaaacag gtgcttttat tgtacatata catttaataa atgctgcttt tgtataagcc     2700
acttttaagc ttgtgttatt ttgggggtgg tgttttaggc cttttaaaac attgaaagcc     2760
tttacacaaa tgcaactctt gactatgggg gtctaacctt tgggaatctt cagcaggggc     2820
tgaagtatct gagacttggg aagagcattg tgattgggat tcagtgcttg atccatgtcc     2880
agagtcttca gtttctgaat cttcttctct tgtgatatca agaatacatt tccccatgca     2940
tatattatat ttcatccttg aaaaagtata catacttatc tcagaatcca gccttttcctt     3000 ccattcaaca attctagatt gtatatctgt tgcaaaatca gctacaggcc taaaccaaat     3060
```

```
tagcagtagc aacaaggtca ttccactttg taaaattctt ttttcaagta agaactctga   3120
gttttgtaag gattttctta aatatatttt gggcctaaaa tctatttgtc ttacaaatct   3180
agcttgcagg gttttaggaa caggatactc attcattgta accaggcctg gtggaaatat   3240
ttgggttctt ttgtttaaat gtttcttttc taaattaacc ttaacacttc catctaaata   3300
atctctcaaa ctgtctaaat tgtttattcc atgtcctgaa ggcaaatcct ttgattcagc   3360
ccctgttcct tttacatctt caaaaacaac catgtactga tctatagcta cacctagttc   3420
aaaggttagc ctttccatgg gtaggtttac atttaaggct ttacctccac acaaatctaa   3480
taaccctgca gctagtgttg ttttttccact atcaatggga cctttaaata accagtatct   3540
tcttttaggt acattaaaaa caatacagtg caaaaaatca aatataacag aatccatttt   3600
aggtagcaaa cagtgcagcc aagcaacacc tgccatatat tgttccagta cagcatttcc   3660
atgagctcca aatattaaat ccattttatc taatatatga ttaaatcttt ctgttagcat   3720
ttcttctctg gtcatatgaa gggtatctac tctttttta gctaaaactg tatctactgc   3780
ttgctgacaa atacttttt gattttact ttctgcaaaa atagtagcat ttgcaaaatg   3840
cttttcatga tacttaaagt gataaggttg gtcttttttc tgacactttt tacactcttc   3900
tacattgtat tgaaattcta aatacatacc caataataaa aacacatcct cacactttgt   3960
ctctactgca tactcagtaa ttaatttcca agacacctgc tttgtttctt caggctcttc   4020
tgggttaaaa tcatgctcct ttaagccccc ttgaatgctt tcttctattg tatggtatgg   4080
atctctagtt aaggcactat atagtaagta ttccttatta acacccttac aaattaaaaa   4140
actaaaggta cacagctttt gacagaaatt attaattgca gaaactctat gtctatgtgg   4200
agttaaaaag aatataatat tatgcccagc acacatgtgt ctactaataa aagttacaga   4260 atattttcc ataagttttt tatacagaat ttgagctttt tctttagtag tatacacagc   4320
aaagcaggca agggttctat tactaaatac agcttgacta agaaactggt gtagatcaga   4380
aggaaagtct ttagggtctt ctacctttct ctttttcttg ggtggtgtgg agtgttgaga   4440
atctgctgtt gcttcttcat cactggcaaa catatcttca tggcaaaata atcttcatc   4500 ccattttca ttaaaggagc tccaccagga ctcccactct tctgttccat aggttggcac   4560
ctataaaaaa aataattact tagggccttt aaatattttc ttatttatct aaatataagt   4620 tagttaccttt aaagctttag atctctgaag ggagtttctc caattatttg gacccaccat   4680
tgcagagttt cttcagttag gtctaagcca aaccactgtg tgaagcagtc aatgcagtag   4740
caatctatcc aaaccaaggg ctcttttctt aaaaattttc tatttaaatg ccttaatcta   4800
agctgacata gcatgcaagg gcagtgcaca gaaggctttt tggaacaaat aggccaatcc   4860
ttgcagtaca gggtatctgg gcaaagagga aaatcagcac aaacctctga gctactccag   4920
gttccaaaat caggctgatg agctaccttt acatcctgct ccatttttt atataaagta   4980 ttcattctct tcattttatc ctcgtcgccc cctttgtcag ggtgaaattc cttcacttc   5040 cttaaatagg cttttctcat taagggaagg tttccccagg cagctctttc aaggcctaaa   5100
aggtccatga gctccatgga ttcttccctg ttaagcactt tatccat        5147
```

<210> SEQ ID NO 50
<211> LENGTH: 5147
<212> TYPE: DNA
<213> ORGANISM: Human polyomavirus 1
<220> FEATURE:
<223> OTHER INFORMATION: Type BK virus

<400> SEQUENCE: 50

```
ttttgcaaaa attgcaaaag aataggatt tccccaaata gttttgctag gcctcagaaa      60
aagcctccac acccttacta cttgagagaa agggtggagg cagaggcggc ctcggcctct    120
tatatattat aaaaaaaaag gccacaggga ggagctgctt acccatggaa tgcagccaaa    180
ccatgacctc aggaaggaaa gtgcatgact gggcagccag ccagtggcag ttaatagtga    240
aaccccgccc ctaaaattct caaataaaca caagaggaag tggaaactgg ccaaaggagt    300
ggaaagcagc cagacagaca tgttttgcga gcctaggaat cttggccttg tccccagtta    360
aactggacaa aggccatggt tctgcgccag ctgtcacgac aagcttctgt gaaagttggt    420
aaaacctgga ctgaacaaa aaaaagagct cagaggattt ttatttttat tttagagctt    480
ttgctggaat tttgtagagg tgaagacagt gtagacggga aaaacaaaag taccactgct    540
ttacctgctg taaaagactc tgtaaaagac tcctaggtaa gtaatccctt ttttttgta    600 tttccaggtt catgggtgct gctctagcac ttttggggga cctagttgcc agtgtatctg    660
aggctgctgc tgccacagga ttttcagtgg ctgaaattgc tgctgggag gctgctgctg    720 ctatagaagt tcaaattgca tcccttgcta ctgtagaggg cataacaagt acctcagagg    780
ctatagctgc tataggccta actcctcaaa catatgctgt aattgctggt gctcctgggg    840
ctattgctgg gtttgctgct ttaattcaaa ctgttagtgg tattagttcc ttggctcaag    900
tagggtatag gttctttagt gattgggatc acaaagtttc cactgtaggc ctctatcagc    960
aatcaggcat ggctttggaa ttgtttaacc cagatgagta ctatgatatt ctgtttcctg   1020
gtgtaaatac ttttgttaat aatattcaat accttgatcc taggcattgg ggtccttctt   1080
tgtttgctac tatttcccag gctttgtggc atgttattag ggatgatata ccttctataa   1140
cctcacagga attgcagaga agaacagaaa gattttttag agactccttg gctagatttt   1200
tggaggaaac tacctggacc attgtaaatg cccctataaa cttttataat tatattcaac   1260
aatattattc tgatctgtcc cctattaggc cctcaatggt tagacaagta gctgaaaggg   1320
aaggtacccg tgtacatttt ggccatactt atagtataga tgatgctgac agtatagaag   1380
aagttacaca aagaatggat ttaagaaatc aacaaagtgt acattcagga gagtttatag   1440
aaaaaactat tgccccagga ggtgctaatc aaagaactgc tcctcaatgg atgttgcctt   1500
tacttctagg cctgtacggg actgtaacac ctgctcttga agcatatgaa gatggcccca   1560
accaaaagaa aaggagagtg tccagggca gctcccaaaa agccaaagga acccgtgcaa   1620
gtgccaaaac tactaataaa aggaggagta gaagttctag aagttaaaac tggggtagat   1680
gctattacag aggtagaatg cttcctaaac ccagaaatgg gggatccgga tccagatgaa   1740
aaccttaggg gctttagtct aaagctaagt gctgaaaatg actttagcag tgatagccca   1800
gagagaaaaa tgcttccctg ttacagcaca gcaagaattc ccctcccaa tttaaatgag    1860 gacctaacct gtggaaatct actgatgtgg gaggctgtaa ctgtacaaac agaggttatt   1920
ggaataacta gcatgcttaa ccttcatgca gggtcacaaa agtgcatga gcatggtgga   1980 ggaaaaccta ttcaaggcag taatttccac ttctttgctg ttggtggaga ccccttggaa   2040
atgcagggag tgctaatgaa ttacaggaca agtacccag atggtactat aacccctaaa   2100
aacccaacag cccagtccca ggtaatgaat actgaccata aggcctattt ggacaaaaac   2160
aatgcttatc cagttgagtg ctgggttcct gatcccagta gaaatgaaaa tactaggtat   2220
tttgggactt tcacaggagg ggaaaatgtt ccccagtac ttcatgtgac caacacagct   2280
accacagtgt tgctagatga acagggtgtg gggcctcttt gtaaagctga tagcctgtat   2340
```

```
gtttcagctg ctgatatttg tggcctgttt actaacagct ctggaacaca acagtggaga    2400
ggccttgcaa gatattttaa gatccgcctg agaaaaagat ctgtaaagaa tccttaccca    2460
atttcctttt tgctaagtga cctcataaac aggagaaccc agagagtgga tgggcagcct    2520
atgtatggta tggaatccca ggtagaagag gttagggtgt ttgatggcac agaaagactt    2580 ccagggga ccagatatgat aagatatatt gacaaacagg gacaattgca aaccaaaatg    2640
ctttaaacag gtgctttat tgtacatata catttaataa atgctgcttt tgtataagcc    2700
acttttaacc ttgtgttatt ttggggg tgg tgttttaggc cttttaaaac actgaaagcc    2760
tttacacaaa tgtaactctt gactatgggg gtctgacctt tgggaatctt cagcagggggc    2820 tgaagtatct gagacttggg aagagcattg tgattgggat tcagtgcttg atccatgtcc    2880
agagtcttca gtttctgaat cctcttctct tgtgatatca agaatacatt tccccatgca    2940
tatattatat ttcatccttg aaaaagtata catacttatc tcagaatcca gcctttcctt    3000
ccattcaaca attctagatt gtatatctgt tgcaaaatca gctacaggcc taaaccaaat    3060
tagcagtagc aacaaggtca ttccactttg tagaattctt ttttcaagta agaactctga    3120
gttttgtaag gattttctta aatatatttt gggcctaaaa tctatttgtc ttacaaatct    3180
agcttgcagg gttttaggga caggatactc attcattgta accaagcctg gtggaaatat    3240
ttgggttctt ttgtttaaat gttttttttttc taaatttacc ttaacacttc catctaaata    3300
atctcttaaa ctgtctaaat tgtttattcc atgtcctgaa ggcaaatcct ttgattcagc    3360
ccctgtccct tttacatctt caaaaacaac catgtactga tctatagcca cacctagctc    3420
aaaggttagc ctttccatgg gtaggtttac atttaaggct ttacctccac acaaatctaa    3480
taaccctgca gctagtgttg ttttttccact atcaatggga cctttaaata accagtatct    3540
tcttttaggt acattgaaaa caatacagtg caaaaaatca aatataacag aatccatttt    3600
aggtagcaaa cagtgcagcc aagcaacacc tgccatatat tgttctagta cagcatttcc    3660
atgagctcca aatattaaat ccattttatc taatatatga ttgaatcttt ctgttagcat    3720
ttcttccctg gtcatatgaa gggtatctac tctttttta gctaaaactg tatctactgc    3780
ttgctgacaa atactttttt gattttact ttctgcaaag ataatagcat ttgcaaagtg    3840
cttttcatga tacttaaagt gataaggttg gtcttttttc tgacactttt tacactcctc    3900
tacattgtat tgaaattcta atacatacc taataataaa aacacatcct cacactttgt    3960
ctctactgca tactcagtaa ttaatttcca agacacctgc tttgtttctt caggctcttc    4020
tgggttaaaa tcatgctcct ttaagccccc ttgaatgctt tcttctatag tatggtatgg    4080
ctctctagtt aaggcactat acagtaagta ttccttatta acacccttac aaattaaaaa    4140
actaaaggta cacagctttt gacagaagtt attaattgca gaaactctat gtctatgtgg    4200
agttaaaaag aatataatat tatgcccagc acacatgtgt ctactaataa aagttacaga    4260 atattttttcc ataagttttt tatacaggat ttgagctttt tctttagtag tatacacagc    4320
aaagcaggca agggttctat tactaaatac agcttgacta agaaactggt gtagatcaga    4380
gggaaagtct ttagggtctt ctacctttct tttttttcttg ggtggtgttg agtgttgaga    4440
atctgctgtt gcttcttcat cactggcaaa catatcttca tggcaaaata agtcttcatc    4500
ccatttttca ttaaaggaac tccaccagga ctcccactct tctgttccat aggttggcac    4560
ctataaaaaa aataattact tagggccttt taatattttta ttatttatct aaatataagt    4620
tagttacctt aaagctttag atctctgaag ggagtttctc caattatttg gacccaccat    4680
tgcagagttt cttcagttag gtctaagcca aaccactgtc tgaagcagtc aatgcagtag    4740
```

| caatctatcc aaaccaaggg ctctttcctt aaaaattttc tatttaaatg ccttaatcta | 4800 |
| agctgacata gcatgcaagg gcagtgcaca gaaggctttt tggaacaaat aggccattcc | 4860 |
| ttgcagtaca gggtatctgg gcaaagagga aaatcagcac aaacctctga gctactccag | 4920 |
| gttccaaaat caggctgatg agctaccttt acatcctgct ccattttttt atataaagta | 4980 |
| ttcattctct tcatttatc ctcgtcgccc cctttgtcag ggtgaaattc cttacacttc | 5040 |
| cttaaataag cttttctcat taagggaaga tttccccagg cagctctttc aaggcctaaa | 5100 |
| aggtccatga gctccatgga ttcttccctg ttaagcactt tatccat | 5147 |

<210> SEQ ID NO 51
<211> LENGTH: 5148
<212> TYPE: DNA
<213> ORGANISM: Human polyomavirus 1
<220> FEATURE:
<223> OTHER INFORMATION: Type BK virus

<400> SEQUENCE: 51

| ttttgcaaaa attgcaaaag aatagggatt cccccaaat agttttgcta ggcctcagaa | 60 |
| aaagcctcca caccctact acttgagaga aagggtggag gcagaggcgg cctcggcctc | 120 |
| ttatatatta taaaaaaaaa ggccacaggg aggagctgct tacccatgga atgcagccaa | 180 |
| accatgacct caggaaggaa agtgcatgac tgggcagcca gccagtggca gttaatagtg | 240 |
| aaaccccgcc cctgaaattc tcaaataaac acaagaggaa gtggaaactg ccaaaggag | 300 |
| tggaaagcag ccagacagac atgttttgcg ggcctaggaa tcttggcctt gtccccagtt | 360 |
| aaactggaca aaggccatgg ttctgcgcca gctgtcacga caagcttctg tgaaacttgg | 420 |
| taaaacctgg actggaacaa aaaaagagc tcagaggatt tttatttta ttttagagct | 480 |
| tttgctggaa ttttgtagag gtgaagacag tgtagacggg aaaaacaaaa gtaccactgc | 540 |
| tttacctgct gtaagagact ctgtaaaaga ctcctaggta agtaatccct ttttttttgt | 600 |
| atttccaggt tgatgggtgc tgctctagca cttttggggg acctagttgc cagtgtatct | 660 |
| gaggctgctg ctgccacagg attttcagtg gctgaaattg ctgctgggga ggctgctgct | 720 |
| gctatagaag ttcaaattgc atcccttgct actgtagagg cataacaag tacctcagag | 780 |
| gctatagctg ctataggcct aactcctcaa acatatgctg taattgctgg tgctcctggg | 840 |
| gctattgctg ggtttgctgc tttaattcaa actgttactg gtattagttc cttggctcaa | 900 |
| gtagggtata ggttttttag tgattgggat cacaaagttt ccactgtagg cctctatcag | 960 |
| caatcaggca tggctttgga attgtttaac ccagatgagt actatgatat attgtttcct | 1020 |
| ggtgtaaata cttttgtaaa taatattcaa taccttgatc ctaggcattg gggtccttct | 1080 |
| ttgtttgcta ctatttctca ggctttgtgg catgttatta gggatgatat acctgctata | 1140 |
| acctcacaag aattgcaaag aagaacagaa agatttttta gagactcctt ggctagattt | 1200 |
| ttggaggaaa ctacctggac aattgtaaat gcccctataa acttttataa ttatattcaa | 1260 |
| gaatatatt ctgatctttc ccctattagg ccctcaatgg ttagacaagt agctgaaagg | 1320 |
| gaaggtaccc gtgtacattt tggccatact tatagtatag atgatgctga cagtatagaa | 1380 |
| gaagttacac aaagaatgga cttaagaaat caacaaactg tacattcagg agagtttata | 1440 |
| gaaaaaacta ttgccccagg aggtgctaat caaagaactg ctcctcaatg gatgttgcct | 1500 |
| ttacttctag gcctgtacgg gactgtaaca cctgctcttg aagcatatga agatggcccc | 1560 |
| aacaaaaaga aaggagagt gtccagggc agctcccaaa aagccaaagg aaccccgtgca | 1620 |

```
agtgccaaaa ctactaataa aaggaggagt agaagttcta gaagttaaaa ctgggctaga    1680
tgctataaca gaggtagaat gcttcctaaa cccagaaatg ggggatccgg atccagatga    1740
aaaccttagg ggctttagtc taaagctaag tgctgaaaat gactttagca gtgatagccc    1800
agaaagaaaa atgcttccct gttacagcac agcaagaatt cccctcccca atttaaatga    1860
ggacctaacc tgtggaaatc tactgatgtg ggaggctgta acagtacaaa cagaggtcat    1920
tggaataact agcatgctta accttcatgc agggtcacaa aaagtgcatg agcatggtgg    1980
aggtaaacct attcaaggca gtaatttcca ctttttttgct gttggtggag accccttgga    2040
aatgcaggga gtgctaatga attacaggac aaagtaccca gaaggtacta taaccccaaa    2100
aaacccaaca gcccagtccc aagtaatgaa tactgaccat aaggcctatt tggacaaaaa    2160
caatgcttat ccagttgagt gctggattcc tgatcccagt agaaatgaaa atactaggta    2220
ttttgggact ttcacaggag gggaaaatgt tcccccagta cttcatgtga ccaacacagc    2280
taccacagtg ttgctagatg aacagggtgt ggggcctctt tgtaaagctg atagcctgta    2340
tgtttcagct gctgatatttt gtggcctgtt tactaacagc tctggaacac aacagtggag    2400
aggccttgca agatatttta agattcgcct gagaaaaaga tctgtaaaaa atccttaccc    2460
aatttccttt ttgctaagtg accttataaa caggagaacc cagagagtgg atgggcagcc    2520
tatgtatggt atggaatccc aggtagaaga ggttagggtg tttgatggca cagaaaaact    2580
tccaggggac ccagatatga taagatatat tgacaaacaa ggacaattgc aaaccaaaat    2640
gcttaaaaca ggtgctttta ttgttgatat acatttaata aatgctgctt ttgtataagc    2700
cagttttaag cttgtgttat tttggggtg gtgttttagg cctttaaaa cactgaaagc    2760 ctttacacaa atgcaactct tgactatggg ggtctgacct ttgggaatct tcagcagggg    2820
ctgaagtatc tgagacttgg gaagagcatt gtgattggga ttcagtgctt gatccatgtc    2880
cagagtcttc agtttctgaa tcttcttctc ttgtgatatc aagaatacat tttcccatgc    2940
atatattata tttcatcctt gaaaaagtat acatacttat ctcagaatcc agcctttcct    3000
tccattcaac aattctagat tgtatatctg ttgcaaaatc agctacaggc taaaccaaa    3060 ttagcagtag caacaaggtc attccacttt gtagaattct tttttcaagt aagaactctg    3120
agttttgtaa ggattttctt aaatatattt tgggcctaaa atctatctgt cttacaaatc    3180
tagcctgcag ggttttaggg acaggatact cattcattgt aaccaggcct ggtgaaata    3240 tttgggttct tttgtttaaa tgtttctttt ctaaattaac cttaacactt ccatctaaat    3300
aatctctcaa actgtctaaa ttgtttattc catgtcctga aggcaaatcc tttgattcag    3360
ctcctgttcc ttttacatct tcaaaaacaa ccatgtactg atctatagct acacctagtt    3420
caaaggttag ccttttccatg ggtaggttta catttaaagc tttacctcca cacaaatcta    3480
ataaccctgc agctagtgtt gttttttccac tatcaatggg acctttaaat aaccagtatc    3540
ttcttttagg tacattaaaa acaatacagt gcaaaaaatc aaatataaca gaatccattt    3600
taggtagcaa acagtgcagc caagcaacac ctgccatata ttgttctaat acagcatttc    3660
catgagcccc aaatattaaa tccatttttat ctaatatatg attaaatctt tctgttagca    3720
tttcttctct agtcatatga aggctatcta ctctttttt agctaaaact gtatctactg    3780
cttgctgaca aatactttt tgattttac tttctgcaaa gatagtagca tttgcaaaat    3840
gcttttcatg atacttaaag tgataaggtt ggtcttttt ctgacacttt ttacactcct    3900
ctacattgta ttgaaattct aaatacatac ctaataataa aaacacatcc tcacactttg    3960
tttctactgc atactcagta attaatttcc aagagacctg ctttgttct tcaggctctt    4020
```

-continued

```
ctgggttaaa atcatgctcc tttaagcccc cttgaatgct ttcttctatt gtatggtatg      4080
gatctctagt taaggcacta tatagtaagt attccttatt aacaccctta caaattaaaa      4140
aactaaaggt acacagcttt tgacagaaat tattaattgc agaaactcta tgtctatgtg      4200
gagttaaaaa gaatataata ttatgcccag cacacatgtg tctactaata aaagttacag      4260 aatattttc cataagtttt ttatacagaa tttgagcttt ttctttagta gtatacacag       4320
caaagcaggc gagggttcta ttactaaata cagcttgact aagaaactgg tgtagatcag      4380
aaggaaagtc tttagggtct tctacctttc ttttttttctt gggtggtgtt gagtgttgag    4440
aatctgctgt tgcttcttca tcactggcaa acatatcttc atggcaaaat aaatcttcat      4500
cccatttttc attaaaggaa ctccaccagg actcccactc ttctgttcca taggttggca      4560
cctataaaac aaataattac ttagggcctt taaatatttt attatttatc taaatataag     4620
gtagttacct taaagcttta gatctctgaa gggagtttct ccaattattt ggacccacca     4680
ttgcagagtt tcttcagtta ggtctaagcc aaaccactgt gtgaagcagt caatgcagta     4740
gcaatctatc caaaccaagg gctctttttct taaaaatttt ctatttaaat gccttaatct    4800
aagctgacat agcatgcaag ggcagtgcac agaaggcttt tggaacaaa taggccattc      4860 cttgcagtac agggtatctg ggcaaagagg aaaatcagca caaacctctg agctactcca    4920
ggttccaaaa tcaggctgat gagctacctt tacatcttgc tccatttttt tatataaagt    4980
attcattctc ttcattttat cctcgtcgcc cccttttgtca gggtgaaatt ccttacactt   5040
ccttaaatag gcttttctca ttaagggaag gtttccccag gcagctcttt caaggcccaa    5100
aaggtccatg agctccatgg attcttccct gttaagcact ttatccat                 5148
```

<210> SEQ ID NO 52
<211> LENGTH: 5147
<212> TYPE: DNA
<213> ORGANISM: Human polyomavirus 1
<220> FEATURE:
<223> OTHER INFORMATION: Type BK virus

<400> SEQUENCE: 52

```
ttttgcaaaa attgcaaaag aatagggatt tccccaaata gttttgctag gcctcagaaa       60
aagcctccac acccttacta cttgagagaa agggtggagg cagaggcggc ctcggcctct     120
tatatattat aaaaaaaaag gccacaggga ggagctgctt acccatggaa tgcagccaaa     180
ccatgacctc aggaaggaaa gtgcatgact gggcagccag ccagtggcag ttaatagtga     240
aaccccgccc ctgaaattct caaataaaca caagaggaag tggaaactgg ccaaaggagt     300
ggaaagcagc cagacagaca tgttttgcgg gcctaggaat cttggccttg tccccagtta     360
aactggacaa aggccatggt tctgcgccag ctgtcacgac aagcttctgt gaaacttggt     420
aaaacctgga ctggaacaaa aaaagagct cagaggattt ttattttat tttagagctt     480 ttgctggaat tttgtagagg tgaagacagt gtagacggga aaaacaaaag taccactgct    540
ttacctgctg taaaagactc tgtaaaagac tcctaggtaa gtaatccctt ttttttgta    600 tttccaggtt gatgggtgct gctctagcac ttttggggga cctagttgcc agtgtatctg    660
aggctgctgc tgccacagga ttttcagtgg ctgaaattgc tgctggggag ctgctgctg     720 ctatagaagt tcaaattgca tcccttgcta ctgtagaggg cataacaagt acctcagagg    780
ctatagctgc tataggccta actcctcaaa catatgctgt aattgctggt gctcctgggg    840
ctattgctgg gtttgctgct ttaattcaaa ctgttactgg tattagttcc ttggctcaag    900
```

```
tagggtatag gttttttagt gattgggatc acaaagtttc cactgtaggc ctctatcagc      960
aatcaggcat ggctttggaa ttgtttaacc cagatgagta ctatgatata ttgtttcctg     1020
gtgtaaatac ttttgtaaat aatattcaat accttgatcc taggcattgg ggtccttctt     1080
tgtttgctac tatttctcag gctttgtggc atgttattag ggatgatata cctgctataa     1140
cctcacaaga attgcaaaga agaacagaaa gattttttag agactccttg gctagatttt     1200
tggaggaaac tacctggaca attgtaaatg cccctataaa cttttataat tatattcaag     1260
aatattattc tgatctttcc cctattaggc cctcaatggt tagacaagta gctgaaaggg     1320
aaggtacccg tgtacatttt ggccatactt atagtataga tgatgctgac agtatagaag     1380
aagttacaca aagaatggac ttaagaaatc aacaaactgt acattcagga gagtttatag     1440
aaaaaactat tgccccagga ggtgctaatc aaagaactgc tcctcaatgg atgttgcctt     1500
tacttctagg cctgtacggg actgtaacac ctgctcttga agcatatgaa gatggcccca     1560
acaaaaagaa aaggagagtg tccaggggca gctcccaaaa agccaaagga acccgtgcaa     1620
gtgccaaaac tactaataaa aggaggagta gaagttctag aagttaaaac tgggctagat     1680
gctataacag aggtagaatg cttcctaaac ccagaaatgg gggatccgga tccagatgaa     1740
aaccttaggg gctttagtct aaagctaagt gctgaaaatg actttagcag tgatagccca     1800
gaaagaaaaa tgcttcccct gttacagcaca gcaagaattc ccctcccccaa tttaaatgag     1860 gacctaacct gtggaaatct actgatgtgg gaggctgtaa cagtacaaac agaggtcatt     1920
ggaataacta gcatgcttaa ccttcatgca gggtcacaaa aagtgcatga gcatggtgga     1980
ggtaaaccta ttcaaggcag taatttccac ttttttgctg ttggtggaga ccccttggaa     2040
atgcagggag tgctaatgaa ttacaggaca agtacccag aaggtactat aaccccaaaa     2100
aacccaacag cccagtccca agtaatgaat actgaccata aggcctattt ggacaaaaac     2160
aatgcttatc cagttgagtg ctggattcct gatcccagta gaaatgaaaa tactaggtat     2220
tttgggactt tcacaggagg ggaaaatgtt cccccagtac ttcatgtgac caacacagct     2280
accacagtgt tgctagatga acagggtgtg gggcctcttt gtaaagctga tagcctgtat     2340
gtttcagctg ctgatatttg tggcctgttt actaacagct ctggaacaca acagtggaga     2400
ggccttgcaa gatattttaa gattcgcctg agaaaaagat ctgtaaaaaa tccttaccca     2460
atttcctttt tgctaagtga ccttataaac aggagaaccc agagagtgga tgggcagcct     2520
atgtatggta tggaatccca ggtagaagag gttagggtgt ttgatggcac agaaagactt     2580 ccagggggacc cagatatgat aagatatatt gacaaacaag gacaattgca aactaaaatg     2640
gtttaaacag gtgcttttat tgttgatata catttaataa atgctgcttt tgtataagcc     2700
agttttaagc ttgtgttatt ttgggggtgg tgttttaggc ctttttaaaac actgaaagcc     2760 tttacacaaa tgcaactctt gactatgggg gtctgacctt tgggaatctt cagcaggggc     2820
tgaagtatct gagacttggg aagagcattg tgattgggat tcagtgcttg atccatgtcc     2880
agagtcttca gtttctgaat cttcttctct tgtgatatca agaatacatt ttcccatgca     2940
tatattatat ttcatccttg aaaaagtata catacttatc tcagaatcca gcctttcctt     3000
ccattcaaca attctagatt gtatatctgt tgcaaaatca gctacaggcc taaaccaaat     3060
tagcagtagc aacaaggtca ttccactttg tagaattctt ttttcaagta agaactctga     3120
gttttgtaag gattttctta aatatatttt gggcctaaaa tctatctgtc ttacaaatct     3180
agcctgcagg gttttaggga caggatactc attcattgta accaggcctg gtggaaatat     3240
ttgggttctt ttgtttaaat gtttcttttc taaattaacc ttaacacttc catctaaata     3300
```

```
atctctcaaa ctgtctaaat tgtttattcc atgtcctgaa ggcaaatcct tgattcagc    3360 tcctgttcct tttacatctt caaaaacaac catgtactga tctatagcta cacctagttc   3420
aaaggtcagc ctttccatgg gtaggtttac atttaaagct ttacctccac acaaatctaa   3480
taaccctgca gctagtgttg ttttttccact atcaatggga cctttaaata accagtatct  3540 tctttaggt acattaaaaa caatacagtg caaaaaatca aatataacag aatccatttt    3600
aggtaacaaa cagtgcagcc aagcaacacc tgccatatat tgttctaata cagcatttcc   3660
atgagcccca aatattaaat ccattttatc taatatatga ttaaatcttt ctgttagcat   3720
ttcttctcta gtcatatgaa ggctatctac tcttttttta gctaaaactg tatctactgc   3780
ttgctgacaa atacttttt gatttttact ttctgcaaag atagtagcat ttgcaaaatg    3840
cttttcatga tacttaaagt gataaggttg gtcttttttc tgacactttt tacactcctc   3900
tacattgtat tgaaattcta aatacatacc taataataaa aacacatcct cacactttgt   3960
ttctactgca tactcagtaa ttaattcca agagacctgc tttgtttctt caggctcttc    4020
tgggttaaaa tcatgctcct ttaagccccc ttgaatgctt tcttctattg tatggtatgg   4080
atctctagtt aaggcactat atagtaagta ttccttatta acacccttac aaattaaaaa   4140
actaaaggta cacagctttt gacagaaatt attaattgca gaaactctat gtctatgtgg   4200
agttaaaaag aatataatat tatgcccagc acacatgtgt ctactaataa agttacaga    4260 atattttcc ataagttttt tatacagaat ttgagctttt tctttagtag tatacacagc    4320
aaagcaggca agggttctat tactaaatac agcttgacta agaaactggt gtagatcaga   4380
aggaaagtct ttagggtctt ctacctttct ttttttcttg ggtggtgttg agtgttgaga   4440
atctgctgtt gcttcttcat cactggcaaa catatcttca tggcaaaata aatcttcatc   4500 ccattttca ttaaaggaac tccaccagga ctcccactct tctgttccat aggttggcac    4560
ctataaaaca ataattact tagggccttt aaatatttta ttatttatct aaatataagg    4620
tagttacctt aaagctttag atctctgaag ggagtttctc caattatttg gacccaccat   4680
tgcagagttt cttcagttag gtctaagcca aaccactgtg tgaagcagtc aatgcagtag   4740
caatctatcc aaaccaaggg ctctttttctt aaaaattttc tatttaaatg ccttaatcta   4800
agctgacata gcatgcaagg gcagtgcaca gaaggctttt tggaacaaat aggccattcc   4860
ttgcagtaca gggtatctgg gcaaagagga aaatcagcac aaacctctga gctactccag   4920
gttccaaaat caggctgatg agctaccttt acatcttgct ccatttttt atataaagta    4980 ttcattctct tcattttatc ctcgtcgccc cctttgtcag ggtgaaattc cttacacttc   5040
cttaaatagg cttttctcat taagggaagg tttccccagg cagctctttc aaggcccaaa   5100
aggtccatga gctccatgga ttcttccctg ttaagcactt tatccat                 5147
```

<210> SEQ ID NO 53
<211> LENGTH: 5148
<212> TYPE: DNA
<213> ORGANISM: Human polyomavirus 1
<220> FEATURE:
<223> OTHER INFORMATION: Type BK virus

<400> SEQUENCE: 53

```
ttttgcaaaa attgcaaaag aatagggatt tcccccaaat agtttgcta ggcctcagaa      60 aaagcctcca caccttact acttgagaga aagggtggag gcagaggcgg cctcggcctc    120
ttatatatta taaaaaaaaa ggccacaggg aggagctgct tacccatgga atgcagccaa   180
```

```
accatgacct caggaaggaa agtgcatgac tgggcagcca gccagtggca gttaatagtg    240 aaacccccgcc cctgaaattc tcaaataaac acaagaggaa gtggaaactg gccaaaggag    300
tggaaagcag ccagacagac atgttttgcg ggcctaggaa tcttggcctt gtccccagtt    360
aaactggaca aaggccatgg ttctgcgcca gctgtcacga caagcttctg tgaaacttgg    420
taaaacctgg actggaacaa aaaaaagagc tcagaggatt tttatttta ttttagagct    480 tttgctggaa ttttgtagag gtgaagacag tgtagacggg aaaaacaaaa gtaccactgc    540
tttacctgct gtaagagact ctgtaaaaga ctcctaggta agtaatccct ttttttttgt    600
atttccaggt tgatgggtgc tgctctagca cttttgggg acctagttgc cagtgtatct    660
gaggctgctg ctgccacagg attttcagtg gctgaaattg ctgctgggga ggctgctgct    720
gctatagaag ttcaaattgc atcccttgct actgtagagg gcataacaag tacctcagag    780
gctatagctg ctataggcct aactcctcaa acatatgctg taattgctgg tgctcctggg    840
gctattgctg ggtttgctgc tttaattcaa actgttactg gtattagttc cttggctcaa    900
gtagggtata ggttttttag tgattgggat cacaaagttt ccactgtagg cctctatcag    960
caatcaggca tggctttgga attgtttaac ccagatgagt actatgatat attgttttcct   1020 ggtgtaaata cttttgtaaa taatattcaa taccttgatc ctaggcattg gggtccttct   1080
ttgtttgcta ctatttctca ggctttgtgg catgttatta gggatgatat acctgctata   1140
acctcacaag aattgcaaag aagaacagaa agatttttta gagactcctt ggctagattt   1200
ttggaggaaa ctacctggac aattgtaaat gcccctataa acttttataa ttatattcaa   1260
gaatattatt ctgatctttc ccctattagg ccctcaatgg ttagacaagt agctgaaagg   1320
gaaggtaccc gtgtacattt tggccatact tatagtatag atgatgctga cagtatagaa   1380 gaagttcac aaagaatgga cttaagaaat caacaaactg tacattcagg agagtttata   1440
gaaaaaacta ttgccccagg aggtgctaat caaagaactg ctcctcaatg gatgttgcct   1500
ttacttctag gcctgtacgg gactgtaaca cctgctcttg aagcatatga agatggcccc   1560
aacaaaaaga aaaggagagt gtccaggggc agctcccaaa aagccaaagg aacccgtgca   1620
agtgccaaaa ctactaataa aaggaggagt agaagttcta gaagttaaaa ctgggctaga   1680
tgctataaca gaggtagaat gcttcctaaa cccagaaatg ggggatccgg atccagatga   1740
aaaccttagg ggctttagtc taaagctaag tgctgaaaat gactttagca gtgatagccc   1800
agaaagaaaa atgcttccct gttacagcac agcaagaatt cccctcccca atttaaatga   1860
ggacctaacc tgtggaaatc tactgatgtg ggaggctgta acagtacaaa cagaggtcat   1920
tggaataact agcatgctta accttcatgc agggtcacaa aaagtgcatg agcatggtgg   1980
aggtaaacct attcaaggca gtaatttcca ctttttgct gttggtggag accccttgga   2040
aatgcaggga gtgctaatga attacaggac aaagtaccca gaaggtacta accccaaa    2100 aaacccaaca gcccagtccc aagtaatgaa tactgaccat aaggcctatt tggacaaaaa   2160
caatgcttat ccagttgagt gctggattcc tgatcccagt agaaatgaaa atactaggta   2220
ttttgggact ttcacaggag gggaaaatgt tcccccagta cttcatgtga ccaacacagc   2280
taccacagtg ttgctagatg aacagggtgt ggggcctctt tgtaaagctg atagcctgta   2340
tgtttcagct gctgatattt gtggcctgtt tactaacagc tctggaacac aacagtggag   2400
aggccttgca agatatttta agattcgcct gagaaaaaga tctgtaaaaa atccttaccc   2460
aatttccttt ttgctaagtg acctttataaa caggagaacc cagagagtgg atgggcagcc   2520
tatgtatggt atggaatccc aggtagaaga ggttagggtg tttgatggca cagaaaaact   2580
```

```
tccagggggac ccagatatga taagatatat tgacaaacaa ggacaattgc aaaccaaaat    2640
gctttaaaca ggtgctttta ttgttgatat acatttaata aatgctgctt ttgtataagc    2700
cagttttaag cttgtgttat tttggggggtg gtgttttagg ccttttaaaa cactgaaagc    2760
ctttacacaa atgcaactct tgactatggg ggtctgacct tgggaatct tcagcagggg    2820 ctgaagtatc tgagacttgg gaagagcatt gtgattggga ttcagtgctt gatccatgtc    2880
cagagtcttc agtttctgaa tcttcttctc ttgtgatatc aagaatacat tttcccatgc    2940
atatattata tttcatcctt gaaaaagtat acatacttat ctcagaatcc agcctttcct    3000
tccattcaac aattctagat tgtatatctg ttgcaaaatc agctacaggc ctaaaccaaa    3060
ttagcagtag caacaaggtc attccacttt gtagaattct ttttttcaagt aagaactctg    3120 agttttgtaa ggattttctt aaatatattt tgggcctaaa atctatctgt cttacaaatc    3180
tagcttgcag ggttttaggg acaggatact cattcattgt aaccaggcct ggtggaaata    3240
tttgggttct tttgtttaaa tgtttctttt ctaaattaac cttaacactt ccatctaaat    3300
aatctctcaa actgtctaaa ttgtttattc catgtcctga aggcaaatcc tttgattcag    3360
ctcctgttcc ttttacatct tcaaaaacaa ccatgtactg atctatagct acacctagtt    3420
caaaggttag ccttttccatg ggtaggttta catttaaagc tttacctcca cacaaatcta    3480
ataaccctgc agctagtgtt gttttttccac tatcaatggg acctttaaat aaccagtatc    3540
ttcttttagg tacattaaaa acaatacagt gcaaaaaatc aaatataaca gaatccattt    3600
taggtagcaa acagtgcagc caagcaacac ctgccatata ttgttctaat acagcatttc    3660
catgagcccc aaatattaaa tccattttat ctaatatatg attaaatctt tctgttagca    3720
tttcttctct agtcatatga aggctatcta ctctttttttt agctaaaact gtatctactg    3780
cttgctgaca aatactttttt tgatttttac tttctgcaaa gatagtagca tttgcaaaat    3840
gcttttcatg atacttaaag tgataaggtt ggtctttttt ctgacacttt ttacactcct    3900
ctacattgta ttgaaattct aaatacatac ctaataataa aaacacatcc tcacactttg    3960
tttctactgc atactcagta attaatttcc aagagacctg ctttgtttct tcaggctctt    4020
ctgggttaaa atcatgctcc tttaagcccc cttgaatgct ttcttctatt gtatggtatg    4080
gatctctagt taaggcacta tatagtaagt attccttatt aacaccctta caaattaaaa    4140
aactaaaggt acacagcttt tgacagaaat tattaattgc agaaactcta tgtctatgtg    4200
gagttaaaaa gaatataata ttatgcccag cacacatgtg tctactaata aaagttacag    4260
aatatttttc cataagtttt ttatacagaa tttgagcttt ttctttagta gtatacacag    4320
caaagcaggc gagggttcta ttactaaata cagcttgact aagaaactgg tgtagatcag    4380
aaggaaagtc tttagggtct tctacctttc tttttttctt gggtggtgtt gagtgttgag    4440
aatctgctgt tgcttcttca tcactggcaa acatatcttc atggcaaaat aaatcttcat    4500 cccattttttc attaaaggaa ctccaccagg actcccactc ttctgttcca taggttggca    4560
cctataaaac aaataattac ttagggcctt taaatatttt attatttatc taaatataag    4620
gtagttacct taaagcttta gatctctgaa gggagtttct ccaattattt ggacccacca    4680
ttgcagagtt tcttcagtta ggtctaagcc aaaccactgt gtgaagcagt caatgcgta    4740 gcaatctatc caaaccaagg gctctttttct taaaaatttt ctatttaaat gccttaatct    4800
aagctgacat agcatgcaag ggcagtgcac agaaggcttt ttggaacaaa taggccattc    4860
cttgcagtac agggtatctg ggcaaagagg aaaatcagca caaacctctg agctactcca    4920
```

```
ggttccaaaa tcaggctgat gagctacctt tacatcttgc tccatttttt tatataaagt    4980
attcattctc ttcattttat cctcgtcgcc ccctttgtca gggtgaaatt ccttacactt    5040
ccttaaatag ctttttctca ttaagggaag gtttccccag gcagctcttt caaggcccaa    5100
aaggtccatg agctccatgg attcttccct gttaagcact ttatccat                5148

<210> SEQ ID NO 54
<211> LENGTH: 5111
<212> TYPE: DNA
<213> ORGANISM: Human polyomavirus 1
<220> FEATURE:
<223> OTHER INFORMATION: Type BK virus

<400> SEQUENCE: 54
ttttgcaaaa attgcaaaag aatagggatt tccccaaata gttttgctag gcctcagaaa      60
aagcctccac acccttacta cttgagagaa agggtggagg cagaggcggc ctcggcctct     120
tatatattat aaaaaaaaag gccacaggga ggagctgctt acccatggaa tgcagccaaa     180
ccatgacctc aggaaggaaa gtgcatgact gggcaggcag ccagtggcag ttaatagtga     240
aaccccgccc ctaaaattct caaataaaca caagaggaag tggaaactgg ccaaaggagt     300
ggaaagcagc cagacagaca tgttttgcga gcctaggaat cttggccttg tccccagtta     360
aactggacaa aggccatggt tctgcgccag ctgtcacgaa caaaaaaaag agctcagagg     420
atttttattt ttatttttaga gcttttgctg aatttttgta gaggtaaaga cagtgtagac     480
gggaaaaaca aaagtaccac tgctttacct gctgtaaaag actctgtaaa agactcctag     540
gtaagtaatc cctttttttt tgtatttcca ggttcatggg tgctgctcta gcacttttgg     600
gggacctagt tgccagtgta tctgaggctg ctgctgccac aggattttca gtggctgaaa     660
ttgctgctgg ggaggctgct gctgctatag aagttcaaat tgcatccctt gctactgtag     720
agggcataac aagtacctca gaggctatag ctgctatagg cctaactcct caaacatatg     780
ctgtaattgc tggtgctcct ggggctattg ctgggtttgc tgctttaatt caaactgtta     840
gtggtattag ttccttggct caagtagggt ataggttctt tagtgattgg gatcacaaag     900
tttccactgt aggcctctat cagcaatcag gcatggcttt ggaattgttt aacccagatg     960
agtactatga tattctgttt cctggtgtaa atactttttgt taataatatt cataccttg    1020 atcctaggca ttggggtcct tctttgtttg ctactatttc ccaggctttg tggcatgtta    1080
ttagggatga tatccttct ataacctcac aggaattgca gagaagaaca gaaagatttt    1140
ttagagactc cttggctaga ttttgggagg aaactacctg gaccattgta aatgccccta    1200
taaactttta taattatatt caacaatatt attctgattt gtcccctatt aggccctcaa    1260
tggttagaca gtagctgaa agggaaggta cccgtgtaca ttttggccat acttatagta    1320
tagatgatgc tgacagtata aagaagtta cacaaagaat ggatttaaga aatcaacaaa    1380
gtgtacattc aggagagttt atagaaaaaa ctattgcccc aggaggtgct aatcaaagaa    1440
ctgctcctca atggatgttg cctttacttc taggcctgta cgggactgta acacctgctc    1500
ttgaagcata tgaagatggc cccaaccaaa agaaaaggag agtgtccagg ggcagctccc    1560
aaaaagccaa aggaacccgt gcaagtgcca aaactactaa taaaggagg agtagaagtt    1620 ctagaagtta aaactggggt agatgctatt acagaggtag aatgcttcct aaacccagaa    1680 atggggatc cggatccaga tgaaaacctt aggggcttta gtctaaagct aagtgctgaa    1740
aatgacttta gtagtgatag cccagagaga aaaatgcttc ctgttacag cacagcaaga    1800 attcccctgc ccaatttaaa tgaggaccta acctgtggaa atttactgat gtgggaggct    1860
```

-continued

```
gtaactgtac aaacagaggt tattggaata actagcatgc ttaaccttca tgcagggtca    1920
caaaaagtgc atgagcatgg tggaggaaaa cctattcaag gcagtaattt ccacttcttt    1980
gctgttggtg gagacccctt ggaaatgcag ggagtgctaa tgaattacag gacaaagtac    2040
ccagatggta ctataacccc taaaaaccca acagcccagt cccaggtaat gaatactgac    2100
cataaggcct atttggacaa aaacaatgct tatccagttg agtgctgggt tcctgatccc    2160
agtagaaatg aaaatactag gtattttggg actttcacag gaggggaaaa tgttcccccca    2220
gtacttcatg tgaccaacac agctaccaca gtgttgctag atgaacaggg tgtggggccc    2280
ctttgtaaag ctgatagcct gtatgtttca gctgctgata tttgtggcct gtttactaac    2340
agctctggaa cacaacagtg gagaggcctt gcaagatatt ttaagatccg cctgagaaaa    2400
agatctgtaa agaatcctta cccaatttcc tttttgctaa gtgaccttat aaacaggaga    2460
acccagagag tggatgggca gcctatgtat ggtatggaat cccaggtaga ggaggttagg    2520
gtgtttgatg gcacagaaag acttccaggg gacccagata tgataagata tattgacaaa    2580
cagggacaat tgcaaaccaa aatgctttaa acaggtgctt ttattgtaca tatacattta    2640
ataaatgctg cttttgtata agccactttt aagcttgtgt tattttgggg gtggtgtttt    2700
aggtctttta aaacactgaa agcctttaca caaatgtaac tcttgactat ggggtctga    2760
cctttgggaa tcttcagcag gggctgaagt atctgagact tgggaagagc attgtgattg    2820
ggattcagtg cttgatccat gtccagagtc ttcagtttct gaatcctctt ctcttgtgat    2880
atcaagaata catttcccca tgcatatatt atatttcatc cttgaaaaag tatacatact    2940
tatctcagaa tccagccttt ccttccattc aacaattcta gattgtatat ctgttgcaaa    3000
atcagctaca ggcctaaacc aaattagcag tagcaacaag gtcattccac tttgtagaat    3060
tcttttttca agtaaaaact ctgagttttg taaggatttt cttaaatata ttttgggcct    3120
aaaatctatt tgtcttacaa atctagcttg cagggtttta gggacaggat actcattcat    3180
tgtaaccaag cctggtggaa atatttgggt tcttttgttt aaatgtttct tttctaaatt    3240
tactttaaca cttccatcta aataatctct caaactgtct aaattgttta ttccatgtcc    3300
tgaaggcaaa tcctttgatt cagcccctgt cccttttaca tcttcaaaaa caaccatgta    3360
ctgatctata gctacaccta gctcaaaggt tagccttttcc atgggtaggt ttacatttaa    3420
ggctttacct ccacacaaat ctaataaccc tgcagctagt gttgttttttc cactatcaat    3480
gggacctttca ataaccagt atcttctttt aggtacattg aaaacaatac agtgcaaaaa    3540
atcaaatata acagaatcca ttttaggtag caaacagtgc agccaagcaa cacctgccat    3600
atattgttct agtacagcat ttccatgagc tccaaatatt aaatccattt tatctaatat    3660
atgattgaat cttctgtta gcatttcttc cctggtcata tgaagggtat ctactctttt    3720
cttagctaaa actgtatcta ctgcttgctg acaaatactt ttttgatttt tactttctgc    3780
aaagataata gcatttgcaa agtgcttttc atgatactta aagtgataag gttggtcttt    3840
tttctgacac ttttttacact cctctacatt gtattgaaat tctaaataca tacctaataa    3900
taaaaacaca tcctcacact ttgtctctac tgcatactca gtaattaatt tccaagacac    3960
ctgctttgtt tcttcaggct cttctgggtt aaaatcatgc tcctttaagc ccccttgaat    4020
gctttcttct atagtatggt atggctctct agttaaggca ctatatagta agtattcctt    4080
attaacaccc ttcaaaatta aaaaactaaa ggtacacagc ttttgacaga agttattaat    4140
tgcagaaact ctatgtctat gtggagttaa aaagaatata atattatgcc cagcacacat    4200
```

```
gtgtctacta ataaaagtta cagaatattt ttccataagt tttttataca gaatttgagc    4260 tttttctttta gtagtataca cagcaaagca ggcaagggtt ctattactaa atacagcttg   4320
actaagaaac tggtgtagat cagagggaaa gtctttaggg tcttctacct ttcttttttt   4380
cttgggtggt gttgagtgtt gagaatctgc tgttgcttct tcatcactgg caaacatatc   4440
ttcatggcaa ataagtctt catcccattt ttcattaaag gaactccacc aggactccca    4500
ctcttctgtt ccataggttg gcacctataa aaaaataat tacttagggc cttttaatat    4560
tttattattt atctaaatat aagttagtta ccttaaagct ttagatctct gaagggagtt   4620
tctccaatta tttggaccca ccattgcaga gtttcttcag ttaggtctaa gccaaaccac   4680
tgtgtgaagc agtcaatgca gtagcaatct atccaaacca agggctcttt tcttaaaaat   4740
tttctattta aatgccttaa tctaagctga catagcatgc aagggcagtg cacagaaggc   4800
tttttggaac aaataggcca ttccttgcag tacagggtat ctgggcaaag aggaaaatca   4860
gcacaaacct ctgagctact ccaggttcca aaatcaggct gatgagctac ctttacatcc   4920
tgctccattt ttttatataa agtattcatt ctcttcattt tatcctcgtc gccccctttg   4980
tcagggtgaa attccttaca cttccttaaa taagcttttc tcattaaggg aagatttccc   5040
caggcagctc tttcaaggcc taaaaggtcc atgagctcca tggattcttc cctgttaagc   5100
actttatcca t                                                       5111

<210> SEQ ID NO 55
<211> LENGTH: 119
<212> TYPE: DNA
<213> ORGANISM: Human polyomavirus 1

<400> SEQUENCE: 55
aacaaaaaaa agagctcaga ggattttat ttttatttta gagcttttgc tggaattttg      60
tagaggtgaa gacagtgtag acgggaaaaa caaaagtacc actgctttac ctgctgtaa    119

<210> SEQ ID NO 56
<211> LENGTH: 72
<212> TYPE: DNA
<213> ORGANISM: Human polyomavirus 1

<400> SEQUENCE: 56
ttgccccagg aggtgctaat caaagaactg ctcctcaatg gatgttgcct ttacttctag     60
gcctgtacgg ga                                                        72

<210> SEQ ID NO 57
<211> LENGTH: 101
<212> TYPE: DNA
<213> ORGANISM: Human polyomavirus 1

<400> SEQUENCE: 57
ggaaagtctt tagggtcttc tacctttctc tttttcttgg gtggtgtgga gtgttgagaa     60
tctgctgttg cttcttcatc actggcaaac atatcttcat g                       101

<210> SEQ ID NO 58
<211> LENGTH: 95
<212> TYPE: DNA
<213> ORGANISM: Human polyomavirus 1

<400> SEQUENCE: 58
atgggtgctg ctctagcact tttgggggac ctagttgcca gtgtatctga ggctgctgct     60
gccacaggat tttcagtggc tgaaattgct gctgg                               95
```

```
<210> SEQ ID NO 59
<211> LENGTH: 63
<212> TYPE: DNA
<213> ORGANISM: Human polyomavirus 1

<400> SEQUENCE: 59
gggctgaagt atctgagact tgggaagagc attgtgattg ggattcagtg cttgatccat    60
gtc                                                                  63
```